US010548960B2

(12) United States Patent
Pfeil et al.

(10) Patent No.: US 10,548,960 B2
(45) Date of Patent: Feb. 4, 2020

(54) **MALARIA VACCINES BASED ON PRE-ERYTHROCYTIC ANTIGENS FROM *P. FALCIPARUM***

(71) Applicant: Ruprecht-Karls-Universitat Heidelberg, Heidelberg (DE)

(72) Inventors: Johannes Pfeil, Heidelberg (DE); Kirsten Heiss, Dossenheim (DE); Ann-Kristin Müller, Dossenheim (DE)

(73) Assignee: RUPRECHT-KARLS-UNIVERSITÄT HEIDELBERG, Heidelberg (DE)

( * ) Notice: Subject to any disclaimer, the term of this patent is extended or adjusted under 35 U.S.C. 154(b) by 0 days.

(21) Appl. No.: 15/274,767

(22) Filed: Sep. 23, 2016

(65) Prior Publication Data

US 2017/0072039 A1 Mar. 16, 2017

Related U.S. Application Data

(63) Continuation of application No. 13/988,339, filed as application No. PCT/EP2011/006110 on Dec. 6, 2011, now abandoned.

(60) Provisional application No. 61/419,906, filed on Dec. 6, 2010.

(51) Int. Cl.
*A61K 39/015* (2006.01)
*A61K 39/00* (2006.01)

(52) U.S. Cl.
CPC ........ *A61K 39/015* (2013.01); *A61K 2039/57* (2013.01)

(58) Field of Classification Search
None
See application file for complete search history.

(56) References Cited

FOREIGN PATENT DOCUMENTS

| | | | |
|---|---|---|---|
| EP | 0570489 | A1 | 11/1993 |
| WO | 9641877 | A2 | 12/1996 |
| WO | WO 2011/066995 | A1 | 6/2011 |

OTHER PUBLICATIONS

Cummings, J. F. et al., "Recombinant Liver Stage Antigen-1 (LSA-1) formulated with AS01 or AS02 is safe, elicits high titer antibody and induces IFN-gamma/IL-2 CD4+ T cells but does not protect against experimental Plasmodium falciparum infection." *Vaccine*, Jul. 2010, 28(31): Abstract, doi: 10. 1016/j.vaccine.2009.08.046.

Benmohamed, L. et al., "Long-Term Multiepitopic Cytotoxic-T-Lymphocyte Responses Induced in Chimpanzees by Combinations of Plasmodium falciparum Liver-Stage Peptides and Lipopeptides," 2004, *Infection and Immunity*, vol. 72, No. 8, p. 4376-4384.

Boslego et al (Vaccines and Immunotherapy, 1991, Chapter 17).

Cifuentes, G. et al., "Structural characteristics of immunogenic liver-stage antigens derived from P. falciparum malarial proteins," 2009, *Biochemical and Biophysical Research Communications*, vol. 384, p. 455-460.

Cowman, A. F. et al., "Functional analysis of Plasmodium falciparum merozoite antigens: implications for erythrocyte invasion and vaccine development," 2002, *The Royal Society*, vol. 357, p. 25-33.

Ellis (Vaccines, W.B. Saunders Company, Chapter 29, 1988, pp. 568-574).

Gardner, M. J. et al., "Genome sequence of the human malaria parasite Plasmodium falciparum," 2002, *Nature*, vol. 419, p. 498-511.

Hall, N. et al., "Sequence of Plasmodium falciparum chromosomes 1, 3-9 and 13," 2002, *Nature*, vol. 419, p. 527-531.

Mueller, A. K. et al., "Genetically Attenuated Plasmodium berghei Liver Stages Persist and Elicit Sterile Protection Primarily via CD8 T Cells," 2007, *The American Journal of Pathology*, vol. 171, No. 1, p. 107-115.

Remarque, E. J. et al., "Apical membrane antigen 1: a malaria vaccine candidate in review," 2007, *Trends in Parasitology*, vol. 24, No. 2, p. 74-84.

Shi, Y. P. et al., "Immunogenicity and in vitro protective efficacy of a recombinant multistage Plasmodium falciparum candidate vaccine," 1999, *Proc. Natl. Acad. Sci*., vol. 96, p. 1615-1620.

Skolnick et al. (Trends in Biotechnology 18:34-39, 2000).

Aidoo, M. et al. "Identification of conserved antigenic components for a cytotoxic T lymphocyte-inducing vaccine against malaria," Lancet 345:1003-1007, 1995.

Carralot, Jean-Philippe et al. "Mass spectrometric identification of an HLA-A*0201 epitope from Plasmodium falciparum MSP-1," International Immunology 20(11):1451-1456, Sep. 2008.

Ellis, Ruth D. et al. "Blood stage vaccines for Plasmodium falciparum," Human Vaccines 6(8):627-634, Aug. 2010.

Hodgson, Susanne H. et al. "Evaluation of the Efficacy of ChAd63-MVA Vectored Vaccines Expressing Circumsporozoite Protein and ME-TRAP against Controlled Human Malaria Infection in Malaria-Naive Individuals," The Journal of Infectious Diseases 211:1076-1086, Apr. 1, 2015.

Sedegah, M. et al. "Naturally acquired CD8+ cytotoxic T lymphocytes against the Plasmodium falciparum circumsporozoite protein," J. Immunol. 149(3):966-971, Aug. 1, 1992.

*Primary Examiner* — Robert A Zeman
(74) *Attorney, Agent, or Firm* — Saliwanchik, Lloyd & Eisenschenk

(57) ABSTRACT

The present invention relates to polypeptides or fragments thereof for use as malaria vaccines. It also relates to nucleic acid molecules coding for the polypeptides of the invention. It further relates to compositions comprising such polypeptides or fragments thereof or the nucleic acid molecules, in particular combinations of such polypeptides or fragments thereof, and the use of such compositions as malaria vaccines.

8 Claims, 10 Drawing Sheets

Specification includes a Sequence Listing.

SEQUENCE LISTING

```
<160> NUMBER OF SEQ ID NOS: 89

<210> SEQ ID NO 1
<211> LENGTH: 2743
<212> TYPE: PRT
<213> ORGANISM: Plasmodium falciparum

<400> SEQUENCE: 1

Met Asn Tyr Lys Leu Lys Glu Asn Val Pro Pro Asn Glu Asp Val Asp
```

-continued

```
1               5                   10                  15

Ile Tyr Glu Lys Leu Lys Thr Cys Val Ile Asn Arg Asn Val Glu Asp
            20                  25                  30

Phe Tyr Glu Glu Cys Val Ser Thr Phe Leu Glu Lys Val Lys Asn Ile
        35                  40                  45

Gly Asp Thr Asn His Ile Ile Cys His Asp Asn Tyr Ser Asp Ile Ile
    50                  55                  60

Asn Phe Phe Tyr Leu Asn Leu Phe Val Asp Asn Ser Glu Phe Val Arg
65                  70                  75                  80

Val Val Ala Val Ser Gln Asp Asn Asn Glu Asn Ala Lys Ile Cys Lys
                85                  90                  95

Arg Tyr Ile His Asp Lys Asn Glu Lys Asp Val Thr Glu Lys Ser Glu
            100                 105                 110

Leu Leu Gln Glu Leu Gly Leu Tyr Leu Lys Asn Ile Lys Leu Lys Tyr
        115                 120                 125

Ser Glu Lys Leu Lys Lys Ile Lys Asn Val Ile Ile Asp Asn Ile Ser
    130                 135                 140

Thr Cys Gln Lys Cys Ile Met Ile Tyr Tyr Phe Leu Gln Lys Lys Leu
145                 150                 155                 160

Val Glu Lys Ile Ser Ser Asn Ile Asn Lys Lys Asp Asp Asn Val Thr
                165                 170                 175

Asn Ile Ile Lys Lys Glu Ile Phe Glu Phe Asn Phe Tyr Arg Ile Ile
            180                 185                 190

Asn Lys Ile Thr Cys Pro Ile Gly Tyr Asn Asn Val Asp Ser Val Ile
        195                 200                 205

Leu Glu Leu Met Leu Asn Gly Ser Lys Ile Phe Gln Met Asp Leu Asn
    210                 215                 220

Tyr Ile Leu Glu Tyr Asn Lys Ile Asn Lys Val Asn Leu Lys Ile Phe
225                 230                 235                 240

Lys Glu Lys Phe Ile Asn Tyr Asp Asn Asp Glu Ile Tyr Arg Ile Ile
                245                 250                 255

Lys Glu Tyr Val Asp Tyr Asp Ser Leu Ile Phe Phe Cys Asn Leu Leu
            260                 265                 270

Phe Lys Glu Phe Lys Arg Met Lys Asn Leu Leu Leu Gln Asn Asp Asn
        275                 280                 285

Tyr Asn Asn Gly Asn Asp Thr Ser Ile Ile Asn Glu Asn Ile Ser Asn
    290                 295                 300

Asn Asn Asn Asn Asn Asn Asn Asn Asn Asn Asp Pro Leu Cys Asn Asp
305                 310                 315                 320

Asn Thr Leu Tyr Asn Tyr Asn Ile Gln Cys Leu Leu Pro Tyr Ile Tyr
                325                 330                 335

Ile His Ile Phe Ile Leu Leu Lys His Lys Gln Val Glu Glu Thr Val
            340                 345                 350

Arg Arg Val Leu Lys Glu Arg Ile Ile Leu Tyr Ser Leu Met Ile Asn
        355                 360                 365

Ser Leu Arg Tyr Ser Asp Asn Phe Ile Gln Leu Ile Ile Phe Lys Ile
    370                 375                 380

Ile Asn Asn Ile Phe Ile Asn Glu Glu Glu Phe Leu Lys Asp Ser Asn
385                 390                 395                 400

Lys Lys Leu Ile Ser Ser Ile Phe Ser Tyr Trp Ile Lys Leu Ser Asp
                405                 410                 415

Gly Cys Ile Val Lys Met Ile Asn Ala Ser Ile Thr Asp Glu Ser Ser
            420                 425                 430
```

-continued

```
Thr Ser His Asn Asn Leu Ser Arg Ser Ser Ser Asn Asn Thr Lys His
        435                 440                 445

Asn Ser Asn Lys Leu Tyr Asn Asn Ser Cys Ile Lys Lys Thr Lys Thr
    450                 455                 460

Asp Asp Glu Asn Phe Leu Lys Asn Asn Phe Thr Asp Tyr Asp Ile Tyr
465                 470                 475                 480

Lys Tyr Met Gln Ser Leu Ile Cys Gly Leu Tyr Leu Leu Thr Leu Ile
                485                 490                 495

Arg Lys Lys Lys Asn Asn Asp His His Tyr Asn Asn Lys Ser Asp Asn
            500                 505                 510

Thr Asn Gln Phe Ser Ser Leu Lys Glu Tyr Asn Ile Asp Met Leu Ser
        515                 520                 525

Leu Asn His Phe Phe Ile Asn Met Asp Asn Tyr Ile Tyr Leu Ile Gly
    530                 535                 540

Phe Met Phe Ser Glu Asn Lys Asp Thr Ile Asn Asn Leu Phe Asn Leu
545                 550                 555                 560

Ile Phe Lys Leu Leu Tyr Phe Ile Lys Tyr Leu Lys Ser Tyr Ile Ile
                565                 570                 575

Gln Asn Arg Asn Leu Lys Asn Lys Tyr Phe Glu Asp Thr Cys Ile Tyr
            580                 585                 590

Ser Ser Ile Asn Ile Leu Tyr Asn Ile Leu Glu Val Thr Lys Lys Phe
        595                 600                 605

Phe Ile Ser Tyr Phe Arg Ile Asp Glu Tyr Thr Lys Asn Leu Tyr Lys
    610                 615                 620

Asn Tyr Phe Arg Asp Arg Pro Leu Thr Phe Glu Asn Met Ala Phe Tyr
625                 630                 635                 640

Val Ile Pro Leu Phe Ile Asn His Glu Asp Tyr Tyr Ile Arg Ile Tyr
                645                 650                 655

Ser Ile Lys Ile Leu Ile Ile Leu Leu Ser Asp Thr Asn Ile Arg Asp
            660                 665                 670

Ser Leu Asp Lys Lys Asn Leu Phe Arg Ile Phe Asp Leu Leu Ile Asn
        675                 680                 685

Ile Glu Gly Tyr Lys Ser Leu Ser Gln Asp Glu Glu Glu Glu Glu Lys
    690                 695                 700

Lys Asn Ile Asn Gln Leu Leu Leu Leu Leu Phe Lys Cys Asn Ile Asn
705                 710                 715                 720

Asp Asn Lys Leu Ser Ser Asn Ile Thr Asn Leu Ile Phe Ser Glu Lys
                725                 730                 735

Gln Lys Ile Phe Ile Lys Tyr Ile Leu Arg Leu Cys Lys Asp Glu Glu
            740                 745                 750

Tyr Ser Ile Ile His Met Lys Asn Phe Phe Asp Tyr Phe Phe Val Leu
        755                 760                 765

Leu Val Lys Leu Ile Asn Ile Ile Ile Arg Arg Ala Gln Cys Ser Leu
    770                 775                 780

Asn Ile Glu Lys Tyr Lys Asp Phe Phe Met Asn Ile Tyr Glu Val Val
785                 790                 795                 800

Glu Ile Phe Met Lys Glu Leu Lys Lys Glu Lys Leu Lys Lys His Lys
                805                 810                 815

Leu Leu Phe Leu Ser Ser Gly Ile Tyr Leu Cys His Leu Ile Thr Asn
            820                 825                 830

Ser Ile Tyr Lys Gly Lys Ile His Ser Ser Val Pro Tyr Leu Asn Val
        835                 840                 845
```

-continued

```
Val Ile Ser Leu Ile Lys Asn Ile Glu His His Leu Asn Phe Ile Gln
    850                 855                 860

Asp Asp Leu Ile Tyr Ile Asn Lys Ile Ser Lys Asp Ile Ile Ser Asp
865                 870                 875                 880

Lys Lys Leu Ser Ile His Ser Glu Asp Glu Asp Asn Lys Asp Asp Asp
                885                 890                 895

Ser Lys Ser Val Lys Asp Leu His Val Leu Tyr Phe Tyr Asn Asn Val
            900                 905                 910

Tyr Ser Glu Glu Leu Gly Lys Asn Val Gly Asn Asn Asn Asn Met Ala
        915                 920                 925

Asn Asn Asn Asn Asn Asp Asn Asn Asp Asn Asn Ile Asn Asn Asn Asn
    930                 935                 940

Asn Asn Asn Asn Gly Glu Asn Ile Glu His Lys Cys Val Lys Ser Thr
945                 950                 955                 960

Tyr Lys Glu Asn Lys Asn Asn Asp Ile Asn Cys Lys Asn Lys Gln Thr
                965                 970                 975

Asn Asp Lys Asn Leu Lys Ser Asn Pro Ser Asp Asn Lys Gly Thr Asn
            980                 985                 990

Asn Ser Glu Ile Val Lys Lys Leu  Asn Lys Tyr Asp Lys  Phe Met Lys
        995                 1000                1005

Met Cys  Leu Leu Gln Asn Lys  Asn Asn Asp Glu Ile  Ile Tyr Asn
    1010                1015                1020

Tyr Ile  Asn Cys Leu Phe Tyr  Leu Cys Val Ser Asn  Met Asn Lys
    1025                1030                1035

Arg Thr  Arg Lys Asn Val Ile  Lys Ser Tyr Asp Leu  Val Val Lys
    1040                1045                1050

Tyr Ile  Leu Lys Asp Glu Tyr  Lys Leu His Arg Val  Lys Lys Lys
    1055                1060                1065

Ser Leu  Leu Phe Ser Met Pro  Ile Tyr Ile Ile Arg  Asp Val Glu
    1070                1075                1080

Asn Glu  Gly Lys Arg Tyr Asn  Leu Ile Ile Asp Lys  Tyr Asp Tyr
    1085                1090                1095

Ile Leu  Arg Ser Tyr Ile Ile  Asp Phe Phe Lys Cys  Lys Lys Tyr
    1100                1105                1110

Leu Pro  Cys Leu Leu Leu Ser  Cys Leu Ser Phe Thr  Asn Thr Met
    1115                1120                1125

Ile Leu  Phe Leu Lys Lys Lys  Asn Phe Ile Asn Ser  Thr Thr Asn
    1130                1135                1140

Asn Asn  Ile Thr Glu Lys Glu  Asp Met Leu Asp Cys  Phe Met Leu
    1145                1150                1155

Val Asn  Ser Lys Thr Trp Phe  Tyr Phe Asn Val Leu  Val Glu Cys
    1160                1165                1170

Ile Cys  Asp Tyr Phe Met Thr  Ser Gln Ser Lys Met  Asp Val Lys
    1175                1180                1185

Ser Gln  Gln Ile Lys Glu Gln  Gln Asn Glu His Thr  Gln Lys Cys
    1190                1195                1200

Asn Asn  Lys Asn Lys Asn Asn  Asn Asn Asn Asn Asn  Asn Asp Asp
    1205                1210                1215

Asp Asp  Val His Lys Phe Ser  Trp Gln Ile Ile Asn  Leu Ile Ile
    1220                1225                1230

Asp Ser  Ile Trp Lys Ile Leu  Ile Tyr Ile Phe Tyr  Asn Ile Lys
    1235                1240                1245

Ile Asn  Ile Phe Ser Ile Lys  Val Lys Thr Phe Ser  Ile Asn Ile
```

-continued

```
    1250                1255                1260

Tyr Gly  Arg Ala Ala Leu Leu  Met Phe Leu Gln Phe  Tyr Glu Ser
    1265                1270                1275

Trp Ile  Val Phe Ile Lys Thr  Phe Leu Thr Ser Glu  Lys Gln Ile
    1280                1285                1290

Phe Ile  Ser Arg Asn Ile Leu  Leu Pro Asp Leu Phe  Tyr Lys Lys
    1295                1300                1305

Phe Gly  Phe Leu Ser Ser Gln  Ile Leu Ser Tyr Phe  His Phe Ile
    1310                1315                1320

Glu Ser  Asn Phe Phe Val Asp  Ser Gln Asn Glu Val  Asn Leu Arg
    1325                1330                1335

Leu Leu  Glu Lys Gln Lys Asp  Val Met Asn Asn Ile  Leu Asp Val
    1340                1345                1350

Leu Ile  Tyr Phe Ile Lys Asp  Lys Asp Pro Lys Gly  Tyr Val Asn
    1355                1360                1365

Glu Leu  Asn Ser Phe Ser Gln  Phe Lys Leu Arg Ile  Lys Lys Leu
    1370                1375                1380

Thr Phe  Pro Lys Lys Leu Gln  Asp Gly Phe Leu Ser  Cys Thr Tyr
    1385                1390                1395

Asp His  Leu Phe Lys Lys Ala  Lys Glu Leu Leu Leu  Arg Val Glu
    1400                1405                1410

Lys Ser  Lys Thr Leu Gln Met  Asp Glu Cys Arg Gly  Glu Asp Pro
    1415                1420                1425

Asn Ile  Asn Ser Asn Ser Leu  Gln Met Asp Lys Gly  Asp Asp Asn
    1430                1435                1440

Glu Asn  Val Ile Asn Ile Asn  Asn Ser Asp Ile Ile  Val Glu Lys
    1445                1450                1455

Asp Ser  Lys Thr Ile Ile Arg  Ile Asp Ser Asn Ser  Lys Asp Ala
    1460                1465                1470

Asn Ala  Val Glu Arg Asp Asp  Asn Lys Glu Gly Lys  Lys Val Phe
    1475                1480                1485

Ser Leu  Glu Gln Ala Lys Lys  Ile Ile Glu Lys Asn  Ala Ala Ser
    1490                1495                1500

Lys Asn  Thr Lys Arg Ala Ile  Val Leu Asn Glu Asn  Leu Ala Glu
    1505                1510                1515

Lys Asn  Lys Gln Gln Ile Phe  Lys Glu Met Lys Glu  Lys Arg Lys
    1520                1525                1530

Glu Ala  Glu Asn Ile Leu Met  Lys Tyr Phe Ile Met  Ile Gln Glu
    1535                1540                1545

Phe Leu  Asn Trp Asp Phe Phe  Asn Leu Asp Asn Ile  Asp Lys Tyr
    1550                1555                1560

Lys Asn  Ser Ile Ser Glu Glu  Leu Pro Ile Arg Phe  Glu Asn Glu
    1565                1570                1575

Glu Glu  Tyr His Lys Phe Phe  Arg Pro Met Ala Leu  Glu Glu Cys
    1580                1585                1590

Arg Cys  Ser Met Leu Asn Asn  Met Met Gly Asp Ile  Asn Lys Tyr
    1595                1600                1605

Val Ile  Ser Ile Val Gly Lys  Lys Lys Met Pro Tyr  Trp Val Val
    1610                1615                1620

Trp His  Val Ser Ser Ser Ser  Glu Asn Lys Arg Asn  Leu Asp Asn
    1625                1630                1635

Ile Lys  Pro Met Asp Leu Ile  Ala Leu Ile Pro Tyr  Asp Glu Asp
    1640                1645                1650
```

-continued

Arg Asn Asn Asn Thr His Ala Asp Asn Asn Asp Thr Ser Ile Lys
1655 1660 1665

Tyr Asp Lys Leu Lys Asp Met Leu Lys Cys Thr Lys His Val Ile
1670 1675 1680

Gly Leu Val Asp Ile Gly Ser Asn Lys Phe Asp Asn Ile Phe Asp
1685 1690 1695

Ile Lys Leu Ile Asn Glu Asp Asn Leu Pro Ser Lys Val Asn Asn
1700 1705 1710

Glu Lys Thr Arg Leu Lys Leu Asn Phe Ile Thr Cys Asn Lys Phe
1715 1720 1725

His Ala Tyr Val Leu Cys Asn Leu Met Thr Asn Ile Arg Glu Phe
1730 1735 1740

Gln Ser Ile Tyr Leu Ser Arg Asn Cys Pro Leu Phe Asn Leu Ile
1745 1750 1755

Leu Asn Pro Val Gly Glu Asn Lys Val Glu Lys Gly Leu Cys Asn
1760 1765 1770

Met Asn Ile Asn Asn Asn Tyr Ile Asn Asp Cys Asp Lys Asp Lys
1775 1780 1785

Asn Asp Lys Leu Lys Lys Glu Leu Glu Lys Leu Thr Arg Gln Glu
1790 1795 1800

Lys Leu Ile Leu Lys Ile Leu Ser Lys Tyr Asn Leu Leu Asn Lys
1805 1810 1815

Ser Gln Ile Glu Ala Val Lys Leu Ile Leu Leu Asn Lys Asn Asn
1820 1825 1830

Ile Ser Leu Ile Gln Gly Pro Pro Gly Thr Gly Lys Thr Lys Thr
1835 1840 1845

Val Ile Gly Ile Val Ser Val Leu Tyr Ala Leu Leu Tyr Lys Lys
1850 1855 1860

Asn Tyr Glu Lys Asp Lys Lys Lys Lys Asp Leu Leu Tyr Asn Glu
1865 1870 1875

Gln Ile Asn Asn Thr Lys Lys Lys Lys Lys Ile Leu Val Cys Ser
1880 1885 1890

Pro Ser Asn Ser Ala Ile Asp Glu Ile Ala Lys Arg Ile Leu Asn
1895 1900 1905

Glu Gly Leu Leu Asn Phe Thr Asn Leu Ile Asn Ser Tyr Glu Asn
1910 1915 1920

Lys Ile Lys Lys Asn Asn Ile Thr Ser Gln Lys Cys Gly Ser Asn
1925 1930 1935

Asn Lys Lys Lys Ile Leu Leu Gly Asp Asn Asp Leu Tyr Asn Ser
1940 1945 1950

Ser Asp Ile Ser Asp Phe Leu Gly Glu Asp Gln Pro Ser Asn Phe
1955 1960 1965

Ser Asn Asp Lys Lys Glu Lys Ser Ser Lys Gly Met Val Leu Leu
1970 1975 1980

Lys Gly Leu Lys Asn Val Asp Lys Leu Asn Asn Asn Asn Ile Ser
1985 1990 1995

Ser Glu Lys Met Asn Gln Phe Lys Lys Gln Thr Ile Ala Pro Lys
2000 2005 2010

Cys Ile Arg Ile Gly Leu Ser Lys Arg Thr His Glu Glu Ile Gln
2015 2020 2025

Arg Ile Ser Leu Asp Tyr Ile Phe Asn Lys Lys Lys Ser Ser Asp
2030 2035 2040

-continued

```
Glu Asn  Leu Tyr His Val His  Phe Glu Lys Arg Lys  Ser Lys Leu
    2045                 2050                 2055

Thr Tyr  Ser Ile Glu Ala Val  Asp Tyr Thr Lys Leu  Lys Ile Asn
    2060                 2065                 2070

Glu Met  Lys Asn Asp Leu Ser  Leu Asn Asn Ser Glu  Lys Tyr Ser
    2075                 2080                 2085

Phe Asp  Cys Asn Asp Ile Asn  Gly Lys Phe Met Phe  Gln Lys Val
    2090                 2095                 2100

Glu Phe  Ile Glu Arg Phe Phe  Ser Asp Glu Tyr Ile  Asn Asn Leu
    2105                 2110                 2115

Asp Lys  Lys Tyr Leu Glu Asn  Leu Leu Tyr Leu Tyr  Asn Glu Ser
    2120                 2125                 2130

Ser Ser  His Tyr Asp Trp Ser  Ile Gln Lys Leu Ile  Ser Glu Arg
    2135                 2140                 2145

Asn Tyr  Leu Asp Glu Cys Met  Thr Arg Leu Ile Glu  Thr Asp Glu
    2150                 2155                 2160

Gln Ile  Gly Ser Phe Tyr Thr  Ser Asn Asn Lys Glu  Asn Met Leu
    2165                 2170                 2175

Phe Asp  Ser Glu Ile Ile Phe  Ser Thr Leu Ser Gly  Ser Ala Ser
    2180                 2185                 2190

Pro Val  Ile Glu Asn Leu Glu  Phe Glu Tyr Leu Ile  Ile Asp Glu
    2195                 2200                 2205

Ala Cys  Gln Cys Val Glu Leu  Ser Cys Leu Ile Pro  Phe Arg Leu
    2210                 2215                 2220

Lys Val  Lys Asn Ile Ile Met  Val Gly Asp Pro Lys  Gln Leu Pro
    2225                 2230                 2235

Ala Thr  Thr Phe Ser Ser Asp  Cys Arg Lys Tyr Gly  Tyr Ser Arg
    2240                 2245                 2250

Ser Leu  Phe Glu Arg Leu Leu  Leu Cys Asn Val Ser  Ser Val Leu
    2255                 2260                 2265

Leu Asn  Ile Gln Tyr Arg Met  Arg Pro Glu Ile Cys  Tyr Phe Pro
    2270                 2275                 2280

Asn Asn  Tyr Phe Tyr Asn Gly  Leu Ile Lys Asn Ala  Asp Ile Leu
    2285                 2290                 2295

Ser Asn  Lys Pro Phe Phe Tyr  Tyr Phe Gln Asp Leu  Asp Phe Phe
    2300                 2305                 2310

Gly Cys  Tyr Lys Phe Ile Asn  Ile Asp Gly Ile Glu  Ser Met Thr
    2315                 2320                 2325

Tyr Asn  Lys Ser Tyr Ile Asn  Tyr Val Glu Ala Tyr  Phe Ile Tyr
    2330                 2335                 2340

Lys Leu  Val Leu Tyr Ile Lys  Asn Ile Ile Ser Lys  His Gln Asp
    2345                 2350                 2355

His Thr  Lys Ser Val Pro Asn  Leu Tyr Lys Leu Pro  Val His Phe
    2360                 2365                 2370

Ser Leu  Lys Asp Ile Gly Ile  Ile Cys Pro Tyr Gln  Ser Gln Val
    2375                 2380                 2385

His Leu  Ile Arg Asn Met Phe  Glu Glu Ser Phe Glu  Asp Lys Ile
    2390                 2395                 2400

Pro Phe  Pro Glu Val Ser Thr  Val Asp Ala Phe Gln  Gly Arg Glu
    2405                 2410                 2415

Lys His  Ile Ile Ile Phe Ser  Cys Val Arg Ser Lys  Leu Glu Val
    2420                 2425                 2430

Leu Glu  Asn Ser Lys Leu Leu  His Lys Met Gly Thr  Tyr Lys Lys
```

-continued

```
    2435                2440                2445

Ala Asp  Asp Lys Trp Lys Lys  Thr Lys Glu Arg Tyr  Val Ile Tyr
    2450                2455                2460

Asp Ser  Asp Asp Asn Ala Glu  Tyr Ser Met Asn Glu  Asn Glu Asp
    2465                2470                2475

Asn Ser  Asp Asn Asp Asp Asp  Asn Asp Asp Asp Asn  Asp Asn Asp
    2480                2485                2490

Asp Asp  Asn Asn Lys Glu Trp  Lys Tyr Asp Tyr Asn  Asp Gly Val
    2495                2500                2505

His Thr  Lys Lys Trp Ile Ser  Ser Lys Met Pro Asn  Ile Lys Asn
    2510                2515                2520

Glu Asn  Asp Phe Arg Ala Ile  Gln Lys Phe Gly Asn  Asn Ile Gly
    2525                2530                2535

Phe Leu  Lys Asp Glu Arg Arg  Leu Asn Val Ala Leu  Thr Arg Ala
    2540                2545                2550

Lys Asp  Tyr Leu Trp Ile Ile  Gly Asn Arg Lys Asn  Leu Glu Met
    2555                2560                2565

Asn Glu  Thr Trp Asp Cys Leu  Ile Gln Asn Ala Ile  Ile Arg Lys
    2570                2575                2580

Cys Tyr  Leu Asp Leu Lys Ile  Asn Phe Glu Asn Ser  Thr Thr Glu
    2585                2590                2595

Asn Ile  Ile Lys Glu Lys Val  Asn Asp Phe Phe Ile  His Leu Glu
    2600                2605                2610

Asn Asp  Ile Asn Glu Lys Lys  Tyr Glu Ser Ser Glu  Met Ser Ser
    2615                2620                2625

Asn Leu  Ser Ser Asn Ser Cys  Ile Ile Lys Glu Glu  His Asp Glu
    2630                2635                2640

Glu Glu  Asn Tyr Asp Glu Ile  Ile Val Asp Asp Asp  Lys Leu Phe
    2645                2650                2655

Lys Asn  Lys Asn Lys Phe Arg  Leu Asn Lys Asn Lys  Tyr Lys Gln
    2660                2665                2670

Asn Thr  Ile Trp Asn Asn Ser  Gly Asp Asn Glu Phe  Ser Phe Ser
    2675                2680                2685

Arg Ala  Tyr Thr Gly Asn Ser  Tyr Trp Ser Asn Tyr  Ser Asn Lys
    2690                2695                2700

Glu Arg  Glu Lys Asn Lys Asn  Tyr Asp Lys Lys Gly  Lys Arg Lys
    2705                2710                2715

Ile Asn  Asp Ser Leu Leu Asp  Asp Asp Leu Leu Thr  Lys Arg Arg
    2720                2725                2730

Lys Tyr  Asp Pro Tyr Asp Asn  Ser Asn Val
    2735                2740
```

<210> SEQ ID NO 2
<211> LENGTH: 1653
<212> TYPE: PRT
<213> ORGANISM: Plasmodium falciparum

<400> SEQUENCE: 2

```
Met Ser Thr Gly Trp Asn Phe Asn Phe Lys Lys Lys Asn Gly Arg Arg
1               5                   10                  15

Lys Lys Gly Asp Leu Lys Tyr Val Gln Leu Phe Ser Arg Ser Gly Ile
            20                  25                  30

Ser Thr Leu Lys Asn Glu Asn Val Ile Phe Glu Lys Gly Leu Asn Cys
        35                  40                  45
```

-continued

```
Gly Pro Ala Gly Arg Asn Ala Leu Ile Arg Trp Ile Glu Tyr Asn Tyr
    50                  55                  60

Lys Met Lys Asn Asp Glu Glu Asn Ser Tyr Pro Ala Val Asn Ala Cys
65                  70                  75                  80

Lys Ile Trp Gln Lys Thr Gln Ser Phe Gln Asp Val Val Leu Ser Gly
                85                  90                  95

Met Val Asp Phe Leu Lys Phe Leu Asn Val Pro Lys His Val Thr Tyr
            100                 105                 110

Lys Asn Val Phe Asp Asn Tyr Leu Ser Pro Asn Phe Ile Asn Lys Ile
        115                 120                 125

Asn Ser Ile Gly Asn Ser Gln Lys Ser Leu Ile Arg Leu Ala Ser Lys
    130                 135                 140

Met Thr Pro Met Phe Gln Val Arg Glu Ile Gln Pro Leu Phe Ser Val
145                 150                 155                 160

Leu Leu Glu Lys Ile Asn Val Ile Pro Val Lys Ile Leu Asn Ile Leu
                165                 170                 175

Val Glu Asp Thr Pro Ala Ala Gln Tyr Phe Tyr Glu Ile Thr Cys Leu
            180                 185                 190

Asn Val Lys Arg Lys Ile Trp Val Met Trp Ala Gln Lys Phe Tyr Glu
        195                 200                 205

Glu Ile Glu Gln Leu Val Glu Glu Ile Ile Ile His Met Lys Leu Asn
    210                 215                 220

Asp Asn His Glu Tyr Ile Asn Asn Leu Ile Asn Lys Ile Ile Asp Phe
225                 230                 235                 240

Ile Gly Asp Gly Thr Glu Lys Tyr Tyr Leu Tyr Asn Leu Cys Ile His
                245                 250                 255

Ile Ile Arg Leu Lys Ser Val Asn Thr Ile Leu Asn His Asn Glu Tyr
            260                 265                 270

Leu Ser Ser Asn His Tyr Asn Asp Asn Leu Lys Tyr Asp Glu His His
        275                 280                 285

Asn Ile Thr Met Thr Asn Gln Thr Asn Asn Ile Asn Lys Ile Ser Lys
    290                 295                 300

Asn Ile Asp Ile Tyr Asn Asn Asn Ile Ile Ile Asn Asp Lys Lys Asn
305                 310                 315                 320

Lys Glu Pro Asn Lys Asn Tyr Leu Lys Leu Asn Leu Asn Phe Asn Asn
                325                 330                 335

Ile Ser Glu Asn Gln Asp Leu Gln Gln Lys Leu Ile Lys Leu Gln Ser
            340                 345                 350

Cys Phe Asp Asn Ile Met Asn Asn Asn Asn Asn Lys Glu Ser Asp Asp
        355                 360                 365

Gln Lys Glu Met Ile Tyr Ser Lys Glu Asn Thr Pro Tyr Tyr Leu Gln
    370                 375                 380

Leu His Glu Tyr Tyr His Asn Ser Thr Ser Phe Lys Tyr Leu Lys Lys
385                 390                 395                 400

Arg Lys Asn Glu Lys Tyr Gly Lys Asp Ile Asn Ile Ile Asn Asp Glu
                405                 410                 415

Lys Ile Leu Leu Asn Lys Met Glu Arg Glu Thr Asp Ser Met Arg Leu
            420                 425                 430

Ile Lys Asn Pro Gln Tyr Ile His Lys Glu Asp Thr Ile Cys Lys Arg
        435                 440                 445

Ile Leu Tyr Gln Asn Arg Asp Asp Asn Arg Val Lys Lys Ile Lys Tyr
    450                 455                 460

Asn Met His Asp Lys Asp Glu Asp Asn Glu Leu Glu Asn Ile Val Tyr
```

-continued

```
465                 470                 475                 480

Met Glu Arg Asn Lys Ile Glu Glu Lys Thr Lys Asp Ala Leu Val Lys
                485                 490                 495

Asp Lys Glu Asn Val Glu Glu Asp Asn Leu Glu Asn Ile Thr Asn Lys
            500                 505                 510

Asn Met Asn Asn Asn Asn Asn Lys Ile Ser Arg Ser Asn Ile Cys His
        515                 520                 525

Asp Asn Ile Thr Asp Thr Lys Glu Lys Phe Gln Lys Thr Arg Lys Ile
    530                 535                 540

Lys Thr Asn Asn Asn Ala Tyr Tyr Asp Lys Lys Asn Ser Leu Pro Phe
545                 550                 555                 560

Asp Asn Met Phe Tyr Ser Lys Leu Arg Leu Leu Leu Cys Met Gln Tyr
                565                 570                 575

Lys Glu Lys Tyr Asn Val Val Asp Asn Glu Met Ile Lys Ile Asp Lys
            580                 585                 590

Tyr Phe Tyr Phe Ile Glu Phe Ile Asn Asn Ile Ile Lys Asp Gly Ile
        595                 600                 605

Val Asn Phe Ile Asp Glu Phe Lys Thr Lys Glu Ile Ile Lys Lys Met
    610                 615                 620

Gln Tyr Asn Phe Lys Ile Thr Asn Ile Asp Asp Leu Tyr Glu Tyr Ser
625                 630                 635                 640

Leu Leu Leu Asn Asn Ile Gln Leu Lys Phe Ser Ile Ile Glu Gly Ile
                645                 650                 655

Cys Phe Asn Phe His Lys Asn Asn Phe Asp Met Ile Thr Gln Lys Cys
            660                 665                 670

Asn Val His Phe Trp Ile Ser Leu Phe Tyr Leu Gly Ile Tyr Asn Asn
        675                 680                 685

Phe Phe Ser Leu Ile Lys Tyr Ala Ile Asp Lys Arg Glu Ser Ile Gly
    690                 695                 700

Thr Lys Lys Lys Asp Ile Lys Lys Asp Gln Asn Asp Arg His Ile Ile
705                 710                 715                 720

Lys Gly Glu Val Asp Ser Asp Ile Asn Thr His Val Tyr Asn Glu Ile
                725                 730                 735

Ile His Thr Glu Glu Glu Lys Asp Tyr Tyr Glu Asn Lys Glu Asn Val
            740                 745                 750

His Glu Glu Val Lys Leu Gln Asn Asp Ile Lys Glu Ile Glu Glu Glu
        755                 760                 765

Glu Gln Asn Glu Tyr Ala Gly Lys Asp Glu Ile Val Arg Asp Lys His
    770                 775                 780

Leu Asn Asn Tyr Gln Asp Glu Lys Asp Val Gln His Leu His Ile Tyr
785                 790                 795                 800

Glu Phe Tyr Glu Asn Gly Gln Tyr Tyr Gln Asn Tyr Asp Asp Gly Met
                805                 810                 815

Lys Phe Phe Glu Glu Lys Glu Glu Pro Asp Arg Lys Asp Glu Cys Asp
            820                 825                 830

Glu Asn Lys Asn Asp Asp Asp Glu Glu Glu Glu Glu Asp Asp Asp Glu
        835                 840                 845

Glu Glu Glu Glu Asp Asp Asp Glu Glu Glu Glu Glu Asp Asp Asp Glu
    850                 855                 860

Glu Glu Asp Asp Asp Asp Glu Gln Glu Asp Asp Asp Asp Glu Glu Asp
865                 870                 875                 880

Asp Asp Asp Glu Glu Asp Asp Glu Glu Glu Asp Asp Asp Asp Glu Gln
                885                 890                 895
```

-continued

```
Glu Asp Asp Asp Glu Glu Asp Asp Asp Asp Asp Asp Asp Asp Asp Asp
            900                 905                 910

Glu Glu Asp Asp Asp Asp Asp Asp Asp Asp Asn Tyr Asn Asp Thr Tyr
        915                 920                 925

Asn Asp Asp Asp Asp Tyr Asn Asn Ile Asn His Glu Tyr Asn Lys Glu
    930                 935                 940

His Pro Lys Lys Ile Ser Asn Gly Gly Asn Asn Lys Lys Tyr Gly His
945                 950                 955                 960

Val Phe Pro Lys Val Tyr Pro His His Thr Ile Tyr Asn Asp Tyr Asn
                965                 970                 975

Lys Arg Asn Asn Tyr Tyr Glu Ser Gln Glu Lys Glu Asp Thr Trp Lys
            980                 985                 990

Asn Gln Lys His Lys Gly Ile Asn  Lys His Lys Asp Asp  Ser His Glu
        995                 1000                 1005

Asp Asp  Ser His Glu Asp Asp  Ser His Glu Asp Asp  Ser His Glu
    1010                 1015                 1020

Asp Asp  Ser His Glu Asn Asp  Ser His Glu Asp Asp  Ser His Glu
    1025                 1030                 1035

Asp Asp  Ser His Glu Asn Asp  Ser His Glu Glu Lys  Glu Gln Tyr
    1040                 1045                 1050

Ile Tyr  Asn Lys Glu Leu Tyr  Glu Lys Ile Lys Lys  Lys Pro Gly
    1055                 1060                 1065

Lys Asn  Met Asn Lys Glu Ile  Tyr Tyr Lys Lys Asn  Ile Lys Glu
    1070                 1075                 1080

Glu Cys  Met Gly Asn Asp Gln  Asn Arg Asn Asn Asn  Asn Asp Asn
    1085                 1090                 1095

Asn Asn  Asn Asn Tyr Asn Asn  Ile Asp Asp Ile Lys  Asn Asp Lys
    1100                 1105                 1110

Tyr Lys  Leu Phe Phe Asn Phe  Cys Lys Asp Ser Tyr  Leu Lys Ile
    1115                 1120                 1125

Pro Ile  Ile Asn Ile Leu Arg  Tyr Ile Val Ile Ser  Asn Asp Ile
    1130                 1135                 1140

Pro Asn  Glu Phe Phe Ser Phe  Phe Asp Phe Phe Lys  Glu Asp Asn
    1145                 1150                 1155

Ile Glu  Glu Leu Lys Ser Ile  Lys Glu Lys Asn Thr  Ile Leu Leu
    1160                 1165                 1170

Leu Ser  Ala Leu Leu Asn Ile  Pro Gln Ile Asp Tyr  Ile Lys Val
    1175                 1180                 1185

Lys Asn  Phe Phe Ser Ile Ile  Glu Glu Phe Phe Tyr  Leu Glu Lys
    1190                 1195                 1200

Lys Lys  Lys Thr Pro Asn Leu  Gln Ser Asp Asn Asn  Asn Asn Asn
    1205                 1210                 1215

Met Arg  Asp Asn Phe His Asn  Arg Tyr Ser Thr Glu  Met Ile Asn
    1220                 1225                 1230

Val Glu  Glu Gly Lys Lys Tyr  Leu Leu Asn Glu Ile  Cys Leu Asp
    1235                 1240                 1245

Lys Asn  Asn Ile Arg Asp Ile  Gln Ile Ser Ala Glu  Asp Leu Glu
    1250                 1255                 1260

Tyr Ser  Asp Asn Asn Asn Val  Asp Ser Gly Tyr Asp  Ser Asp Ile
    1265                 1270                 1275

Asn Ser  Asn Lys Tyr Asn Ser  Asn Asn Asn Lys Gln  Gln Gln Lys
    1280                 1285                 1290
```

-continued

```
Ile Asn  Asn Asn Asn Ile Asn  Asn Asn Asn Asn Asn  Asn Asn Asn
    1295                 1300                 1305

Ile Asp  Ser Asn Asn Ile Arg  Asp Asn Val Asp Ile  Asn Tyr Lys
    1310                 1315                 1320

Asp Ala  Ile Asn Gln Asn Asp  Ile Arg Thr Ser Phe  Gln Ile Tyr
    1325                 1330                 1335

Glu Asn  Val Asn Leu Glu Phe  Asp Lys Glu Lys Met  Phe Asn Glu
    1340                 1345                 1350

Gln Lys  Glu Glu Ser Ile Lys  Asn Ile Asp Asn Gly  Asn Val Asp
    1355                 1360                 1365

Ser Leu  Asn Asn Lys Tyr Leu  Phe Glu Lys Leu Gly  Arg Lys Leu
    1370                 1375                 1380

Ile Asn  Thr Ile Tyr Asn Met  Ser Lys Glu Ile Ser  Asp Asn Lys
    1385                 1390                 1395

Phe Leu  Ile Asn Asn Asn Ile  Cys Ser Ile Tyr Ile  Tyr Leu Asn
    1400                 1405                 1410

Asn Cys  Cys Lys Lys Lys Asn  Met Gln Lys Gln Asn  Asn Ile Ser
    1415                 1420                 1425

Phe Trp  Asn Lys Asp Lys Asn  Ile His Thr Ser Phe  Asp Glu Asn
    1430                 1435                 1440

Ser Ile  Leu Tyr Met Pro Lys  Glu Met Asn Glu Lys  Phe Tyr Asn
    1445                 1450                 1455

Cys Asn  Asn Leu Val Lys Lys  Tyr Phe Pro Tyr Ile  Leu Lys Ser
    1460                 1465                 1470

Ser Phe  Phe Ile Phe Asn Ile  Leu Lys Lys Lys Arg  Leu Ile His
    1475                 1480                 1485

Ile Tyr  Ile Lys Tyr Met Tyr  Leu Tyr Glu Tyr Leu  Tyr His Met
    1490                 1495                 1500

Ile Leu  Asn Arg Ile Leu Tyr  Ile Ser Thr Ile Lys  Phe Tyr Pro
    1505                 1510                 1515

Phe Leu  Gln Asn Ile Ile Leu  Lys Glu Leu Asn Tyr  Tyr Phe His
    1520                 1525                 1530

Asp Phe  Lys Asn Val Thr Ile  Lys Asn Phe Trp Lys  Phe Tyr Leu
    1535                 1540                 1545

Tyr Ala  His Thr Leu Ile Asp  Ile Asn Asn Ser Lys  Ile Ile Leu
    1550                 1555                 1560

Thr Lys  Lys Leu Phe His Asn  Asn Ala Ile Gln Tyr  Phe Ile Lys
    1565                 1570                 1575

Leu Phe  Tyr Tyr Leu Ser Phe  Tyr Asn Pro Ile Phe  Ser Ile Leu
    1580                 1585                 1590

Phe Leu  Asn Leu Ile Arg Thr  Pro Leu Phe His Lys  Asn Ile Glu
    1595                 1600                 1605

Asn Lys  Arg Leu Glu Ile Leu  Gln Asn Ile Trp Asn  Gly Ala His
    1610                 1615                 1620

Glu Arg  Tyr Phe Leu Phe Leu  Ser Lys Arg Lys Ile  Tyr Ser Ile
    1625                 1630                 1635

Glu Tyr  Lys Ile Trp Leu Asp  Glu Tyr Asn Lys Cys  Ser Glu Lys
    1640                 1645                 1650
```

<210> SEQ ID NO 3
<211> LENGTH: 1550
<212> TYPE: PRT
<213> ORGANISM: Plasmodium falciparum

<400> SEQUENCE: 3

```
Met Asn Leu Leu Val Ile Cys Ile Tyr Tyr Leu Phe Phe Leu Asn Ile
1               5                   10                  15

Glu Lys Asn Ile Ser Cys Ser Cys Ser Thr Thr Lys Asn Lys Ser Thr
            20                  25                  30

Phe Val Ser Leu Trp Asp Lys Phe Arg Gln Leu Phe Lys Asp Lys Glu
        35                  40                  45

Ile Glu Lys Glu Lys Asn Ile Ile Thr Tyr Asn Phe Ile Lys His Tyr
    50                  55                  60

Asn Asp Glu Lys Tyr Val Ile Glu Glu Asn Lys Lys Asn Arg Tyr Phe
65                  70                  75                  80

Thr Gly Tyr Glu Ile Asn His Ile Asn Arg Leu Ile Tyr Met Asn Ser
                85                  90                  95

Phe Lys Thr Tyr Ile Leu Ser Ala Tyr Ile Pro Tyr Ile Tyr Met Ser
            100                 105                 110

Val Arg Asp Ile Tyr Ile Val Leu Lys Lys Ile Lys Glu Leu Asn Phe
        115                 120                 125

Asn Thr Val Tyr Thr Phe Leu Phe Trp Pro Glu Asn Glu Tyr Leu Glu
    130                 135                 140

Asp Glu Tyr Asp Met Asn Asn Ser Lys Leu Phe Tyr Leu Leu Asn Phe
145                 150                 155                 160

Cys Ala Ser Asn Gly Leu Phe Val Ile Leu Asp Ile Gly Pro Tyr Ile
                165                 170                 175

Asn Asn Ile Tyr Asn Ser Asn Ile Pro Thr Tyr Ile Leu Phe Asn Lys
            180                 185                 190

Lys Leu Asn Asp Tyr Ile Arg Asn Lys Tyr Ile Glu Arg Lys Ala Asp
        195                 200                 205

Leu Tyr Lys Tyr Phe Leu Ser Pro Trp Glu Asn Ile Trp Lys Arg Lys
    210                 215                 220

Arg Asn Ser Leu Ile Lys Glu Thr Arg Asn Leu Asn Arg Gln Ile Ile
225                 230                 235                 240

Glu Lys Asn Ile Asn Asn Thr Lys Ser Phe Tyr Lys Lys Asn Asn Tyr
                245                 250                 255

Thr Tyr Asn Asn Ile Tyr Ser Leu Tyr Tyr Phe Asn Arg Val Ile Lys
            260                 265                 270

Trp Tyr Asn Tyr Ile Leu Pro Gln Leu Lys Lys Tyr Met Asn Ile Asn
        275                 280                 285

Asn Gly Pro Ile Ile Tyr Leu Asn Ile Asp Lys Thr Phe Asp Asn Tyr
    290                 295                 300

Tyr Met Tyr Ile Ile Ile Asp Leu Lys Arg Lys Lys Ile Phe Asn Asn
305                 310                 315                 320

Ile Cys Asn Ala Gln His Tyr Met Glu Arg Ser Asn Val Ser Tyr Tyr
                325                 330                 335

Asn Asn Lys Ile Ile Asp His Asp Asn Ile Ser Ser Ile Asn Lys Ser
            340                 345                 350

Ser Ser Ser Glu Phe Phe Leu Asn Cys Val Ile Ser Phe Phe Arg Arg
        355                 360                 365

Ile Arg Arg Ser Tyr Ile Met Thr Leu Gly Tyr Leu Leu Tyr Ile Lys
    370                 375                 380

Phe Asn Lys Tyr Leu Arg Val Ile Tyr Glu Tyr Asp Leu Gly Leu Leu
385                 390                 395                 400

Phe Ile Asn Glu Ile Asn Lys Leu Val Gln Lys His Leu Thr Lys Val
                405                 410                 415
```

-continued

```
Asn Ile Leu Thr Thr Asn Tyr Pro Tyr Ile Asn Asp Glu Phe Ile Asn
            420                 425                 430

Ser Tyr Ala Gly Asn Asn Cys Tyr Asn His Phe Leu Lys Asn Asn Trp
        435                 440                 445

Phe Asp Asn Glu Cys Ile Asn Leu Asn Lys Pro Cys Ile Trp Ser Gln
    450                 455                 460

Val Trp Thr Gly Ala Lys Tyr Ser Ile His Asn Val Asn Ser Ser Ser
465                 470                 475                 480

Ile Leu Lys Arg Lys Tyr Asp Asp His Ile Leu Tyr Thr Ser Pro Tyr
                485                 490                 495

Val Asn Ile Glu Asn Lys Val Asp Lys Ile Ser Ser Pro His Pro Asp
            500                 505                 510

His Asp Lys Ala Asn Asp Lys Lys Gly Asn Gln Pro Thr Glu Lys Lys
        515                 520                 525

Asp Lys Gln Lys Asn Ile Asp Asn Lys Lys Asn Asn Asn Asn Asn Lys
    530                 535                 540

Asn Asn Asn Asn Asn Asn Asn Asn Asn Asn Asn Asn Asn Lys Asn Asn
545                 550                 555                 560

Asn Asn Asn Asn Asn Asn Tyr Tyr Ser Val Asp Lys Gly Gly Ser Val
                565                 570                 575

Gln Asn Lys Glu Glu Leu Ser His Gly Lys Asp Asp Gly Ile Thr Asn
            580                 585                 590

Asn Tyr Lys Asp Ser Lys Lys Cys Tyr Lys Asp Lys Lys Ile Asn Met
        595                 600                 605

Asp Asp Ile Asn Ser Asn Val Lys Lys Arg Arg Ile Gln Ile Asn Lys
    610                 615                 620

Asn Asn Asn Tyr Tyr Asn Asn Asn Tyr Ile Gly His Ile Arg Asn Phe
625                 630                 635                 640

Lys Asp Leu Thr Phe Asn Ile Val Val Phe Ile Ala Lys Gly Gly Val
                645                 650                 655

Phe Leu Asn Ile Phe Pro Tyr Tyr Ser Gly Asn Asn Ile Asn Asn Ile
            660                 665                 670

His Ser Tyr Ile Glu His Tyr Ser Lys Glu Thr Gly Gln Pro Leu Asp
        675                 680                 685

Leu Tyr Phe Asn His Lys Glu Pro Leu Tyr Ser His Ile Lys Arg Ile
    690                 695                 700

Phe Lys Ile Leu Tyr Lys Tyr Gly Asn Tyr Leu Leu Lys Asp Glu Tyr
705                 710                 715                 720

Tyr Ile Asn Pro Ile Lys Ile Ser Asn Asn Ile Glu Leu Tyr Asp Tyr
                725                 730                 735

Asp Ile Ile Lys Ile Ile Cys Asn Tyr Asn Ile Lys Gly Ser Thr Phe
            740                 745                 750

Val Lys Ile Gly His Val Asn Tyr Asn Ile Asn Ser Phe Ser Cys Ile
        755                 760                 765

Ile Tyr His Glu Tyr Lys Lys Lys Ile Ile Tyr Asp Thr Ser Tyr Asn
    770                 775                 780

Tyr Ser Tyr Glu Tyr Ser Tyr Ile Asn Lys Lys Glu Thr Tyr Lys Pro
785                 790                 795                 800

Ile Asp Lys Tyr Leu Tyr Ser Leu Asn Thr Ile Asn Thr Gly Pro Leu
                805                 810                 815

Met Cys Ile Lys Glu Lys Gln Gln Lys Ile Ile Lys Pro Ser Asn Lys
            820                 825                 830

Asn Lys Asn Lys Leu Ser Lys Asn Ile Asn Ile Tyr Lys Lys Ile Phe
```

-continued

```
        835                 840                 845

Thr Tyr Leu Phe Pro Asn Asn Phe Phe His Ser Val Tyr Glu Ile Asn
    850                 855                 860

Val Leu Asn His Phe Tyr Leu Thr Met Asp Phe Thr Lys Phe Gln Trp
865                 870                 875                 880

Tyr Ile Leu Ser Phe Lys Asn Thr Met Asn Tyr Val Lys Leu Phe Ile
                885                 890                 895

Ser Asn Tyr Ser Leu Tyr Ile Tyr Ile Tyr Ala Asp Asn Lys Phe Ile
            900                 905                 910

Tyr Gly Gly Phe Asn Glu Tyr Lys Phe Ile Glu Ile Met Asn Cys Lys
        915                 920                 925

His Ile Tyr Ile Ile Cys Val Asn Leu Gly Leu Gly Phe Pro Lys Glu
    930                 935                 940

Gln Val Arg Thr Glu Phe Phe Asn Tyr Ile Asn Phe Asn His Leu Lys
945                 950                 955                 960

Tyr Asn Tyr Gln Glu Asn Asn Phe Asn Ser Ser Ser His Thr Ser Ile
                965                 970                 975

Asn Ser Asp His Asn Met Asn Asp Gln Gly Gly Pro Tyr Phe Asn Met
            980                 985                 990

Asn Lys Ser Ala Ser Ser Lys Asn  Lys Arg Gly Ile Gln  Glu Thr Gly
        995                 1000                1005

Lys Gly  Asn Ser Lys Asn Lys  Met Asp His Asp Asn  Arg Lys Glu
    1010                1015                1020

Val Val  Asn Ser Asp Lys Asp  Glu Lys His Leu Lys  Glu Gln Lys
    1025                1030                1035

Asp Pro  Lys Val Met Asn Lys  Leu Asp Lys Asn His  Pro Asn Gly
    1040                1045                1050

Asn Asn  Asn Asn Asn Lys Lys  Asn Tyr Asn Asn Ser  Lys Asn Tyr
    1055                1060                1065

Asn Lys  Asp Lys Asn Phe Asn  Asn Asn Val Ser Ser  Asn Gly Tyr
    1070                1075                1080

Thr Ile  Phe Asp Asp Leu Tyr  Asp Tyr Tyr Lys Asn  Lys Thr Glu
    1085                1090                1095

Gln Asn  His Asn Ile Tyr Asn  Asn Phe Met Tyr Asp  Glu Lys Asn
    1100                1105                1110

Tyr Asn  Met His Asn Tyr Tyr  Asp Glu Asp Ser Thr  Asn Thr Tyr
    1115                1120                1125

Ile Phe  Ile Val Thr Arg Asn  Glu Tyr Glu Leu Phe  Asn Cys Val
    1130                1135                1140

Gly Leu  Asn Gly Glu Ile Ile  Lys Asn Glu Lys His  Met Asn Glu
    1145                1150                1155

Tyr Lys  Lys Met Tyr Asn Phe  Leu Asp Tyr Ser Phe  Val Lys Thr
    1160                1165                1170

Tyr Leu  Met Asn Thr Gln Ser  Ser Asn Thr Asn Asp  Val Ser Glu
    1175                1180                1185

Gln Asn  Lys Asn Lys Asn Lys  Asn Lys Asn Lys Asn  Lys Lys Asp
    1190                1195                1200

Asn Lys  Gly Asn Asn Asn Asn  His Asp Asp Asp Asp  Asp Asp Asp
    1205                1210                1215

Asn Asp  Asn Asn Lys Val Ile  Ser Lys Asp Thr Asn  Asn Asn Asp
    1220                1225                1230

Lys Asn  Tyr Ile Gln Ser Asn  Asp Asn Ile Gln Ile  Asn Asn Gln
    1235                1240                1245
```

```
Pro Asn  Gln Ile Asn Arg Asp  Tyr Gln Asn Tyr His  Asn Asn Asn
    1250                 1255                 1260

Phe Lys  Ser Leu Leu Thr Asn  Lys Lys Ile Glu Met  Lys Ser Ile
    1265                 1270                 1275

Thr Lys  Ala Phe Leu Asn Leu  Cys Thr Ser Gly Phe  Phe Ser Phe
    1280                 1285                 1290

Ile Phe  Asn Lys Ile Lys Tyr  Tyr Cys Lys Thr Gly  Ile Phe Lys
    1295                 1300                 1305

Tyr Leu  Ser Thr Phe Asn Lys  Val Asn Lys Asn Asn  Thr Ser Thr
    1310                 1315                 1320

Pro Leu  Thr Trp Tyr Thr Leu  Leu Tyr Phe Ile Lys  Asn Ile Asp
    1325                 1330                 1335

Phe Leu  Arg Ser Lys Tyr Ser  Leu Lys Leu Ser Thr  Tyr Asp Lys
    1340                 1345                 1350

Lys Thr  Lys Asn Ile Asp Gly  Leu Phe Arg Gly Phe  Val Tyr Ile
    1355                 1360                 1365

Asn Asn  His Phe Leu Gly Ser  Phe Trp Ile Thr Asp  Asp Val Asp
    1370                 1375                 1380

Ser Tyr  Glu Lys Glu Ile Asn  Glu Asp Glu Lys Leu  Lys Asn Gly
    1385                 1390                 1395

Lys Lys  Ile Lys Lys Glu Lys  Ser Lys Phe Leu Asn  Asn Glu Asn
    1400                 1405                 1410

Leu Ile  His Ile Pro Leu Thr  Arg Tyr Met Arg Ile  Pro Thr Asp
    1415                 1420                 1425

Trp Leu  Val Glu Gly Thr Asn  Ile Val Ile Leu Phe  Asp Glu Phe
    1430                 1435                 1440

Gly Gly  Asn Pro Tyr Lys Val  Glu Ile Val Arg Glu  Ile Leu His
    1445                 1450                 1455

Gly Gly  Val Tyr Arg Leu Thr  Lys Lys Glu Lys Tyr  Val Asn Trp
    1460                 1465                 1470

Ile Leu  Phe Leu Phe Ile Leu  Ser Ile Ile Val Phe  Ile Thr Tyr
    1475                 1480                 1485

Phe Phe  Phe Lys Ala Leu His  Asn Tyr Phe Lys Thr  Lys Glu Glu
    1490                 1495                 1500

Lys Glu  Arg Asn Lys Gln Asn  Tyr Gln Asn Ile Ile  Glu Asn Ile
    1505                 1510                 1515

Ile Thr  His Asn Ile Tyr Ile  Asn Ser Ser Tyr Asp  Asp Ile Thr
    1520                 1525                 1530

Glu Glu  Thr Asn Thr Glu Asn  Ile Gln Asn Val Ser  Asp Phe Leu
    1535                 1540                 1545

Asp Ser
    1550
```

<210> SEQ ID NO 4
<211> LENGTH: 1207
<212> TYPE: PRT
<213> ORGANISM: Plasmodium falciparum

<400> SEQUENCE: 4

```
Met Phe Ile His Ser Cys Asn Phe Tyr Leu Phe Leu Leu Phe Tyr Phe
1               5                   10                  15

Ile Phe Ile Asn Cys Ser Tyr Ile His Phe Arg Lys Glu Lys Ser Asn
            20                  25                  30

Met Asn Asn His Lys Asn Tyr Cys Tyr Asp Gly Ser Ile Lys Asp Ala
```

```
        35                  40                  45

Cys Ile His Val Lys Glu Asn Pro Ser Ser Tyr Asp Asn Asn Asn Ile
    50                  55                  60

Glu His Met Asn Gln Ile Trp Asn Asn Ser Pro Thr Asn Ile Ile Asn
65                  70                  75                  80

Thr Lys Lys Val Ser Asn Val Glu Gln Asn Leu Gln Lys Asp Thr Lys
                85                  90                  95

Lys Tyr Asp Leu His Asp Arg Asn Tyr Pro Asn Ile Ile Lys Glu Glu
            100                 105                 110

Glu Asn Ile Phe Leu Leu Thr Cys Lys Lys Phe Val Asn Phe Thr Ile
        115                 120                 125

Gln Lys Arg Phe Phe Val Val Leu Ser Ile Leu Ile Gly Phe Leu Leu
    130                 135                 140

Leu Met Leu Val Ser Ile Pro Leu Tyr Glu Thr Met Ile Ser Asn Lys
145                 150                 155                 160

Ile Glu Thr Ser Phe Val Thr Phe Asp Asn Ser Leu Lys Tyr Ile Arg
                165                 170                 175

Asn Ile Tyr Pro Leu Thr Phe Glu Ile Lys Lys Ala Gly Asp Val Leu
            180                 185                 190

Thr Gln Ser Ser Asp Lys Leu Gly Asn Asn Thr Asn His Phe Ile Asn
        195                 200                 205

Ile Tyr Lys Lys Asp Lys Thr Ala Thr Leu Met Phe Phe Ser Glu Asn
    210                 215                 220

Asn Asn Asn Lys Glu Asn His Ile Leu Asp Tyr Asn Thr Leu Lys Asp
225                 230                 235                 240

Ile Phe Phe Leu Leu Gln Tyr Phe Lys Gln Ile Thr Ile Leu Lys Asp
                245                 250                 255

Gln Lys Glu Ile Tyr Trp Lys Asp Ile Cys Lys Lys Tyr Asp Thr Pro
            260                 265                 270

Leu Ser Asn Pro Lys Cys Phe Val Leu Gly Leu Phe Thr Ile Ser Glu
        275                 280                 285

Leu Thr Asn Ile Asn Tyr Asn Asn Ile Glu Lys Trp Asn Val Phe Phe
    290                 295                 300

Asp Lys Ile Ile Lys Glu Asp Thr Lys Tyr Ile Lys Arg Phe Phe Ser
305                 310                 315                 320

Gln Ala Leu Tyr Phe Leu Pro Asn Phe Leu Tyr Ile Pro Asn His Phe
                325                 330                 335

Ile Tyr Lys Ile Glu Glu Gln Gln Asn Met His Asn Ile Ile Asn Lys
            340                 345                 350

Ile Tyr Thr Asn Ile Lys Gly Leu Leu Phe Val Tyr Thr Phe Asp Asp
        355                 360                 365

Asn Ile Ser Asn Glu Leu Leu Asp Asn Trp Tyr Asn Lys Leu Asn Glu
    370                 375                 380

Tyr Ile Gln Leu Ile Asn Asn Asn Lys Leu Ser Tyr Ile Asn Ile Lys
385                 390                 395                 400

Asn Pro Asp Gly Thr Ile Tyr Thr His Ile Leu Lys Tyr Asn Lys Met
                405                 410                 415

Trp Asn Val Leu Thr Ile Asn Asp Lys Leu Leu Gln Asp Glu Glu Gln
            420                 425                 430

Asn Ser Ile Leu Leu Gly Phe Gln Ser Asn Tyr Leu Phe Ile Ile Leu
        435                 440                 445

Ser Leu Leu Phe Ile Phe Phe Tyr Ile Asn Ile Asn Leu Ser Thr Phe
    450                 455                 460
```

-continued

```
Val Thr Tyr Thr Lys Lys Ile Val Leu Leu Ile Cys Val Tyr Leu Leu
465                 470                 475                 480

Thr Phe Phe Ser Leu Ser Ser Thr Phe Phe Ile Tyr Leu Ile Phe Lys
                485                 490                 495

Leu Tyr Ile Met Arg Ile Phe Leu Leu Asn Tyr Phe Val Leu Phe Phe
            500                 505                 510

Leu Ser Val Leu Phe Cys Cys Val Asn Ile Phe Tyr Tyr Asn Gln Tyr
        515                 520                 525

Cys Thr Ser Pro Gly Lys Asp Ser His Asn Asn Asn Ile Tyr Glu Asn
    530                 535                 540

Leu Asn Asn His Ile Tyr Asn Ser Ser Tyr Pro Ile Ser Asp Asn His
545                 550                 555                 560

Met Glu Thr Phe Tyr Tyr Leu Gln Ala Thr Tyr Lys Ser Leu Tyr Phe
                565                 570                 575

Asn Gly Lys Ile Thr Leu Val Leu Ile Ser Ile Tyr Thr Ile Gly Leu
            580                 585                 590

Phe Cys Ser Tyr Thr Ile Thr Lys Trp Phe Cys Leu Asn Thr Ile Phe
        595                 600                 605

Ser Leu Ile Ser Leu Tyr Ile Tyr Tyr Val Phe Phe Phe Asn Asn Ile
    610                 615                 620

Phe Ser Tyr Leu Leu Tyr Val Lys Gly Lys Asn Asn Asn Ile Asn Tyr
625                 630                 635                 640

Asn Pro Asn Asp Gln Ile Lys Val Ile Asp Tyr Ser Lys Val Asn Asn
                645                 650                 655

Glu Glu Asp Lys Lys Glu Met Ile Ile Phe Phe Asn Ala Gln Gln Asn
            660                 665                 670

Val Asn Asn Asn Asn Cys Asn Asn Ile Glu Glu Asn Asn Tyr Pro Phe
        675                 680                 685

Thr Asn Asn Asn Ile His Thr Asn Asn Asp Ile Leu Lys Asn Asn Asp
    690                 695                 700

Ile Leu Lys Asn Asn Asp Ile Leu Lys Asn Asn Asp Ile Leu Lys Asn
705                 710                 715                 720

Asn Asp Ile Leu Lys Asn Asn Asp Met Leu Lys Asn Asn Asp Met Leu
                725                 730                 735

Lys Asn Asn Asp Thr His Met Tyr Thr Lys Lys Cys Val Thr Asn His
            740                 745                 750

Phe Asp Lys Met Asn Thr Phe Gln Asn Asn Thr Gln Tyr Thr Glu His
        755                 760                 765

Lys Met Phe Asn Lys Pro Lys Lys Tyr Asn Glu Lys Pro Phe His Ile
    770                 775                 780

Phe Lys Lys Ile Ser Leu Leu Leu Leu Leu Ile Leu Ser Phe Leu Ile
785                 790                 795                 800

Leu Tyr Leu Tyr Ile Phe Ile Asn Asn Lys Thr Gln Phe Ser Ile Phe
                805                 810                 815

Arg Tyr Met Asn Lys Asn Ser Asn Val Arg Met Phe Ile Glu Ile Phe
            820                 825                 830

Glu Gly Ile Ala Asn His Val Ile Glu Pro Gly Tyr Leu Val Leu Pro
        835                 840                 845

Glu Ser Phe Asn Tyr Glu Lys Glu Asp Asn Leu Ile Asn Val Val Lys
    850                 855                 860

Leu Ile Glu Asp Leu Lys Lys Glu Lys Cys Ile Tyr Asn Pro Ile Ile
865                 870                 875                 880
```

-continued

Ser Trp Ile Ser Thr Phe Glu Leu Leu Lys Asn Asp Cys Thr Asn Ile
885 890 895

Asp Phe Phe Asp Thr Gln Tyr Glu Leu Asp Asn Asn Ser Glu Glu Cys
900 905 910

Ile Asn Tyr Asn Leu Gln Asn Val Gly Lys Lys Asn Lys Lys Leu Tyr
915 920 925

Leu Glu Leu Leu Ser Ala Gln Phe Cys Lys Asn Ile Gln Lys Pro Leu
930 935 940

Cys Asp Thr Phe Asn Lys Ile Ile Tyr Asn Trp Ile His His Lys Asn
945 950 955 960

Asp Asp Ile Tyr Glu Ser His Met Phe Gln Ile Lys Thr Ser Tyr Asn
965 970 975

Asp Asn Ile Asp Gln Ile Leu Pro Gln Tyr His Thr Ile Ser Pro His
980 985 990

Ile Phe Tyr Asp Lys Tyr Ile Lys Met Asp Glu Asn Tyr Asn Ile Leu
995 1000 1005

Asn Ser Arg Ile Gly Ser Ile Phe His Asn Tyr Pro Ser Ser Tyr
1010 1015 1020

Asn Lys Asn Ile Glu Thr Ile Glu Lys Ile Asn Asn Val Ile Lys
1025 1030 1035

Asn Ser Asn Ile Glu Asn Ile Tyr Phe Tyr Ser Glu Thr Tyr Val
1040 1045 1050

Leu Tyr Gln Gln Ala Met Lys Phe Leu Lys Glu Phe Lys Phe Met
1055 1060 1065

Phe Phe Phe Tyr Ile Phe Ile Tyr Ile Ile Ser Ile Tyr Ile Phe
1070 1075 1080

Asn Lys Met Gly Val Pro Ile Ile Phe Pro Phe Leu Leu Phe Asn
1085 1090 1095

Ser Leu Ser Met Leu Tyr Phe Thr Tyr Phe Phe Ser Ile Asn Thr
1100 1105 1110

Asp Ala Ile Thr Ile Ile Leu Leu Lys Ile Thr Thr Ala Ile Ser
1115 1120 1125

Leu Ser Asn Tyr Leu Tyr Ser Thr Leu Tyr Phe Asn Lys Thr Lys
1130 1135 1140

Asn Gly Thr Leu His Phe Asp Asn Thr Ile Lys Lys Ser Leu Pro
1145 1150 1155

Tyr Leu Leu Phe Leu Ile Leu Tyr Leu Ile Ser Phe Ser Ala Gly
1160 1165 1170

Asp Tyr Ile Ser Asn Val Val Arg Leu Tyr Ile Leu Asn His Val
1175 1180 1185

Leu Trp Tyr Ile Leu Tyr Ser Leu Thr Ile Phe Cys Ile His Arg
1190 1195 1200

Ile Met Tyr Lys
1205

<210> SEQ ID NO 5
<211> LENGTH: 227
<212> TYPE: PRT
<213> ORGANISM: Plasmodium falciparum

<400> SEQUENCE: 5

Met Gly Ser Lys Lys Asn Ser Asn Thr Val Asp Ser Ser Glu Asn Val
1 5 10 15

Glu Glu Val Val Asp Asn Leu Thr Ser Glu Lys Asn Lys Glu Ser Leu
20 25 30

```
Lys Lys Asp Lys Arg Lys Lys Lys Glu Lys Lys Asn Asn Asp Val Asp
        35                  40                  45

Asp Ile Asn Glu Glu Glu Asp Glu Glu Gly Asn Asp Glu Asp Thr Met
    50                  55                  60

Lys Lys Phe Ser Val Asp Thr Ser Glu Asn Glu Asp Asp Lys Glu Asp
65                  70                  75                  80

Asp Asp Asp Asp Glu Asp Asp Asp Asp Asp Asp Asp Asp Asp Asp Asp
                85                  90                  95

Glu Asp Asp Asp Asp Glu Asp Asp Asp Asp Asp Asp Asp Asp Asp Asp
            100                 105                 110

Asp Asp Asp Asp Asp Asp Asp Glu Asp Asp Asp Asp Asp Asp Asp Asp
        115                 120                 125

Asp Glu Asp Asp Asp Asp Glu Asp Asp Glu Asp Asp Asp Asp Asp Asp
    130                 135                 140

Glu Asp Asp Asp Asp Asp Phe Asp Asp Met Asp Glu Asp Asp Asp Asp
145                 150                 155                 160

Asp Asp Asp Asp Asp Glu Asp Asp Asp Asp Glu Glu Asp Tyr Asp Asp
                165                 170                 175

Asp Asp Asp Asp Asp Asp Asp Asp Asp Glu Asp Asp Asp Glu Asp Asp
            180                 185                 190

Asp Glu Asp Asp Asp Asp Glu Asn Asp Gln Asn Glu Tyr Ala Gly Asp
        195                 200                 205

Asp Lys Lys Asp Glu Asp Gly Asp Ala Lys Lys Gly Ser Asp Asp Glu
    210                 215                 220

Gly Phe Asp
225


<210> SEQ ID NO 6
<211> LENGTH: 468
<212> TYPE: PRT
<213> ORGANISM: Plasmodium falciparum

<400> SEQUENCE: 6

Met Gly Lys His Ile Arg Ile Leu Lys Asn Gln Tyr Leu Gln Phe Met
1               5                   10                  15

Ser Lys Arg Cys Ile Gln Ser Lys Ala Ala Phe Asn Ile Cys Gly Lys
            20                  25                  30

Ile Asn Val Glu Asn Pro Ile Val Glu Leu Asp Gly Asp Glu Met Thr
        35                  40                  45

Arg Ile Ile Trp Lys Asp Ile Lys Glu Lys Leu Ile Leu Pro Tyr Val
    50                  55                  60

Asn Leu Lys Ile Lys Tyr Phe Asp Leu Ser Ile Glu Asn Arg Asp Lys
65                  70                  75                  80

Thr Asn Asp Gln Val Thr Ile Glu Ala Ala Glu Glu Ile Lys Lys Thr
                85                  90                  95

Ser Val Gly Ile Lys Cys Ala Thr Ile Thr Pro Asp Ala Ala Arg Val
            100                 105                 110

Lys Glu Phe Asn Leu Lys Glu Met Trp Lys Ser Pro Asn Gly Thr Ile
        115                 120                 125

Arg Asn Ile Leu Asp Gly Thr Val Phe Arg Thr Pro Ile Leu Ile Lys
    130                 135                 140

Asn Ile Pro Lys Leu Val Pro Asn Trp Lys Lys Pro Ile Val Ile Gly
145                 150                 155                 160

Arg His Ala Tyr Ala Asp Gln Tyr Lys Gln Lys Ser Leu Lys Ile Glu
```

```
                165                 170                 175

Lys Ser Gly Lys Phe Glu Ile Val Phe Thr Pro Asp Asp Asn Ser Gln
            180                 185                 190

Val Leu Arg Glu Thr Val Phe His Phe Lys Ser Pro Gly Val Cys Leu
        195                 200                 205

Gly Met Tyr Asn Thr Glu Glu Ser Ile Arg Asn Phe Ala Leu Ser Cys
    210                 215                 220

Phe Gln Tyr Ala Leu Asp Leu Lys Met Pro Val Tyr Met Ser Thr Lys
225                 230                 235                 240

Ser Thr Ile Leu Lys Ile Tyr Asp Gly Leu Phe Lys Asp Ile Phe Asp
                245                 250                 255

Glu Ile Tyr Glu Lys Gln Phe Lys Lys Ser Phe Glu Gln His Asn Leu
            260                 265                 270

Trp Tyr Glu His Lys Leu Ile Asp Asp Met Val Ala Gln Val Leu Lys
        275                 280                 285

Ser Glu Gly Gly Phe Leu Trp Ala Cys Lys Asn Tyr Asp Gly Asp Ile
    290                 295                 300

Gln Ser Asp Ala Val Ala Gln Gly Tyr Gly Ser Leu Gly Leu Met Ser
305                 310                 315                 320

Ser Val Leu Leu Cys Pro Asp Gly Val Thr Cys Val Ser Glu Ala Ala
                325                 330                 335

His Gly Thr Val Thr Arg His Tyr Arg Ala Tyr Gln Lys Gly Glu Lys
            340                 345                 350

Thr Ser Thr Asn Pro Ile Ala Ser Ile Phe Ala Trp Thr Lys Gly Leu
        355                 360                 365

Glu His Arg Ala Lys Leu Asp Lys Asn Asp Asn Leu Lys Gln Phe Cys
    370                 375                 380

Tyr Ala Leu Glu Lys Ala Cys Ile Glu Thr Val Glu Asp Gly Leu Met
385                 390                 395                 400

Ser Lys Asp Leu Ala Gly Cys Ile Lys Gly Ile Lys Asn Val Thr Glu
                405                 410                 415

Lys Asp Tyr Ile Phe Thr Gln Asp Leu Ile Asn Ala Ile Asn Glu Lys
            420                 425                 430

Leu Lys Leu Lys Ile Leu Gln Asn Gln Ser Lys Asn Asp Pro Gln Ala
        435                 440                 445

Thr Ser Tyr Lys Leu Lys Asn Asp Asn Trp Asn Phe Tyr Ala Pro Gln
    450                 455                 460

Glu His Ser Thr
465
```

<210> SEQ ID NO 7
<211> LENGTH: 481
<212> TYPE: PRT
<213> ORGANISM: Plasmodium falciparum

<400> SEQUENCE: 7

```
Met Lys Lys Leu Asn Leu Leu Ile Gly Cys Ile Ser Leu Tyr Ser Ile
1               5                   10                  15

Ile Phe Tyr Thr Ala Lys Ile Ser Cys Thr Val Gln Val Lys Asn Gly
            20                  25                  30

Gly Ile Glu Asn Leu Ala Ser Ser Ser Gly Leu Leu Lys Asn Val Leu
        35                  40                  45

Lys His Ser Pro Arg Ile Ser Glu Glu Glu Ile Lys Glu Ser Glu Ile
    50                  55                  60
```

-continued

```
Lys Ile Ile Lys Asn Ala His Glu Glu Glu Lys Lys Ile Leu Asp Lys
65                  70                  75                  80

Tyr Gly Lys Cys Leu Lys Asp Tyr Thr Leu Pro Cys Pro Asn Tyr Trp
                85                  90                  95

Lys Arg Arg Thr Asp Lys Tyr Gly Lys Asn Val Cys Ile Ala Asn Glu
            100                 105                 110

Glu Tyr Asn Gly Phe Cys Glu Gln Val Gln Ile Phe Asp Glu Phe Ser
        115                 120                 125

Glu His Glu Lys Met Ser Tyr Glu Ser Ser Cys Asn Val Glu Trp Gly
    130                 135                 140

Cys Lys Gly Ser Ser Lys Glu Ile Cys Glu Ser Gly Lys Arg Asp Tyr
145                 150                 155                 160

Asn Val Pro Cys Pro Glu Gly Phe Leu Val Gln Asn Asp Asn Ser Cys
                165                 170                 175

Lys Ala Asp Ile Ser Val Tyr Arg Gly Met Cys Asn Asn Glu Thr Ile
            180                 185                 190

Asn Phe Thr His Leu Thr Ser Ser Glu Lys Glu Asn Trp Ser Ile Ala
        195                 200                 205

Cys Glu Ala Tyr Trp Pro Cys Tyr Thr Asp Cys Ile Ser Glu Glu Tyr
    210                 215                 220

Ile Ser Asp Cys Pro Lys Asn Trp Lys Gln Val Asn Lys Tyr Asp Cys
225                 230                 235                 240

Ile Pro Asp Lys Asn Tyr Lys Gly Pro Cys Arg Asn Ile Lys Asn Phe
                245                 250                 255

Lys Tyr Phe Thr Leu Ser Met Lys Lys Asp Phe Glu Glu Lys Cys Lys
            260                 265                 270

Thr Lys Phe Glu Cys Asn Asn Ile Cys Glu Lys Asn Tyr Glu Gln Glu
        275                 280                 285

Cys Pro Leu Asn Trp Lys Val Glu Lys Gly Tyr Cys Leu Ala Pro Asp
    290                 295                 300

Thr Phe Asp Leu Cys Lys Arg Lys Lys Ile Ser Ile Glu Asn Met Thr
305                 310                 315                 320

Arg Lys Glu Lys Glu Asn Ile Glu Lys Glu Cys Phe Val Ser Trp Pro
                325                 330                 335

Cys Ile Asn Asn Lys Asn Thr Asn Lys Pro Asn Cys Gln Ile Asn Trp
            340                 345                 350

Leu Ala Asp Cys Pro Phe Gly Trp Asp Arg Lys Lys Glu Asp Lys Arg
        355                 360                 365

Asp Gln Lys Lys Asp Glu Tyr Val Cys Ile Leu Pro Thr Glu Lys Gln
    370                 375                 380

Ile Tyr Thr Glu Glu Asn Lys Phe Asn Ser Leu Asn Lys Glu Lys Cys
385                 390                 395                 400

Thr Asn Ile Phe Leu Lys Lys Asn Ser Asp Glu Val Ile Lys Arg Glu
                405                 410                 415

Ile Ala Ser Val Cys Asn Thr Pro Trp Pro Cys Leu Asn Asn Glu Lys
            420                 425                 430

Ile Tyr Ile Ser His Asn Val Asp His Glu Gln Lys Glu Glu Asn Glu
        435                 440                 445

Lys Leu Asn Gly Pro Leu Thr Asn Glu Gly Lys Ile Tyr Lys Asn Gly
    450                 455                 460

Lys Tyr His Ile Val Glu Glu Gly Asn Phe Ser Leu Ser Asp Ile Met
465                 470                 475                 480

Lys
```

<210> SEQ ID NO 8
<211> LENGTH: 2072
<212> TYPE: PRT
<213> ORGANISM: Plasmodium falciparum

<400> SEQUENCE: 8

```
Met Glu Lys Tyr Phe Met Lys Lys Ile Lys Gly Val Phe Ser Thr Phe
1               5                   10                  15

Lys Lys Asp Asn Pro Asn Ile Asn Asn Asn Asn His Asn Asn Thr
            20                  25                  30

Asn Asn Asn Asn Asn Asn His Asn Lys Ser Asn Asn Asn Asn Ser Thr
        35                  40                  45

Asn Ser Asn Arg Asn Asp Asp Asp Asn Ile Asn Arg Gln Ser Thr Gln
    50                  55                  60

Glu Asn Asn Ser Thr Val Gly Asn Lys Arg Ile Val Gly Met Thr Asn
65                  70                  75                  80

Asp Thr Tyr Lys Gln Glu Lys Asp Leu Asn Tyr Phe Phe Ser Glu Asn
                85                  90                  95

Lys Glu Arg Lys Glu Glu Ser Asn Ser Asn His Lys Lys Lys Asn Leu
            100                 105                 110

Lys Asn Lys Gly Gln Lys Lys Leu Asp Ser Asn Glu Lys Asp Met Pro
        115                 120                 125

Glu Phe Ser Lys Lys Met Lys Tyr Thr Lys Leu Tyr Gln Lys Glu Asn
    130                 135                 140

Met Leu Ser Ile Asp Asn Tyr Ile Lys Ile Asn Lys Lys His Ser Leu
145                 150                 155                 160

His Phe Val Lys Arg Lys Tyr Thr Lys Arg Lys Leu Met Ala Ser Asn
                165                 170                 175

Ile Gln Asn Ile Cys Asn Phe Ile Thr Asp Lys Asn Lys Asn Glu Asn
            180                 185                 190

Ser Arg Thr Lys Lys Val Glu Ser Leu Asp Asp Tyr Lys Glu Glu Asn
        195                 200                 205

Lys Asn Thr Pro Asn Lys Val Asp Glu Glu Lys Lys Met Asn Leu Gln
    210                 215                 220

Tyr Glu Gln Glu His Asn Asn Thr Asn Val Ala Gln Glu Thr Lys Gly
225                 230                 235                 240

Gly Lys Lys Lys Lys Lys Lys Asn Val Asp Arg Asn Gln Asn Asn Leu
                245                 250                 255

Lys Glu Asp Asn Leu Asn Asn Asp Leu Leu Asn Glu Asp Ile Leu Thr
            260                 265                 270

Lys Gly Gln Tyr Asp His Asp Asn Asn Asn Lys Lys Asn Asn Ser Ser
        275                 280                 285

Asn Ser Ser Asn Asn Asn Asn Asn Asn Ser Asn Asn Ser Met Asn Glu
    290                 295                 300

Tyr Asn Ile Leu Asp Asp Ser Ser Asn Ile Gln Phe His Lys Lys Glu
305                 310                 315                 320

Thr Pro Ser Lys Asn Gln Gly Lys Asn Lys Tyr Ile Phe Lys Asn Val
                325                 330                 335

Glu Arg Lys Asn Thr Ala Val Tyr Asp Lys Asn Lys Asn Thr Ser Leu
            340                 345                 350

Asn Asn Tyr Gly Gln Gln Gln Lys Lys Ile Asn Arg Ile Asp Glu Ile
        355                 360                 365

Phe Lys Asn Leu Ile Glu Lys Arg Lys Lys Lys Glu Met Arg Gln Lys
```

-continued

```
    370                 375                 380

Tyr Met Leu Lys Lys Lys Phe Leu Met Asn Asn Tyr Lys Gly Lys Thr
385                 390                 395                 400

Asn Glu Asn Tyr Glu His Glu Gln Arg Glu Gly Glu Lys Glu Glu Lys
                405                 410                 415

Gln Lys Glu Asn Asp Thr Tyr Gly Asp Phe Glu Glu Leu Asp Glu Glu
            420                 425                 430

Ile Glu Lys Asp Gly Glu Glu Lys Glu Glu Glu Glu Asp Asp Lys Asn
        435                 440                 445

Glu Glu Val Glu Glu Gln Asn Glu Glu Val Val Glu Lys Lys Glu Asn
    450                 455                 460

Val Glu Lys Gln Lys Asn His Gln Asn Asn Lys Thr Ser Asn Asn Ile
465                 470                 475                 480

Tyr Asp Asn Lys Ser Tyr Asp His His Gly Arg Asn Thr His Leu Leu
                485                 490                 495

Lys Lys Glu Lys Lys Gln Arg Thr Lys Gln Ile Ser Asn Lys Asn Val
            500                 505                 510

Pro Met Ile Asp Glu Ser Thr Ile Glu Lys Cys Tyr Lys Gln Met Arg
        515                 520                 525

Ile Phe Ala Glu Lys Phe Ser Ser Phe Lys Asn Lys Phe Asp Gln Tyr
    530                 535                 540

Tyr Asn Thr Ser Glu His Trp Asn Leu Lys Lys Lys Gly Lys Lys Arg
545                 550                 555                 560

Lys Asn Ser Val Asn Thr Ser Asp Lys Glu Asn Met Glu Asn Tyr Phe
                565                 570                 575

Phe Asp Glu Asp Ser Met Lys Lys Glu Thr Asn Glu Leu Glu Glu Leu
            580                 585                 590

Asn Lys Asn Ile Gln Lys Leu Leu Asn Ala Asn Met Ser Asn Asp Ile
        595                 600                 605

Asn Val Asp Lys Ile Asn Glu Ile Lys Lys Tyr Thr Gln Asp Asn His
    610                 615                 620

Asn Lys Ser Leu Met Lys Asn Ile Asn Ile Ser Glu Ser Ile Tyr Phe
625                 630                 635                 640

Asp Cys Glu Asn Thr Ser Ala Lys Lys Arg Lys Cys Ser Asp Asn Ala
                645                 650                 655

Ser Val Ser Thr Asn Glu Glu Asn Leu Asn Lys Leu Leu Glu Tyr Ala
            660                 665                 670

Thr Asn Lys Lys Asn Asn Met Ile Asn Ser Glu Asp Asp Ile Lys Thr
        675                 680                 685

Asp Gln Glu Tyr Glu Arg Asp Lys Arg Lys Lys Asn Lys Arg Lys Lys
    690                 695                 700

Asn Ile Tyr Asp Asp Leu Gln Lys Ser Asn Glu Asn Asn Ser Glu Glu
705                 710                 715                 720

Val Ile His Leu Leu Arg Glu Asn Glu Glu Glu Glu Lys Glu Glu Asn
                725                 730                 735

Lys Gln Thr Asn Met Glu Lys Arg Lys Lys Gly Arg Lys Lys Lys Lys
            740                 745                 750

Thr Glu Asp Ile Gln Ser Asp Lys Val Lys Ile Glu Asn Val Gln Ser
        755                 760                 765

Asp Lys Val Lys Ile Glu Asn Val Gln Ser Asp Lys Val Lys Val Glu
    770                 775                 780

Asn Val Gln Met Glu Asn Val Gln Ile Glu Asn Val Gln Thr Glu Asn
785                 790                 795                 800
```

-continued

```
Val Gln Met Glu Asn Val Gln Met Glu Asn Val Gln Met Glu Asn Val
                805                 810                 815

Gln Met Glu Asn Val His Thr Glu Lys Ala Gln Asn Glu Asn Ile Gln
            820                 825                 830

Ile Glu Asn Val His Thr Glu Lys Ala Gln Asn Glu Lys Ile Gln Thr
        835                 840                 845

Gln Asn Ile Gln Thr Asp Asn Val Lys Thr Gln Asn Ala Gln Pro Asp
    850                 855                 860

Asn Val Gln Thr Gln Asn Ala Gln Pro Asp Asn Val Gln Thr Gln Asn
865                 870                 875                 880

Ala Gln Pro Asp Asn Val Gln Thr Gln Asn Ala Gln Pro Asp Asn Val
                885                 890                 895

Gln Thr Gln Asn Ala Gln Pro Asp Asn Thr Gln Tyr Lys Asn Glu Pro
            900                 905                 910

Phe Lys Ile Glu Ala Ile Glu Asn Val Leu Glu Glu Lys Glu Asn Leu
        915                 920                 925

Ser Asp Lys His Leu Glu Asn Gln Val Glu Val Ala Asn Val Ser Asn
    930                 935                 940

Glu Val Phe Glu Thr Glu Met Lys Asn Phe Asn Asn Ser Asn Gly Asn
945                 950                 955                 960

Met Asp Lys Asp Ile Asn Ile Ile Asp Ile Pro His Glu Asp Leu Asn
                965                 970                 975

Lys Tyr Ile Lys Asp Glu Leu Asn Asn Asn Asp Asn Asn Asn Asn Leu
            980                 985                 990

Leu Asn Ile Gln Asn Val Glu Ile  Met Glu Tyr Ala Glu  Ser Ile Lys
        995                 1000                1005

Ser Asp  Asn Ile Ile Asn Asp  Thr Lys Glu Asp Ala  Leu Pro Arg
    1010                1015                1020

Asn Glu  Thr Leu Asn Phe Leu  Lys Gln Glu Tyr Val  Ser Ser Lys
    1025                1030                1035

Glu Gln  Glu Glu Lys Lys Asp  Glu Glu Lys Asn Ile  Leu Asn Glu
    1040                1045                1050

Gln Glu  Leu Asn Asp Ile Asn  Glu Lys Met Lys Gln  Gln Asn Asn
    1055                1060                1065

Val Asp  Ser Lys Leu Pro His  Phe Ala Ile Glu Gln  Arg Lys Lys
    1070                1075                1080

Leu Ile  Lys Glu Thr Asn Arg  Phe Phe Lys Met Tyr  Asn Leu His
    1085                1090                1095

Leu Lys  Ile Glu Lys Leu Pro  Ile Asn Ile Pro Asn  Asp Leu Lys
    1100                1105                1110

Ile Leu  Met Gln Lys Lys Lys  Lys Ile Val Asp Ile  Ile Asn Asp
    1115                1120                1125

Tyr Lys  Ile Val Phe Lys Thr  Leu Gln Lys Tyr Ala  Glu Lys Glu
    1130                1135                1140

Lys Asn  Ile Ser Glu Glu Gln  Asp Gly Glu Glu Arg  Lys Leu Ser
    1145                1150                1155

His Asp  Asn Leu Asp Lys Gln  Lys Glu Gln Gln Asn  Asp Glu His
    1160                1165                1170

Asp Asn  Asn Asn Asp Ser Asn  Asn Asn Glu Asn Asn  Asn Asn Glu
    1175                1180                1185

Asn Asn  Asn Asn Asp Asn Ile  Asn Asn Asp Asn Asn  Asn Asn Asp
    1190                1195                1200
```

-continued

Asn Ile Asn Asn Asn Asp Ile Cys Ile Asp His Lys Val Thr Asn
1205 1210 1215

Asn Met Val Leu Asn Thr Asp Gly Asp Glu Gln Asn Lys Glu Gln
1220 1225 1230

Asn Ile Ser Ser Gln Thr Asp Lys Gly Asn Val Ile Leu Thr Thr
1235 1240 1245

Lys Asp Glu Thr Val Val Asn Lys Asn Asp Ile Ser Ser Val Leu
1250 1255 1260

Lys Glu Glu Asn Glu Asp Lys Glu Asn Lys Glu Asn Ser Thr His
1265 1270 1275

Lys Asp Pro Asp Leu Ser Leu Asp Val Asn Ala Glu Thr Lys Glu
1280 1285 1290

Lys Val Pro Arg Arg Arg Gly Arg Lys Lys Lys Leu Glu Lys Glu
1295 1300 1305

Ile Glu Val His Val Gly Lys Arg Arg Gly Arg Lys Arg Gln Thr
1310 1315 1320

Glu Asp Ile Leu Asn Asp Asn Asn Ile Asn Asp Asp Ser Leu Tyr
1325 1330 1335

Tyr Leu Ser Asp Ser Ser Lys Glu Leu Ile Glu Lys Glu Phe Asn
1340 1345 1350

Lys Phe Met Asn Ile Phe Glu Asn Ile Asn Arg Asn Lys Pro Asn
1355 1360 1365

Glu Ser Asn Glu Ser Asn Glu Pro Asn Glu Ser Asn Glu Pro Asn
1370 1375 1380

Glu Pro Asn Glu Pro Asn Glu Pro Asn Glu Pro Asn Glu Pro Asn
1385 1390 1395

Glu Ser Asn Lys Pro Asn Glu Ser Asn Val Pro Asn Glu Ser Asn
1400 1405 1410

Val Pro Asn Glu Ser Asn Glu Ser Asn Val Pro Asn Glu Ser Asn
1415 1420 1425

Glu Ser Asn Val Pro Asn Glu Pro Asn Val Pro Asn Glu Asn Asn
1430 1435 1440

Glu Ser Asn Glu Lys Asn Met Lys Thr Phe Ser Asn Met Asn Asp
1445 1450 1455

Thr Phe Asn Asp Gln Gln Lys Asp Glu Val Ile Asp Asp Ala Thr
1460 1465 1470

Thr Cys Thr Phe Met Asp Leu Asn Asn Cys Thr Tyr Gly Asp Asn
1475 1480 1485

Lys Asn Asn Thr Ser Glu Tyr Asn Lys Asn Asp Lys Gln Thr Asn
1490 1495 1500

Lys Glu Gln Tyr Arg Pro Ile Asp Tyr Asp Val Glu Lys Glu Ile
1505 1510 1515

Gln Asn Ser Glu Lys Ser Glu Tyr Phe Asp Lys Tyr Glu Asn Ser
1520 1525 1530

Phe Ile His Gln Leu Ile Asn Asp Leu Ile His Asn Asn Leu Glu
1535 1540 1545

Glu Glu Asn Tyr Ile Gln Phe Ser Asn Ile Asp Asn Glu Glu Ile
1550 1555 1560

Lys Tyr Arg Lys Leu Lys Glu Val Ile Thr Asn Leu Lys Ile Lys
1565 1570 1575

Glu Lys Lys Ile Asp Leu Ile Leu Ser Asn Asn Leu Ser Phe Phe
1580 1585 1590

Lys Tyr Ser Cys Met Tyr Arg Lys Arg Gln Leu Leu His Glu Lys

```
    1595                1600                1605

Met Leu Gly Asn Trp Ser Tyr Val Glu Asn Thr Ile Asn Lys Arg
    1610                1615                1620

Asp Asp Ile Arg Asn Lys Asn Leu Pro Phe Gln Leu Leu Lys Leu
    1625                1630                1635

Glu Gln Asn Met Leu Glu Asn Ile Ser Lys Cys Tyr Asp Asp Ile
    1640                1645                1650

Leu Leu Glu Asp Phe Ser Gly Ile Ile Ile Thr Leu Asn Thr Asn
    1655                1660                1665

Ser Phe Glu Arg Glu Thr Asp Gly Lys Ile Ile Lys Val Ser Lys
    1670                1675                1680

Val Ile Cys Gly Cys Leu Ile Glu Tyr Leu Asp Asn Thr Ser Glu
    1685                1690                1695

Leu Asn Ile Lys Cys Ile Trp Ala His Pro Phe Leu Asn Thr Lys
    1700                1705                1710

Ser Thr Tyr Tyr Ile Leu Cys Ala Phe Leu Pro Arg Val Ile Leu
    1715                1720                1725

Glu Ala Phe Leu Asn Ser Lys Gly Ile Leu His Asn Asp Ile Asn
    1730                1735                1740

Asp Lys Asp His Ile Asn Met Val Asn Ser Val Lys Gly Glu Gly
    1745                1750                1755

Leu Glu Asn Met Asn Ser Glu Met Cys Glu Phe Lys Asn Ser Glu
    1760                1765                1770

Lys Lys Lys Lys Lys Lys Lys Ser Phe Tyr Asp Arg Leu Asn Glu
    1775                1780                1785

Leu Asp Met Glu Lys Ile Lys Asn Asp His His Glu Asn Asp Asn
    1790                1795                1800

Ile Asn Asn Ser His Asn Asn Ile Ile Lys Leu Glu Gln Ala Tyr
    1805                1810                1815

Phe Ser Asn Tyr Ser Thr Tyr Glu Tyr Pro Leu Thr His Leu Leu
    1820                1825                1830

Asn Phe Asn Lys Glu Cys Ala Tyr Ala Leu Asn Tyr Asn Glu Asn
    1835                1840                1845

Leu Phe Lys Asp Asn Glu Asn Lys Gln Asp Asn Ile Asn Thr Cys
    1850                1855                1860

Asn Asn Met Lys Gly His Asn Asn Cys Asn Asp Asn Thr Ser Leu
    1865                1870                1875

Ser Ser Lys Asp Ser Asn Asn Lys Phe Leu Tyr Ile Ile Phe Ser
    1880                1885                1890

Asp Ile Asp Ile Phe Pro Arg Gln Cys Tyr Leu Ile Leu Cys Ser
    1895                1900                1905

Tyr Lys Tyr Met Cys Leu Asn Met His Tyr Asp Thr Asp Asn Tyr
    1910                1915                1920

Ser Val His Tyr Asp Leu Glu Asn Met Lys Lys Glu Asn Val Gly
    1925                1930                1935

Lys Thr Thr Glu Leu Ser Asn Ser Cys Pro Cys Lys Cys Met Lys
    1940                1945                1950

Ser Ile Pro Asp Asp Ser Glu Glu Ser Tyr Glu Arg Ile Ile Gly
    1955                1960                1965

Leu Ser Glu Leu Tyr Met Tyr Tyr Met Ile Pro Lys Arg Glu Glu
    1970                1975                1980

Arg Glu Asn Leu Gly Leu Leu Lys Arg Asn Gly Trp Arg Asp Leu
    1985                1990                1995
```

```
Ile Cys  Ser Thr Phe Leu Glu  Asp Val His Glu Asn  Ile Ser Ser
    2000                 2005                 2010

Ile Leu  Lys Ile Lys Thr His  Ile Asn Lys Val Ser  Glu His Ile
    2015                 2020                 2025

Ser Val  Gln Asn Arg Ile Tyr  Glu Lys Arg Tyr Thr  Pro Ile Tyr
    2030                 2035                 2040

Ile Asn  Lys Tyr Glu Trp Cys  Gly Leu Lys Leu Lys  Asp Ile Arg
    2045                 2050                 2055

Asn Met  Leu Asn Glu Asp Phe  Asn Tyr Asp Gly Asn  Asp Lys
    2060                 2065                 2070


<210> SEQ ID NO 9
<211> LENGTH: 1236
<212> TYPE: PRT
<213> ORGANISM: Plasmodium falciparum

<400> SEQUENCE: 9

Met Ile Asn Ala Glu Gly Asn Lys Tyr Glu Leu Pro Lys Asp Glu Glu
1               5                   10                  15

Ile Glu Asp Phe Leu Gln Lys Val Glu Glu Val Ser Asn Lys Ile Asn
            20                  25                  30

Gly Leu Ile Lys Gly Thr Ile Ser Ile Glu Glu Leu Asp Lys Glu Glu
        35                  40                  45

Lys Lys Leu Arg Leu Glu Lys Arg Ile Lys Glu Ile Lys Glu Glu Glu
    50                  55                  60

Lys Lys Glu Tyr Glu Lys Lys Arg Phe Leu Met Gly Ile Glu Gly Lys
65                  70                  75                  80

Gly Asn Glu Asp Asn Tyr Leu Phe Phe Cys Ser Phe Cys Phe Ile Leu
                85                  90                  95

Tyr Asn Tyr Asp Leu Thr Asn Cys Val Arg Cys Asn Lys Lys Val Ile
            100                 105                 110

Ser Lys Glu Lys Arg Lys Lys Glu Ile Asn Asp Lys Val Gln Lys Tyr
        115                 120                 125

Lys Ile Leu Lys Asn Lys Arg Asn Ile Arg Arg Asn Arg Trp Asn Thr
    130                 135                 140

Tyr Leu Lys Glu Gln Glu Lys Lys Asn Asn Lys Pro Thr Tyr Lys Asn
145                 150                 155                 160

Tyr Thr Asn Tyr Glu Lys Trp Asn His Tyr Glu Pro Ser Ser Asp Thr
                165                 170                 175

Phe Asp Glu His Glu Lys Met Leu Cys Leu Pro Lys Asn Asn Glu Gln
            180                 185                 190

Phe Lys Gln Phe Glu Asn Lys Leu Asn Gln Asp Ile Gln Lys Lys Lys
        195                 200                 205

Asp Arg Gln Gln Ile Ala Tyr Ser Ile Lys Ile Lys Gly Asn Glu Tyr
    210                 215                 220

Phe Lys Gln Lys Lys Tyr Ile His Ala Ile Glu Cys Tyr Asn Asn Ala
225                 230                 235                 240

Leu Asp Leu Cys Lys Asp Tyr Leu Asp Leu Tyr Val Asn Ile Ala Leu
                245                 250                 255

Cys Gln Ile Lys Ile Tyr Gln Tyr Glu Asn Ala Ile Leu Asn Cys Asn
            260                 265                 270

Gln Val Ile Gln Tyr Tyr Asn Thr Phe Arg Thr Asp Leu Lys Phe Asn
        275                 280                 285

Leu Ser Ile Ile Phe Lys Ala Tyr Ala Arg Lys Ala Leu Ala Leu Phe
```

-continued

```
    290                 295                 300

Ile Leu Phe Gln Phe Lys Asp Ser Leu Thr Asn Phe Thr Gln Ala Leu
305                 310                 315                 320

Glu Phe Asn Lys Asn Asp Glu Gln Val Asn Glu Tyr Ile Gln Lys Cys
                325                 330                 335

Lys His Ile Leu Asn Asp Gln Leu Asn Ser His Tyr Gly Gln Lys Gln
            340                 345                 350

Ile Gln Tyr Leu Ser Cys Gly Asn Pro Ser His Ala Lys Leu Lys Asn
        355                 360                 365

Ala Gln Ser Glu Pro Glu Ala Lys Gln Thr Lys Gln Asn Ile Glu Gly
    370                 375                 380

Glu Lys Cys Val Glu Asn Lys Lys Asn Met Glu Cys Glu Glu Asn Lys
385                 390                 395                 400

Asn Asn Ile Glu Cys Ile Glu Cys Val Glu Cys Val Glu Cys Val Glu
                405                 410                 415

Cys Val Glu Cys Val Glu Cys Val Glu Cys Val Glu Ser Val Glu Asn
            420                 425                 430

Ile Lys Asn Val Glu Tyr Asn Asn Asn Asp Thr Asn Ile His Ile Pro
        435                 440                 445

Phe Asn Ser Asn Asn Gln Asn Asn Ala Phe Leu Leu His Asn Leu Lys
    450                 455                 460

Asn Ser Glu Ile Asn Lys Asn Ile Met Met Glu Leu Ser Lys Lys Asp
465                 470                 475                 480

Ile Asn Lys Glu Pro Asn Leu Phe Ile Ile His Leu Lys Gly Ile Arg
                485                 490                 495

Lys Asn Ile Lys Lys Asp Glu Ile Thr Lys Leu Ile Phe Cys Ser His
            500                 505                 510

Val Tyr Asp Leu Glu Lys Glu Asp Tyr Asn Asn Pro Lys Gln Ser Thr
        515                 520                 525

Lys Lys Arg Lys Tyr Ile Thr Met Leu Ser Phe Phe Ala Asp Lys Leu
    530                 535                 540

Asn Asp Ile Leu Phe Tyr Ile Lys Arg Lys Ser Gln Asn Asn Asp Cys
545                 550                 555                 560

Leu Phe Tyr Thr Gln Asn Ile Asn Asn Lys Ile Phe Lys Ile Asn Lys
                565                 570                 575

Asn Val Lys Lys Cys Thr His Leu Ile Ile Asp Ile Leu Ile Phe Ile
            580                 585                 590

Leu Glu Asn His Phe Tyr Tyr Ala Asp Phe Cys Leu Asn Ala Ile Lys
        595                 600                 605

Pro Ile Phe Thr Phe Tyr Phe Leu Arg Asn Val Lys Val Ser Lys Cys
    610                 615                 620

Leu His Leu Leu Tyr Ser Ile Ile Ser Asn Asn Asn Glu Gly Lys Lys
625                 630                 635                 640

Met Ile Cys Gln Met Leu Glu Glu Lys His Ile Ile Leu Lys Glu Leu
                645                 650                 655

Phe Asn Lys Leu Asn Asn Phe Ile Leu His Glu Arg Asn Thr Tyr Thr
            660                 665                 670

Asn Glu Lys Ile Lys Ile Met Glu Asn Leu Lys Thr His Ile Leu Thr
        675                 680                 685

Cys Thr Tyr Val Lys Lys Tyr Leu Asn Val Gln Glu Ile Asn Glu Leu
    690                 695                 700

Ala Ser Gln Lys Ser Glu Phe Met Lys Glu Asn Glu Tyr Lys Asn Met
705                 710                 715                 720
```

-continued

```
Glu His Met Glu Glu Tyr Ile Lys Ser Asn Glu Lys Glu Lys Leu Gly
                725                 730                 735

Tyr Asn Thr Lys Ile Asn Lys Glu Met Lys Lys Arg Asn Ser Asp Lys
            740                 745                 750

Asn Tyr Asp Asn Ile Leu Leu Tyr Gly Tyr Glu Lys Lys Lys Glu Ile
        755                 760                 765

Cys Met Ser Val Leu Lys Asp Ile Met Ser Ile Asp Met Leu Lys Lys
    770                 775                 780

Glu Asn Glu Asn Asn Arg Ser Leu Ile Asn Glu Ala Ser Lys Gly Ser
785                 790                 795                 800

Leu Phe Cys Asn Ile Asn Asp Met Glu Lys Arg Val Glu Thr Tyr Ile
                805                 810                 815

Lys Asn Ile Met Lys Asn Thr Met Lys Asn Gln Asp Glu Glu Gln Asn
            820                 825                 830

Glu Cys Leu Thr Leu Phe Ser Phe Leu Ser Tyr Leu Ile Val Phe Pro
        835                 840                 845

Asn Ile Leu Asn Ile Ile Glu Lys Cys Cys Met Gln Asn Met Ile Asn
    850                 855                 860

Ile Ile Ile Tyr Ile Asn Glu Lys Met Tyr Asp Tyr Lys Asn Met Lys
865                 870                 875                 880

Cys Asn Tyr Ile Leu Phe Leu Leu Asn Phe Val Ser His Ile Lys Val
                885                 890                 895

Arg Pro Phe Ile Leu Thr Cys Ser Leu Ser Asn Met Leu Phe Tyr Ile
            900                 905                 910

Glu Lys Asn Glu Asn Asp Asn Leu Leu Lys Asn Ile Leu Ser Val Leu
        915                 920                 925

Phe Asn Leu Thr Ile Thr Trp Leu Asn Glu Met Asp Ser Lys Asn Phe
    930                 935                 940

Ile Val Leu Ser Tyr Tyr Gly Glu Ile Lys Glu Ser Thr Phe Arg Lys
945                 950                 955                 960

Leu Ile Asn Ala Met Glu Ser Thr Asp Lys Arg Val Cys Glu Leu Ser
                965                 970                 975

Met Ile Leu Leu Ser Arg Phe Tyr Leu Tyr Met Tyr Cys Phe Asn Asp
            980                 985                 990

Lys Ile Lys Val Gln Lys Asn Ile  Arg Asp Thr Lys Asn  Lys Pro Asp
        995                 1000                1005

Asp Val  Leu Glu Gln Val Pro  Leu Ile Phe Asn Lys  Asp Gly Ile
    1010                1015                1020

Asp Ile  Lys His Phe Tyr Asp  Glu Lys Thr Gln Gln  Lys Asn Glu
    1025                1030                1035

Ser Leu  Met Asn Lys Leu Lys  Glu Lys Ile Lys Lys  Glu Asn Glu
    1040                1045                1050

Lys Leu  Tyr Glu Leu Asp Asn  Ile Ser Phe Leu Tyr  Leu Lys Arg
    1055                1060                1065

Asn Ile  Met Asn Cys Leu Ser  Ile Val Asn Ile Gln  Asn Asp Leu
    1070                1075                1080

Leu Ile  Ile Asn Ala Cys Ile  Lys Leu Val Tyr Asn  Leu Ser Ile
    1085                1090                1095

Tyr Thr  Asn Phe Ile Phe Lys  Asn Ile Ile Tyr Asp  Gln Thr Asn
    1100                1105                1110

Thr Asn  Glu Tyr Tyr Phe Lys  Gln Leu Ile Ser Gln  Ile Ser Ser
    1115                1120                1125
```

Ile Leu Leu Asp Ile Thr Leu Asp Glu Lys Glu Lys Asn Val Asn
1130 1135 1140

Lys Ser Ile Tyr Val Leu Ile Asn Asn Ile Ile Met Phe Phe Ile
1145 1150 1155

Gln Ser Leu Lys Phe Ile Cys Ile His Asn Ile His Lys Glu Glu
1160 1165 1170

Ser Ile Tyr Ile Ile Arg Thr Ile Gln Ser Ile Ile Pro Tyr Ala
1175 1180 1185

Ile Lys Ile Ser Asn Ser Asn Glu Lys Lys Leu Asn Lys Asn Ile
1190 1195 1200

Ser Met Phe Val Ser Tyr Cys Phe Leu Asn Lys Asp Leu Lys Lys
1205 1210 1215

Thr Ile Leu Glu Leu Tyr Asp Asn Asp Ile Arg Lys Val Glu His
1220 1225 1230

Leu Ile Lys
1235

<210> SEQ ID NO 10
<211> LENGTH: 1254
<212> TYPE: PRT
<213> ORGANISM: Plasmodium falciparum

<400> SEQUENCE: 10

Met Glu Asn Glu Ser Phe Asn Pro Leu Ser Leu Leu Asp Lys Asn Gln
1 5 10 15

Ala Phe Asp Ala Glu Lys Leu Lys Leu Leu Asp Asn Val Val Glu Ala
20 25 30

Leu Leu Asp Thr Lys Asp Lys Asn Arg Arg Asp Phe Ala Gln Asn Leu
35 40 45

Leu Asn Gln Phe Lys Met Leu Asp Thr Ser Trp Arg Ser Val Ser Ile
50 55 60

Ile Leu Glu His Ser Glu Asn Val Asn Thr Lys Phe Tyr Gly Leu Gln
65 70 75 80

Ile Leu Glu Glu Cys Ile Asn Asn Arg Trp Asn Ile Leu Pro Ser Glu
85 90 95

Glu Lys Glu Gly Met Lys Asn Phe Ile Ala Cys Tyr Thr Ile Thr Leu
100 105 110

Ser Thr Glu Gly Thr Thr Val Gly Val Asp Arg His Leu Leu Asn Lys
115 120 125

Leu Asp Glu Thr Leu Ile Gln Ile Val Lys Gln Glu Trp Pro Asp Ser
130 135 140

Trp Ser Ser Phe Ile Pro Asp Ile Val Asn Ser Ala Lys Leu Asn Gln
145 150 155 160

Asn Val Cys Glu Asn Asn Met Lys Leu Leu Asn Met Leu Ser Glu Glu
165 170 175

Val Phe Glu Phe Gly Asn Glu Thr Leu Val Lys Lys Lys Lys Glu Lys
180 185 190

Leu Arg Asn Glu Tyr Ala Ser Gln Phe Gln Glu Val Tyr Asn Leu Cys
195 200 205

Leu Tyr Ile Leu Glu Ala Asn Val Tyr Asn Lys Arg Ser Thr Asn Thr
210 215 220

Ser Leu Ile Lys Gln Thr Leu His Cys Leu Ser Asn Phe Phe Lys Trp
225 230 235 240

Ile Pro Leu Thr Tyr Ile Phe Asp Lys Tyr Lys Phe Asn Asp Asn Asn
245 250 255

-continued

```
Ile Gln Ile Ile Asp Leu Leu Phe Asp His Phe Trp Asp Asp Ile Ser
            260                 265                 270

Tyr Lys Ile Glu Cys Val Lys Cys Ile Gln Glu Ile Val Met Leu Lys
        275                 280                 285

Ile Asp Glu Lys Asn Ile Leu Tyr Phe Asp Asn Val Phe Ile Asn Leu
    290                 295                 300

Trp Thr Lys Leu Val Ser Lys Ile Lys Leu Leu Pro Asn Ala Asn Glu
305                 310                 315                 320

Met Lys Asn Ile Pro Pro Glu Leu Lys Ile Phe Trp Glu Gln Tyr Phe
                325                 330                 335

Leu Gln Leu Ser Ile Cys Ile Thr Ser Phe Leu Lys Asn Tyr Arg Glu
            340                 345                 350

Lys Ile Val Glu Lys Asn Asn Asn Thr Asn Asp Val Asn Ile Val Phe
        355                 360                 365

Lys Phe Leu Asn Met Leu Ala Asn Ser Asn Met Glu Glu Val Phe Leu
    370                 375                 380

Ile Ile Ile Asp Tyr Tyr Asn Ile Phe Thr Glu Gln Leu Ile Arg Glu
385                 390                 395                 400

Leu Ile Thr Arg Leu Glu Gln Glu His Asn Phe Lys Asn Lys Asn Asp
                405                 410                 415

Met Asn Ser Ser Ser Leu Asp Met Lys Asn Thr Leu Thr Thr Asn Met
            420                 425                 430

Asn Leu Asp Ser Ser Ser Leu Thr Asn Arg Lys Ser Tyr Ser Phe Val
        435                 440                 445

Thr Met Asn Asn Asp Ile Asn Leu Leu Asn Asn Asn Asn Asn Asn Asn
    450                 455                 460

Asn Ser Asn Asn Met Asn Ser Ser Asn Met Asn Ser Asn Met Val Ile
465                 470                 475                 480

Asn Ile Asn Glu Tyr Ser Ser Ile Leu Asp Lys Ile Asp Leu Asn Pro
                485                 490                 495

Ser Asp Ile Lys Lys Met Cys Pro Arg Ile Lys Leu Tyr Glu Phe Ile
            500                 505                 510

Leu Asn Asp Ile Arg Lys Thr Val Ile Glu Lys Met Ala Lys Pro Gln
        515                 520                 525

Glu Ile Tyr Ile Ser Tyr Asp Asn Glu Thr Gly Glu Val Val Arg Asp
    530                 535                 540

Phe Glu Pro Asp Thr Thr Glu Ile Ser Leu Tyr Asn Thr Met Lys Thr
545                 550                 555                 560

Thr Leu Val Tyr Leu Thr Tyr Leu Gly Ser Glu Lys Thr Met Glu Leu
                565                 570                 575

Ile Val Glu Leu Leu Asn Lys Glu Ser Glu Lys Ser Leu Lys Asn Thr
            580                 585                 590

Asn Lys Asn Glu Val Trp Asn Ser Thr Lys Thr Asn Arg Ile Ser Tyr
        595                 600                 605

Ala Val Gly Ser Ile Ser Met Cys Met Thr Leu Lys Lys Glu Gln Asp
    610                 615                 620

Phe Leu Met Tyr Ile Leu Arg Ile Tyr Leu His Met Ile Glu Val Lys
625                 630                 635                 640

Asn Gly Glu Glu Asn Arg Ala Ile Leu Ala Ser Cys Val Met Tyr Ile
                645                 650                 655

Val Ser Gln Tyr His Arg Phe Leu Lys Leu His Trp Arg Phe Leu Lys
            660                 665                 670
```

-continued

```
Thr Val Met Lys Lys Leu Phe Glu Phe Ala Glu Asn Glu Lys Val Gln
        675                 680                 685

Asp Met Ala Ala Glu Thr Ile Leu Lys Ile Cys Lys Gln Cys Lys Asn
    690                 695                 700

Val Ile Ala Lys Asn Asn His Asn Asn Asp Asn Asn Glu Ser Phe Phe
705                 710                 715                 720

Ser Thr Phe Ile Lys Phe His Asn Asn Ile Met His Lys Leu Pro Glu
                725                 730                 735

Lys Leu Asn Leu Leu Leu Tyr Glu Ala Ile Ala His Val Ile Ser Cys
            740                 745                 750

Phe Pro Tyr Glu Glu Lys Gln Glu Ser Ile Lys Val Leu Met Ser Lys
        755                 760                 765

Leu Met Asn Leu Trp Asn Ser Leu Ile Tyr Ala Asn Asn Asn Gly Ala
    770                 775                 780

Ile Lys Asp Met Asn Asn Thr Asn Ser Leu Asn Asn Asn Asn Ile Asn
785                 790                 795                 800

Asn Asn Asn Asn Ile Asn Ile Asn Asn Asp Asp Met Lys Asn Leu Glu
                805                 810                 815

His Leu Cys Thr Tyr Glu Asn Ser Lys Leu Ile Ile Thr Phe Val Arg
            820                 825                 830

Val Asn Cys Arg Leu Ala Tyr Ala Leu Ser Tyr Phe Tyr Tyr Glu Gln
        835                 840                 845

Leu Ala Leu Val Phe Leu Asp Phe Leu Lys Ile Tyr Gln Leu Tyr Ser
    850                 855                 860

Lys Phe Ile Asn Leu Glu Val Glu Ala Asn Gly Thr Lys Arg Ile Lys
865                 870                 875                 880

His Ala Gln Phe Arg Asn Leu Phe Leu Met Lys Arg Glu Phe Leu His
                885                 890                 895

Leu Ile Glu Thr Thr Ile Glu Arg Ser Cys Tyr Asn Ile Gln Asp Leu
            900                 905                 910

Glu Lys Glu Leu Leu Lys Arg Glu Gln Lys Lys Leu Lys Asn Glu Ile
        915                 920                 925

Asp Glu Ser Met Glu Ile His Leu Pro Thr Ile Glu Glu Ala Lys Gln
    930                 935                 940

Ile Asn Phe Gln Met Thr Ser Asn Ile Leu Asn Val Leu Leu Glu Thr
945                 950                 955                 960

Ile Leu Val Asp Tyr Arg Asp Ser Asn Pro His Ile Lys Asp Ala Glu
                965                 970                 975

Val Phe Ser Leu Leu Ser Thr Val Phe Lys Lys Ile Glu Asn Val Thr
            980                 985                 990

Cys Pro Ile Leu Pro Thr Val Leu  Asn Tyr Val Leu Leu  Pro Thr Ile
        995                 1000                1005

Asp Met  Ile Lys Asn Asp Phe  Ser Ser Tyr Pro Glu  His Arg Glu
    1010                1015                1020

Lys Phe  Tyr Asn Phe Leu Asp  Ala Cys Val Arg His  Cys Phe Asp
    1025                1030                1035

Tyr Leu  Phe Thr Leu Asp Ser  Glu Ile Phe Asn Thr  Phe Ile Gln
    1040                1045                1050

Ser Leu  Leu Trp Ala Ile Lys  His Glu His Pro Ser  Val Ala Asp
    1055                1060                1065

His Gly  Leu Arg Ile Thr Gln  Gln Phe Leu His Asn  Ile Ile Ile
    1070                1075                1080

Lys Lys  Lys Glu Tyr Leu Glu  Glu Phe Cys Lys Ala  Phe Tyr Tyr
```

```
    1085                1090                1095

Ile Ile  Leu Asn Glu Ile Leu  Lys Thr Leu Thr Asp  Ser Phe His
    1100                1105                1110

Lys Ser  Gly Phe His Tyr Gln  Thr Ile Ile Leu Met  Asn Leu Leu
    1115                1120                1125

Arg Leu  Leu Glu Phe Glu Val  Val Asn Ile Pro Glu  Val Glu Ile
    1130                1135                1140

Thr Lys  Pro His Ile Ile Lys  His Val Gln Asn Phe  Leu Thr Gln
    1145                1150                1155

Ser Phe  Glu Asn Leu Asn Gln  Lys Gln Ile Glu Thr  Phe Ser Val
    1160                1165                1170

Asp Met  Phe Asn Phe Cys Val  Glu Ser Pro Ser Ala  Phe Arg Ser
    1175                1180                1185

Phe Val  Arg Asp Leu Leu Ile  Ser Leu Lys Glu Phe  Ala Thr Asn
    1190                1195                1200

Gln Asp  Glu Leu Tyr Glu Ala  Asp Arg Gln Glu Ala  Leu Gln Arg
    1205                1210                1215

Ala Lys  Met Ala Glu Asp Asn  Lys Leu Ile Lys Leu  Arg Gly Leu
    1220                1225                1230

Met Lys  Glu Asp Val Pro Ser  Phe Ser Ala Ile Asp  Val Asp Asp
    1235                1240                1245

Glu Cys  Ile Asn Val Glu
    1250


<210> SEQ ID NO 11
<211> LENGTH: 1374
<212> TYPE: PRT
<213> ORGANISM: Plasmodium falciparum

<400> SEQUENCE: 11

Met Asn Glu Tyr Ser Val Tyr Asn Lys Pro Asn Ser Asn Asn Ile Ser
1               5                   10                  15

Val Ser Lys Gly Thr Ser Arg Ile Phe Lys Lys Ile Lys Thr Asn Lys
            20                  25                  30

Asn Tyr Gly Ser Leu Ala Ile Lys Lys Glu Thr His Asn Glu Leu Asn
        35                  40                  45

Gly Asn Thr Lys Arg Asn Val Ser Asp Lys Leu Ile Tyr Glu Asn Glu
    50                  55                  60

Thr Lys Thr Met Ile Asn Asn Asn Asn Asn Asn Met Asn Asp Asn Asn
65                  70                  75                  80

Asn Asn Tyr Arg Leu Asp Ile Leu Thr Gly Ser Glu Glu Tyr Glu Lys
                85                  90                  95

Asn Asp Ile Ser Tyr Val Gln Glu Asp Ser Asp Ile Met Glu His Ile
            100                 105                 110

Lys Leu Glu Gly Asn Glu Ile Asp Tyr Glu Lys Met Val Tyr Gly Asn
        115                 120                 125

Asp Lys Glu Arg Ser Lys Glu Lys Lys Lys Ile Asn Asn Tyr Asp Lys
    130                 135                 140

Asn Ile Gln Gly Ile Lys Ile Glu Glu Asp Ile Asn Glu Tyr Lys Lys
145                 150                 155                 160

Val Lys Lys Cys Asp Val Ala Lys Asn Arg Val Lys Arg Leu Glu Leu
                165                 170                 175

Val Ile Asp Ile Glu Glu Tyr Asn Asp Asn Lys Leu Glu Asn Glu Asn
            180                 185                 190
```

-continued

```
Leu Leu Gln Lys Asn Tyr Ala Lys Asn Ile Ser Ser Asp Glu Lys Lys
        195                 200                 205

Tyr Tyr Tyr Asn Asn Tyr Ile Phe Asn Asp Asp Leu Tyr Asn Gly Lys
    210                 215                 220

Leu Asn Cys Leu Thr Lys Thr Leu Asp Phe Leu Ala Lys Glu Glu His
225                 230                 235                 240

Ile Asn Pro Asn Gly Asn Leu Asp Asp Gln Glu Asp Ser Glu Ser Val
                245                 250                 255

Cys Val Ile Glu Lys Arg Thr Ile Lys Asn Ser Ser Ser Cys Asp Glu
            260                 265                 270

Lys Glu Leu Ile Glu Lys Ile Asn Leu Lys Asp Asn Tyr Val Phe Phe
        275                 280                 285

Asn Asn Asn Asn Lys Glu Lys Asn Lys Asn Lys Leu Lys Asp Lys Asn
    290                 295                 300

Lys Thr Asn Lys Ile Asn Lys Arg Lys Lys Pro Asn His Ser Lys Thr
305                 310                 315                 320

Asn Asp Asn Asp Gln Thr Glu Ile Tyr Lys Lys Thr Lys Lys Met Asn
                325                 330                 335

Asn Lys Asn Asn Asn Gly Lys Asn Lys Asn Asn His Met Asn Val Leu
            340                 345                 350

Glu Asn Phe Asn Ala Lys His Asn Met Asn Ser Thr Thr Arg Gln Asn
        355                 360                 365

Asn Asn Asn Ile Lys Lys Ile Lys Ser Asn Asn Asn Asn Asn Asn Asn
    370                 375                 380

Asn Asp Asn Asn Tyr Cys Tyr Tyr Tyr Lys Ser Ile Asp Lys Asn Val
385                 390                 395                 400

Ser Tyr Tyr Asn Ser Arg Ser Ser Ser Lys Ser Asp Phe Asn Leu Tyr
                405                 410                 415

Ser Asn Thr Thr Ser Thr Gln Asn Ser Tyr Ser Ser Ile Tyr Asn Asp
            420                 425                 430

Asn Asp Asn Asp Asn Cys Ile Asn Ser Cys Asp Ser Asn Tyr Asn Asn
        435                 440                 445

Asn Tyr Asn Asn Ile Tyr Asn Asn His Cys Asn Asn Asn Phe Asn Asn
    450                 455                 460

Asn Asn Lys Leu Pro Ser Ser Asn Tyr Thr Lys Ile Met Asn Asp Thr
465                 470                 475                 480

Asn Tyr Val Ser Ser Asn Asp Asp Ser Thr Lys Ile His Ile Gly Ile
                485                 490                 495

Lys Glu Glu Lys Lys Tyr Ile Met Lys Pro Glu Glu His Leu Glu Asn
            500                 505                 510

Phe Ile Lys Asn Asn Arg Ile Tyr Asn Asp Ser Gly Cys Tyr Val Ile
        515                 520                 525

Ser Asp Asp Cys Val Ile Pro Asn Tyr Lys Tyr Glu Gln Asp Asp Val
    530                 535                 540

Tyr Val Glu Ile Ile Glu Asn Asn Asn Ile Thr Asp Gly Tyr Asn Asn
545                 550                 555                 560

Leu Gln Asp Ser Phe Glu Lys Ile Lys Glu Phe Trp Ser Ser Ser Asn
                565                 570                 575

Val Thr Ser Thr Thr Asn Lys Asn Asn Asn Asn Lys Lys Asn Ile Ile
            580                 585                 590

Leu Tyr Asp Glu Gln Lys Asp Asp Asn Glu Ile Asp His Arg Lys Thr
        595                 600                 605

Ser Lys Asn Ser Asn Asp Asn Leu Lys Lys Ser Gln Asn Ile Asn Asp
```

-continued

```
    610                 615                 620

Gly Met Lys Thr Ala Asn Ser Ser Ile Lys Asn Asp Thr Lys Asp Glu
625                 630                 635                 640

Glu Glu Tyr Lys Lys Ser Ile Lys Ser Lys Asn Asn Lys Asn Asn Arg
                645                 650                 655

Asn Asn Asp Asp Asp Tyr Met Lys Glu Glu Asp Gln Ile Asn Ser Phe
            660                 665                 670

Leu Pro Ser Asn Glu Asn Asn Asn Asn Asn Asn Asn Asn Asn Asn Asn
        675                 680                 685

Asn Asn Asn Asn Asn Asn Asn Asn Asn Asn Asn Asn Asn Asn Asn Asn
    690                 695                 700

Asn Asn Asn Asn Asn Asn Asp Cys Asp Thr Lys Tyr Asp Ala Asn Ile
705                 710                 715                 720

Asn Ser Lys Cys Asn Arg Asn Asn Ile Tyr Asn Ile Asn Ser Tyr Leu
                725                 730                 735

Asn Val Val Gly Tyr Asn Asp Asn Lys Lys Asn Asp Thr Ile Asn Asp
            740                 745                 750

Lys Asn Asn Asn Asn Asn Met Lys Asn Asp Lys Pro Glu Asp Glu Cys
        755                 760                 765

Thr Lys Lys Lys Asp Ile Asn Asn Ser Asn Asn Lys Asn Tyr Ser Ser
    770                 775                 780

Asn Asp Asn Ile Asn Asn Gly Asn Asn Lys Asn Tyr Asn Gly Asn Asn
785                 790                 795                 800

Lys Asn Tyr Asn Gly Asn Asn Lys Asn Tyr Asn Gly Asn Asn Lys Asn
                805                 810                 815

Tyr Asn Gly Asn Asn Lys Asn Cys Asn Gly Asn Asn Lys Asn Cys Asn
            820                 825                 830

Gly Asn Asn Lys Asn Tyr Asn Gly Asn Asn Lys Asn Cys Asn Gly Asn
        835                 840                 845

Asn Lys Asn Tyr Asn Ser Asn Asn Lys Asn Tyr Asn Ser Lys His Asn
    850                 855                 860

Ser Asn Lys Gly His Ser Lys Asp His Asn Asn Gly His Ser Lys Asp
865                 870                 875                 880

His Asn Asn Gly His Ser Lys Asp His Asn Asn Gly His Ser Lys Asp
                885                 890                 895

His Asn Asn Gly His Ser Lys Asp His Asn Asn Gly His Ser Lys Asp
            900                 905                 910

His Asn Asn Gly His Ser Lys Asp His Asn Asn Gly His Asn Asp Asp
        915                 920                 925

His Asn Asn Asp His Asn Asn Asn Asn Asp Ser Phe Lys Cys Glu Glu
    930                 935                 940

Asn Val Phe Gln Glu Phe Asn Glu Phe Met Arg Lys Lys Met Trp Met
945                 950                 955                 960

Glu Lys Tyr Leu His Asn Gln Ile Asn Cys Tyr Asp Val Leu Leu Glu
                965                 970                 975

Ile Arg Lys Arg Val Pro Arg Trp Gly Asp Tyr Lys Cys Asn Phe Phe
            980                 985                 990

Phe His Trp Lys Lys Ile Met Glu  Leu Asn Asn Glu Glu  Leu Lys Ile
        995                 1000                1005

Tyr Ile  Leu Ile Phe Arg Ser  Leu Cys Asn Glu Asn  Ile Lys Lys
    1010                1015                1020

Ile Asp  Phe Tyr Ile Leu Lys  Ile Ile Leu Asn Glu  Leu Asp Glu
    1025                1030                1035
```

Leu Arg Lys Val Asn Glu Pro His Tyr Val Ser Phe Glu Phe Thr
1040 1045 1050

Gln Asp Cys Ile Asn Asn Gly Glu Thr Lys Tyr Val Asp Ser Ser
1055 1060 1065

Asp Val Tyr Phe Asn Met Asn Gln Phe Val Gln Pro Trp Tyr Leu
1070 1075 1080

Lys Asn Leu Asn Lys Ser Met Asp Ile Lys Lys Phe Leu Asn Ser
1085 1090 1095

Leu Asp Ile Leu Glu Asn Gln Lys Lys Lys Thr Tyr Ile Val His
1100 1105 1110

Gly Met Glu Ile Pro Glu Gln Ile Phe Asn Met Tyr Asn Thr Ser
1115 1120 1125

Lys Lys Lys Ala Lys Lys Lys Lys Lys Cys Ser Lys Ile Asn Thr
1130 1135 1140

Asn Glu His Leu Tyr Asp Gln Pro Ser Thr His Ser Asp Val Pro
1145 1150 1155

Leu Asn Asn Gln Leu Lys Asn Asn Leu Gln Lys Lys Ser Gln Asn
1160 1165 1170

Asn Ile Tyr Asn Arg Asp Glu Asn Arg Gln Ala Lys Asn Cys Lys
1175 1180 1185

Tyr Leu Lys Lys Thr Asn Thr Leu Leu Asn Asn Glu His Ile Asn
1190 1195 1200

Asn Met Val Ser Asn Leu Asp Asn Thr Lys Thr Lys Asp Ile Asn
1205 1210 1215

Lys Asn Lys Asn Ile Asn Glu Ser Val Lys Lys Ala Ser Ile Lys
1220 1225 1230

Asn Tyr Asn Lys Asn Val Lys Asn Asn Asn Lys Lys Cys Asp Asn
1235 1240 1245

Thr Asn Asp Asn Lys Asn Asp Asn Lys Asn Asp Asn Thr Asn Asp
1250 1255 1260

Asn Lys Asn Asp Asn Lys Cys Glu Lys Thr Thr Lys Asp Tyr Glu
1265 1270 1275

Ala Lys Gln Val Asn Lys Thr Leu Lys Lys Asn Ala Asn Ser Pro
1280 1285 1290

Asn Asn Ser Lys Gly Lys Lys Arg Thr Gly Phe Tyr Asp Leu Glu
1295 1300 1305

Ile Asp Gly Val Ile Ser Ser Phe Glu Ala Arg Lys Gly Val Tyr
1310 1315 1320

Tyr Asp Lys Ser Arg Lys Leu Trp Arg Ala Asn Trp Lys Glu Asn
1325 1330 1335

Gly Lys Ile Gln Thr Lys Gly Phe Ser Val Asn Glu Tyr Lys Ser
1340 1345 1350

Val Gln Leu Ala Arg Gln Lys Ala Ile Glu Trp Arg Glu Lys Lys
1355 1360 1365

Glu Ala Glu Leu Leu Leu
1370

<210> SEQ ID NO 12
<211> LENGTH: 246
<212> TYPE: PRT
<213> ORGANISM: Plasmodium falciparum

<400> SEQUENCE: 12

Met Ala Arg Arg Tyr Asp Ser Arg Thr Thr Thr Phe Ser Pro Glu Gly 1 5 10 15

Arg Leu Tyr Gln Val Glu Tyr Ala Leu Glu Ala Ile Asn Asn Ala Ser
20 25 30

Ile Thr Ile Gly Leu Ile Thr Lys Asp Gly Val Ile Leu Gly Ala Asp
35 40 45

Lys Val Phe Ile Ser Lys Leu Ile Asp Lys Ala Asn Asn Tyr Glu Lys
50 55 60

Ile Tyr Lys Ile Asp Lys His Ile Phe Cys Gly Val Ala Gly Leu Asn
65 70 75 80

Ala Asp Ala Asn Ile Leu Ile Asn Gln Ser Arg Leu Tyr Ala Gln Arg
85 90 95

Tyr Leu Tyr Asn Tyr Asn Glu Val Gln Pro Val Ser Gln Leu Val Val
100 105 110

Gln Ile Cys Asp Ile Lys Gln Ser Tyr Thr Gln Tyr Gly Gly Leu Arg
115 120 125

Pro Tyr Gly Val Ser Phe Leu Ile Gly Gly Tyr Asp Thr Lys Asp Gly
130 135 140

Tyr Gln Leu Tyr His Thr Asp Pro Ser Gly Asn Tyr Ser Gly Trp Phe
145 150 155 160

Ala Thr Ala Ile Gly Thr Asn Asn Leu Thr Ala Ser Ser Val Leu Lys
165 170 175

Gln Glu Trp Lys Asn Asp Met Thr Leu Glu Glu Gly Leu Leu Leu Ala
180 185 190

Leu Lys Thr Leu Ala Lys Ser Thr Asp Thr Glu Ile Pro Lys Ser Glu
195 200 205

Lys Ile Glu Leu Ala Tyr Leu Thr Asn Lys Asp Gly Glu Val Tyr Gln
210 215 220

Lys Tyr Leu Thr Glu Lys Glu Ile Glu Glu Leu Ile Lys Leu Tyr Thr
225 230 235 240

Gln Lys Tyr Ile Lys Glu
245

<210> SEQ ID NO 13
<211> LENGTH: 448
<212> TYPE: PRT
<213> ORGANISM: Plasmodium falciparum

<400> SEQUENCE: 13

Met Gly Asn Thr Pro Gly Gly Met Asn Asn Pro Tyr Gly Phe Leu Gly
1 5 10 15

Lys Lys Glu Asp Lys Asp Lys Gly Lys Asp Lys Asp Lys Glu Lys Lys
20 25 30

Lys Leu Glu Ser Val Pro Ile Ser His Met Gly Lys Lys Lys Lys Lys
35 40 45

Asn Lys Gly Thr Ser Gly His Ser Lys Leu Pro Asn Val Thr Pro Asn
50 55 60

Thr Lys Cys Arg Leu Lys Leu Leu Lys Leu Glu Arg Ile Lys Asp Tyr
65 70 75 80

Leu Leu Leu Glu Glu Glu Tyr Ile Thr Asn Gln Glu Gln Ile Lys Ser
85 90 95

Ser Asp Asp Lys Asn Tyr Val Lys Leu Lys Ile Asp Asp Leu Arg Gly
100 105 110

Ser Pro Val Ser Val Gly Thr Leu Glu Glu Leu Ile Asp Glu Asn His
115 120 125

-continued

Gly Ile Ile Ala Thr Ser Val Gly Pro Glu Tyr Tyr Val Asn Ile Leu
130 135 140

Ser Phe Val Asp Lys Asp Leu Leu Glu Pro Gly Cys Ser Val Leu Leu
145 150 155 160

Asn Asn Lys Thr Asn Ser Val Val Gly Ile Leu Leu Asp Glu Val Asp
165 170 175

Pro Leu Val Ser Val Met Lys Val Glu Lys Ala Pro Leu Glu Ser Tyr
180 185 190

Ala Asp Ile Gly Gly Leu Glu Ser Gln Ile Gln Glu Ile Lys Glu Ala
195 200 205

Val Glu Leu Pro Leu Thr His Pro Glu Leu Tyr Glu Asp Ile Gly Ile
210 215 220

Lys Pro Pro Lys Gly Val Ile Leu Tyr Gly Pro Pro Gly Thr Gly Lys
225 230 235 240

Thr Leu Leu Ala Lys Ala Val Ala Asn Glu Thr Ser Ala Thr Phe Leu
245 250 255

Arg Val Val Gly Ser Glu Leu Ile Gln Lys Tyr Leu Gly Asp Gly Pro
260 265 270

Lys Leu Val Arg Glu Met Phe Lys Val Ala Glu Glu His Ala Pro Ser
275 280 285

Ile Val Phe Ile Asp Glu Ile Asp Ala Val Gly Thr Lys Arg Tyr Glu
290 295 300

Ala Thr Ser Gly Gly Glu Arg Glu Ile Gln Arg Thr Met Leu Glu Leu
305 310 315 320

Leu Asn Gln Leu Asp Gly Phe Asp Ser Arg Gly Asp Val Lys Val Ile
325 330 335

Met Ala Thr Asn Arg Ile Asp Ser Leu Asp Pro Ala Leu Ile Arg Pro
340 345 350

Gly Arg Ile Asp Arg Lys Ile Gln Leu Pro Asn Pro Asp Thr Lys Thr
355 360 365

Lys Arg Arg Ile Phe Gln Ile His Thr Ser Lys Met Thr Met Ser Pro
370 375 380

Asp Val Asp Leu Glu Glu Phe Val Met Ser Lys Asp Glu Leu Ser Gly
385 390 395 400

Ala Asp Ile Lys Ala Ile Cys Thr Glu Ala Gly Leu Leu Ala Leu Arg
405 410 415

Glu Arg Arg Met Lys Ile Thr Gln Ala Asp Leu Arg Lys Ala Arg Asp
420 425 430

Lys Ala Leu Phe Gln Lys Lys Gly Asn Ile Pro Glu Gly Leu Tyr Leu
435 440 445

<210> SEQ ID NO 14
<211> LENGTH: 235
<212> TYPE: PRT
<213> ORGANISM: Plasmodium falciparum

<400> SEQUENCE: 14

Met Ala Asp Gly Glu Tyr Ser Phe Ser Leu Thr Thr Phe Ser Pro Thr
1 5 10 15

Gly Lys Leu Val Gln Ile Glu Tyr Ala Leu Asn Arg Val Ser Ser Ser
20 25 30

Ser Pro Ala Leu Gly Ile Arg Ala Lys Asn Gly Val Ile Ile Ala Thr
35 40 45

Glu Lys Lys Ser Pro Asn Glu Leu Ile Glu Glu Asn Ser Ile Phe Lys
50 55 60

Ile Gln Gln Ile Ser Glu His Ile Gly Ile Val Tyr Ala Gly Met Pro
65 70 75 80

Gly Asp Phe Arg Val Leu Leu Lys Arg Ala Arg Lys Glu Ala Ile Arg
85 90 95

Tyr Ser Leu Gln Tyr Gly Ser Glu Ile Leu Val Lys Glu Leu Val Lys
100 105 110

Ile Ile Ala Ser Ile Val Gln Glu Phe Thr Gln Thr Gly Gly Val Arg
115 120 125

Pro Phe Gly Leu Ser Leu Leu Ile Cys Gly Val Asp Val Tyr Gly Tyr
130 135 140

His Leu Tyr Gln Ile Asp Pro Ser Gly Cys Tyr Phe Asn Trp Met Ala
145 150 155 160

Thr Cys Val Gly Lys Asp Tyr Gln Asn Asn Met Ser Phe Leu Glu Lys
165 170 175

Arg Tyr Asn Lys Asp Ile Glu Ile Glu Asp Ala Ile His Thr Ala Ile
180 185 190

Leu Thr Leu Lys Glu Ser Tyr Glu Gly Val Leu Asn Glu Lys Asn Ile
195 200 205

Glu Ile Gly Val Ala Tyr Asp Asn Lys Pro Phe Lys Ile Leu Thr Gln
210 215 220

Asn Glu Ile Lys Asp Tyr Leu Ile Glu Ile Glu
225 230 235

<210> SEQ ID NO 15
<211> LENGTH: 149
<212> TYPE: PRT
<213> ORGANISM: Plasmodium falciparum

<400> SEQUENCE: 15

Met Ala Asp Lys Leu Thr Glu Glu Gln Ile Ser Glu Phe Lys Glu Ala
1 5 10 15

Phe Ser Leu Phe Asp Lys Asp Gly Asp Gly Thr Ile Thr Thr Lys Glu
20 25 30

Leu Gly Thr Val Met Arg Ser Leu Gly Gln Asn Pro Thr Glu Ala Glu
35 40 45

Leu Gln Asp Met Ile Asn Glu Ile Asp Thr Asp Gly Asn Gly Thr Ile
50 55 60

Asp Phe Pro Glu Phe Leu Thr Leu Met Ala Arg Lys Leu Lys Asp Thr
65 70 75 80

Asp Thr Glu Glu Glu Leu Ile Glu Ala Phe Arg Val Phe Asp Arg Asp
85 90 95

Gly Asp Gly Tyr Ile Ser Ala Asp Glu Leu Arg His Val Met Thr Asn
100 105 110

Leu Gly Glu Lys Leu Thr Asn Glu Glu Val Asp Glu Met Ile Arg Glu
115 120 125

Ala Asp Ile Asp Gly Asp Gly Gln Ile Asn Tyr Glu Glu Phe Val Lys
130 135 140

Met Met Ile Ala Lys
145

<210> SEQ ID NO 16
<211> LENGTH: 374
<212> TYPE: PRT
<213> ORGANISM: Plasmodium falciparum

<400> SEQUENCE: 16

Met Val His Asn Asn Cys Asn Lys Glu Glu Asn Tyr Phe Phe Glu Phe
1 5 10 15

Gln Tyr Lys Lys Lys Asn Lys Asn Glu Tyr Phe Asn Leu Glu Ile Ile
20 25 30

Ile Gly Ser Ile Ile Asn Asn Arg Asp Lys Lys Lys Arg Glu Thr Phe
35 40 45

Phe Thr Phe Arg Lys Ile Leu Ile Tyr Ile Ile Phe Ile Tyr Ile Leu
50 55 60

Tyr Phe Ile Asp Tyr Lys Tyr Leu Leu Asn Asn His Ser His Glu Gln
65 70 75 80

Tyr Glu Ile Tyr Lys Ile Ser Ser Asn Lys Lys Trp Arg Gln Leu Ser
85 90 95

Glu Ser Tyr Asp Tyr Phe Gln Asp Pro Leu Asp Tyr Phe Glu Asn Val
100 105 110

Gln Asn Arg Val Lys Leu Phe Tyr Asn Ile Asp Asn Ile Asp Glu Leu
115 120 125

Asp Ile Asn Phe Leu Tyr Lys Asn Ile Leu Asp Lys Ser Lys Leu Thr
130 135 140

Asp Lys Lys Arg Ile Asn His Tyr Glu Ser Ser Asn Ser Tyr Met Gly
145 150 155 160

Asp Lys Ala Asn Ile Ser Tyr Asp Asp Asn Ile Ser Ser Ile Asn Ile
165 170 175

Met Cys Cys Asn Asn Ile Lys Thr His Asn Asn Asn Pro Ser Asn Asn
180 185 190

Tyr Asn Ile Tyr Asn Gln Asn Ile Ile Arg Tyr Asp Asn Asn Gly Lys
195 200 205

Thr Asn Leu Tyr Asp Thr Asn Asn Asp Phe Phe Lys His Lys Tyr Lys
210 215 220

Ser Asn Glu Ser Phe Asp Thr Phe Leu Thr Asn Asp His Asn Glu Asn
225 230 235 240

Gly Asn Phe Gln Val Tyr Glu Ile Ser Asp Asp Glu Ile Ile Leu Thr
245 250 255

Asn Ile Lys Thr His Asp Met Lys Phe Glu Lys Asn Thr Asn Asn Lys
260 265 270

Ser Lys Gln Lys Arg Phe Asn Thr Ile Asp His Glu Ile Ser His Leu
275 280 285

Asn Lys Asp Ser Ser Thr Asn Lys Asn Leu Leu Lys Asn Ile Ser Ile
290 295 300

Leu Lys Tyr Ile Tyr Asn Asn Gly Lys Cys Asn Ile Lys Pro Lys Lys
305 310 315 320

Ile Tyr Ala Lys Cys Ile Lys Lys Ile Lys Lys Ile Lys Phe Lys Lys
325 330 335

Ile Ile Tyr His Ile Leu Tyr Met Leu Gly Ser Ala Leu Thr Thr Tyr
340 345 350

Leu Phe Leu Gly Ala Leu Gly Pro Glu Met Val Asn Arg Ile Gly Val
355 360 365

Ser Leu Ile Ala Tyr Gly
370

<210> SEQ ID NO 17
<211> LENGTH: 355
<212> TYPE: PRT
<213> ORGANISM: Plasmodium falciparum

<400> SEQUENCE: 17

```
Met Tyr Asn Phe Val Lys Ile Phe Gln Ser Asn Phe Ile Asp Ile Asn
1               5                   10                  15

Lys Leu Ser Lys Phe Glu Ile Phe Leu Lys Thr Ile Phe Arg Ile Tyr
            20                  25                  30

Ser Ser Pro Gly Arg Thr His Leu Leu Ala His Ala Ala Asp Ile Ser
        35                  40                  45

Ala Lys Tyr Ala Val Arg Lys Ile Tyr Glu Tyr Met Arg Thr Asp Glu
    50                  55                  60

Glu Gly Ile Arg Ile Leu Lys Glu Lys Pro Leu Leu Ile Arg Gln Asp
65                  70                  75                  80

Ile Cys Phe Asn Glu Leu Lys Lys Leu Pro Lys Asn Thr Leu Gly Tyr
                85                  90                  95

Lys Tyr Met Glu Phe Leu Glu Thr Tyr Lys Leu His Ala His Asp Arg
            100                 105                 110

Glu Val Ser His Phe Ile Lys Asp Ile Asn Glu Ser Tyr Ile Leu Thr
        115                 120                 125

Arg Tyr Arg Gln Ile His Asp Ile Ala His Val Val Tyr Asn Leu Asn
    130                 135                 140

Ile Ser Ile Glu Ala Glu Ala Ala Leu Lys Leu Ile Glu Leu Ile Gln
145                 150                 155                 160

Thr Lys Leu Pro Ile Thr Leu Leu Ala Ile Leu Ile Ala Pro Phe Met
                165                 170                 175

Thr Pro Leu Tyr Arg Phe Gln Tyr Ile Phe Glu His Asn Ile Pro Ser
            180                 185                 190

Asn Phe Leu Cys Pro Asn Phe Asp Tyr Thr Tyr Asn Asp Asp Tyr Asn
        195                 200                 205

Tyr Ile Asp Glu Met Ser Leu Lys Gln Tyr Glu Tyr Tyr Leu Thr Asp
    210                 215                 220

Tyr Phe His Val Glu Lys Arg Glu Ser Gln Ser Phe Tyr Tyr Lys Leu
225                 230                 235                 240

Tyr Lys Tyr Tyr Phe Asp Asn Leu Asn Asn Ser Ser His Val Arg Gly
                245                 250                 255

Ser Ile Ile Tyr Gly Tyr Gln Asn Lys Asn Tyr Asn Asp Ile His Tyr
            260                 265                 270

Asp Lys Leu Asn Asn Glu Tyr Leu Tyr Leu Lys Asn Asn Ile Lys Asn
        275                 280                 285

Tyr Phe His Phe Gln Tyr Lys Pro Arg Lys Leu Leu Leu Thr Asn Leu
    290                 295                 300

Tyr Pro Trp Ala Tyr Lys Thr Ala Ile Gln Thr Asn Lys Pro Leu His
305                 310                 315                 320

Ser Ile Tyr Val Glu Lys Trp Phe Asp Lys Asp Ile Asp Leu Phe Arg
                325                 330                 335

Lys Lys Tyr Asn Ile Thr Pro Leu Pro Ser Asn Leu Asn Leu Met Ala
            340                 345                 350

Gly Ile Asn
        355
```

<210> SEQ ID NO 18
<211> LENGTH: 419
<212> TYPE: PRT
<213> ORGANISM: Plasmodium falciparum

<400> SEQUENCE: 18

-continued

```
Met Asp Ser Glu Glu Thr Ile Asn Leu Ala Val Lys Tyr Ala Lys Glu
1               5                   10                  15

Ala Val Val Glu Asp Glu Lys Lys Asn Tyr Lys Glu Ala Leu Asn Leu
            20                  25                  30

Tyr Ile Gln Ser Leu Gln Tyr Phe Asn Phe Phe Cys Lys Tyr Glu Lys
        35                  40                  45

Asn Ser Asn Ile Arg Asp Leu Ile Leu Lys Lys Met Glu Val Tyr Met
    50                  55                  60

Thr Arg Ala Glu Asn Leu Lys Glu Met Leu Asn Lys Lys Asp Ser Ile
65                  70                  75                  80

Glu Asn Lys Glu Lys Ile Thr Asn Thr Glu Glu Thr Lys Glu Asn Met
                85                  90                  95

Lys Lys Gln Ile Lys Gln Phe Ile Leu Asn Lys Asn Asn Asn Ile Lys
            100                 105                 110

Trp Ser Asp Val Cys Gly Leu Glu Thr Ala Lys Glu Val Leu Lys Glu
        115                 120                 125

Ala Ile Ile Phe Pro Leu Lys Phe Pro Lys Leu Phe Asn Ser Ser Thr
    130                 135                 140

Leu Pro Tyr Lys Gly Ile Leu Leu Tyr Gly Pro Pro Gly Thr Gly Lys
145                 150                 155                 160

Thr Phe Leu Ala Leu Ala Cys Ser Asn Glu Cys Asn Met Asn Phe Phe
                165                 170                 175

Asn Val Ser Ser Ser Asp Leu Val Ser Lys Tyr Gln Gly Glu Ser Glu
            180                 185                 190

Lys Tyr Ile Lys Cys Leu Phe Glu Thr Ala Lys Glu His Ser Pro Ala
        195                 200                 205

Ile Ile Phe Ile Asp Glu Ile Asp Ser Leu Cys Gly Ser Arg Thr Asp
    210                 215                 220

Gly Glu Asn Glu Ser Thr Arg Arg Ile Lys Thr Glu Phe Leu Ile Asn
225                 230                 235                 240

Met Ser Gly Leu Thr Asn Tyr Lys Asn Asn Ile Ile Val Met Gly Ala
                245                 250                 255

Thr Asn Thr Pro Trp Ser Leu Asp Ser Gly Phe Arg Arg Arg Phe Glu
            260                 265                 270

Lys Arg Ile Tyr Ile Pro Leu Pro Asn Ile Tyr Ala Arg Ala Lys Ile
        275                 280                 285

Phe Glu Lys Tyr Ile Asn Gln Asn Glu Asn Asn Asn Ile Ser Lys Glu
    290                 295                 300

Asp Ile Lys Gln Phe Ala Thr Leu Thr Glu Asn Tyr Thr Gly Ala Asp
305                 310                 315                 320

Ile Asp Ile Leu Cys Arg Asp Ala Val Tyr Met Pro Val Lys Lys Cys
                325                 330                 335

Leu Leu Ser Lys Phe Phe Lys Gln Val Lys Lys Asn Asn Lys Ile Cys
            340                 345                 350

Tyr Thr Pro Cys Ser Pro Gly Asp Ser Asp Pro Thr Lys Val Glu Lys
        355                 360                 365

Asn Val Met Ser Leu Ser Glu Asn Glu Leu Ser Leu Pro Pro Leu Thr
    370                 375                 380

Val Gln Asp Phe Lys Thr Ala Ile Ser Asn Ala Lys Pro Ser Leu Ser
385                 390                 395                 400

Val Asp Asp Ile Lys Lys Tyr Glu Glu Trp Thr His Gln Tyr Gly Met
                405                 410                 415

Asn Gly Thr
```

<210> SEQ ID NO 19
<211> LENGTH: 1043
<212> TYPE: PRT
<213> ORGANISM: Plasmodium falciparum

<400> SEQUENCE: 19

```
Met Asn Ile Val Val Thr Asn Tyr Gly Ile Leu Arg Lys Asn Phe Ile
1               5                   10                  15

Arg Thr Tyr Leu Ala Asn Lys Ile Asn Thr Ile Lys Gly Thr Tyr Lys
            20                  25                  30

Asn Ile Cys Ile Tyr His Val Asp Ile Lys Arg Tyr Cys His Tyr Lys
        35                  40                  45

Ser Arg Ser Lys Ile Lys Cys Lys Asn Asn Gly Val Met Asn Lys Asp
    50                  55                  60

Met Asn Phe Ile Cys Asp Glu Leu Lys Glu Lys Tyr Ile Asp Asn Asn
65                  70                  75                  80

His Met Asn Asn Val His Asn Asn Asn Ser Tyr Asn Asn Phe Asn Thr
                85                  90                  95

Phe Tyr Glu Asn Gly Asn Asn Lys Asp Asn Phe Asn Val Ser Lys Lys
            100                 105                 110

Cys Val Gly Lys Lys Val Ile Arg Asp Thr Phe Ile Asn Lys Ile Lys
        115                 120                 125

Glu Gly Thr Leu Ser Leu Leu Asn Leu Glu Ile Glu Glu Leu Asn Tyr
    130                 135                 140

Glu Glu Leu Leu Lys Tyr Lys Asn Ile Lys Lys Val Val Val Met Lys
145                 150                 155                 160

Asn Lys Leu Thr Ile Leu Lys Tyr Phe Asn Ser Tyr Leu Leu Lys Asn
                165                 170                 175

Asn Lys Gly Lys Tyr Tyr Ile Leu Lys Val Leu Met Phe Cys Ile Val
            180                 185                 190

Lys Asp Ile His Lys Tyr Lys Asn Asn Glu Leu Ile Tyr Ile Leu Tyr
        195                 200                 205

Ile Tyr Lys Tyr His Asn Tyr Leu Asn Pro Phe Leu Ile Leu His Ile
    210                 215                 220

Ile Asp Lys Leu Cys Cys Asp Asn Tyr Ile Tyr Asn Met Asn Ile Lys
225                 230                 235                 240

Glu Phe Val Phe Leu Leu Asp Ile Leu Asn Val Pro Leu Val Met Thr
                245                 250                 255

Asn Lys Phe Ile Gln Asn Ile Met Asp Tyr Ile Asn Ile Asn Gln Asn
            260                 265                 270

Lys Ile Lys Tyr Cys Lys Tyr Tyr Phe Asp Ile Ala Tyr Phe Leu Ala
        275                 280                 285

Lys Asn Asn Leu Tyr Asn Lys Tyr Ile Phe Asp Thr Ile Ala Gln Tyr
    290                 295                 300

Tyr Thr Ser His Ser Tyr Asn Phe Glu Leu Ser Ile Leu Tyr Met Phe
305                 310                 315                 320

Asn Asn Glu His Lys Asn Ile Asn Arg Asn Asn Asn Ala Phe Pro Ile
                325                 330                 335

Lys Gly Ser Tyr Asn Ile Asn Asn Asn Ile Val Asp Ile Asn Ile Cys
            340                 345                 350

Glu Glu Leu Ile Asn Asn Asp Asp Tyr Leu Asn Val Lys Gln Arg Asn
        355                 360                 365

Met Leu Lys Lys Val Glu Ser Asp Asn Gly Cys Tyr Asp Asn Thr Tyr
```

```
    370                 375                 380

Asp Asn Asn Asn Ile Ile Asn Phe Lys Arg Glu Ile His Lys His Leu
385                 390                 395                 400

Tyr Ile Leu Ser Lys Tyr Gly Tyr Lys Asn Ile Gln Ile Tyr Asn Asn
                405                 410                 415

Met Phe Lys Ile Ile Ile Phe Ser Cys Asn His Phe Lys Pro Phe Glu
            420                 425                 430

Val Ser Ser Ile Phe Lys Ser Leu Lys Asn Ile Asn Tyr Phe Asn Ile
        435                 440                 445

Val Leu Leu Glu Lys Leu Thr Ser Thr Leu Lys Lys Asn Ile Ser Gln
    450                 455                 460

Tyr Lys Thr Ser Leu Leu Leu Asp Cys Leu Asn Thr Leu Ser Tyr Phe
465                 470                 475                 480

Asn Tyr Lys Asp Asp Asn Ile Ile Thr Thr Ile Leu Ile Asn Leu Pro
                485                 490                 495

Arg Asn Ile Ser Thr Tyr Thr Ser Asn Gln Phe Leu Lys Leu Val Tyr
            500                 505                 510

Phe Met Asp Asn Phe Ile Pro Phe Ser Ile Tyr Phe Asn Ile Phe Leu
        515                 520                 525

Asn Lys Gln Ile Cys Ile Phe Ser Ser Ser Phe Gly Leu Cys His Leu
    530                 535                 540

Ile Ser Leu Leu Lys Ile Phe Thr His Gln Asn Leu Ile Ser Asn Pro
545                 550                 555                 560

Ile Leu Tyr Leu Leu Arg Ile Lys Ile Ser Lys Tyr Asn Lys Ser Leu
                565                 570                 575

Thr Tyr Asn Asp Ile Lys Ser Lys His Ile Asn Glu Lys Pro Asp Glu
            580                 585                 590

Ile Phe Pro Ser Ile Asn Tyr Thr Gly Asn Ile Lys Ile Ser Tyr Lys
        595                 600                 605

Asp Ile Tyr Ser Ile Phe Tyr His Met His Leu Met Arg Val Gln Tyr
    610                 615                 620

Met Asp Leu Ala Ile Lys Cys Ile Glu Cys Ile Phe Phe Met Glu Lys
625                 630                 635                 640

Asn Phe Lys Asn Ile Phe Ser Glu Asp Ile Glu Tyr Ile Thr Asn Ser
                645                 650                 655

Cys Cys Tyr Phe Leu Leu Leu Asn Asp Asn Tyr Asp Asp Pro Phe Leu
            660                 665                 670

Arg Lys Phe Ile Asn Val His Ile Glu Asn Phe Phe Ser Phe Val Ala
        675                 680                 685

Ser Asn Phe Val Lys Asn Glu Ser Leu Glu Lys Lys Asn Glu Cys Ile
    690                 695                 700

Asn Gly Asn Met Glu Met Glu Lys Ile Asn Asp Asn Asn Asn Asn Asn
705                 710                 715                 720

Lys Lys Lys Lys Lys Tyr Lys Thr Tyr Asn Ile Lys Met Asp Asp Ile
                725                 730                 735

Lys Met Asp Asp Ile Lys Met Asp Asp Ile Lys Met Gly Asp Ile His
            740                 745                 750

Phe Ala His Tyr Glu Lys Asn Asn Gly Thr Ile His Phe Asn Asn Lys
        755                 760                 765

Ile Asn Tyr Asn Glu Gln Ile Ile Asp Ile Gln Asn Asn Asn Asn Asp
    770                 775                 780

Lys Lys Asn Leu Tyr Leu Ala Phe Asn Lys Lys Lys Asn Val Tyr Ala
785                 790                 795                 800
```

Ile Ile Ile Leu Thr Leu Ile Asn Glu Leu Val Tyr Gln Asn Ser Ile
805 810 815

Lys Lys Ile Ser Asn Ile Ile His Asn Phe Asn Leu Glu Tyr Ile Lys
820 825 830

Asn Asn Ile Tyr Val Phe Leu Gln His Phe Asn Asn Glu Lys Asn Glu
835 840 845

Lys Glu Lys Cys Asp Thr Ile Tyr Ile Leu Glu Lys Leu Phe Pro Leu
850 855 860

Leu Tyr Phe Pro Lys Ile Asn Asn Val His Leu Lys Asn Ile Ser Arg
865 870 875 880

Asn Asn Phe Asn Ile Ser Thr Phe Asn Leu Thr Tyr Val Gln Asn Gly
885 890 895

Tyr Asn Asn Tyr Leu Lys Ser Glu His Ile Lys Lys Glu Ile Ile Ser
900 905 910

Asn Gln Tyr Ile Leu Asn Glu Ile Tyr Lys Ile Leu Arg Ser Leu Lys
915 920 925

Gln Lys Asn Tyr Ile Phe Lys Leu Ile Asn Lys Ser His Thr Lys Ser
930 935 940

Phe Phe Leu Tyr Asn His Tyr Ile Tyr Val Lys Asn Ile Arg Asn Gly
945 950 955 960

Asp Lys Ile Ala Ile Leu Phe Ala Ser Lys Asn Tyr Tyr Tyr Asn Thr
965 970 975

Ile Asp Asp Ala Asn Leu Gly Leu Thr Ser Lys Met Gly Lys Lys Ile
980 985 990

Phe Glu Lys Lys Lys Phe Thr Lys Glu Ala Ile Thr Gln Ile Glu Tyr
995 1000 1005

Phe Lys Ile Tyr Phe Asn Lys Val Tyr Leu Val Glu Phe Tyr Thr
1010 1015 1020

Trp Glu Asn Met Ile Asn Ile Gln Glu Lys Lys Asp Tyr Leu Val
1025 1030 1035

Asn Leu Leu Asn Ile
1040

<210> SEQ ID NO 20
<211> LENGTH: 759
<212> TYPE: PRT
<213> ORGANISM: Plasmodium falciparum

<400> SEQUENCE: 20

Met Asp Ile His Ala Gln Glu Asn Gln Thr Gly Ile Arg Phe Ser Trp
1 5 10 15

Asn Leu Trp Pro Pro Thr Lys Ala Glu Ala Ala Lys Ile Glu Val Pro
20 25 30

Leu Gly Cys Leu Tyr Thr Val Leu Lys Arg Thr Asp Asp Ser Ser Val
35 40 45

Lys Leu Val Glu Tyr Glu Pro Leu Lys Cys Lys Thr Ser Asn Cys Ile
50 55 60

Leu Asn Pro Tyr Cys Asn Ile Asp Phe Arg Asn Lys Thr Trp Thr Cys
65 70 75 80

Pro Phe Ser Asn Ile Lys Asn Pro Phe Pro Leu His Tyr Ala Glu His
85 90 95

Ile Ser Glu Lys Asn Leu Pro Ala Asp Val Met Tyr Ser Asn Ile Glu
100 105 110

Tyr Ile Gln Pro Ser Asn Val Gly Asp Ile Pro Pro Pro Thr Phe Leu

-continued

```
        115                 120                 125

Phe Val Ile Asp Thr Cys Leu Leu Glu Glu Glu Leu Glu Gln Leu Lys
    130                 135                 140

Asp Ser Ile Gln Gln Cys Ile Ser Leu Met Pro Gly Asp Ala Tyr Ile
145                 150                 155                 160

Gly Ile Ile Thr Phe Gly Asn Met Cys Tyr Val His Glu Ile Gly Phe
                165                 170                 175

Asn Asp Cys Leu Lys Ser Tyr Val Phe Lys Gly Asn Lys Glu Ile Ser
            180                 185                 190

Ala Gln Asp Leu Gln Lys Gln Leu Asn Leu Gly Ser Arg Asn Asp Pro
        195                 200                 205

Arg Ser Ser Thr Thr Ser Ala Ser Ala Arg Arg Phe Leu Gln Pro Val
    210                 215                 220

Ser Glu Cys Glu Tyr Asn Ile Asn Met Leu Leu Glu Asp Ile Gln Lys
225                 230                 235                 240

Asp Asn Trp Pro Thr Pro Pro Asp Gln Arg Ala Lys Arg Cys Thr Gly
                245                 250                 255

Val Ala Leu Ser Val Ala Ile Gly Leu Leu Glu Cys Cys Cys Asn Gln
            260                 265                 270

Leu Ser Gly Arg Val Met Met Phe Ile Gly Gly Ala Asp Thr Thr Ser
        275                 280                 285

Pro Gly Lys Ile Val Asp Thr Pro Leu Ser Glu Ser Leu Arg His His
    290                 295                 300

Leu Asp Leu Gln Lys Glu Asn Ser Asn Ala Arg His Val Lys Lys Ala
305                 310                 315                 320

Leu Lys Tyr Tyr Val Ser Leu Ala Asn Arg Ala Val Ala Ser Gly His
                325                 330                 335

Ala Ile Asp Ile Phe Ala Cys Ser Leu Asp Gln Ile Gly Leu Tyr Glu
            340                 345                 350

Met Lys Val Cys Cys Glu Lys Thr Asn Gly Phe Met Val Met Ala Asp
        355                 360                 365

Ser Phe Ser Met Asn Val Phe Lys Asp Ser Phe Lys Lys Ile Phe Glu
    370                 375                 380

Thr Asp Ser Thr Glu Tyr Ile Lys His Gly Tyr Asn Ala Lys Leu Thr
385                 390                 395                 400

Val Ile Cys Ser Lys Glu Phe Arg Val Cys Gly Ala Ile Gly Ala Cys
                405                 410                 415

Ser Ser Asn Lys Lys Thr Ala Asn Tyr Val Ser Asp Thr Cys Val Gly
            420                 425                 430

Glu Gly Gly Thr Cys Glu Trp Thr Ile Cys Ala Leu Asp Arg Gln Ser
        435                 440                 445

Thr Ile Ala Phe Tyr Phe Glu Ile Val Asn Gln Asn Leu Ala Ser Leu
    450                 455                 460

Pro Pro Asp Arg Gln Ala Tyr Leu Gln Phe Gln Thr Leu Tyr Gln His
465                 470                 475                 480

Pro Ser Gly Arg Arg Arg Leu Arg Val Thr Thr Ile Ser Tyr Arg Phe
                485                 490                 495

Ala Glu Pro Asn Ile Ala Glu Ile Ser Gln Gly Phe Asp Gln Glu Thr
            500                 505                 510

Ala Ala Val Ile Met Ala Arg Phe Ala Val Leu Lys Ala Glu Thr Asp
        515                 520                 525

Glu Pro Ile Asp Val Leu Arg Trp Leu Asp Arg Lys Leu Ile Arg Leu
    530                 535                 540
```

Val Ser Thr Phe Ala Asp Tyr Gln Lys Asp Asp Ile Asn Ser Phe His
545 550 555 560

Leu Ser Ser Glu Phe Ser Ile Tyr Pro Gln Phe Met Tyr His Leu Arg
565 570 575

Arg Ser His Phe Leu Gln Thr Phe Asn Ala Ser Pro Asp Glu Thr Ala
580 585 590

Tyr Tyr Arg Ser Ile Leu Leu Arg Glu Asn Val Met Asn Ser Leu Ile
595 600 605

Met Ile Gln Pro Ala Leu Leu Gln Tyr Ser Phe Asp Ser Pro Thr Pro
610 615 620

Ile Pro Val Leu Leu Asp Ala Gln Ser Leu Lys Ser Asn Val Ile Leu
625 630 635 640

Leu Leu Asp Ser Tyr Phe His Ile Val Ile Trp Tyr Gly Glu Met Ile
645 650 655

Tyr Gln Trp Arg Glu Gln Gly Phe His Glu Lys Pro Glu Tyr Glu His
660 665 670

Phe Arg Gln Leu Leu Asn Ala Pro His Glu Asp Ala Lys Ser Ile Leu
675 680 685

Glu Asp Arg Phe Pro Ile Pro Lys Phe Val Leu Cys Asn Ser Gly Gly
690 695 700

Ser Gln Ser Arg Phe Leu Leu Ala Lys Val Asn Pro Ser Thr Thr His
705 710 715 720

Asn Ser Leu Ser Gly Ser Thr Phe Gly Thr Ser Ser Asn Glu Ser Tyr
725 730 735

Ile Ile Asn Thr Asp Asp Val Ser Leu Lys Ile Phe Met Asp His Leu
740 745 750

Val Lys Leu Ala Val Gln Thr
755

<210> SEQ ID NO 21
<211> LENGTH: 1353
<212> TYPE: PRT
<213> ORGANISM: Plasmodium falciparum

<400> SEQUENCE: 21

Met Glu Gly Tyr Glu Glu Val Ser Asp Leu Ile Gln Lys Phe Lys Lys
1 5 10 15

Asp Thr Tyr Val Leu Asn Tyr Tyr Lys Arg Ile Tyr Glu Leu Asn Lys
20 25 30

Cys Lys Ser Tyr Arg Ser Ile Met Ile Lys Asp Ile Gln Asn Lys Ile
35 40 45

Asp Tyr Lys Lys Glu Gln Glu Lys Asn Ile Lys Lys Lys Lys Lys Lys
50 55 60

Asp Glu Asn Asp Asp Glu Ile Ile Asn Asp Asp Glu Ile Ile Asn Glu
65 70 75 80

Asp Glu Asn Asp Lys Lys Glu Tyr Tyr Tyr Asn Ser Glu Glu Asn Ala
85 90 95

Thr Thr Leu Gly Arg Glu Thr Ser Lys Asp Lys Ile His Thr Leu His
100 105 110

Glu Asn Tyr Asn Asp Asp Asn Asn Asn Asp Ile Met Lys Thr Ile Leu
115 120 125

Lys Ser Ile Asp Asn Lys Leu Tyr Lys Tyr Thr Asn Glu Val Leu Glu
130 135 140

Tyr Phe Asp Gly Gln Asp Lys Glu Thr Leu Asn Thr Asn Tyr Gln Ile

-continued

```
145                 150                 155                 160

Asn Asn Cys Ile Glu Ala His Ala Tyr Ile Asp Asn Ile Leu Ile Thr
                165                 170                 175

Asn Gln His Asp Ile Gln Tyr Ile Cys Lys Asp Ile Asn Asn Ile Glu
            180                 185                 190

Lys Leu Thr Gln Ser Ile Asn Asn Lys Leu Thr Asn Arg Lys Ile Ile
        195                 200                 205

Leu Glu Leu Leu Asn Thr Tyr Ile Lys Ile Ile Ile Ile Thr Pro Gln
    210                 215                 220

Leu Ile Arg Asn Ile Ile Tyr Gly Asp Ile Asn Gln Glu Phe Ile Lys
225                 230                 235                 240

Asn Ile His Ile Leu Thr Asn Lys Ile Glu Asn Cys Lys His Cys Leu
                245                 250                 255

Tyr Asp Ile Tyr Pro Ser Ile Lys Tyr Ser Tyr Ile Glu Leu Glu Lys
            260                 265                 270

Leu Lys Lys Lys Ser Val Asp Arg Ile Tyr Phe Phe Phe Leu Glu Lys
        275                 280                 285

Ile Asn Asn Ile Lys Asn Lys Asn Thr Asp Ile Tyr Ile Ile Gln Gln
    290                 295                 300

Asn Leu Leu Thr Phe Phe Glu Leu Asn Thr Phe Leu Phe Asn Asn Asn
305                 310                 315                 320

Arg His Val Tyr Asn Tyr Leu Leu Lys Glu Tyr Ile His Val Met Asn
                325                 330                 335

Lys Lys Tyr Phe His Leu Phe Lys Asn Tyr Ile Thr Asn Met Gln Lys
            340                 345                 350

Lys Ile Lys Asn Asn Lys Asn Cys Thr Phe Ile Asn Asn Ser Asn Val
        355                 360                 365

Gly Phe Thr Asn Asn Tyr Asn Ser Gln Val Glu Arg Asn Val Asn Asn
    370                 375                 380

Lys Ile Ser Val Asn Arg Asn Ile Asn Ile Asn Asn Ile Asn Ile Asn
385                 390                 395                 400

Asn Ile Asn Ile Asn Asn Ile Asn Ile Asn Asn Ile Asn Ile Asn Asp
                405                 410                 415

Val Asp Ile Asn Asn Ile Asn Ile Asn Asn Asn Asn Asn Asn Tyr Asn
            420                 425                 430

Tyr Asn Asn Tyr Asn Asn Tyr Tyr Tyr Asn Asn Ser Cys Ser Asn Asn
        435                 440                 445

His Leu Asp Ile Ile Ser Ser Asn Met Asn Asn Val Thr Phe Gln Asn
    450                 455                 460

Ala Lys Lys Thr Met Met Asn Phe Leu Gly Ile Asn Pro Lys Asn Asp
465                 470                 475                 480

Asn Thr Cys Asn Thr Tyr Glu Glu Pro Asp Glu Asn Ile Phe Ser Leu
                485                 490                 495

Asn Cys Arg His Lys Val Leu Tyr Asp Met Cys Tyr Phe Asn Lys Thr
            500                 505                 510

Lys Glu Glu Lys Lys Asn Asp Ile Asn Ile Asn Asp Asp Asn Ile Asn
        515                 520                 525

Asp Asp Asn Ile Asn Asp Asp Asn Ile Asn Asp Asp Asn Ile Asn Asp
    530                 535                 540

Asp Asn Ile Asn Asp Asp Asn Ile Asn Asp Asp Asn Ile Asn Asp Asp
545                 550                 555                 560

Asn Ile Asn Asp Asp Asn Ile Asn Asp Asp Asn Ile Asn Asp Asp Asn
                565                 570                 575
```

-continued

```
Ile Asn Asp Asp Asn Ile Asn Asp Asp Asn Ile Asn Asp Asp Asn Ile
            580                 585                 590

Asn Asp Asp Asn Ile Tyr Asp Asp Asn Ile Asn Asp Asp Asn Ile Asn
        595                 600                 605

Asp Asn Asn Asn Asp Asn Asn Asn Glu Asn Ile Ile Met Asn Asn Tyr
    610                 615                 620

Asn Tyr Ile Lys Asn Tyr Asn Arg Ile Asn Asn Glu Lys Thr Phe Glu
625                 630                 635                 640

Asn Lys Ile Asn Lys Glu Tyr Pro Val Ser Leu Ile Ser Asp Leu Asp
                645                 650                 655

Asn Leu Ile Tyr His Phe Glu Glu Ile Tyr Lys Ser Ile Asn Lys Leu
            660                 665                 670

Phe Leu Asp Thr Gly Ser Leu Glu Tyr Tyr Phe Ile Leu Asn Phe Phe
        675                 680                 685

Lys Asp Tyr Glu Ser Pro Asp Phe Leu Phe Leu Glu Ile Tyr Ser Lys
    690                 695                 700

Thr Ile Ser Leu Cys Phe Asp Phe Ile Tyr Phe Tyr Thr Ile Gln Thr
705                 710                 715                 720

Tyr Asp Val Ile Ser Leu Tyr Cys Val Tyr Ile Met Asn Leu Tyr Tyr
                725                 730                 735

Ala Tyr Ile Met Tyr Lys Arg Asn Ile Val Thr Leu Tyr Val Tyr Ile
            740                 745                 750

Gln Arg Ile Gln Thr Phe Leu Trp Asp Lys Ile Tyr Tyr Ile Ile Gln
        755                 760                 765

Glu Asn Leu Asp Ser Leu Asn Lys Lys Arg Leu Asp Glu Lys Lys Tyr
    770                 775                 780

Val Ser Ser Asn Phe Asn Ala Lys Ile Asn Thr Asn Glu Leu Glu His
785                 790                 795                 800

Tyr Gln Asn Lys Thr Cys His Ile Asn Asn Leu Thr Phe Asp Lys Phe
                805                 810                 815

Glu Asn Phe Thr Asn Val His Ser Asn Asn Tyr Gln Asn Gly Asp Asn
            820                 825                 830

Lys Gly Asp Asn Glu Asp Asn Asn Met Asp Asn Glu Asn Lys Lys Leu
        835                 840                 845

Asp Asn Glu Asp Lys Lys Ser Asp Asn Glu Asp Lys Lys Ser Asp Asn
    850                 855                 860

Glu Asp Asn Asp Lys Asp Lys Asp Asn His Tyr Asn Asn Asn Ile Ser
865                 870                 875                 880

Gln His Tyr Tyr His Asn His Asn Asn Tyr Cys Met Asn Lys Asn Ile
                885                 890                 895

Glu Leu Thr Asn Asn Leu Gly Ile Tyr Lys Thr Gln Ala Asn Lys Asn
            900                 905                 910

Thr His Leu Val Asn Ile Lys Gln Asn Asp Ile Thr Asn Lys His Leu
        915                 920                 925

Asn Thr Asn Leu Asn Asn Gln Glu Glu Lys Lys His Ser Leu His Phe
    930                 935                 940

Ser Thr Ile Leu Lys Thr Gln Glu Val His Ser Val Thr Lys Lys Phe
945                 950                 955                 960

Thr Asp Phe Tyr Cys Ser Val Val Ile Leu Ser Asn Leu Cys Phe His
                965                 970                 975

Ile Asp Thr Tyr Tyr Lys Glu Lys Ile Asp Lys Gln Lys Val Lys Val
            980                 985                 990
```

-continued

```
Gly Tyr Gln Glu Gln Lys Leu Lys  Glu Asn Lys Asn Gln  His Leu Met
        995                 1000                 1005

Asn Met  Glu Glu Lys Val Asp  Lys Ile Glu Met Asp  Arg Lys Asn
    1010                 1015                 1020

Tyr Asn  Asp Gln Lys Gly Cys  Asn Ile Leu His Gly  Glu Ala Asp
    1025                 1030                 1035

Lys Asn  Lys Leu Ser Asn Glu  Gln Phe Lys Glu Asp  Ile Ile Met
    1040                 1045                 1050

Glu Asn  Leu Tyr Asp Lys Asn  Val Asn Phe Val Lys  His Asn Asn
    1055                 1060                 1065

Glu Gly  Ile Glu Lys Asn Lys  Asp Glu Ser Lys Ile  Thr Thr Glu
    1070                 1075                 1080

Lys Arg  Lys His Asn Asn Asn  Asn Asn Ile Cys Ala  His Ser Asn
    1085                 1090                 1095

Glu Asn  Ser Tyr Leu Asn Lys  Ile Tyr Asp Glu Asn  Val Thr Met
    1100                 1105                 1110

Glu Asp  Lys Leu Lys Asn Asp  Lys Glu Val Asn Asn  Thr Ser Ile
    1115                 1120                 1125

Ser Asp  Lys Lys Asn Asn Tyr  Phe Leu Lys Tyr Lys  Lys Ile Thr
    1130                 1135                 1140

Asn Leu  Ile Ser Lys Leu Glu  Gly Ala Ile Ile His  Thr Leu Ile
    1145                 1150                 1155

Ser Ile  Asp Asn Glu Leu Val  Cys Pro Lys Glu Lys  Leu Leu Phe
    1160                 1165                 1170

Leu Ile  Asn Asn Tyr Tyr Tyr  Ile Ile Tyr Ile Leu  Lys Gln Asn
    1175                 1180                 1185

Lys Leu  Gln Glu Lys Ile Cys  Thr Phe Glu Lys Leu  Leu Lys Lys
    1190                 1195                 1200

Glu Ile  Thr Thr Tyr Ile Glu  Tyr Glu Leu Asn Ile  Tyr Ile Lys
    1205                 1210                 1215

Asp Ile  Ile Leu Phe Val Asn  Lys His Glu Asn Ile  Ile Asn Thr
    1220                 1225                 1230

Ile Lys  Glu Asp Ile Tyr Asn  Lys Asn Ile Lys Asn  Asn Asn Asn
    1235                 1240                 1245

Asp Asp  His His Asn Tyr Tyr  Leu Ser His Val Asp  Phe Ile Ser
    1250                 1255                 1260

Met Glu  Asn Ile Ala Ile Gln  Phe Thr Lys Asn Trp  Lys Leu Leu
    1265                 1270                 1275

Phe Lys  Asn Ile Arg Asn Asn  Ile Ile Thr Ser Phe  Ile Asn Ile
    1280                 1285                 1290

Asp Asn  Ala Phe Asn Ile Leu  Lys Leu Leu Asn Thr  Gln Ile Leu
    1295                 1300                 1305

Leu Tyr  Phe Thr Arg Phe Tyr  Gln Leu Thr Lys Lys  Ile Phe Ser
    1310                 1315                 1320

Asn Ile  Gln Pro Pro Leu Tyr  Ile Gln Asn Leu Pro  Ser Val Asp
    1325                 1330                 1335

Val Ile  Met Ile Gln Ile Lys  Lys Asp Ala Lys Asn  Val Gly Ser
    1340                 1345                 1350
```

<210> SEQ ID NO 22
<211> LENGTH: 740
<212> TYPE: PRT
<213> ORGANISM: Plasmodium falciparum

<400> SEQUENCE: 22

```
Met Lys Ile Lys Glu Leu Leu Tyr Asn Glu Leu Ile Ile Ile Lys Ile
1               5                   10                  15

Thr Glu Phe Leu Thr Ile Leu Glu Ile Gln Asn Met Ile Ile Ser Leu
            20                  25                  30

Arg Ile Asn Val Lys Arg Asn Ile Tyr Phe Met Arg Glu Cys Leu Ser
        35                  40                  45

Leu Met Asn Leu Asp Thr Asp Gly Tyr Asn His Asn Val Ser Asn Lys
    50                  55                  60

Asn Thr Pro Asn Lys Asn Lys Asn Lys Asn Thr Ser Thr Thr Glu Pro
65                  70                  75                  80

Leu Leu Leu Ser Ser Ser Val Asn Leu Thr Thr Asp Ile Asp Asp Tyr
                85                  90                  95

Val His Asn Ala Thr Ser Tyr Val Gly Asp Gln His Phe Leu Gln Gln
            100                 105                 110

Glu Gly Leu Asn Leu Ile Thr Tyr Asp Asp Glu Tyr Asp Glu Tyr Ile
        115                 120                 125

Phe Asn Asp Tyr Asn Glu Gly Gly Asn Asn Val Asp Asn Val Asn Asn
    130                 135                 140

Phe Asp Asn Val Asn Asn Ile Asp Asn Val Asn Asn Phe Asp Asn Asp
145                 150                 155                 160

Asn Asn Met Tyr Asn Tyr Ser Asn His Asp Ile Tyr Asn Asn Thr Ser
                165                 170                 175

Tyr Tyr Asn Thr Arg Ala Asp Glu Asn Phe Asp Glu Asn Phe Met Tyr
            180                 185                 190

Asn Thr Lys Tyr Ser His Tyr Glu Asp Thr Leu Asn Asp Met Thr His
        195                 200                 205

Leu Met Ser Thr Tyr Thr Asp Asn Asn Ile Asn Tyr Tyr Glu Thr Asn
    210                 215                 220

Lys Thr Asn Phe Gly Ala Leu Tyr Glu Ile Lys Lys Tyr Leu Asn Phe
225                 230                 235                 240

Phe Glu Gln Glu Lys Glu Gly His Val Gln Lys Cys Phe Asn Asn Val
                245                 250                 255

Trp Ile Tyr Ile His Leu Lys Asn Glu Leu Ile Asp Ile Lys Lys Asn
            260                 265                 270

Leu Glu Thr Tyr Phe Met Arg Ile Lys Met Asn Thr Gln Val Asn Arg
        275                 280                 285

Asn Lys Arg Ile Arg Ile Asp Ile Phe Gln Leu Phe Lys Tyr Asn His
    290                 295                 300

Thr Tyr Tyr Ser Phe Tyr Asp Met Pro Trp Val Ser Ile Tyr Tyr Asp
305                 310                 315                 320

Phe Phe Leu Asn Ser Ile Cys Thr Leu Cys Asn Ile Lys Leu Asp His
                325                 330                 335

Arg Ser Ile Cys Leu Phe Ser Glu Lys Phe Asn Leu Ile Gln Thr Asn
            340                 345                 350

Asp Lys Leu Leu Lys Tyr Ile Asn Ser Met Ser Asp Asp Ile Val Ser
        355                 360                 365

Asn Arg Lys Asn Glu Lys Lys Arg Asp His Gln Lys Val Asp Met Leu
    370                 375                 380

Phe Gly Glu Asp Val Glu Arg Glu Lys Thr Lys Lys Lys Thr Asp Met
385                 390                 395                 400

Ile Asn Asn Asp Asn Lys Asn Asp Ser Asn Asn Tyr Asp Asn Asn Asn
                405                 410                 415
```

```
Asp Ser Asn Asn Tyr Asp Asn Asn Asn Asp Ser Asn Asn Tyr Asp Asn
            420                 425                 430

Lys Asn Asp Ser Asn Asn Tyr Asp Asn Asn Asn Asp Ser Asn Asn Tyr
        435                 440                 445

Asp Asn Lys Asn Asp Ser Asn Asn Tyr Asp Asn Lys Asn Asp Ser Asn
    450                 455                 460

Asn Tyr Asp Asn Met Tyr Asn Leu His Asp Asp Tyr Asn Gln His Gln
465                 470                 475                 480

Glu Thr Leu Ala Glu Ile Lys Leu Asn Lys Asp Ile Phe Ser Cys Lys
                485                 490                 495

Asn Lys Ile Asn Thr Tyr Asp Glu Glu Phe Ile Phe Ile Arg Lys Thr
            500                 505                 510

His Ile Phe Cys Glu Glu Cys Thr Lys Ile Ile Asp Tyr Lys Met Asn
        515                 520                 525

Ile Asn Ser Leu Leu Glu Ser Ile Lys Lys Asp Tyr Glu Leu Leu Lys
    530                 535                 540

Lys Ile Arg Ile Ile Tyr Lys Met Ile Asp Ile Pro Ser Asp Leu Phe
545                 550                 555                 560

Cys Phe Cys Asn Tyr Phe Phe Phe Lys Glu Lys Tyr Ile Thr Phe Phe
                565                 570                 575

Lys Asn Val Ser Asn Asp Leu Gln Asn Leu Arg Lys Ala Leu Lys Lys
            580                 585                 590

Lys Leu Thr Asn Asn Phe Ile Leu Asn Phe Ser Ile Asn Phe Tyr Lys
        595                 600                 605

Phe Val Ile Ser Ser Leu Ile Leu Cys Asp Glu Lys Lys Leu Phe Ser
    610                 615                 620

Gln Glu Asn Ile Phe Leu Phe Gly Phe Tyr Ile Lys Tyr Arg Asn Ile
625                 630                 635                 640

Leu Lys Leu Phe Ser Ser Pro Arg Cys Thr His Ile Tyr Phe Ser Phe
                645                 650                 655

Asn Ile Ile Tyr Gln Lys Ile Val Lys Phe Gln Ser Phe Phe Lys His
            660                 665                 670

Lys His Phe Ser Lys Leu Ser Lys Val Leu His Phe Asp Val Ile Thr
        675                 680                 685

Ile Leu Glu Lys Leu Lys His Ser Lys Thr Lys Met Leu Tyr Lys Asn
    690                 695                 700

Ile Ala Val Tyr Leu Tyr Gln His Leu Asn Asp Lys Ile Leu Arg Lys
705                 710                 715                 720

Tyr Asn Tyr Asp Glu Ala Tyr Ala Tyr Phe Phe Gln Cys Leu Gln Arg
                725                 730                 735

Tyr His Phe Ser
            740
```

<210> SEQ ID NO 23
<211> LENGTH: 481
<212> TYPE: PRT
<213> ORGANISM: Plasmodium falciparum

<400> SEQUENCE: 23

```
Met Ala Leu Ile Asn Phe Lys Glu Lys Ile Gln Ile Leu Leu Lys Leu
1               5                   10                  15

Lys Glu Ser Leu Ile Pro Gln Ile Asp Gly Asn Phe Ile Gly Gln Trp
            20                  25                  30

Glu Met Glu Ala Leu Lys Tyr Gln Asn Thr Ser Glu Asn Ile Met Ile
        35                  40                  45
```

```
Glu Leu Lys Asn Val Asn Phe Ile Glu Thr Leu Val Ser Ala Ile Ser
    50                  55                  60

Ser Gln Leu Ser Tyr Leu Arg Ile Asn Leu Gln Asn Tyr Ala Lys Met
65                  70                  75                  80

Asn Glu Gln Glu Lys Asp Lys Phe Lys Arg Leu Tyr Val Leu Ala Ala
                85                  90                  95

Leu Gly Leu Ile Ala Lys Leu Lys Leu Ile Leu Phe Phe Ser Thr Tyr
            100                 105                 110

Val Asn Ser Arg Asn Glu Thr Asn Asn Ser Lys Ala Phe Pro Ile Ile
        115                 120                 125

Asn Glu Asn Thr Tyr Pro Ser Gln Leu Ser Pro Asn Met Glu Asn Asn
    130                 135                 140

Tyr Asp Met Thr Ile Ser Leu Asn Met Asn Asn Asn Asn Asn Asn Asn
145                 150                 155                 160

Asn Asn Asn Asn Asn Ile Asn Asn Met Asn Asn Asn Ile Asn Cys Asn
                165                 170                 175

Asn Asn Asn Asn His Ser Glu Asn Phe Ile Asn Pro Lys Glu Ser Gln
            180                 185                 190

Ser Ile Asn Met Tyr Asn Asn Asn Val Asp Glu Phe Tyr Val His Tyr
        195                 200                 205

Gln Asn Asn Thr Glu Gln Tyr Asn Asp Asn Phe Thr Lys Ser Ile Thr
    210                 215                 220

Gln Asn Asn Met Met Asn Phe Asn Ala Pro Val Asn Asn Val Thr Ser
225                 230                 235                 240

Asn Asn Asn Ile Asn Asn Leu Asn Ile Asn Asn Met Asn Val Asn Asn
                245                 250                 255

Met Asn Val Asn Asn Met Asn Ile Asn Asn Val Ser Asn Ile Asn Asn
            260                 265                 270

Val Asn Asn Asn Ser Lys Lys Asn Asn Lys Ser Ser Asn Asn Asn Asn
        275                 280                 285

Asn Asn Ile Asn Cys Asn Asn Ser Gly Asn Asn Phe Ser Ser His Phe
    290                 295                 300

Thr Thr Asn Asn Thr Glu Asp Ile Gln Leu Asn Val Leu Asn Asn Phe
305                 310                 315                 320

Val Thr Thr Lys Asn Glu Asn Leu Ile Asn Ala Pro Leu His Thr Ser
                325                 330                 335

Lys Lys Arg Ser Leu Thr Ile Ala Gln Pro Gln Asn Asn Asn Lys Ser
            340                 345                 350

Ile Asn Tyr Ile Lys Asn Leu Gln Thr Ile Asn Gly Thr Lys Asn Ile
        355                 360                 365

Thr Asn Glu His Met Ile Asn Tyr Asn Glu His Val Ile Asn Asp Asp
    370                 375                 380

Pro Gln Arg Phe Leu Gln Gln Asn Gln Tyr Thr Lys Tyr Thr Asn Asn
385                 390                 395                 400

Asn His Gln Asn Val Thr Ala Thr Asn Asn Asp Asn Asn Glu Leu Thr
                405                 410                 415

Asn Cys Ser Ile Asn Phe Asn Asn Tyr Tyr Gln His Gln Asn Asn Gly
            420                 425                 430

Asn Asn Ser Ile Asn Asn Asn Asn Asn Asn Asn Asn Asn Asn Asn Asn
        435                 440                 445

Asn Asn Asn Ser Ile Gln Asp Lys Thr Ile Leu Gln Ser Tyr Asn Asn
    450                 455                 460
```

Asn Asn Met Tyr Thr Phe Arg Asp Asp Ile Tyr Lys Asn Ser Tyr Tyr
465 470 475 480

Ile

<210> SEQ ID NO 24
<211> LENGTH: 1904
<212> TYPE: PRT
<213> ORGANISM: Plasmodium falciparum

<400> SEQUENCE: 24

Met Arg Ser Ile Ser Val Gly Phe Thr Ile Tyr Glu Ala Gln Asn Leu
1 5 10 15

Glu Val Asp Asp Lys Asn Leu Leu Asp Pro Leu Val Val Val Arg Cys
20 25 30

Cys Asn Asn Glu Tyr Ile Thr Lys Lys Lys Lys Lys Lys Tyr Asn Ala
35 40 45

Val Asn Trp Glu Glu Ser His Ile Trp Asp Arg Ile Ile Leu Ser Glu
50 55 60

Ile Glu Trp Asn Val Ser Lys Ile Glu Phe Glu Val Gln Ser Ala Asn
65 70 75 80

Ile Leu Trp Arg Asn Asp Ile Ile Gly Val Ile Ser Phe Glu Leu Lys
85 90 95

Leu Ile Lys Asn Lys Arg Asn His Gln Ile Gln Gly Ile Tyr Pro Ile
100 105 110

Leu Cys Lys Asn Gly Thr Glu Ile Arg Gly Gln Leu Arg Leu Lys Val
115 120 125

Met Val Cys Asp Glu Asn Asp Tyr Ile Ser Asn Asn Asn Ile Phe Asn
130 135 140

Asp Leu Thr Glu Asn Asn Asn Glu Asn Arg Ile Glu Asp Asn Glu Glu
145 150 155 160

Ile Tyr Asn Asp Leu Thr Lys Ala Val Val Glu Glu Asn Leu Val Thr
165 170 175

Leu Arg Asp Glu Lys Ser Arg Phe Tyr Tyr Leu Tyr Val Asn Ile His
180 185 190

Lys Ile Glu Asp Ile Tyr Thr Asp Ile Ser Lys Lys Glu Tyr Arg Asp
195 200 205

Leu Tyr Ile Thr Cys Asp Phe Asn Gly Cys His Leu Lys Ser Ser Gln
210 215 220

Ala Arg Asn Cys Ile Asn Tyr Thr Phe Asn Glu Cys Phe Lys Ile Pro
225 230 235 240

Ile Ala Thr Pro Ile Leu Asp Asp Ser Ile Ile Leu Lys Ile Trp Asp
245 250 255

Trp Asn Tyr Leu Ser Asn Asp Glu Leu Ile Ala Ile Gly Val Leu Ser
260 265 270

Phe Asn Gln Ile Lys Asn Glu Cys Leu Asn Pro Thr Trp Leu Asn Leu
275 280 285

Tyr Gly Phe His Lys Lys Glu Phe Asp Leu Glu Lys Ile Thr Asn Asn
290 295 300

Tyr Thr Asn Lys Asn Asn Ser Asn Asn Tyr Tyr Asp Ile Cys Asn Asp
305 310 315 320

Tyr Asn Leu Leu Leu Glu Gly Asn Phe Tyr Leu Gly Arg Ile Cys Ile
325 330 335

Ser Ser Tyr Val Glu Arg Ile Asn Asn Phe Asp Asn Leu Asn Ile Ala
340 345 350

```
Ile Thr Gln Ser Cys Leu Ala Tyr Asp Asp Pro Leu Tyr Ile Pro Ile
        355                 360                 365

Thr Leu Leu Cys Asp Val Tyr Leu Val Thr Gly Ile Leu Ser Lys Asn
    370                 375                 380

Ile Tyr Val Glu Leu Thr Cys Gly Pro His Arg Lys Lys Thr Gln Cys
385                 390                 395                 400

Val Ser Val Asn Glu Met Leu Gln Asp Val Met Gly Lys Gln Thr Asn
                405                 410                 415

Gln Lys Lys Lys Thr Lys Lys Lys Lys Ile Ile Lys Gly Ile His Asn
            420                 425                 430

Ser Tyr Ile Asp Asn Glu Ile Val Asn Asn Asn Tyr Asp Asn Thr Ile
        435                 440                 445

Tyr Thr Tyr Asn Gln Lys Thr Asn Pro Leu Phe Thr Phe Asp Glu Ile
    450                 455                 460

Leu Asn Leu Asp Asn Val Phe Asn Lys Val Thr Glu Lys Gln Gln Ile
465                 470                 475                 480

Ile Glu Asn Asn Glu His Thr Glu Phe Tyr Phe Ser Ala Asn Lys Gly
                485                 490                 495

Lys Ile Glu Asn Met Lys Leu Cys Val Val Gln Glu Glu Tyr Gln Gln
            500                 505                 510

Trp Asp Ile Ile Ile Asn Val Tyr Glu Lys Val Tyr Asn Asn Ser Tyr
        515                 520                 525

His Glu Asn Asn Phe Leu Pro Ser Leu Leu Tyr Asn Asn Glu Glu Thr
    530                 535                 540

Lys Asn Asp Asp Tyr Ser Lys Leu Thr Glu Tyr Gln Lys Tyr Gln Lys
545                 550                 555                 560

Lys Lys Glu Glu Ile Asp Gln Tyr Glu Gln Asn Ile Pro Asn His Ile
                565                 570                 575

Asp Arg Arg Ile Ala Tyr Tyr Arg Met Pro Leu Lys Asn Val Leu Leu
            580                 585                 590

Tyr Asn Glu Lys Ile Ser Arg Cys Pro Ile Trp Ile Pro Leu Lys Asn
        595                 600                 605

Ile Pro Lys Asn Val Gln Gly Asp Phe Asn Cys Met Tyr Asn Ile Phe
    610                 615                 620

Gln Asn Gly Ser Ile Leu Leu Asn Leu Glu Lys Ser Phe Asp Val Gln
625                 630                 635                 640

Leu Gly Ile Asn Arg Arg Lys Lys Leu Ile Pro Val Asn Tyr Glu Leu
                645                 650                 655

Arg Cys Tyr Ile Tyr Ala Cys Arg Asn Val Ile Ser His Phe Asn Asp
            660                 665                 670

Ser Pro Asn Thr Phe Val His Ile Ser Cys Ala Gly Lys Met Lys Ile
        675                 680                 685

Thr Ser Leu Ser Leu Asn Ser Cys Asn Pro Val Tyr Leu Gln Cys Leu
    690                 695                 700

Lys Leu Asn Ile Asn Ile Leu Thr Asp Tyr Ser Ile Gly Leu Pro Thr
705                 710                 715                 720

Ile Pro Leu Ile Ile Val Thr Leu Tyr Glu Phe His Asn Asp Thr Phe
                725                 730                 735

Tyr Tyr Ile Gly Arg Cys Tyr Cys Asn Tyr Asp Ile Tyr Leu Lys Gln
            740                 745                 750

Ser Gly Asn Lys Tyr Asn Phe Thr Glu Lys Gly Ser Lys Tyr Asn Val
        755                 760                 765

Val Glu Gln Ile Lys Pro Lys Trp Ile Lys Leu Lys Gly Ser Lys Tyr
```

```
    770                 775                 780

Thr Lys Ala Met Tyr Ala Asn Asn Leu Trp Gln His Asn Gly Asn Asp
785                 790                 795                 800

Lys Arg Ile Met Gln Glu Tyr Leu Tyr Glu Lys Gln Gln Glu Leu Ile
                805                 810                 815

Asn Asn Ser Thr Ile Asn Lys Asn Asn Asn Asn Asn Asn Lys Lys Asp
            820                 825                 830

Asn Asn Asn Lys Lys Asp Asn Asn Asn Lys Lys Asp Asn Asn Asn Asn
        835                 840                 845

Asn Asn Asn Asn Tyr Tyr Tyr Asn Ser Ser Asn Val Tyr Gln Tyr Asn
    850                 855                 860

Asp Leu Leu Tyr Gly Glu Arg Val Gly Asp Ile Leu Leu Tyr Phe Glu
865                 870                 875                 880

Leu Val Gln Ser Lys Asp Ala Met Lys Phe Pro Ile Tyr Pro Met Ile
                885                 890                 895

Thr Glu Ile Lys Lys Cys Thr Leu Ser Phe Phe Cys Met Ser Leu Glu
            900                 905                 910

Asn Leu Ile Leu Met Lys Lys Ala Asn Phe Leu Lys Thr Leu Ser Phe
        915                 920                 925

Glu Arg Asn Asn Lys Tyr Gln Ile Ser Thr Pro Ile Ile Leu Leu Ser
    930                 935                 940

Ile Thr Ser Tyr Ser Ser Tyr Gly Lys Lys Lys Asn Glu Leu Met Ile
945                 950                 955                 960

Lys Tyr Glu Lys Thr Leu Lys Ala Asn Thr Arg Ile Gln Leu Lys Asn
                965                 970                 975

Trp Lys Asn Ser Phe Asn Gln Gln Ser Phe Glu Met Phe Ser Ile Glu
            980                 985                 990

Asn Met Asn Ile Asp Ile Pro Leu  Asp Pro Ile Phe Asp  Pro Ile Leu
        995                 1000                1005

Asn Ile  Lys Val Tyr Asn Lys  Lys Val Lys Ser Lys  Tyr Phe Ile
    1010                1015                1020

Gly Glu  Thr Asn Ile Ser Leu  Val Pro Tyr Leu Pro  Trp Ile Lys
    1025                1030                1035

Asn Ile  Asp Glu Val Leu Tyr  Tyr Leu Gln Ala His  Asp Asp Tyr
    1040                1045                1050

Ser Glu  Thr Ile Asn Met Lys  Asn Ile Asp Asn Thr  Phe Asn Ile
    1055                1060                1065

Tyr Lys  Asn Lys Asn Ala Ala  Leu Val Ile Ser Ala  Ile Ser Leu
    1070                1075                1080

Ala Asp  Cys Glu Asp Thr Leu  Ser Leu Lys Glu Glu  Ile Asn Lys
    1085                1090                1095

Tyr Glu  Asn Asp Asp Asp Glu  Ala Trp Lys Glu Ile  Pro Leu Phe
    1100                1105                1110

Asn Leu  Asp Gln Glu Asn Gln  Lys Glu Asp Asn Lys  Asn Thr Ser
    1115                1120                1125

Ser Gln  His Gly Asn Val Thr  Asn Asn Tyr Asp Gly  Tyr Asn Asn
    1130                1135                1140

Gly Ala  Tyr Glu Met Gly Met  Tyr Asn Met Glu Thr  Tyr Asn Ile
    1145                1150                1155

Lys Asn  Asn Asp Asn Asn Asn  Asn Asn Asn Tyr Asn  Asn Tyr Asn
    1160                1165                1170

Asn Asn  Ser Tyr Asn Asn Asn  Asn Tyr Tyr Tyr Asn  Asn Tyr Ala
    1175                1180                1185
```

Ala Pro Tyr Thr Ser Tyr Asn Asn Asn Val Leu Gln Asn Asp Thr
1190 1195 1200

Arg Asn Asn Val Arg Tyr Asn His Ser Asn Asn Met Met Ile Asn
1205 1210 1215

Asn Met Tyr Lys Asn Asn Ile Tyr Asn Ala Ser Gln Phe Gly Val
1220 1225 1230

Ile Asn Tyr Asn Asn Tyr Asn Asn Tyr Tyr Asp Lys Gly Asn Thr
1235 1240 1245

Leu Asn Phe Asn Asn Asn Asn Ile His His Phe Asn Lys Leu Ser
1250 1255 1260

Asn Asn Lys Phe Asp Ser Tyr Leu Ser Arg Ile Gln Lys Asp Thr
1265 1270 1275

Tyr Asn Ile Lys Tyr Asn Asn Ser Ile Tyr Lys Leu Phe Asp Asp
1280 1285 1290

Gly Ile Pro Glu Ile Ile Lys Leu Ser Tyr Asn Val Lys Asn Tyr
1295 1300 1305

Pro Tyr Ile Lys Ile Leu Thr Ser Lys Tyr Ile Leu Asn Val His
1310 1315 1320

Ile Pro Pro Arg Phe Ile Leu Tyr Val Glu Gly Asp Lys Leu Asn
1325 1330 1335

Ile Glu Lys Phe Ile Lys Asn Ile Asn Arg Val Ser Val Asp Gly
1340 1345 1350

Ile Leu Glu Asn Tyr Leu Asp Asp Ile Leu Ile Pro Ser Leu Pro
1355 1360 1365

Leu Ile Lys Lys Cys Asn Asp Ile Ser Cys Asp Asn Asn Tyr Asn
1370 1375 1380

Glu Asn Lys Ile Glu Lys Gln Gly Ile Lys Phe Gly Cys Phe Glu
1385 1390 1395

Gln Phe Pro Phe Val Glu Ile Ile Gly Gly Gln Ile Lys Cys Phe
1400 1405 1410

Thr Lys Ile Lys Tyr Arg Asn Leu Glu Ser Glu Asn Met Pro Leu
1415 1420 1425

Ser Leu Lys Asp Ile Thr Asn Gln Asn Ile Phe Arg Asn Lys Phe
1430 1435 1440

Arg Gly Lys Asn Lys Ile Pro Leu Tyr Leu Lys Ile Arg Val Tyr
1445 1450 1455

Val Leu Arg Gly Ile Gly Leu Tyr Gly Ile Asn Asn Glu Tyr Thr
1460 1465 1470

Ala Asn Pro Tyr Leu Ile Phe Ser Leu Gly Glu Lys Thr Ser Asn
1475 1480 1485

Leu Arg Asn Ala Phe Lys Arg Ser Asn Ile Asn Pro Glu Phe Gly
1490 1495 1500

Cys Leu Trp Glu Ser Glu Ala Ile Phe Pro Glu Asp Glu Ile Leu
1505 1510 1515

Thr Ile Ser Val Tyr Ser Ala Glu Asp Asn Tyr Asp Lys Gln Ile
1520 1525 1530

Asn Asp Ile Tyr Ile Gly Ser Thr Glu Ile Asn Leu Phe Asp Arg
1535 1540 1545

Trp Met Ser Lys Glu Trp Arg His Met Met Lys Lys Asn Lys Ile
1550 1555 1560

Pro Val Glu Tyr Arg Pro Leu Tyr Ser Asn Tyr Ile Lys His Pro
1565 1570 1575

```
Lys Met Val Ser Ser Asn Asn Tyr Asn Thr Met Asn Ser Trp Asn
    1580                1585                1590

Asn Ile Phe Ser Phe Phe Asp Ile Phe Asn Tyr Leu Met Thr Tyr
    1595                1600                1605

Thr Ser Pro Thr Lys Gly Asn Asn Asn Asn Asn Asn Asp Asn Asn
    1610                1615                1620

Asn Asn Asn Ser Asn Ile Tyr Gly Asn His Ser Leu Lys Asp Thr
    1625                1630                1635

His Ser Asn Ile Ser Phe Gly Asn Ser Gln Lys Arg Asn Asn Gly
    1640                1645                1650

Ile Leu Glu Met Trp Val Glu Ile Met Asp Tyr Glu Gln Ser Lys
    1655                1660                1665

Lys Ile Pro Ile His Lys Met Val Pro Pro Lys Lys Thr Glu Ile
    1670                1675                1680

Glu Ile Arg Ile Ile Ile Trp Arg Cys Thr Met Leu Thr Asn Lys
    1685                1690                1695

Asp Asn Ile Asn Lys Thr Met Asp Leu Thr Val Thr Ser Glu Leu
    1700                1705                1710

Asp Cys Ile Thr Tyr Asn Gly Lys Asn Pro Thr Met Gln Ser Thr
    1715                1720                1725

Asp Val His Tyr Asn Cys Lys Thr Gly Thr Ala Ile Phe Asn Trp
    1730                1735                1740

Arg Ile Val Tyr Pro Asn Ile Thr His Pro Leu Asn Thr Cys Phe
    1745                1750                1755

Leu Gln Leu Ala Ala Tyr Asn Asn Asn Asn Val Gly Val Ser Glu
    1760                1765                1770

Phe Leu Gly Glu Val Asn Leu Glu Leu Ser Lys Tyr Ile Gln Lys
    1775                1780                1785

Ala Ser Gln Ile Leu Asn Lys Phe Glu Leu Asp Ala Glu Leu Lys
    1790                1795                1800

Leu Arg Lys Lys Thr Asp Thr Asp His Asn Lys Asn Thr Tyr Asn
    1805                1810                1815

Gly Tyr Ile Gln Val Thr Val Gln Phe Ile Pro Gln Asn Lys Ala
    1820                1825                1830

Asn Ile Lys Pro Val Gly Leu Gly Arg Asp Glu Pro Asn Arg Asn
    1835                1840                1845

Pro Tyr Leu Lys Thr Pro Asp Ser Gly Arg Glu Trp Asn Asp Phe
    1850                1855                1860

Met Tyr Ser Ile Gly Phe Asn Asp Ile Tyr Lys Pro Phe Trp Asn
    1865                1870                1875

Ser Leu Lys Leu Ala Phe Ile Cys Leu Leu Val Ile Trp Val Phe
    1880                1885                1890

Val Leu Ser Phe Val Tyr Pro Ser Leu Leu Arg
    1895                1900
```

<210> SEQ ID NO 25
<211> LENGTH: 1704
<212> TYPE: PRT
<213> ORGANISM: Plasmodium falciparum

<400> SEQUENCE: 25

```
Met Ser Ser Ile Ala Lys Lys Thr Gln Tyr Asn Ile Lys Val Asp Ile
1               5                   10                  15

His Glu Val Lys Asp Leu Ser Phe Arg Glu Ser Ala Asn Glu Lys Glu
            20                  25                  30
```

-continued

```
Ile Ile Pro Asn Pro Tyr Ile Glu Val Thr Val Asn Asn Glu Lys Lys
        35                  40                  45

Ser Thr Thr Lys Lys Asn Gln Ala Val Asn Val Val Tyr Asn Thr Ser
    50                  55                  60

Phe Asn Phe Ser Gln Asp Leu Thr Asp Tyr Lys Phe Glu Arg Thr Ser
65                  70                  75                  80

Val Asp Val Cys Val Leu His Lys Tyr Thr Ile Gln Ser Ala Leu Ile
                85                  90                  95

Gly Lys Cys Ser Phe Gly Leu Asn Phe Val Tyr Ser Lys Val Gln His
            100                 105                 110

Trp Leu Tyr Arg Ile Trp Val Lys Leu Arg Asn Pro Asp Leu Pro Leu
        115                 120                 125

Asp Asp Val Gly Phe Leu Leu Ile Ser Val Gly Val Tyr Gly Pro Gly
    130                 135                 140

Asp Ser Ile Pro Ile Val Asn Asp Ser Val Lys Thr Asp Ile His Glu
145                 150                 155                 160

Asp Val Phe Ser Asn Lys Gly Leu Asp Ile His Ile Thr His Tyr Asp
                165                 170                 175

Leu Cys Leu Asn Ile Phe Arg Gly Gln Asp Ile Glu Leu Ile Gly Asn
            180                 185                 190

Ser Thr Leu Phe Ser Asn Ile Leu Glu Pro Tyr Val Lys Val Ser His
        195                 200                 205

Asn Gly Phe Glu Glu Cys Thr Lys Val Ile Arg Asn Asp Pro Asn Pro
    210                 215                 220

Val Trp Asn Leu Ser Ile His Ile Pro Thr Cys Thr Pro Cys Tyr Asp
225                 230                 235                 240

Lys Asn Ile Leu Val Glu Leu Ile Asn Gly Glu His Asn Gly Ile Val
                245                 250                 255

Ile Tyr Ser Ile Leu Leu Asp Phe Phe Glu Ile Leu Lys Arg Glu Leu
            260                 265                 270

Ala Pro Arg Trp Phe Asn Ile Tyr Tyr Asn Pro Gln Asn Gln Ile Met
        275                 280                 285

Pro Arg Tyr Ser Glu Tyr Met Gln Asn Gly Ser Ile Gln Ile Asn Leu
    290                 295                 300

Asn Ser Thr Thr Thr Asn Asn Asn Asn Asn Asn Ser Thr Ala Ile Asn
305                 310                 315                 320

Pro Leu Gly Asn Tyr Leu Phe Ser Gly Ala Ala Glu Lys Ile Phe Lys
                325                 330                 335

Asn Ala Thr Gln Ala Ile Asn Ile Asn Asp Ile Leu Gly Val Thr Lys
            340                 345                 350

Val Gln Asn Met Phe Thr Asp Asp Thr Leu Lys Glu Phe Tyr Leu Tyr
        355                 360                 365

Gly Gly Arg Ile Phe Leu Ser Ala Asn Ala Thr Lys Thr His Ser Pro
    370                 375                 380

Gly Pro Ile Cys Ile Lys Ser Ala Lys Val Glu Val Asp Ala Pro Asn
385                 390                 395                 400

Lys Glu Tyr Ile Phe Cys Ala Asp Ile Tyr Glu Ile Leu Ser Val Arg
                405                 410                 415

Asn Asn Lys Met Gly Asn Tyr Asp Asp Tyr Asp Gly Gly Tyr Thr Thr
            420                 425                 430

Thr Asn Asn Asn Asn Lys Asn Lys Asn Asn Asn Asn Glu Asn Asn Asn
        435                 440                 445
```

-continued

```
Asn Asp Asn Asn Asp Asn Ile Tyr Asn Ser Asn Asn Ile Tyr Asn Ser
    450                 455                 460

Ala Ser Glu Lys Arg Arg Ser Arg Tyr Asn Asn Asn Tyr Asp Ala Ser
465                 470                 475                 480

Gly Glu Ser Ile Ile Cys Val Cys Ala Leu Gly Pro His Lys Leu Lys
                485                 490                 495

Thr Ile Pro Leu Leu Pro Asn Glu Val Gly Ser Tyr Val Leu Asn Glu
            500                 505                 510

Asn Val Gly Arg Ile Asp Glu Phe Arg Ile Phe Leu Pro Gln Asn Asn
        515                 520                 525

Asn Glu Gln Ile Tyr Asp Ile Phe Leu Tyr Ile Tyr Ile Lys Ser Asn
    530                 535                 540

Leu Ala Val Thr Asn Trp Ile Asn Asn Arg Arg Ser Ile Tyr Asn Ser
545                 550                 555                 560

Val Leu Leu Asn Asn Glu Tyr Glu Ser Gly Asp Arg Asn Lys Lys Gln
                565                 570                 575

Gly Leu His Lys Met Gly Ser Ile Asn Asn Ile Ser Glu Asp Ile Met
            580                 585                 590

Gln Asp Ser Asp Phe Leu Asn Asn Tyr Lys Leu Thr Ser Tyr Val Arg
        595                 600                 605

Ile Pro Tyr Lys Tyr Leu Leu Leu Asn Glu Asn Lys Pro Lys Trp Phe
    610                 615                 620

Ser Met Lys Asn Ile Glu Thr Asn Val His Glu Tyr Asn Ile Ser Phe
625                 630                 635                 640

Phe Ala Asn Leu Ile Pro Tyr His Ala Tyr Lys Lys Arg Pro Lys Arg
                645                 650                 655

Leu Glu Tyr Lys Leu Ser Arg Tyr Phe Phe Arg Ala Leu Ile Tyr Glu
            660                 665                 670

Gly Leu His Phe Pro Ala Lys Gly Tyr Asn Ala Phe Pro Asp Pro Tyr
        675                 680                 685

Ile Lys Ile Glu Leu Ala Gly Gln Val Ile Lys Thr Ser Thr Ile Leu
    690                 695                 700

His Thr Leu Asn Pro Asn Tyr Tyr Glu Ala Tyr Glu Val Gln Val Ile
705                 710                 715                 720

Leu Pro Thr Asn Leu Asn Leu Ala Pro Asp Ile Ser Ile Glu Ala Leu
                725                 730                 735

Ser Val Asn Lys Ser Phe Leu Tyr Asn Asp Asp Ile Leu Leu Gly Ser
            740                 745                 750

Cys Thr Phe Pro Ile Met Lys Val Pro Thr Glu Trp Lys Lys Ser Pro
        755                 760                 765

Ile Trp Ile Pro Leu Lys Ser Ser Gln Tyr Lys Lys Cys Lys Ala Lys
    770                 775                 780

Leu Leu Val Ala Phe Glu Leu Val Pro Val Glu Lys Val Leu Asp Asp
785                 790                 795                 800

Thr Tyr Pro Phe Tyr Asp Asp Ile Arg Pro Ser Thr Leu Pro Gly His
                805                 810                 815

Val Ser Leu Phe Leu Ile Gly Ile Arg Met Phe Lys Pro Leu Lys Asp
            820                 825                 830

Pro Ser Val Thr Val Cys Phe Gly Arg Asp Val Asp Asp Thr Ser Gln
        835                 840                 845

Phe Leu Trp His Glu Thr Thr Asn Lys Val Ile Ser Gly Lys Glu Gly
    850                 855                 860

Asn Trp Asn Phe Leu Lys Tyr Phe Ser Leu Asp Val Met Leu Pro Lys
```

-continued

```
865                 870                 875                 880

Arg Met Gln His His Ser Phe Leu Glu Val Arg Ile Glu Asp Arg Ile
                885                 890                 895

Leu Asn Ser Gly Phe Thr Gly Thr Ala Ser Ser Asn Met His Ala Val
            900                 905                 910

Asn Ala Thr Asn Asn Asn Leu Leu Ile Gly Thr Ala Tyr Ile Thr Leu
        915                 920                 925

Asn Pro Leu Leu Pro Trp Leu Asp Asn Tyr Glu Lys Asn Glu Cys Val
    930                 935                 940

Glu Leu Phe Lys Leu His Leu Leu Glu Glu Val Leu Ile Glu Asp Ala
945                 950                 955                 960

Glu Met Asp Arg Lys Ser Tyr Asn Ser Ala Leu Ile Tyr Lys Lys Ser
                965                 970                 975

Ser Ile Met Ser Arg Lys Leu Ser Asn Asp Asn Phe Glu Thr Gln Gln
            980                 985                 990

Met Gly Glu Glu Asn Gly Ile Phe  Asn Asp Ile Pro Met  Asn Thr Leu
        995                 1000                1005

Glu Glu  Asn Val Thr Ile Lys  Gly Asp Asp Ser Ser  Asp Asp Glu
    1010                 1015                 1020

Lys Asp  Asn Ser Tyr Asp Asp  Glu Lys Asp Asn Ser  Tyr Asp Asp
    1025                 1030                 1035

Glu Lys  Asp Asn Ser Tyr Asp  Asp Glu Lys Asp Asn  Ser Tyr Asp
    1040                 1045                 1050

Gly Asp  Asp Lys Ser Gly His  Tyr Tyr His Thr Trp  Glu Asp Asn
    1055                 1060                 1065

Asn Asn  Asn Asn Asn Asn Asn  Val Thr Ser Asp His  Thr Cys Lys
    1070                 1075                 1080

His Lys  Asn Glu His Asn Asn  Asn Lys Lys Glu Asp  Glu Lys Arg
    1085                 1090                 1095

Lys Arg  Glu Lys Lys Asn Thr  Tyr Thr Thr Asn His  Asp Lys Arg
    1100                 1105                 1110

Glu Asn  Asn Asn Thr His Ile  Asn Asn Asn Tyr Lys  His Val Ile
    1115                 1120                 1125

Asp Ile  Lys Lys Lys Lys Arg  Lys Lys Asn Ile Lys  Lys Tyr Ile
    1130                 1135                 1140

Asn Asn  Glu Tyr Val Pro Tyr  Asn Asp Pro Asp Phe  Ser Asn Val
    1145                 1150                 1155

Arg Ile  Glu Glu Thr Leu Glu  His Val Cys Phe Lys  Ile Asn Asp
    1160                 1165                 1170

Leu Thr  Lys Lys Glu Asn Thr  Tyr Ile Tyr Tyr Asn  Asp Glu Gln
    1175                 1180                 1185

Glu Thr  Leu Cys Asp Ser Ile  Ser Ser Glu Lys Arg  Lys Lys Leu
    1190                 1195                 1200

Lys Asp  Ile His Phe Phe Lys  Gly Gly Lys His Asp  Asp Lys Glu
    1205                 1210                 1215

Lys Lys  Ser Thr Ile Ile Asp  Gly Lys Gln Pro Thr  Thr Ile Tyr
    1220                 1225                 1230

Gly Phe  Asn Glu Asp Met Leu  Asn Phe Gln Leu Ser  Leu Ala Asp
    1235                 1240                 1245

Asp Asp  Glu Gln Glu Glu Ile  Gln Arg Asp Glu Met  Leu Tyr Glu
    1250                 1255                 1260

Tyr Glu  Val Asp Met Asn Thr  Asp Asp Leu Pro Tyr  Leu Arg Ala
    1265                 1270                 1275
```

-continued

```
Thr Ile  Phe Arg Cys Thr Asp  Ser Gly Val Pro Glu  Ala Val Gly
    1280                 1285                 1290

Tyr Leu  Lys Tyr Ile Cys Asn  Val Tyr Asp Glu Lys  Thr Met Tyr
    1295                 1300                 1305

Leu Lys  Lys Glu Met Ile Lys  Lys Cys Asp Asp Leu  Val Arg Glu
    1310                 1315                 1320

Tyr Arg  Leu Thr Arg Asn Leu  Val Val Arg Ala Tyr  Ile Ile Gln
    1325                 1330                 1335

Ala Arg  Gly Leu Asn Pro Pro  Ser Gly Ala Thr Asp  Ile Thr Thr
    1340                 1345                 1350

Tyr Ile  Trp Ile Lys Asn Ser  Asn Asp Met Thr Asn  Ile Pro Gly
    1355                 1360                 1365

Gly Leu  Ser His Asn Ile Lys  Asp Thr Gly His Thr  Lys Lys Gln
    1370                 1375                 1380

Gly Tyr  Lys Pro Glu Phe Asn  Arg Cys Tyr Gln Leu  Leu Cys Ser
    1385                 1390                 1395

Phe Pro  Asp Glu Ser Ile Val  Gln Val Cys Ile Met  Asn Gln Gly
    1400                 1405                 1410

Ser Leu  Ser Asp Glu Ile Ile  Gly Tyr Thr Tyr Ile  Asp Met Glu
    1415                 1420                 1425

Asp Arg  Tyr Phe Asn Gln Lys  Ile Arg Gln Leu Met  Ile Asp Asp
    1430                 1435                 1440

Leu Met  Pro Ile Glu Leu Arg  Ser Leu Lys Leu Glu  Asn Ser Thr
    1445                 1450                 1455

Ile Ser  His Gly Ser Leu Arg  Cys Trp Phe Glu Ile  Phe Asn Glu
    1460                 1465                 1470

Glu Phe  Ala Gln Leu Asn Pro  Ile Lys Val Leu Cys  Ser Asn Glu
    1475                 1480                 1485

Pro Asp  Asp Tyr Gln Leu Arg  Leu Val Ile Trp Lys  Val Asn Asn
    1490                 1495                 1500

Ala Ala  Met Asp Asp Asn Ser  Thr Ile Ser Leu Phe  Val Arg Cys
    1505                 1510                 1515

Ile Tyr  Thr Asp Glu Asp Arg  Glu Asp Ile Arg Asp  Thr Asp Thr
    1520                 1525                 1530

His Tyr  Asn Ser Lys Asp Gly  Lys Gly Ile Phe Asn  Trp Arg Phe
    1535                 1540                 1545

Val Tyr  Asn Ile Lys Ile Pro  Thr Asn Ala Thr Asn  Ile Lys Ile
    1550                 1555                 1560

Gln Ile  His Asn Tyr Ala Leu  Leu Ser Ser Asn Glu  Pro Ile Gly
    1565                 1570                 1575

Glu Ala  Thr Leu Asp Leu Ser  Ala His Phe Tyr Arg  Ala Arg Lys
    1580                 1585                 1590

Lys Lys  Gly Tyr Tyr Pro Ile  Pro Arg Phe Trp Leu  Ser Cys Lys
    1595                 1600                 1605

His Pro  Ala His Lys Asn Lys  Val Arg Gly Asn Val  Glu Ile Glu
    1610                 1615                 1620

Gly Ser  Ile Leu Ile Lys Ser  Glu Ala Glu Leu Asp  Pro Val Gly
    1625                 1630                 1635

Asn Gly  Arg Asp Glu Pro Asn  Lys Asp Pro Tyr Leu  Pro Pro Val
    1640                 1645                 1650

Thr Glu  Asn Arg Thr Tyr Val  Asp Trp Val Met Ile  Asn Glu Lys
    1655                 1660                 1665
```

```
Phe Gly  Ala Ala Thr Ala Ser  Ile Met His Gly Leu  Lys Trp Thr
    1670                1675                1680

Gly Val  Trp Ile Val Val Gly  Val Ile Val Ile Gly  Ile Phe Phe
    1685                1690                1695

Leu Ile  Phe Leu Phe Lys
    1700
```

<210> SEQ ID NO 26
<211> LENGTH: 9
<212> TYPE: PRT
<213> ORGANISM: Artificial Sequence
<220> FEATURE:
<223> OTHER INFORMATION: fragment of MALS_A

<400> SEQUENCE: 26

```
Ser Leu Ile Cys Gly Leu Tyr Leu Leu
1               5
```

<210> SEQ ID NO 27
<211> LENGTH: 10
<212> TYPE: PRT
<213> ORGANISM: Artificial Sequence
<220> FEATURE:
<223> OTHER INFORMATION: fragment of MALS_A

<400> SEQUENCE: 27

```
Ile Leu Tyr Ser Leu Met Ile Asn Ser Leu
1               5                   10
```

<210> SEQ ID NO 28
<211> LENGTH: 10
<212> TYPE: PRT
<213> ORGANISM: Artificial Sequence
<220> FEATURE:
<223> OTHER INFORMATION: fragment of MALS_A

<400> SEQUENCE: 28

```
Leu Ile Cys Gly Leu Tyr Leu Leu Thr Leu
1               5                   10
```

<210> SEQ ID NO 29
<211> LENGTH: 9
<212> TYPE: PRT
<213> ORGANISM: Artificial Sequence
<220> FEATURE:
<223> OTHER INFORMATION: fragment of MALS_B

<400> SEQUENCE: 29

```
Val Leu Leu Glu Lys Ile Asn Val Ile
1               5
```

<210> SEQ ID NO 30
<211> LENGTH: 10
<212> TYPE: PRT
<213> ORGANISM: Artificial Sequence
<220> FEATURE:
<223> OTHER INFORMATION: fragment of MALS_B

<400> SEQUENCE: 30

```
Tyr Leu Ser Pro Asn Phe Ile Asn Lys Ile
1               5                   10
```

<210> SEQ ID NO 31
<211> LENGTH: 9
<212> TYPE: PRT
<213> ORGANISM: Artificial Sequence
<220> FEATURE:
<223> OTHER INFORMATION: fragment of MALS_C

<400> SEQUENCE: 31

Ile Leu His Gly Gly Val Tyr Arg Leu
1 5

<210> SEQ ID NO 32
<211> LENGTH: 9
<212> TYPE: PRT
<213> ORGANISM: Artificial Sequence
<220> FEATURE:
<223> OTHER INFORMATION: fragment of MALS_C

<400> SEQUENCE: 32

Ile Leu Phe Leu Phe Ile Leu Ser Ile
1 5

<210> SEQ ID NO 33
<211> LENGTH: 10
<212> TYPE: PRT
<213> ORGANISM: Artificial Sequence
<220> FEATURE:
<223> OTHER INFORMATION: fragment of MALS_C

<400> SEQUENCE: 33

Leu Leu Phe Ile Asn Glu Ile Asn Lys Leu
1 5 10

<210> SEQ ID NO 34
<211> LENGTH: 10
<212> TYPE: PRT
<213> ORGANISM: Artificial Sequence
<220> FEATURE:
<223> OTHER INFORMATION: fragment of MALS_F

<400> SEQUENCE: 34

Ser Leu Ile Ser Leu Tyr Ile Tyr Tyr Val
1 5 10

<210> SEQ ID NO 35
<211> LENGTH: 9
<212> TYPE: PRT
<213> ORGANISM: Artificial Sequence
<220> FEATURE:
<223> OTHER INFORMATION: fragment of MALS_F

<400> SEQUENCE: 35

Phe Leu Leu Leu Met Leu Val Ser Ile
1 5

<210> SEQ ID NO 36
<211> LENGTH: 9
<212> TYPE: PRT
<213> ORGANISM: Artificial Sequence
<220> FEATURE:
<223> OTHER INFORMATION: fragment of MALS_Cal

<400> SEQUENCE: 36

Phe Leu Thr Leu Met Ala Arg Lys Leu
1 5

<210> SEQ ID NO 37
<211> LENGTH: 9
<212> TYPE: PRT
<213> ORGANISM: Artificial Sequence
<220> FEATURE:

<223> OTHER INFORMATION: fragment of MALS_E

<400> SEQUENCE: 37

Asn Leu Leu Asp Pro Leu Val Val Val
1               5

<210> SEQ ID NO 38
<211> LENGTH: 9
<212> TYPE: PRT
<213> ORGANISM: Artificial Sequence
<220> FEATURE:
<223> OTHER INFORMATION: fragment of MALS_E

<400> SEQUENCE: 38

Leu Leu Leu Glu Gly Asn Phe Tyr Leu
1               5

<210> SEQ ID NO 39
<211> LENGTH: 9
<212> TYPE: PRT
<213> ORGANISM: Artificial Sequence
<220> FEATURE:
<223> OTHER INFORMATION: fragment of  MALS_E

<400> SEQUENCE: 39

Lys Leu Ile Pro Val Asn Tyr Glu Leu
1               5

<210> SEQ ID NO 40
<211> LENGTH: 9
<212> TYPE: PRT
<213> ORGANISM: Artificial Sequence
<220> FEATURE:
<223> OTHER INFORMATION: fragment of MALS_E

<400> SEQUENCE: 40

Ile Leu Ile Pro Ser Leu Pro Leu Ile
1               5

<210> SEQ ID NO 41
<211> LENGTH: 8232
<212> TYPE: DNA
<213> ORGANISM: Plasmodium falciparum

<400> SEQUENCE: 41
atgaattata aattaaaaga aaacgtaccg cctaatgaag atgtggatat atatgaaaag     60
ttaaaaactt gtgttataaa tagaaatgtg gaagacttct atgaagaatg tgtaagtacc    120
tttttggaaa aagtaaaaaa tataggagat actaatcata taatatgtca tgataattat    180
tctgacatta taaatttttt ttatttaaac ttatttgttg acaattcaga gtttgtacgt    240
gttgtagcag tatcacaaga taataatgaa aatgctaaga tttgtaaaag atatatacat    300
gataagaatg aaaaggatgt taccgaaaag agtgaattat tacaagaatt agggttgtat    360
ttaaaaaaca ttaaattaaa atattccgaa aaattaaaga agataaaaaa tgtgattatc    420
gataatatta gtacttgcca aaaatgtatt atgatatatt attttttaca gaaaaaattg    480
gttgaaaaaa tatcgtctaa tataaataag aaagatgata atgttacgaa tataataaaa    540
aaggaaatat ttgaatttaa tttttaccgt ataattaata aaataacatg tcctataggt    600
tacaacaacg ttgattctgt tatattagag ttaatgttaa atggttccaa aatatttcag    660
atggatttaa attatatatt agaatataat aaaataaata aagtaaattt aaaaaatattt    720 aaagaaaaat ttattaatta tgataatgat gaaatatata gaatcataaa agaatatgtt    780

-continued

```
gattatgatt ctttaatttt tttctgtaat cttttattta aagaatttaa aagaatgaaa    840
aatttattat tacaaaatga taactataat aatggaaatg atacaagtat aataaatgaa    900
aatattagta ataataataa taataataat aataataata atgatccatt atgtaatgat    960
aatacattat ataattacaa tatacaatgt ttattaccat atatttatat acacattttt   1020
attcttttaa aacacaaaca agttgaagaa actgttagaa gggttttaaa agaaagaata   1080
attttatatt ctttaatgat taattcttta agatattctg ataattttat acaattaatt   1140
atatttaaaa tcataaataa tatttttata aatgaagaag aatttttaaa agattcaaat   1200
aaaaaattaa tatcatctat tttttcctat tggatcaaat tatccgatgg gtgtatcgtc   1260
aaaatgataa atgcaagtat aaccgatgaa tcctcaacta gccataataa tttaagtcgt   1320
agtagtagta ataatacaaa acataatagt aacaaattat ataataatag ttgtataaaa   1380
aaaacaaaaa ctgatgatga aaatttttta aaaaataatt ttacagatta tgatatatat   1440
aaatacatgc aaagcttaat ttgcggtctt tatttattaa ctttaataag aaaaaaaaaa   1500
aataatgatc atcattataa taataaaagt gataacacga atcaattttc ttctttaaaa   1560
gaatacaata tagatatgtt atccttaaat cactttttta ttaatatgga taattatata   1620
tatcttatag gatttatgtt ttctgagaac aaggatacaa taaataatct atttaattta   1680
attttcaaat tattatattt tattaaatat ttaaaatcgt atattattca aaatagaaac   1740
ttaaaaaata aatatttcga agatacatgt atatattcat caataaatat attatataat   1800
atcttagaag taaccaagaa atttttata agttattttc gtatagatga atatacaaaa   1860
aatttgtata aaaattattt tagagacagg ccattgactt ttgagaacat ggccttttat   1920
gtaatcccct tgtttataaa ccatgaggat tattatatac gtatatattc aattaagatt   1980
ttgataatcc tcctgtccga tacaaacatt cgggattctc ttgataaaaa aaaccttttc   2040
aggatcttcg atttattaat aaatatagaa ggatataaaa gtttatcaca agatgaagaa   2100
gaggaagaga aaaaaaatat caaccaactt cttctgctat tatttaaatg caatattaat   2160
gataataagt tatcatctaa tataacaaat ttaatattta gtgaaaaaca aaaaatattt   2220
attaaatata ttttacgtct atgtaaagat gaggagtatt caataataca tatgaagaat   2280
tttttgatt atttttttgt tttattagta aaattaatta atataataat acgaagagca   2340
caatgtagtt taaatataga aaagtataaa gatttcttta tgaatatata tgaagttgtt   2400
gaaatattta tgaaggaatt aaaaaaagaa aaactaaaaa aacacaaatt attattttta   2460
tcctcaggaa tatatctatg tcatttaata acgaatagta tatataaagg taaaattcat   2520
tcatccgttc cttatttaaa tgttgtaata agtttaatta aaaatataga acaccattta   2580
aattttatac aggatgattt aatttatatt aataaaatat ctaaggatat aatatcagat   2640
aaaaaattat ccattcattc tgaggacgaa gataataaag atgacgattc aaaaagtgta   2700
aaggatttac acgtcttgta tttttataat aacgtatata gtgaagaatt gggcaaaaat   2760
gtgggtaata ataataatat ggctaataac aataataatg ataataatga taataatatt   2820
aataataata ataataacaa taatggagaa aatattgagc ataaatgtgt taagagtacc   2880
tataaagaaa ataaaaataa tgatattaat tgtaagaata aacagactaa tgataaaaac   2940
ctcaaatcta acccgtcgga taacaaagga acgaataatt cagaaatagt aaaaaaatta   3000
aataaatatg ataagtttat gaaaatgtgt cttttacaaa ataagaataa tgatgaaatt   3060
atttataatt atataaattg cctttttat ttgtgtgtca gtaatatgaa taaaagaaca   3120
```

-continued

```
aggaaaaatg tgattaaatc gtatgatttg gttgttaaat atattttgaa agatgaatat   3180
aagttgcatc gagtaaaaaa gaaaagttta cttttttcca tgccaattta tattattaga   3240
gatgttgaaa atgaggggaa aaggtacaat ttaataattg acaaatatga ttatatatta   3300
agaagttata taattgattt ttttaaatgc aaaaaatact taccttgttt acttttatca   3360
tgtttaagtt ttacaaatac tatgatatta tttttaaaaa agaaaaactt tataaatagt   3420
acaacaaaca ataatatcac ggagaaggaa gatatgttag attgtttcat gttagtaaat   3480
tccaaaactt ggttttattt taacgtgttg gttgaatgta tatgtgacta ttttatgacg   3540
tcccaaagca aaatggatgt aaaaagtcaa caaataaaag aacaacaaaa tgaacataca   3600
caaaaatgta ataataaaaa taaaaataat aataataata ataataatga tgacgatgat   3660
gtacataaat tttcatggca aattattaat ttaataatag acagcatatg gaaaatactt   3720
atatatattt tttataatat aaaaatcaat atattcagta taaaagtcaa aacattcagt   3780
ataaatatct atggcagagc agcattatta atgttcttac aattttatga atcgtggatt   3840
gtatttatca aaaccttttt gacatcagaa aaacaaatat tcatatctag aaatatatta   3900
ttacctgact tattttataa aaagtttggt tttctatcat cccaaatatt aagctatttt   3960
cattttattg aatccaattt ttttgtggat agtcaaaatg aagttaattt aagattatta   4020
gaaaagcaaa aagatgtcat gaataatatt ttggatgttt taatatattt tataaaggat   4080
aaggatccaa agggttatgt gaatgagtta aacagttttt cacaatttaa attgaggata   4140
aagaaattaa cgtttccaaa aaagttacaa gatggttttt tatcgtgcac atatgaccat   4200
ctttttaaga aggccaagga gttattatta cgtgtagaga agtcgaaaac gttacaaatg   4260
gatgaatgcc gcggtgaaga tccaaatatc aactcaaatt cgttgcaaat ggacaaggga   4320
gatgataacg aaaatgtaat taatattaat aattctgata taattgtgga aaaagattca   4380
aaaaccatta ttaggatcga ttcaaattct aaggatgcaa atgcagttga aagagatgat   4440
aataaagaag ggaaaaaagt attttcttta gaacaagcta aaaaaattat agaaaaaaat   4500
gcagcttcaa aaaatacaaa gagagcaata gtattgaatg aaaatcttgc agaaaagaat   4560
aaacaacaaa tttttaaaga gatgaaagaa aaacgaaaag aagcagaaaa tatcttaatg   4620
aaatatttta ttatgataca agaattttttg aattgggatt tttttaattt agataatatt   4680
gataaatata aaaattctat tagcgaagaa ttacccatac gttttgaaaa tgaggaggaa   4740
tatcacaagt tttttcgacc catggctttg gaagagtgca ggtgtagtat gctcaataac   4800
atgatgggag atataaacaa atatgtcata agtattgtgg gtaagaaaaa aatgccttat   4860
tgggtagtat ggcatgtatc atcgagtagt gagaacaagc gcaatttgga taacataaaa   4920
ccaatggatt taatagcttt aattccttat gatgaggaca gaaacaataa tacacatgca   4980
gataataatg atacaagtat aaaatatgac aaattaaaag acatgttgaa atgtactaaa   5040
catgttattg gattagttga tattggatcg aataaatttg ataatatatt tgatattaaa   5100
ttaattaatg aagacaattt accttctaag gtgaataatg agaaaactcg tttaaaatta   5160
aattttatta cttgtaataa attccatgca tatgtattat gtaatctaat gacaaatatt   5220
agggaatttc aaagtatata tttgagtaga aattgtcctc tttttaattt aatattaaat   5280
cctgtaggag aaaataaagt agaaaaaggt ttatgtaata tgaacattaa taataattat   5340
ataaatgatt gtgataagga taaaaatgat aaattaaaaa aagaattaga gaaattaacc   5400
agacaggaga aactaatatt aaaaatttta agtaaatata atttattaaa taaatcacaa   5460
atcgaagctg tgaaattaat tcttttaaat aaaaataata tatctttaat acaaggcccc   5520
```

-continued

```
ccaggtacag gtaaaaccaa aacagttata ggaatagtgt ctgttttata tgcattatta   5580
tataaaaaga attatgaaaa agataagaaa aaaaaagatt tgttatataa tgaacaaatt   5640
aataatacaa agaaaaaaaa aaagattttg gtttgttctc catccaattc agcaattgat   5700
gaaattgcta agaggatatt aaatgaggga ttactaaatt ttactaactt aataaattct   5760
tatgaaaata agataaaaaa gaataaatatc acatcgcaaa aatgtggtag taataataag   5820
aagaagatat tgttagggga taatgattta tataattcct ctgatatcag tgattttctt   5880
ggtgaagatc aaccttccaa cttttctaat gataagaaag aaaaatcatc caagggtatg   5940
gtattattaa aaggtttgaa aaatgtagat aaattaaata ataacaatat atcaagtgaa   6000
aaaatgaatc aatttaaaaa acaaacgatt gctcctaaat gtatacgtat tggattatcc   6060
aaaagaaccc atgaagaaat ccagcgaatt tcattagatt atatatttaa caagaagaaa   6120
agttctgatg aaaatcttta tcatgtacat tttgaaaaga ggaaaagtaa attaacatat   6180
tccatcgaag cagtagatta tacgaaatta aaaataaacg aaatgaaaaa tgatttgagt   6240
ttgaataatt ctgaaaagta tagttttgat tgtaatgata ttaatggaaa gtttatgttt   6300
cagaaggttg aatttattga acgatttttt tctgatgaat atataaataa tttggataaa   6360
aaatatttag aaaatttgtt atatttatat aatgaatcat catcacatta tgattggagt   6420
atacaaaaat tgatatcaga aagaaattat ttagacgaat gtatgacaag attgattgag   6480
acagatgagc agattggttc tttttataca agtaataata aagaaaatat gttatttgat   6540
agtgaaatta tatttagtac cttatctggt agtgcttccc ctgttattga aaatttagaa   6600
tttgaatatt taattataga tgaggcatgt cagtgtgtag aattaagttg tttaatacca   6660
tttagattga aagtaaaaaa tattataatg gtaggagatc caaaacaatt accagctaca   6720
accttttcat cagattgtag aaagtatggt tatagtcgtt ccttatttga gcgtttatta   6780
ttatgtaatg tttctagtgt tttattaaat attcaatatc gtatgagacc agaaatttgt   6840
tatttcccaa ataattattt ttataatggt ttaattaaga atgctgatat attatcgaat   6900
aaaccatttt tttattattt tcaagatttg gatttttttg gatgttataa atttattaat   6960
atagatggaa tagaatctat gacatataat aaatcttata taaattatgt tgaagcttat   7020
tttatatata aattagtgtt atatataaaa aatattattt cgaaacatca agatcatacc   7080
aaatcggttc ctaatttata taaattacct gtacatttta gtttgaaaga tattggtatt   7140
atttgcccat atcaatcgca agtacattta ataagaaata tgttcgaaga atcttttgaa   7200
gataaaatcc cattccccga agtatcaaca gttgatgcat ttcagggacg tgagaagcac   7260
atcataatat tttcttgtgt aagatctaaa ttggaggtgt tagaaaatag taagttatta   7320
cataaaatgg gaacttataa aaaagcggat gataaatgga aaaaaacaaa agaaagatat   7380
gtcatatatg acagtgatga taatgctgaa tatagtatga acgaaaatga agataatagt   7440
gataatgatg atgataatga tgatgataat gataatgatg atgataataa taaagagtgg   7500
aaatacgatt acaatgatgg ggtacatacc aaaaaatgga tatcttctaa aatgcctaat   7560
ataaaaaatg agaacgattt tcgagctata caaaagttcg gaaataatat tggtttttta   7620
aaagatgaaa gaagattaaa tgttgctttg acaagagcta aggattattt atggataata   7680
ggaaatcgta aaaatttaga aatgaatgaa acatgggatt gtttaattca gaatgctatc   7740
ataagaaaat gttatttaga tttaaaaatt aattttgaaa acagtaccac agaaaatatc   7800
ataaaagaga aagtcaatga ttttttttata catttggaaa acgacataaa tgaaaaaaaa   7860
```

tatgaatcct cagaaatgag tagtaattta tcttctaatt cgtgtataat aaaagaagaa 7920
cacgatgaag aagaaaatta tgacgaaatt atagtagatg acgacaaatt atttaaaaat 7980
aaaaataaat ttagattaaa taaaaataag tataagcaaa atacaatttg gaataattca 8040
ggggacaacg aatttagttt tagtcgagct tatacaggaa atagttactg gtctaattat 8100
agtaataaag aaagggaaaa aaataaaaat tatgataaaa agggtaaaag gaaaataaat 8160
gactccttac ttgacgatga tttgttaaca aaaagaagaa aatatgaccc atatgataat 8220
tcaaatgtgt ga 8232

<210> SEQ ID NO 42
<211> LENGTH: 4962
<212> TYPE: DNA
<213> ORGANISM: Plasmodium falciparum

<400> SEQUENCE: 42
atgagtactg gttggaattt taattttaaa aaaaaaaatg gaagaagaaa aaaaggtgac 60
ttaaaatacg tgcagctctt tagtagaagt ggcataagta ctttgaaaaa tgaaaatgtt 120
atttttgaaa aaggtttgaa ttgtggacct gcaggaagaa atgcattaat tcgatggatt 180
gaatataact ataaaatgaa aaacgatgaa gagaacagtt accctgctgt taatgcttgc 240
aaaatatggc aaaaaacaca atcatttcaa gatgttgtat tgtctggtat ggtagacttt 300
ctaaaatttt taaacgttcc aaagcacgta acatataaaa atgtttttga taattatcta 360
tctccaaatt ttataaacaa aattaattct attggaaatt ctcaaaaaag cttaataaga 420
ttggctagta aaatgactcc catgttccaa gttagggaaa tccaaccctt attttctgtt 480
ttattagaaa agataaatgt aatacctgta aagatattaa acatattagt agaggatacc 540
cccgctgctc aatactttta cgagataaca tgcctaaatg taaaaaggaa aatttgggta 600
atgtgggccc aaaaatttta tgaagaaatt gaacagttgg ttgaagaaat tattattcat 660
atgaaattaa atgataatca tgaatacata aataatttaa taaataaaat tatagatttt 720
attggagatg gtacagaaaa atattactta tataatttat gtatacatat tataagattg 780
aaatctgtaa atacaatatt aaatcataat gaataccttt catctaatca ttataatgat 840
aatcttaaat atgatgaaca ccataatatt accatgacaa atcaaactaa taatattaac 900
aaaatttcaa aaaatattga tatatataat aataatataa ttataaatga taaaaaaaat 960
aaagaaccaa ataaaaacta tttaaaatta aatttaaatt ttaacaatat atcagaaaat 1020
caagatctac aacaaaaact tatcaaatta caatcatgtt ttgataatat catgaataat 1080
aataataata aagaaagtga tgatcagaaa gaaatgatat atagtaaaga aaataccccca 1140 tattatttac aacttcacga atattatcac aatagtactt catttaaata tttaaagaaa 1200
agaaaaaatg aaaaatatgg aaaagatata aatataataa acgatgaaaa gatattacta 1260
aataaaatgg aaagagagac cgattctatg cgtcttatta aaaatccaca gtatattcat 1320
aaagaggaca caatatgcaa gagaatttta tatcaaaata gggatgacaa tagggttaaa 1380
aaaataaaat ataacatgca tgataaggat gaagataatg agttggaaaa tatagtttat 1440
atggaaagaa ataaaattga agagaaaaca aaagatgccc ttgttaagga taaggagaat 1500
gtagaagagg acaaccttga aaatattaca aataagaata tgaacaataa taataataag 1560
ataagtcgta gtaatatatg ccatgacaat attacagata caaaagagaa atttcaaaaa 1620
acacgtaaaa ttaaaaccaa taacaatgca tattatgata aaaagaactc cttaccattt 1680
gataatatgt tctatagtaa attacgccta cttttgtgca tgcaatataa agagaaatat 1740

```
aatgttgttg ataatgaaat gataaagata gacaaatatt tttattttat agaatttatt   1800
aataatatta ttaaagatgg aatagttaat tttatagatg aatttaaaac aaaagaaata   1860
ataaaaaaaa tgcaatataa ttttaaaatt acaaatatcg atgatctata tgaatattct   1920
ttattactca ataatataca attaaaattt tctattattg aaggaatatg tttcaatttt   1980
cataaaaata attttgatat gataacacaa aaatgtaatg tacacttttg gatatcattg   2040
ttttatttag gtatttacaa taacttcttc tcattaatta aatatgctat cgataaaaga   2100
gagtcgatcg gtacaaaaaa gaaagatata aaaaaagatc agaatgacag acatataatt   2160
aagggggaag tcgattcaga tataaataca catgtttata acgagataat acacactgag   2220
gaagaaaagg attattatga aaataaagaa aatgttcatg aggaagtaaa gctacaaaat   2280
gatatcaaag aaatagagga ggaggagcaa aatgaatatg ctggtaagga tgaaattgtg   2340
agagataaac atttgaataa ttaccaagat gaaaaagatg ttcaacattt acatatatat   2400
gaattttatg aaaatggtca atattatcaa aattatgatg atggcatgaa attttttgag   2460
gagaaggagg aacctgatag aaaggatgaa tgtgatgaaa ataaaaatga tgatgatgaa   2520
gaggaagaag aagatgatga tgaagaggaa gaagaagatg atgatgaaga ggaagaagaa   2580
gatgatgatg aagaggaaga tgatgatgat gaacaggaag acgatgatga cgaagaagat   2640
gatgatgacg aagaagatga tgaagaggaa gatgatgatg atgaacagga agatgatgac   2700
gaagaagatg atgatgacga tgacgatgat gatgacgaag aagatgatga tgacgatgac   2760
gatgataatt ataatgatac ttataatgat gatgatgact ataataatat aaatcatgaa   2820
tataataaag aacaccctaa aaaaataagt aatggtggta ataataaaaa atatggtcat   2880
gtatttccta aggtttatcc acatcataca atttataatg attataataa aagaaataat   2940
tattatgaat ctcaagagaa ggaggacaca tggaaaaatc aaaagcataa aggtataaat   3000
aaacataaag atgattcaca tgaagatgat tcacatgaag atgattcaca tgaagatgat   3060
tcacatgaag atgattcaca tgaaaatgat tcacatgaag atgattcaca tgaagatgat   3120
tcacatgaaa atgattcaca tgaagaaaaa gaacaatata tatataacaa ggaattatat   3180
gaaaaaataa aaaaaaaacc aggaaaaaat atgaataagg aaatatatta taaaaaaaat   3240
ataaaggaag aatgtatggg aaatgaccaa aacaggaaca ataataatga taataataat   3300
aataattata ataatattga tgatataaaa aatgataagt acaaattatt ttttaatttt   3360
tgtaaggata gttatttgaa aattccgata ataaatatac taagatatat agtaatatca   3420
aatgatattc caaatgaatt tttttcattt tttgattttt ttaaagaaga taatatagaa   3480
gaattaaaat caataaaaga aaaaaatact atattgttat tatctgcttt gttaaatata   3540
ccacaaattg attatataaa agtaaaaaat tttttttcta taattgaaga attttttttac   3600
cttgagaaaa aaaaaaaaac cccaaattta cagagtgata ataataataa taatatgaga   3660
gacaattttc ataataggta ttcaactgaa atgattaatg tggaagaagg gaaaaaatac   3720
ttactaaatg aaatttgttt agataaaaat aatataaggg acattcaaat atcagccgaa   3780
gatttagaat atagtgataa taacaatgta gacagtggtt atgatagtga tattaatagt   3840
aataagtata atagtaataa taataaacag cagcaaaaaa taaataacaa taatattaat   3900
aataataata ataataataa taatattgat agtaataata ttagagacaa tgtggacata   3960
aattataaag atgccattaa tcaaaatgat attagaacat cgtttcaaat ttatgaaaat   4020
gtcaacctag aatttgataa ggaaaaaatg tttaatgaac aaaaagaaga gagtataaaa   4080
```

-continued

```
aatatagata atggaaatgt ggatagttta aataataaat atctttttga aaaattagga   4140
agaaaattga taaatactat atataatatg agcaaagaaa ttagtgataa taaattttta   4200
ataaataata atatatgttc catatatata tatttgaata attgttgtaa gaaaaaaaat   4260
atgcaaaaac aaaataatat ttctttttgg aataaagata aaaatataca tacttctttt   4320
gatgaaaatt caattttgta tatgccaaaa gaaatgaacg aaaaattcta taattgtaat   4380
aatcttgtta agaaatattt tccttatatt ttgaaaagtt ccttttttcat ttttaatatt   4440
ttaaaaaaaa aaagattgat acatatttat ataaaatata tgtatttata tgaatattta   4500
taccatatga tattaaatag aatattatat atcagtacaa tcaaattcta tccttttcta   4560
caaaatatta ttttaaaaga attaaattat tattttcatg atttcaaaaa tgtaacaata   4620
aaaaattttt ggaaatttta tttatatgca cacacattaa ttgatatcaa taattcaaaa   4680
attattttaa caaagaaatt atttcataat aatgccattc aatattttat aaagcttttt   4740
tattatctct cattttacaa ccctatcttt tctatccttt ttctaaacct catacggaca   4800
cccctatttc ataaaaatat tgaaaataaa agattggaaa ttttacaaaa tatatggaat   4860
ggagcacatg aaagatattt tttatttttg tctaaaagaa aaatatattc cattgagtat   4920
aaaatatggc tagatgaata caataaatgt tccgaaaaat aa                      4962
```

<210> SEQ ID NO 43
<211> LENGTH: 4653
<212> TYPE: DNA
<213> ORGANISM: Plasmodium falciparum

<400> SEQUENCE: 43

```
atgaaccttc ttgtaatatg tatttattac ctattttttt taaatatcga aaaaaatatt     60
tcctgttcat gttctactac aaaaaataag agtacttttg taagtttatg ggataaattt    120
cgtcaattat ttaaggataa ggaaatagag aaagagaaaa acataataac atataatttt    180
ataaaacatt ataatgatga gaaatatgtt attgaagaaa ataagaagaa taggtatttt    240
acaggatatg aaataaatca tataaatcgt ttaatatata tgaatagttt taaaacatat    300
atattgagtg catatattcc atatatatat atgagtgtac gagatatata tatagtttta    360
aaaaaaatta aagaattaaa ttttaataca gtatatacat ttttattttg gccagaaaat    420
gaatatttag aagatgaata tgatatgaat aattcaaaac tttttttattt attaaatttt    480
tgtgcatcta atggattatt tgttatatta gacataggtc catatattaa taatatatat    540
aattcaaata ttcctacata tattttattt aataaaaaat taaatgatta tataagaaat    600
aaatatatag aaaggaaagc agatttgtat aaatattttt tatcaccatg ggaaaatata    660
tggaaaagaa aaagaaattc tcttattaaa gaaactagaa atttgaatag acaaattata    720
gaaaagaata taaataatac aaaatctttt tataagaaaa ataattacac atataataat    780
atatatagtt tatattattt taatagagtt attaaatggt ataattatat attaccacaa    840
ttaaaaaaat atatgaatat taataatgga ccaattatat atttaaatat agataaaaca    900
tttgataatt attatatgta tataattata gatttaaaaa gaaaaaaaat ttttaataac    960
atatgtaatg cacaacatta tatggaaagg tcaaatgtat cttattataa taataaaata   1020
atagatcatg ataatatatc atctattaac aaatcatcaa gttcagaatt ttttttaaat   1080
tgtgtaatct cttttttttag aagaattcga agaagttata ttatgacttt aggatattta   1140
ttatatataa aatttaataa atatttaaga gtaatatatg aatatgattt aggtttatta   1200
tttataaacg aaattaataa attagtacaa aaacatttaa ctaaggttaa tatattaaca   1260
```

```
accaattatc cttatataaa tgatgaattt attaattcat atgcaggaaa taattgttat   1320
aatcattttt taaaaaataa ttggtttgat aatgaatgta taaatttaaa taaaccatgt   1380
atatggtctc aggtatggac aggggcaaaa tatagtatcc acaacgtgaa ctcttccagt   1440
atattaaaaa ggaaatatga tgatcatata ttatatacct ctccttatgt taacatagaa   1500
aataaggtgg acaaaatatc atctccccat cctgatcatg ataaagcaaa tgataaaaag   1560
gggaaccaac ctactgaaaa aaaggataaa caaaaaaata ttgataataa aaaaaataat   1620
aataataaca aaaataataa taataataat aataataata ataataataa taaaaataat   1680
aataataata ataataatta ttatagtgtt gataaggggg gaagtgtaca aaataaagaa   1740
gagttgtcac acggtaaaga cgatggtata actaataatt ataaagattc aaaaaaatgt   1800
tataaagaca aaaagataaa tatggatgat ataaattcga atgtaaaaaa aagaaggata   1860
caaataaata agaataataa ttattataat aataattata taggtcatat aagaaatttt   1920
aaagatctaa cattcaacat tgtagtattt atagcgaaag gtggagtatt tttaaatatt   1980
tttccatatt atagcggcaa taatattaat aatattcatt cgtatataga acattatagt   2040
aaagaaacag gacaacctct agatttatat tttaatcata aagaaccttt atattcacat   2100
ataaaacgta tctttaaaat attatacaag tatggaaatt atttattaaa agatgaatat   2160
tatattaatc caataaagat atcgaataat atagaattat atgattatga tataataaaa   2220
ataaatatgta attataatat taaaggaagt actttttgtta aaattggaca tgttaattat   2280
aatattaata gttttagctg tattatatat catgaatata aaaagaaaat aatttatgat   2340
acatcctata attattctta tgaatattct tatattaata aaaaagaaac atataaacct   2400
attgacaaat atttatattc attaaataca ataaatactg gtccattaat gtgtataaaa   2460
gaaaaacaac aaaaaattat taaaccatca aataaaaata aaaataaatt atctaaaaat   2520
ataaatattt ataagaaaat atttacatac ctttttccaa ataatttctt tcatagtgtc   2580
tatgaaataa atgtattaaa ccatttttat ttaactatgg actttaccaa atttcagtgg   2640
tatattttat ccttcaagaa tacaatgaat tatgttaaat tatttattag taattatagt   2700
ttatatatat atatatatgc agataataaa tttatatatg gtggatttaa cgaatataaa   2760
tttatagaaa ttatgaactg taagcatata tatattatat gtgtaaatct tggtttggga   2820
tttcccaaag aacaagtaag aacagaattt tttaattata ttaatttcaa tcatttgaaa   2880
tataattatc aggaaaataa ttttaatagt tcatctcata cttccataaa ttcagatcac   2940
aatatgaatg accaaggtgg accatatttc aacatgaata aatctgcatc atcaaaaaat   3000
aagagaggta tccaagaaac tgggaaaggt aattctaaaa ataaaatgga tcatgataac   3060
aggaaggaag ttgtaaattc agacaaggat gaaaaacatc taaaggaaca gaaagatcca   3120
aaggttatga ataaattgga taaaaatcat ccaaacggca acaacaacaa caacaaaaaa   3180
aattataata acagcaaaaa ttataataag gacaaaaatt ttaataataa tgttagtagt   3240
aatggatata ccatttttga cgacttatac gattattata aaaacaagac agaacaaaat   3300
cataatatat ataacaattt tatgtatgat gaaaagaatt ataacatgca taattattat   3360
gatgaagaca gtacgaacac gtatatattt atagtaacga gaaatgagta cgaattattt   3420
aactgtgtag gattaaatgg ggaaataata aaaaatgaaa aacatatgaa tgaatataaa   3480
aaaatgtata actttttgga ttattcattt gtaaagacat atttaatgaa tactcaaagt   3540
agtaatacaa atgatgtaag tgaacaaaat aaaaataaaa ataaaaataa aaacaaaaat   3600
```

```
aaaaaggaca acaagggcaa taataataat catgatgatg atgatgatga tgataatgat   3660
aataataagg tgataagtaa agataccaat aataatgata aaaattatat acagtcaaat   3720
gataatatcc aaattaacaa tcaaccgaat caaataaata gagactacca gaattatcat   3780
aataataatt ttaaatcatt attaacaaat aaaaaaatag aaatgaaaag tattacgaaa   3840
gctttttaa atttgtgtac atctggattt ttttcgttca tatttaataa aataaaatat    3900
tattgtaaaa caggaatttt taaatatttg agtacattca ataaagttaa taaaaataat   3960
acgagtaccc ctttaacttg gtatacatta ttatacttta taaaaaatat cgattttctt   4020
cgttctaagt attctttaaa attgtcaaca tatgataaaa aaacaaaaaa cattgatggg   4080
ttatttagag gttttgtcta tattaataat catttttag gaagtttctg gataactgat    4140
gatgtggata gttatgaaaa agaaattaat gaagatgaaa aattaaaaaa tggaaaaaaa   4200
atcaaaaaag aaaaaagtaa atttttaaat aatgaaaatt taatacatat accattaaca   4260
agatatatga gaataccaac agactggtta gttgaaggta caaatattgt tattctattt   4320
gatgagtttg gaggaaatcc atataaggta gaaattgtaa gagaaatact acatggtggt   4380
gtatatagac taaccaaaaa agaaaaatat gtaaactgga ttctcttcct ttttatttta   4440
agtattattg tttttattac ttatttcttt tttaaagcat tacataatta ttttaaaaca   4500
aaagaagaaa aagaaagaaa caaacaaaat tatcaaaata ttatagaaaa tattataaca   4560
cataatatat atataaatag ttcctatgat gatataactg aagaaacaaa tacggaaaat   4620
atccaaaatg ttagtgactt cttggactca taa                                4653
```

<210> SEQ ID NO 44
<211> LENGTH: 3624
<212> TYPE: DNA
<213> ORGANISM: Plasmodium falciparum

<400> SEQUENCE: 44

```
atgtttatac attcttgtaa tttctattta tttttattat tttattttat atttattaac     60
tgctcatata tacattttag aaaagaaaaa agtaatatga ataatcataa gaattattgt    120
tatgatggga gcataaaaga tgcatgtatc catgtgaagg aaaatccttc atcatatgat    180
aataataata tagaacatat gaatcaaatt tggaataatt cacctacaaa tataataaat    240
actaaaaaag tctcaaatgt ggaacaaaat cttcagaagg atactaaaaa atatgatctt    300
catgatagaa actatccaaa tataattaag gaagaggaaa atattttttt acttacatgt    360
aagaagtttg ttaatttcac aatacagaaa cgtttctttg ttgtgttaag catcttgata    420
ggtttttat tacttatgtt agtaagtata ccattgtacg aaactatgat ttctaataaa     480
atagaaacat cttttgtaac ctttgataat agtttaaaat atattagaaa tatctatcct    540
ctaacatttg aaataaaaaa ggcaggagat gtcttaacac aatcaagtga caagttagga    600
aacaatacca atcattttat aaatatttat aaaaaagata aaacagctac acttatgttt    660
ttttcagaaa ataataataa taaggaaaat cacatattag attataatac tttaaaagat    720
atattttttt tattacaata ttttaaacaa ataactatat tgaaagatca gaaagaaata    780
tactggaaag atatatgtaa aaaatatgat acccctctta gtaatccaaa atgttttgtc    840
ttaggtcttt ttacaataag tgaacttaca aatataaatt ataataatat agaaaaatgg    900
aatgtatttt ttgataaaat aataaaagaa gatacaaaat atatcaaacg ttttttttct    960
caagctctat actttttacc taattttta tatatcccaa atcattttat atataaaata    1020
gaggaacaac aaaatatgca taatataata aataaaatat atactaatat aaaaggtctc   1080
```

```
ttatttgttt atacatttga tgataatata tcaaatgaat tattagataa ttggtataat   1140
aaattaaatg agtatataca attaattaat aataataaat tatcatatat taatattaaa   1200
aatcccgatg gaacaatata tacacatatt ttaaaataca acaagatgtg gaatgtatta   1260
acaataaatg ataaactatt acaagatgaa gaacaaaatt caatactttt aggatttcaa   1320
tcaaattatt tatttattat actttcatta ttatttatat tttttatat aaatattaac    1380
ctatcaacat ttgtaacgta tacaaaaaaa atcgttttac ttatatgtgt atatttatta   1440
actttttttt ctttgtcgtc tacatttttt atatacttaa tatttaaatt gtatataatg   1500
cgtatcttct tgttgaatta ttttgtcttg tttttttga gtgtcttatt ttgttgtgtc    1560
aatattttttt attataatca atattgtacc tcacccggga aggattcaca taataataat   1620
atatatgaaa atttgaataa ccatatttat aattcatcat atcccattag tgataaccat   1680
atggaaactt tctattacct ccaagcaact tataaatcct tatattttaa tgggaaaata   1740
acattggttt taatatctat ttatacaata ggcttatttt gtagttacac gattacaaaa   1800
tggttctgct taaatacaat attttccctt atatctttat atatttacta tgtcttcttt   1860
tttaataaca tattttccta tttattgtat gtcaagggaa aaaacaacaa tattaactat   1920
aatccaaatg atcaaattaa agtaatagat tattccaagg tgaataatga agaagataaa   1980
aaagaaatga ttattttttt taatgcacaa caaaatgtaa ataataataa ttgcaacaat   2040
attgaggaaa ataattatcc gttcacaaat aataacatcc atacaaataa tgatatactt   2100
aaaaataatg atatacttaa aaataatgat atacttaaaa ataatgatat acttaaaaat   2160
aatgatatac ttaaaaataa tgatatgctt aaaaataatg atatgcttaa aaataatgat   2220
acacacatgt atacaaaaaa atgtgtcaca aaccattttg acaaaatgaa tacctttcaa   2280
aataatactc aatatacaga acataaaatg tttaataaac caaaaaaata taatgaaaaa   2340
cctttccaca tttttaaaaa aatatcccta ttacttcttc tcatcttgtc attcctaata   2400
ttatacctat acatatttat taataataaa acacagttta gtatttttag gtatatgaac   2460
aaaaattcta atgttagaat gtttatagaa atatttgaag gtatagctaa ccatgttatc   2520
gaaccaggat atttagtatt gcctgaatca tttaattatg aaaaagaaga taatctaatt   2580
aatgttgtta aattaattga agatttgaaa aaagaaaaat gtatttataa tccaattata   2640
tcatggatat caacatttga acttctaaaa aatgattgta caaatataga ttttttgat    2700
acccaatatg aattagataa taactcagaa gaatgcatta attataattt acaaaatgta   2760
gggaaaaaaa acaaaaaatt atatttagaa ctattaagtg cacaattttg taaaaatata   2820
cagaaaccat tatgtgatac atttaataaa ataatttata attggattca tcataaaaat   2880
gatgatatat atgagagtca tatgtttcaa ataaaaacat cttataacga taatattgat   2940
cagattcttc ctcaatacca tacaatatct cctcatatat tttacgacaa atacataaag   3000
atggacgaga attataacat tttaaatagc aggataggtt ccatttttca taattaccca   3060
agttcttata acaaaaatat agagacaatt gaaaaaataa ataatgttat taaaaatagt   3120
aatatagaga atatatattt ttattcagaa acgtatgttt tataccaaca agccatgaaa   3180
tttcttaaag aattcaaatt tatgttcttt ttttatatat tcatctatat tatttctata   3240
tatatattta ataaaatggg agtcccaata atctttccat tcttattatt taatagttta   3300
agtatgttat attttactta ttttttttct attaatactg acgccataac aattatatta   3360
ttaaaaataa ctactgctat atcattatcc aattatctat attccacttt gtattttaac   3420
```

-continued

```
aaaacaaaaa atggtactct tcattttgat aatacgataa agaaatcgtt accatattta   3480

ttatttctaa tattatattt aattagcttt agtgctggag attacatttc gaatgtcgtg   3540

aggttgtaca tcttaaatca tgttctatgg tatattttat attctcttac catattttgt   3600

atacacagaa ttatgtataa ataa                                          3624
```

<210> SEQ ID NO 45
<211> LENGTH: 684
<212> TYPE: DNA
<213> ORGANISM: Plasmodium falciparum

<400> SEQUENCE: 45

```
atgggtagta aaaaaaatag taacactgtt gattcctcag aaaatgttga ggaagttgtt     60

gataatttaa cgagtgaaaa gaataaagag agtttgaaaa aagataaaag aaaaaaaaaa    120

gaaaagaaga ataatgatgt tgatgatata aatgaagaag aagatgaaga aggaaatgat    180

gaagatacta tgaaaaaatt ttctgttgat actagtgaaa atgaagatga taaggaagat    240

gatgatgatg acgaagatga tgatgatgat gacgatgatg atgatgacga agatgatgat    300

gatgaagatg atgatgatga tgacgacgat gatgatgatg acgacgatga tgatgatgaa    360

gacgatgacg atgatgatga cgatgatgaa gatgatgatg atgaagatga tgaagatgat    420

gatgatgatg atgaagatga tgacgacgat tttgatgata tggatgaaga tgatgacgat    480

gatgatgatg atgatgaaga tgatgatgac gaggaggatt atgatgacga tgatgatgac    540

gatgatgacg atgatgaaga cgatgatgaa gatgatgatg aagatgatga tgatgaaaat    600

gatcaaaatg aatatgcagg agatgataaa aaagatgaag atggagatgc aaaaaaggga    660

agtgacgatg aaggttttga ctaa                                           684
```

<210> SEQ ID NO 46
<211> LENGTH: 1407
<212> TYPE: DNA
<213> ORGANISM: Plasmodium falciparum

<400> SEQUENCE: 46

```
atgggaaagc atatacgaat tttaaaaaat caatacctac aatttatgtc gaagagatgt     60

attcaaagca aggcggcttt taacatatgc ggtaaaatta acgtagaaaa ccctattgta    120

gagttagatg gagatgaaat gactagaata atttggaaag atataaaaga aaaattaatc    180

ttaccatatg ttaacttaaa gataaaatat tttgatttat ctattgaaaa tcgagataag    240

actaatgatc aagttaccat agaagctgct gaagaaataa aaaaaacttc agtaggtata    300

aaatgtgcaa ctataacacc tgatgctgca agagttaaag aatttaattt aaaggaaatg    360

tggaaaagtc caaacggtac tataagaaat atattagatg gtactgtttt tagaacacct    420

atacttatta aaaatatacc taaactagta cctaattgga agaaaccaat tgttatagga    480

agacatgcat atgctgatca atataaacag aaatctttaa aaatcgaaaa aagtgggaaa    540

tttgaaattg tatttactcc agatgataat tcacaagtac ttagagaaac tgtgtttcat    600

tttaaatctc ctggtgtatg tttaggtatg tataatacag aagaatctat acgaaatttt    660

gcattgtctt gttttcaata tgctttagat cttaaaatgc cagtttatat gagtactaaa    720

agtactatac taaaaatata tgatggttta tttaaagata tttttgatga aatttatgaa    780

aaacaattta aaaaatcttt tgaacaacat aatttatggt atgaacataa actaattgat    840

gatatggttg ctcaagtatt aaaatcagaa ggtggatttt tatgggcatg taaaaattat    900

gatggtgata tccaatctga tgctgttgct caaggttatg gaagtttagg attaatgtca    960
```

-continued

```
tctgtgttat tatgtccaga cggtgttacg tgtgtttcag aagctgccca tggtaccgtc   1020

actagacatt atagagctta tcaaaaggga gaaaaaacat caacaaatcc tatagcctct   1080

atttttgcat ggaccaaagg attagaacac agagcaaaat tagataaaaa tgataattta   1140

aaacaatttt gttatgcttt agaaaaggca tgtatcgaaa cggtagaaga tggattgatg   1200

tctaaagatc tagcaggatg tattaaaggt attaaaaatg ttactgagaa ggattatatc   1260

tttactcaag atttaatcaa tgctattaat gaaaaactaa aattaaagat acttcaaaat   1320

caatccaaaa atgatccaca agctacttca tataaattga aaaacgataa ctggaatttt   1380

tatgctcccc aagaacattc aacataa                                       1407
```

```
<210> SEQ ID NO 47
<211> LENGTH: 1446
<212> TYPE: DNA
<213> ORGANISM: Plasmodium falciparum

<400> SEQUENCE: 47

atgaaaaaat taaaccttct tatcggatgt atatccttgt attctataat tttttatact     60

gcaaaaattt cctgcacagt tcaggtgaaa aatggtggta ttgaaaattt ggctagttca    120

agtggacttt taaaaaatgt gttgaagcat tccccaagaa taagtgaaga agaaataaaa    180

gagagtgaaa taaaaataat aaagaatgct catgaggagg aaaagaaaat attggataag    240

tatggaaaat gtttaaagga ttatacatta ccttgtccta attattggaa gagaagaacg    300

gataagtatg gaaagaatgt gtgtatagct aatgaagaat ataatggttt ttgtgagcaa    360

gttcagatat ttgatgaatt tagtgagcat gagaagatgt catatgaatc tagttgtaat    420

gtagagtggg gatgtaaagg ttcatcaaaa gaaatttgtg aaagtggaaa aagagattat    480

aatgttccat gtcctgaagg atttcttgta caaaatgata atagttgtaa agctgatata    540

agtgtgtata gaggtatgtg taataatgag acaataaatt tcactcacct gaccagttca    600

gaaaaagaaa attggagtat tgcatgcgaa gcttattggc cttgttatac agactgtata    660

tctgaagagt atatatctga ttgtccaaaa aattggaaac aagtaaataa atatgattgt    720

atacctgata agaattataa aggtccatgt agaaatataa aaaattttaa atattttact    780

ttgtctatga aaaaagattt tgaagagaaa tgtaagacca agtttgagtg taataatatt    840

tgtgaaaaaa attatgaaca agaatgtcca ctcaattgga aagttgagaa aggatattgc    900

ttagctccgg atactttgga tttatgtaaa agaaaaaaaa tatccattga aaatatgaca    960

agaaaagaaa aagaaaatat tgaaaaagaa tgttttgtat cttggccttg tataaataat   1020

aaaaatacaa acaaaccaaa ttgtcaaata aattggctag ctgactgtcc ttttggatgg   1080

gacagaaaaa aagaagataa acgagatcag aagaaagatg aatatgtttg tatattacca   1140

actgagaaac aaatatatac agaggaaaat aaatttaatt cattaaataa agaaaagtgt   1200

acaaatatat ttttaaaaaa aaattcggat gaagttataa aaagagaaat agcgtctgtt   1260

tgtaacactc cttggccatg tttaaataat gagaagattt atatttccca taatgttgat   1320

catgaacaaa aagaagaaaa tgaaaaatta aatgggcctc ttacaaatga ggggaaaata   1380

tataaaaatg ggaaatatca tattgtggag gagggaaatt tttcgttatc tgacattatg   1440

aagtag                                                              1446
```

```
<210> SEQ ID NO 48
<211> LENGTH: 6219
<212> TYPE: DNA
```

<213> ORGANISM: Plasmodium falciparum

<400> SEQUENCE: 48
atggaaaaat attttatgaa aaaaataaaa ggagtatttt ccacttttaa aaaggataac 60
ccgaacatta ataataataa caatcataat aataccaata ataataataa caatcataat 120
aaaagcaaca ataataatag tactaatagt aatcgtaatg atgatgataa tattaaccga 180
caatctaccc aggaaaacaa ttccaccgtg ggaaacaaaa gaatcgttgg aatgacgaat 240
gatacatata aacaagaaaa agatttgaac tatttctttt ctgagaataa agaaagaaaa 300
gaagaatcaa acagtaatca caaaaagaaa aaccttaaaa acaaaggaca gaagaaattg 360
gatagtaatg agaaggatat gccagagttt agtaaaaaaa tgaaatatac caaattatat 420
caaaaagaaa atatgttgtc aatagataat tatataaaaa taaataagaa acatagttta 480
cattttgtaa aaagaaaata tacaaaaaga aaacttatgg cttccaatat acaaaatata 540
tgtaatttta taacagacaa aaataaaaat gagaatagta gaactaagaa agttgaaagt 600
ttagatgatt ataaggaaga aaataaaaac acacctaaca aggtggatga agaaaaaaaa 660
atgaatttgc aatatgaaca agaacataat aatacaaatg tagcacaaga aacaaaagga 720
gggaaaaaaa aaaagaaaaa aaatgtagat aggaatcaaa ataatttgaa ggaagataat 780
ttaaataatg atttattgaa tgaggatatt ctcacaaagg gacaatatga tcatgataat 840
aataataaga agaataatag tagtaatagt agcaacaata ataataataa tagtaataat 900
agtatgaatg aatataatat acttgatgat tcttccaata ttcaatttca taaaaaagaa 960
acaccatcta aaaaccaagg aaaaaacaaa tatatattca aaaacgtaga aaggaaaaat 1020
actgcagtat atgataaaaa caaaaacaca tctttaaata attatggaca gcaacaaaaa 1080
aaaatcaacc gtattgatga aatttttaaa aacttaatag agaaaaggaa aaaaaaagaa 1140
atgagacaaa aatacatgct caaaaaaaaa tttctaatga ataattataa aggaaaaacg 1200
aatgaaaatt atgaacatga acaaagggaa ggagaaaagg aagaaaaaca aaaggaaaat 1260
gatacttatg gtgattttga agagttagat gaagagatag aaaaagatgg cgaagaaaaa 1320
gaagaagagg aagatgataa aaatgaagaa gtagaagaac aaaatgaaga agtagtagaa 1380
aaaaaggaaa atgtagagaa acaaaagaat catcaaaata acaaaacatc aaataatatt 1440
tatgacaaca aatcatatga tcatcatgga agaaatacac acttattgaa aaaagaaaaa 1500
aaacaacgaa caaaacaaat tagtaataaa aatgttccta tgattgatga aagcactata 1560
gaaaaatgtt acaaacaaat gagaattttt gccgagaaat ttagttcttt caaaaataaa 1620
tttgaccaat attataatac cagtgaacat tggaatttaa agaaaaaagg gaaaaaaaga 1680
aaaaattcag taaacactag tgataaagaa aatatggaaa attatttctt tgatgaagat 1740
tctatgaaaa aagaaacaaa cgaactagaa gaattaaaca aaaatataca gaaacttttta 1800
aatgcaaata tgtctaatga tataaatgta gataaaataa acgaaattaa aaaatataca 1860
caagataacc ataataaaag ccttatgaaa aatataaata tttcagaaag catctatttt 1920
gattgtgaaa atacaagtgc taaaaaaaga aaatgttctg ataatgctag tgtaagtaca 1980
aatgaagaaa atttaaataa acttcttgag tatgctacaa ataaaaaaaa taacatgatc 2040
aattctgaag atgatataaa aactgatcag gaatatgagc gagacaagag gaagaaaaat 2100
aaaagaaaaa agaatatata tgatgatttg caaaaatcaa atgaaaacaa ctcagaggag 2160
gttattcatt tgttaagaga aaatgaagaa gaggaaaaag aagaaaataa acaaactaat 2220
atggaaaaac gaaagaaagg cagaaaaaaa aagaaaactg aagatataca atctgataag 2280
gttaaaatag aaaatgtaca atctgataag gttaaaatag aaaatgtaca atctgataag 2340
gttaaagtag aaaatgtaca aatggaaaat gtacaaattg aaaatgtaca aactgaaaat 2400
gtacaaatgg aaaatgtaca aatggaaaat gtacaaatgg aaaatgtaca aatggaaaat 2460
gtacatactg aaaaagcaca aaatgaaaat atccaaattg aaaatgtaca tactgaaaag 2520
gcacaaaatg aaaaaatcca aactcaaaat atccaaactg acaatgtaaa aactcaaaat 2580
gcccaacctg acaatgtaca aactcaaaat gcccaacctg acaatgtaca aactcaaaat 2640
gcccaacctg acaatgtaca aactcaaaat gcccaacctg acaatgtaca aactcaaaat 2700
gcccaacctg acaatactca atataaaaat gaaccattta aaattgaggc tattgaaaat 2760
gttctagaag aaaaagaaaa cttaagtgat aaacatttgg agaatcaagt agaagtggct 2820
aatgtttcga atgaagtttt tgaaacagaa atgaaaaatt tcaacaactc aaatggtaat 2880
atggataaag atataaatat aatcgatatt ccacacgaag atttaaataa atatataaaa 2940
gatgaactaa ataacaatga caataacaat aatctgttaa atatccaaaa tgttgaaatc 3000
atggaatatg ctgaaagcat aaaaagtgat aacataatta atgatactaa agaggatgct 3060
ctacccagaa acgaaaccct caattttctc aaacaagaat atgtatcaag taaagaacaa 3120
gaagaaaaaa aagacgaaga aaaaaatatt ttaaatgaac aagaattaaa tgacataaac 3180
gaaaaaatga aacaacaaaa taacgttgat tccaaattac ctcattttgc tattgaacaa 3240
agaaaaaaat taattaaaga aacaaaccga ttttttaaaa tgtataattt acatttaaaa 3300
attgaaaagt tacctattaa tattccgaat gatttaaaaa tacttatgca gaaaaaaaag 3360
aaaattgtcg atattattaa tgattacaaa attgttttta aaacattaca gaaatatgct 3420
gaaaaggaaa aaaatatttc ggaagaacaa gatggagaag aaagaaaact gtcacatgat 3480
aatctagata aacaaaaaga acaacaaaat gatgaacatg ataataataa tgatagtaat 3540
aataatgaaa ataataataa tgaaaataat aataatgaca atattaataa tgacaataac 3600
aataatgaca atattaataa taatgatata tgtattgatc ataaagtaac aaataatatg 3660
gtgctaaata cagatggaga tgaacaaaat aaagaacaaa acatatcttc ccaaacggat 3720
aaaggaaatg taattcttac gacaaaggat gaaacagttg ttaataaaaa tgacatatca 3780
tctgtattaa aagaagaaaa tgaagacaaa gaaaataaag aaaattccac acataaagat 3840
ccggatttat ctcttgatgt aaatgctgaa acaaaagaaa aggtacccag aagaagagga 3900
aggaaaaaaa aattagaaaa agaaatagaa gtacatgtag gaaaaagaag aggaagaaaa 3960
agacaaactg aagatatatt aaatgataat aacattaacg atgatagctt atattatttg 4020
agtgatagtt ctaaggaatt aatagaaaag gaatttaata agtttatgaa catatttgaa 4080
aacattaaca gaaataaacc aaacgaatca aatgaatcaa atgaaccaaa tgaatcaaat 4140
gaaccaaatg aaccaaatga accaaatgaa ccaaatgaac caaatgaacc aaatgaatca 4200
aataaaccaa atgaatcaaa tgtaccaaat gaatcaaatg taccaaatga atcaaatgaa 4260
tcaaatgtac caaatgaatc aaatgaatca aatgtaccaa atgaaccaaa tgtaccaaat 4320
gaaaacaacg aatccaatga gaaaaatatg aaaacattct ctaatatgaa tgatactttt 4380
aacgatcaac aaaaagatga agttattgac gatgctacta catgcacttt tatggatcta 4440
aataattgta catatggaga taacaagaat aatacaagtg agtacaacaa gaatgataaa 4500
caaacaaaca aagaacaata ccgaccaatt gattatgatg tagagaagga aatacaaaat 4560
tctgaaaaat cagaatattt tgataaatat gaaaattctt ttattcatca acttataaac 4620
gatttaatac ataataattt agaagaagaa aattatatac aattctcaaa tatagataat 4680
gaagaaataa aatacagaaa attaaaagag gtaataacaa acctaaaaat aaaagaaaaa 4740
aaaatagact taattttaag taataatttg agttttttca aatattcctg tatgtataga 4800
aagcgtcaat tattacatga gaaaatgtta ggaaattgga gttatgtaga aaatacaatt 4860
aataaaagag atgatattag aaataaaaat ttgccttttc aattattaaa actagaacaa 4920
aatatgttag aaaatatttc taaatgttat gatgatatat tattagaaga tttctctggt 4980
attattataa cgttaaatac aaattctttt gaaagagaaa cagatggaaa aattattaag 5040
gtgtcaaaag ttatatgtgg atgtttaatt gaatatctag ataatacatc agaattaaac 5100
ataaaatgta tatgggcaca tccattttta aatacaaaat ctacttatta cattttgtgt 5160
gcattcttac caagggttat tttagaagca tttttaaata gtaaaggaat attacataat 5220
gatataaatg ataaagatca tataaatatg gtcaattctg taaaggggga agggttagaa 5280
aatatgaatt ctgaaatgtg tgaattcaaa aattccgaaa aaaaaaaaaa aaaaaaaaaa 5340
agtttttatg atagattaaa tgaattagat atggaaaaaa tcaagaacga tcatcatgaa 5400
aatgataata ttaataattc tcataacaat attatcaaat tagaacaagc atatttctca 5460
aactattcta catatgaata tcctttaacc catcttttaa attttaataa agagtgtgca 5520
tatgccttaa attataatga gaaccttttc aaagataatg aaaataagca agacaatatc 5580
aacacatgta ataatatgaa aggtcataat aattgtaacg ataatacatc attatcttct 5640
aaagatagta ataacaaatt tttgtatata atatttagtg atattgatat atttccaaga 5700
cagtgctatt taattttatg ttcatacaag tatatgtgtt taaatatgca ctatgataca 5760
gataattatt ctgttcatta tgatttagaa aatatgaaaa aggaaaacgt ggggaaaacg 5820
acagagttat ctaatagttg tccttgcaaa tgtatgaaat ctattcccga tgattctgaa 5880
gaatcctatg agcgtataat aggtttgagt gaactttata tgtattatat gatacccaaa 5940
agggaggaaa gggaaaatct cggcctacta aaaagaaacg gttggagaga tttaatttgc 6000
agcacctttc ttgaagatgt acatgaaaat attagtagta tcttaaaaat taaaacacat 6060
attaataagg tatcagaaca tatatctgta caaaatagaa tttatgaaaa acgctacaca 6120
cctatatata taaataaata tgaatggtgt ggattaaaat tgaaggatat tcgtaacatg 6180
cttaacgaag attttaatta tgatggaaac gataaatga 6219

<210> SEQ ID NO 49
<211> LENGTH: 3711
<212> TYPE: DNA
<213> ORGANISM: Plasmodium falciparum

<400> SEQUENCE: 49
atgataaatg cagagggaaa taaatatgaa ctaccaaaag atgaggagat agaagatttt 60
ttacaaaaag tagaagaagt aagcaataaa atcaatgggt taatcaaagg gactataagt 120
attgaagagc tagacaaaga agagaagaag ttacgtttag aaaaaagaat aaaagaaatt 180
aaggaagaag aaaaaaaaga atatgaaaag aaaagatttc ttatgggtat agaaggaaaa 240
ggtaatgaag acaattattt atttttttgt tctttttgtt ttattttata taattatgat 300
ttgacaaatt gtgtacgatg taataaaaaa gttataagca aagaaaaaag gaaaaaggaa 360
ataaatgata aagtacaaaa gtataaaata ttaaaaaata aaagaaatat tagaagaaat 420
agatggaata catatttaaa agaacaagaa aaaaaaaata ataaaccaac atataaaaat 480
tatacaaatt atgaaaaatg gaatcattat gaaccaagtt cagatacatt tgatgaacat 540

-continued

```
gaaaaaatgt tatgtctacc taaaaataat gaacaattca aacaattcga aaataaatta    600
aatcaagata tacaaaaaaa aaaagataga caacaaattg catattctat caaaataaaa    660
ggaaatgaat attttaaaca aaaaaaatat atacatgcta ttgaatgtta taataatgca    720
ttagatttat gtaaagatta tttagattta tatgttaata tagccctatg ccaaattaaa    780
atatatcaat atgaaaatgc aatacttaat tgtaatcaag ttattcaata ttataatact    840
ttccgaacag atctcaaatt taatctatcc attattttta aagcttatgc aagaaaagct    900
ctagcccttt ttatattatt tcaatttaaa gattcattaa caaattttac tcaagctttg    960
gaatttaata aaaatgatga acaagtcaat gaatatatac aaaagtgtaa acatatttta   1020
aatgatcaac ttaactccca ctatggtcag aagcaaatac aatatctttc gtgtggtaat   1080
ccttctcatg caaaattaaa aaatgcacaa agtgaaccag aagcaaaaca aaccaaacaa   1140
aatatagaag gtgaaaaatg tgtggagaat aaaaaaaata tggaatgtga ggaaaataaa   1200
aacaatatag aatgtataga atgtgtagaa tgtgtagaat gtgtagaatg tgtagaatgt   1260
gtagaatgtg tagaatgtgt agaaagtgtg gaaaatataa aaaatgtaga atacaataat   1320
aatgacacaa atattcatat accgttcaat tcaaataatc aaaataatgc tttcctttta   1380
cacaatttaa aaaattcaga gataaacaaa aatatcatga tggaattgtc aaaaaaagat   1440
attaataaag aaccaaacct ttttatcatc catttaaaag gaataagaaa gaatataaaa   1500
aaagatgaaa taacaaaatt aatattctgc tctcatgtat atgatttaga aaaggaggat   1560
tataataatc cgaagcaatc aacaaaaaaa agaaaataca taactatgtt atctttcttt   1620
gctgataaac tgaatgatat attattctat ataaaaagga aatcacaaaa taatgattgc   1680
ttattctata cacaaaatat aaataataaa attttcaaaa taaacaaaaa tgttaaaaaa   1740
tgtacacatt taattattga tatcttaata ttcatacttg aaaatcattt ttattatgca   1800
gatttctgct taaacgctat caaacccatt tttacctttt actttttaag aaatgtaaaa   1860
gtatcaaagt gcctccatct cttatattct atcatatcta ataataatga aggaaaaaaa   1920
atgatttgcc aaatgttaga agagaaacat atcattttaa aagaactatt taacaaatta   1980
aataatttta tcctacatga aagaaacaca tatacaaatg aaaaaattaa aataatggaa   2040
aatttaaaaa ctcatatatt aacatgtaca tatgtgaaaa agtacctgaa cgttcaggaa   2100
ataaatgaat tagctagcca aaagtcagaa tttatgaaag aaaatgaata taagaatatg   2160
gagcacatgg aggagtacat aaaatctaat gagaaagaaa aactgggata caatacaaaa   2220
ataaataaag agatgaagaa aagaaatagt gataaaaatt atgataatat tttattatat   2280
ggttatgaaa aaaagaagga aatatgtatg tctgttttga aggatattat gtctattgat   2340
atgttgaaaa aggaaaatga aaataataga tcattaataa atgaagcatc aaaaggttct   2400
ttattttgta atattaatga tatggaaaaa agggtagaaa catatataaa aaatattatg   2460
aaaaatacga tgaaaaatca ggatgaagaa caaaacgaat gtttgacttt gttcagtttc   2520
ttatcatatt taattgtatt tccaaacatt ctgaatatta ttgaaaaatg ttgcatgcaa   2580
aatatgataa atattataat ttacataaat gaaaaaatgt atgattataa aaatatgaaa   2640
tgtaactata tattattttt attaaatttc gtaagtcaca tcaaagttcg tccttttata   2700
ttgacatgct cattatcaaa tatgcttttt tatatagaga agaatgaaaa tgataattta   2760
ctgaaaaata tcttatccgt actttttaat ttaacaataa catggctaaa cgaaatggat   2820
agcaagaatt ttattgtttt atcatattat ggagaaataa aagaaagtac atttcgtaaa   2880
```

ttaattaatg ctatggaatc aacagataag cgtgtgtgtg aattgtctat gatactttta 2940
tctagatttt atttatacat gtattgtttt aatgataaaa taaaagtaca gaaaaacata 3000
agggatacta aaaataaacc agatgatgta ttagagcagg tgcctttaat atttaacaag 3060
gatggtatag atattaaaca tttctatgat gaaaagacac aacaaaaaaa tgaaagttta 3120
atgaataaat taaaagaaaa aataaagaaa gaaaatgaaa aattatatga actagataat 3180
atatcatttt tatatttaaa aagaaatatt atgaattgtt tatcaatagt aaatatacaa 3240
aatgatcttc taataataaa tgcatgtata aaacttgtat acaatttatc gatatataca 3300
aattttatat ttaaaaatat aatatatgat caaacaaata caaatgaata ttactttaaa 3360
caattaataa gtcaaatttc ttctatcctt ttggatatta cactggacga aaaagaaaag 3420
aatgtcaaca aatcaatata tgtattaata aataatatta tcatgttctt tattcaaagc 3480
ttaaaattta tttgtataca taacatccat aaagaagaat ctatatatat cataagaaca 3540
attcaaagca ttattcctta tgctatcaaa atttcaaata gtaatgagaa aaaattgaat 3600
aaaaatattt ccatgtttgt atcatattgt tttttgaata aggatttaaa aaaaacaata 3660
cttgagttat atgataatga tataaggaaa gtggagcact taataaaata a 3711

<210> SEQ ID NO 50
<211> LENGTH: 3765
<212> TYPE: DNA
<213> ORGANISM: Plasmodium falciparum

<400> SEQUENCE: 50
atggaaaatg aatcgttcaa tcccctctct ttgttagata aaaaccaagc gtttgatgct 60
gaaaaattga aattgttaga caatgtggtg gaagctttat tagatactaa agataagaat 120
agaagagatt ttgcacagaa tttgttaaat caatttaaga tgttagatac atcatggaga 180
tctgtatcaa taatattaga acatagtgag aatgtgaata caaaatttta tggtttacaa 240
atattagaag aatgtataaa taatcgttgg aatatattac cttcagaaga aaaagaaggt 300
atgaagaatt ttatagcttg ctatactatt actttatcaa ctgaaggtac aacggttggt 360
gtagatagac atttattgaa caaattagat gagacattaa ttcagattgt aaaacaagaa 420
tggcctgatt catggtctag ttttattcct gatatagtaa attcagcaaa attaaatcaa 480
aatgtatgtg agaataatat gaaattatta aatatgttaa gtgaagaagt atttgaattt 540
ggtaatgaga cgttagttaa aaagaagaaa gagaaattga gaaatgaata tgctagtcaa 600
tttcaagaag tttataattt atgtttatat atattagaag caaatgtcta taataaaaga 660
agtacgaata catctttgat taaacagaca ttacattgtt tatctaattt ttttaaatgg 720
attcctttaa catatatatt tgataaatat aaatttaatg ataataatat tcaaataata 780
gatttattgt ttgatcattt ttgggatgat atatcttata aaatagaatg tgttaagtgt 840
atacaagaaa tagtaatgtt aaaaattgat gaaaaaaata tcctctattt tgataatgtg 900
tttataaatt tatggacaaa attagttagt aaaataaaat tattaccaaa tgcaaatgaa 960
atgaaaaaca tcccacccga attaaaaata ttttgggaac aatatttttt acaattaagt 1020
atatgtataa ctagcttttt aaaaaattat cgagaaaaaa ttgttgaaaa aaataataat 1080
actaatgatg taaatattgt attcaaattt ttaaatatgt tagctaatag taatatggaa 1140
gaagtatttt taattataat tgattattat aatattttta cagaacaatt aattagagaa 1200
ttaataactc gtttagaaca agaacataat tttaaaaata aaaatgatat gaattcttca 1260
tctcttgata tgaaaaatac attaacgaca aatatgaatt tagattcatc atctttaaca 1320

-continued

```
aatagaaaat catatagttt tgtaacaatg aataatgata taaatctttt aaacaacaac   1380
aataataata ataatagtaa taatatgaat agtagtaata tgaattcaaa tatggttatt   1440
aatattaatg aatattcttc tattttagat aaaattgatt taaatccatc agatattaag   1500
aaaatgtgcc cacgtataaa attatatgaa tttatattaa acgatattag aaagactgtt   1560
attgaaaaaa tggctaaacc acaagaaatt tatatttctt atgataatga gactggtgaa   1620
gttgttcgag attttgaacc agatactact gaaatttctt tatataatac tatgaaaaca   1680
acattggttt atttaactta tttaggttca gaaaaaacca tggaattaat tgttgaatta   1740
ttaaataaag aatcagagaa atcgttaaaa aatacgaata aaaatgaagt atggaatagt   1800
accaaaacga atagaattag ttatgccgtt ggttctattt ctatgtgtat gactttaaaa   1860
aaagaacaag actttttaat gtacattctc agaatatatt tacatatgat tgaagttaaa   1920
aatggcgaag aaaatagagc cattctagct tcatgtgtta tgtacattgt tagtcaatat   1980
catagatttt taaaacttca ttggagattt cttaaaacgg ttatgaaaaa attatttgaa   2040
tttgctgaga atgaaaaggt acaagatatg gcagctgaaa cgattttaaa aatatgtaaa   2100
caatgtaaaa atgttatagc taaaaataat cataataatg ataataatga atcttttttt   2160
agtacattta ttaaattcca taataatatt atgcataagc taccagaaaa attgaatctt   2220
ttattatatg aagctatagc tcatgttatt tcatgtttcc cttatgaaga aaaacaagaa   2280
agcataaaag tgttaatgag caaattaatg aatttatgga attcattaat atatgcaaat   2340
aataatggtg ctataaaaga tatgaataat acaaattctt taaataataa taatataaat   2400
aataacaata atattaatat taataatgat gatatgaaaa atttagaaca tttatgtact   2460
tatgaaaatt ccaaattgat tattacattt gttagagtaa attgtagatt agcatatgca   2520
ttatcctatt tttattatga acaactagct ttagtttttc tagacttttt aaaaatttat   2580
caactttata gtaaattcat taatttagaa gtagaagcaa atggtacaaa aagaattaag   2640
catgcacaat ttagaaattt gtttttaatg aaaagagaat tcttacatct aatcgaaact   2700
accatagaga gaagttgtta taatatacaa gatttagaaa aggaattgtt aaaaagagag   2760
caaaaaaaat taaaaaatga aattgatgaa tccatggaaa tccatttacc aacaatcgaa   2820
gaagcaaaac aaataaattt tcaaatgact agtaatatat taaatgtatt attagaaact   2880
atattagttg attatagaga tagtaatcca catataaaag atgcagaagt attttcatta   2940
ttatcaacag tctttaaaaa aatcgaaaat gtaacatgtc ctatcttacc tacagtacta   3000
aattatgtat tattaccaac aatagatatg attaaaaatg atttctcatc ttatccagaa   3060
catcgtgaaa aattttataa tttcttagat gcatgtgtaa gacattgttt tgattattta   3120
tttacattag attcagaaat atttaataca tttattcaat ctttattatg ggctataaaa   3180
catgaacatc catcggtagc tgatcatggt ttaagaataa cacagcaatt tcttcataat   3240
attataataa agaaaaaaga atatctagaa gaattttgta aggcttttta ttacattata   3300
ttaaatgaaa tactaaaaac actaacagat tcttttcaca aatctggttt tcattatcaa   3360
accataattt taatgaattt attacgattg ttagaatttg aagtagtaaa tatacctgaa   3420
gtagaaataa caaaaccaca tataataaaa catgtacaaa actttttaac tcaatctttt   3480
gaaaatttaa accaaaaaca aatagagaca ttctccgtcg atatgtttaa tttttgtgtg   3540
gagtctccat cagcctttcg atctttcgtt cgagatttgt taatatcact aaaggaattc   3600
gcaacaaatc aagatgaact ttatgaagcc gacagacaag aagcattaca gagagcaaaa   3660
```

atggcagaag ataataaact tataaagtta agaggattaa tgaaggaaga tgtcccaagc 3720
ttttcagcta tagatgttga tgacgaatgt ataaacgttg aataa 3765

<210> SEQ ID NO 51
<211> LENGTH: 4125
<212> TYPE: DNA
<213> ORGANISM: Plasmodium falciparum

<400> SEQUENCE: 51
atgaacgaat atagtgtata taataaaccg aactctaaca atatttctgt atctaagggt 60
acaagtcgaa tttttaaaaa aatcaaaaca aataaaaatt atggttcctt agctataaaa 120
aaagaaacac ataacgagct taatggtaat actaagagga atgtgtctga taaattaatt 180
tatgaaaatg aaacaaaaac gatgataaat aataataata ataatatgaa cgataataat 240
aataattata gattagatat attgacagga agtgaggaat atgaaaaaaa tgatatttca 300
tatgttcaag aggatagtga cattatggaa catataaaat tagaaggaaa tgaaatagac 360
tacgaaaaga tggtttatgg aaatgataag gaaagaagca aagaaaagaa aaaaataaat 420
aattatgata aaaatataca aggtattaaa atagaagaag atataaatga atataagaaa 480
gtgaaaaaat gtgatgttgc aaagaataga gtaaaaagat tagaattagt aatagacatt 540
gaagaatata atgataataa attagaaaat gaaaatttgt tacaaaaaaa ttatgcaaaa 600
aatatatcat ctgatgaaaa gaaatattat tataataatt atattttaa tgatgattta 660 tataatggga aattaaattg tctaacaaaa acattagatt ttttagcaaa agaagagcat 720
attaatccta atggaaattt agatgaccaa gaagatagtg aaagcgtttg tgttattgaa 780
aaaagaacca taaaaaattc ttcatcatgt gatgaaaaag aacttattga aaaaattaat 840
ttaaaagata actatgtttt ttttaataat aataataaag agaaaaacaa aaataagttg 900
aaagataaaa acaaaacaaa caaaataaac aaaagaaaaa aaccaaacca ctctaaaaca 960
aatgacaatg atcaaacgga gatatataaa aaaacaaaaa aaatgaacaa taagaataat 1020
aatggtaaaa ataaaaataa tcatatgaat gttcttgaaa attttaatgc taaacataac 1080
atgaattcaa caacaagaca aaataataat aatatcaaaa aaattaagag taataataat 1140
aataataata ataatgataa taattattgt tattattata aatcgattga taaaaatgtt 1200
agttactata atagtagatc tagtagtaaa tctgatttta atttgtatag taacaccaca 1260
agtacccaaa atagttacag tagtatttat aatgataatg ataatgataa ttgtattaat 1320
agttgtgata gtaattataa caataattat aataatattt ataacaacca ttgcaataat 1380
aattttaata ataataataa gcttccttct agtaattata ccaaaattat gaatgataca 1440
aattatgtta gttcaaatga tgatagtact aaaatacata taggtataaa agaagaaaaa 1500
aaatatatta tgaaaccaga agaacattta gaaaatttta ttaaaaataa tagaatatat 1560
aatgattcag gttgttatgt gataagtgac gactgtgtaa ttcctaatta taaatatgaa 1620
caagatgatg tttatgttga aattatagaa aataataata ttactgatgg atataataat 1680
ctacaagata gttttgaaaa aattaaagaa ttttggagtt cctccaatgt tactagtaca 1740
acgaataaaa ataataataa taaaaagaat attattttgt atgatgaaca aaaagatgac 1800
aatgaaattg atcataggaa gacatcaaaa aatagcaatg ataatcttaa gaagagtcaa 1860
aatataaatg atggtatgaa gacagcgaat agtagtatta aaaatgatac gaaagatgag 1920
gaggaatata aaaagagtat aaaatcaaaa aataataaaa ataatagaaa taatgatgat 1980
gattatatga aggaggaaga tcaaattaat agctttttac catcaaacga aaataataat 2040

-continued aacaataata ataataataa caataataat aataataaca acaataataa taataataat 2100
aataataata ataataataa taataataac gattgtgata caaagtatga tgctaatatt 2160
aattcgaaat gtaatagaaa taatatttat aatataaata gttatcttaa tgtagttggt 2220
tataatgata ataagaaaaa cgatactatt aatgacaaaa ataataataa caatatgaag 2280
aatgataaac ctgaggatga atgcacaaag aagaaagata ttaataatag taataataaa 2340
aattatagta gtaatgataa tataaataat ggtaataata agaattataa tgggaataat 2400
aagaattata atgggaataa taagaattat aatgggaata ataagaatta taatgggaat 2460
aataagaatt gtaatgggaa taataagaat tgtaatggga ataataagaa ttataatggg 2520
aataataaga attgtaatgg aaataataag aattataata gtaataataa gaattataat 2580
agtaagcata atagtaataa gggtcatagt aaagaccata ataatggtca tagtaaagac 2640
cataataatg gtcatagtaa agaccataat aatggtcata gtaaagacca taataatggt 2700
catagtaaag accataataa tggtcatagt aaagaccata ataatggtca tagtaaagac 2760
cataataatg gtcataatga tgatcataat aatgatcata ataataataa tgattcattt 2820
aaatgtgaag aaaatgtctt ccaagaattt aacgaattta tgagaaaaaa aatgtggatg 2880
gaaaaatatt tacataatca aataaattgt tatgatgtct tattagaaat aagaaaaagg 2940
gtacctagat ggggtgatta taaatgtaat tttttttttc attggaagaa aattatggaa 3000
ttaaataatg aagaattaaa aatttatata ttaatattta ggtccttgtg taatgaaaat 3060
atcaaaaaaa tagattttta tattttaaaa attattttaa acgaattaga tgaattaaga 3120
aaagtgaatg aaccacatta tgtatctttt gaatttacac aagattgtat aaataatgga 3180
gaaacaaaat atgttgattc ttctgatgta tattttaata tgaatcaatt tgtacaacca 3240
tggtatttga aaaatcttaa taaatctatg gatataaaga aattcttgaa ttcattagat 3300
atcttagaaa accaaaagaa aaaaacatat attgttcatg gtatggagat acctgaacag 3360
atattcaaca tgtataatac tagcaaaaaa aaagctaaaa aaaaaaaaaa atgtagtaaa 3420
ataaatacaa atgaacatct atatgatcaa ccaagtacac attctgatgt acctctaaat 3480
aatcagttaa aaaataacct tcagaagaaa tcgcaaaata atatatataa tagagatgaa 3540
aatagacagg caaaaaactg taaatattta aaaaaaacaa atacattatt aaataacgaa 3600
catattaata atatggtatc caatttggat aatacaaaga caaaagatat taataaaaat 3660
aaaaatatca atgaatctgt aaaaaaggca tcaatcaaaa attacaacaa aaatgttaaa 3720
aataataata aaaaatgtga taatacaaat gataataaaa atgataataa aaatgataat 3780
acaaatgata ataaaaatga taataaatgt gaaaaaaacga caaaggatta tgaagccaaa 3840
caagtcaata aaacattaaa aaaaaatgct aactctccca acaattctaa gggtaaaaaa 3900
agaacaggat tttatgattt agaaattgat ggggttattt catcatttga agccagaaaa 3960
ggtgtttatt atgataagtc aagaaaattg tggagagcca attggaagga aaatggaaaa 4020
atacaaacaa aaggtttttc agttaatgaa tataaatcgg ttcaactagc tagacaaaag 4080
gctattgaat ggagagagaa aaaagaagct gaattattgt tataa 4125

<210> SEQ ID NO 52
<211> LENGTH: 741
<212> TYPE: DNA
<213> ORGANISM: Plasmodium falciparum

<400> SEQUENCE: 52

```
atggcaagaa gatatgatag tagaacaact accttttctc cagaaggaag gttatatcaa     60

gtagaatatg ctttggaagc cataaataat gcaagtataa caattggttt aataacaaag    120

gatggagtaa tattaggagc ggataaagtt tttatttcaa aattaattga taaagctaat    180

aattatgaaa aaatatataa aattgataaa cacatatttt gtggtgtagc aggattgaat    240

gctgacgcaa atattttaat aaaccaatct agattatatg cacaaagata tttatataat    300

tataatgaag tacaaccagt atcacaatta gtagttcaaa tatgtgatat caagcaaagt    360

tacacacaat atggtggatt aagaccatat ggtgttagct tttaattgg tggttatgat     420

acaaaagatg gataccaact ttatcatact gatccaagtg gaaattattc aggatggttt    480

gcaacagcta ttggtaccaa taacttaaca gctagttctg tacttaaaca ggaatggaaa    540

aatgacatga ctttggaaga aggtttgtta ttagctttaa aacactagc aaaaagtact     600

gatacggaaa ttcccaaaag tgaaaaaatc gaattagcat atttaacaaa taaagatggg    660

gaagtatatc aaaagtattt aacggaaaag gaaatagaag agttaattaa attgtataca    720

cagaagtata ttaaagaata a                                               741
```

```
<210> SEQ ID NO 53
<211> LENGTH: 1347
<212> TYPE: DNA
<213> ORGANISM: Plasmodium falciparum

<400> SEQUENCE: 53

atgggaaata ctccaggtgg tatgaataat ccttatggat ttttaggaaa aaaagaggat     60

aaggataaag gtaaagacaa agataaggaa aagaaaaagc tggaaagtgt tccaatatct    120

catatgggaa aaaaaaagaa gaaaaacaaa ggaacatcag gtcattcaaa attaccaaac    180

gttacaccta atacaaaatg tcgattaaaa ttattaaaat tagaaaggat aaaagattat    240

ttattattag aagaagaata tataacaaat caagagcaga ttaaaagtag tgatgataag    300

aattatgtga aattgaaaat agatgattta agaggatcac ctgtgagtgt aggtacctta    360

gaagaattaa tagatgaaaa tcatggtatt atagctacat ctgttggtcc agaatattat    420

gtaaatatat tatcatttgt tgataaagat ttattagaac ctggttgttc agttttatta    480

aataataaaa caaatagtgt agtaggaata ttattagatg aagtggatcc attagtatca    540

gttatgaaag tagaaaaagc tccattagaa tcttatgcag atattggtgg gttagaatca    600

caaatacaag aaataaaaga agctgttgaa ttacctctaa cacatccaga actttatgaa    660

gatattggta tcaaaccacc taagggtgtt atcttatatg gtccaccagg tactggtaaa    720

acattattag ctaaagctgt agctaatgaa acctctgcta catttttaag agttgtgggt    780

tctgaattaa tacaaaaata tttaggtgat ggtccaaaat tagttagaga aatgtttaaa    840

gttgcagaag aacatgcacc ttccattgtt tttattgatg aaattgatgc cgtaggtacc    900

aaaagatatg aagctacaag tggaggagaa agagaaattc aaagaactat gttagaacta    960

ttaaaccaat tagatggttt cgattctaga ggtgatgtta aagttattat ggctactaat   1020

agaatcgatt cattagatcc tgcactaatc cgaccaggta gaattgatag aaaaatacaa   1080

ttacctaacc cagataccaa aacaaaaaga agaatctttc aaatacatac tagtaaaatg   1140

actatgtctc ctgatgtaga tttagaagaa tttgttatgt caaaagatga attatcaggt   1200

gctgatataa aagctatatg tacagaagct ggactcctag ctcttagaga aagacgaatg   1260

aaaataacac aagcagattt acgtaaggca cgagataagg cattattcca aaagaaagga   1320

aacataccag aaggtttata cttataa                                       1347
```

<210> SEQ ID NO 54
<211> LENGTH: 708
<212> TYPE: DNA
<213> ORGANISM: Plasmodium falciparum

<400> SEQUENCE: 54
atggcagatg gtgaatatag tttttcttta acaactttta gtccaacagg aaaattagta 60
caaattgaat atgctcttaa tagagtatct agcagttcgc cagctttagg tattagagcc 120
aagaatggtg tgataattgc taccgaaaag aaaagtccaa atgaattaat agaagaaaat 180
agcatattca aaatacaaca aataagtgaa catataggta ttgtatatgc aggaatgcct 240
ggagatttcc gtgtattatt aaaaagggca agaaaagaag ccataagata ttctttacaa 300
tatggaagtg aaatattagt aaaagaatta gtaaaaataa ttgcatcaat agttcaagaa 360
tttacacaaa caggtggggt aagaccattt ggtttatctt tattaatatg tggggttgat 420
gtatatggat accatttata tcaaatcgat ccatctggat gttattttaa ttggatggct 480
acatgtgtag gaaaagatta tcaaaacaat atgtcctttt tagaaaaaag atataataaa 540
gacatcgaaa tagaagatgc aattcataca gctattttaa ctttaaaaga aagttatgaa 600
ggagtattga atgaaaaaaa tattgaaatt ggtgtagcct atgataataa accattcaag 660
attttaacac aaaatgaaat taaagattat ttaatagaaa tagaataa 708

<210> SEQ ID NO 55
<211> LENGTH: 450
<212> TYPE: DNA
<213> ORGANISM: Plasmodium falciparum

<400> SEQUENCE: 55
atggcagaca agttaacaga agaacaaatt tcggaattca aagaagcctt tagtttgttt 60
gataaagatg gagatggaac tataacaact aaggagttag gaacggtcat gagatcttta 120
ggacaaaatc caactgaagc agaattgcaa gatatgatta atgaaattga tacagatggg 180
aacggaacga tcgattttcc cgaatttcta accttaatgg caagaaaatt aaaagatacg 240
gacactgaag aagaattaat tgaagccttc cgagtttttg atagagatgg tgatggatat 300
ataagtgcag atgaactaag gcatgtcatg acaaatttgg gagaaaaatt aacaaatgaa 360
gaagttgatg aaatgataag agaagctgat attgatggtg atggacaaat taattatgaa 420
gagtttgtta aaatgatgat agccaaatga 450

<210> SEQ ID NO 56
<211> LENGTH: 1125
<212> TYPE: DNA
<213> ORGANISM: Plasmodium falciparum

<400> SEQUENCE: 56
atggttcata ataattgtaa caaagaagaa aattattttt ttgaatttca atacaaaaaa 60
aaaaataaaa atgaatattt taatttagaa attattatag gaagtataat aaataacagg 120
gacaaaaaaa aaagagaaac atttttcacg ttcagaaaaa tacttatata tataattttt 180
atttatattc tttattttat agattataag tatttgttaa ataatcatag tcatgaacaa 240
tatgaaatat ataaaatatc gagcaataaa aaatggagac aattatccga atcatatgat 300
tattttcaag accctttaga ctattttgaa aatgtgcaaa acagagtaaa attattttat 360
aatatagata atattgatga acttgatata aatttcttgt ataaaaatat tttagataaa 420
tctaaattaa cagataaaaa aagaataaac cattatgaaa gcagtaatag ttatatgggt 480
gataaagcga atattagtta tgacgataat ataagtagta ttaatattat gtgttgcaat 540
aatattaaaa ctcacaataa taacccgagt aataattata atatttataa ccagaatata 600
ataagatatg ataataatgg taaaacaaat ctatatgata caaataacga ttttttttaaa 660 cacaaatata agtcgaatga aagtttcgat acatttttaa caaatgatca taatgaaaat 720
ggaaattttc aagtctatga aatatcagat gatgaaatta tattaactaa tataaaaact 780
catgatatga aatttgaaaa aaatacaaat aataaatcta aacaaaaaag gtttaataca 840
attgatcatg aaatatctca tttaaataaa gattcaagta caaataaaaa tttattaaaa 900
aatatatcta tattaaaata catatataat aatggtaaat gtaatattaa acccaaaaag 960
atttatgcta aatgtattaa aaaaattaaa aaaatcaaat tcaaaaaaat aatttatcac 1020
atattatata tgcttggtag tgcattaact acatatttgt ttcttggtgc tttaggccca 1080
gaaatggtta atcgtattgg tgttagtctt atagcatatg gttaa 1125

<210> SEQ ID NO 57
<211> LENGTH: 1068
<212> TYPE: DNA
<213> ORGANISM: Plasmodium falciparum

<400> SEQUENCE: 57
atgtacaatt ttgtaaaaat atttcaatct aattttattg atataaataa attgagcaaa 60
tttgaaatat ttttaaagac aatatttcga atttatagtt ctcctggaag aacacattta 120
ttagctcatg ctgctgatat atcagctaaa tatgcagtga ggaaaatata tgaatatatg 180
agaactgacg aagaagggat taggatatta aaagaaaagc ctttattaat acgtcaagat 240
atatgtttta atgaattaaa gaagttacca aaaaatacat taggttataa atatatggaa 300
tttttagaaa cttataaatt acatgcacat gatagagaag tttcacattt tataaaagat 360
ataaacgaat cttatatatt aacaagatat agacaaattc atgatatagc tcatgtagta 420
tataatttaa atatatcaat agaagcagaa gcagcattaa aattaatcga attaatacaa 480
acaaaattac ctataacatt acttgcaatt ttaatagcac catttatgac acctttatat 540
aggttccaat atatatttga gcataatatt ccttctaatt ttttatgtcc taattttgat 600
tatacatata atgatgatta taattatatt gatgaaatgt ctttaaaaca atatgaatat 660
tatttaactg attattttca tgtagaaaaa agagaaagcc aatcctttta ttacaaatta 720
tataaatatt atttcgataa tttaaataat tcttcacatg ttagaggttc tattatatac 780
ggatatcaaa ataagaatta taatgatata cattatgaca aattaaataa tgaatattta 840
tacttaaaaa ataatattaa aaattatttt catttccaat ataaaccaag aaaactacta 900
ttaacaaatt tatatccatg ggcttataaa actgcaatac aaacaaacaa accattacat 960
tcaatatatg tagaaaaatg gtttgataaa gatattgatc tgtttagaaa gaaatataac 1020
ataactcctc taccatccaa cttaaacttg atggccggca ttaattaa 1068

<210> SEQ ID NO 58
<211> LENGTH: 1260
<212> TYPE: DNA
<213> ORGANISM: Plasmodium falciparum

<400> SEQUENCE: 58
atggactctg aagaaacaat aaatttggca gtgaagtatg ccaaagaagc cgttgtggaa 60
gatgaaaaga agaattataa ggaagcacta aatttatata tccaaagttt acagtacttt 120
aatttttttt gtaaatatga aaaaaattca aatataagag atttaatttt gaagaaaatg 180
gaagtatata tgacaagagc cgaaaattta aaagaaatgt taaataaaaa agatagtata 240
gaaaataaag aaaaaataac aaacacagaa gaaacaaaag aaaatatgaa gaaacaaata 300
aaacaattta tattaaataa aaataataat attaaatggt cagatgtatg tggtttagaa 360
accgctaaag aagtattaaa agaggcaatt attttcccat taaagtttcc aaaattattt 420
aattcttcta ctttacctta taaaggcatt ttattatatg gtccacctgg tacagggaaa 480
acattccttg cattagcttg ttcgaatgaa tgcaatatga attttttttaa tgtatcttca 540 tcagatttag ttagtaaata tcaaggagaa agtgaaaaat atattaaatg tttattcgaa 600
acagctaagg aacattctcc tgcaataatc tttattgatg aaattgattc cttatgtgga 660
tcaagaactg acggagagaa tgaatctact agaagaataa aaacggaatt tttaattaat 720
atgagtggac ttacaaatta taaaaataat attattgtta tgggtgcaac taatacacct 780
tggtccttag atagtggatt tagaaggaga tttgaaaaaa gaatttatat acctctacca 840
aatatttatg caagagcaaa aatatttgaa aaatatatca atcaaaatga aaataataat 900
atatcaaaag aggatataaa acaattcgct acattaactg aaaattatac aggtgctgat 960
attgatattc tttgtagaga cgctgtctat atgccagtaa aaaaatgtct tctttccaaa 1020
ttttttaaac aggttaaaaa gaataataaa atatgctata ccccatgctc acctggagat 1080
tcagatccta ctaaagtaga aaaaaatgtc atgtctttaa gtgaaaacga attatcatta 1140
cctccattga ctgtacaaga ttttaaaacg gctatatcaa atgctaaacc gtcattatca 1200
gtagatgata ttaaaaaata tgaagaatgg actcatcaat atggaatgaa cggtacataa 1260

<210> SEQ ID NO 59
<211> LENGTH: 3132
<212> TYPE: DNA
<213> ORGANISM: Plasmodium falciparum

<400> SEQUENCE: 59
atgaatatag tggtgacaaa ttatgggata ttaaggaaaa attttattag aacatattta 60
gcaaataaaa taaatacaat caaagggacg tacaaaaata tttgcatata tcatgtagat 120
ataaaaagat attgccatta caaaagtaga agtaaaataa aatgtaaaaa taatggtgtg 180
atgaataagg atatgaattt tatatgtgat gaactgaaag aaaaatatat agataataat 240
catatgaata atgtacataa caataatagt tataataatt ttaatacttt ttatgaaaat 300
ggaaataata aagacaactt taatgtatca aaaaaatgtg taggaaaaaa agttatacga 360
gatacattta taaataagat taaggaaggc acgttgtccc tactaaattt agaaatagaa 420
gaattaaatt atgaagaact attaaaatat aagaatataa aaaaagttgt agtaatgaaa 480
aataaattga caatattaaa atattttaat agctatttat taaaaaataa taaagggaaa 540
tattatatat taaaagtgtt aatgttttgt attgttaaag atatacataa atataaaaac 600
aatgaattaa tatacatttt atatatatat aaatatcata attatttaaa tccattttta 660
atattacata taatagataa actatgttgt gataattata tatataatat gaatataaaa 720
gaatttgtct ttttattaga tattttaaat gtgccacttg ttatgacaaa taaatttatt 780
caaaatatta tggattatat aaatatcaat caaaataaaa taaaatattg taaatattat 840
tttgatatag cttatttttt agcgaaaaat aatttgtata ataaatatat atttgataca 900
atcgcacaat attatacatc acattcatat aattttgagt tatccatttt gtatatgttt 960

-continued

```
aataatgaac ataaaaatat taataggaat aataatgctt ttcctattaa agggagttac   1020

aacataaata ataacatcgt agatataaac atatgtgaag aattaataaa taatgatgat   1080

tatttaaatg ttaaacaaag gaatatgtta aaaaaagtcg aatctgataa tggttgttat   1140

gataatacat atgataataa taatataata aatttcaaga gagaaataca taaacattta   1200

tatatactat ccaaatatgg atataagaat atccaaatat ataataacat gttcaagatc   1260

ataatttttt catgtaacca ttttaaacct tttgaagtta gttcaatttt caaatctttg   1320

aaaaatataa attattttaa cattgtttta ttagaaaaat tgactagtac attaaaaaaa   1380

aatattagtc aatataagac aagtttatta ttagattgtt taaatacatt atcttatttt   1440

aattacaaag atgataatat tataactaca atattaatta atttaccaag gaatatatca   1500

acatatacgt ctaatcagtt tttaaaatta gtatatttta tggataattt tataccttt   1560

tcaatatatt ttaatatatt tttaaataaa caaatttgta tattttcttc ctcttttgga   1620

ttatgtcatc ttatttcttt attaaaaata tttactcacc aaaatttaat atctaatcct   1680

attttatatt tgttaagaat aaaaattagt aaatataata aatcattaac atataatgat   1740

ataaaaagta aacatataaa tgaaaaaccg gatgaaatct tcccttcaat aaattacaca   1800

ggcaatataa aaataagtta taaagatata tattcaatat tttatcatat gcatttaatg   1860

agagtacagt atatggactt ggctataaaa tgtatagaat gtatattttt tatggaaaaa   1920

aattttaaaa atatatttc tgaggatata gaatatataa caaattcatg ttgttatttc   1980

ttattactta atgataatta tgatgatcca tttttaagaa aatttataaa tgttcatata   2040

gaaaattttt tttctttcgt cgcttcaaat tttgtaaaaa atgaatcact ggaaaaaaaa   2100

aatgaatgta taaatggtaa tatggaaatg gaaaaaataa atgataataa taataataat   2160

aagaagaaga agaaatataa aacgtacaat atcaagatgg acgatatcaa gatggacgat   2220

atcaaaatgg atgatatcaa aatgggtgat atacattttg cacattatga aaaaaacaat   2280

ggaacaatac attttaataa taaaattaat tacaatgaac aaattataga tatacaaaac   2340

aataataatg ataaaaaaaa tctatatttg gcatttaata aaaaaaaaaa tgtttatgca   2400

ataatcatat taacacttat aaatgaatta gtataccaaa attcaataaa aaaaatatcc   2460

aatataatac acaactttaa tttggaatat ataaaaaata atatatatgt ctttttacaa   2520

cactttaata atgaaaaaaa tgagaaagaa aaatgtgata ctatatatat acttgagaaa   2580

ttatttccat tactctattt ccctaagata aataatgtac atttgaaaaa tataagtaga   2640

aataatttta atatatctac tttcaattta acatatgttc aaaatggata taataattat   2700

ttgaaaagtg aacatattaa aaaagaaata atatccaacc aatatatact caatgaaata   2760

tataaaatat tacgaagttt aaaacaaaag aattatattt ttaaattgat aaataaaagc   2820

cacacaaaat ctttcttttt atataatcat tatatatatg taaaaaatat aaggaatgga   2880

gataaaatag ccatcttatt tgcatcaaaa aattattatt ataatacgat agacgatgct   2940

aatttgggat taacttctaa aatggggaaa aaaatatttg aaaagaaaaa atttacaaaa   3000

gaagctataa cacaaataga gtattttaaa atatatttta ataaggtata tttagtagaa   3060

ttttatacat gggaaaatat gataaatatc caggaaaaaa aggattatct tgtaaatttg   3120

ttgaacatat ga                                                        3132
```

<210> SEQ ID NO 60
<211> LENGTH: 2280
<212> TYPE: DNA
<213> ORGANISM: Plasmodium falciparum

<400> SEQUENCE: 60
atggatatac atgcacaaga gaatcagacg ggtattcgtt ttagctggaa cttatggcca 60
cccacaaaag cagaagcagc aaaaatagaa gtacccttag ggtgtttata tacagtatta 120
aaaaggacag atgatagtag cgttaagtta gtagaatatg agcctttaaa atgtaaaact 180
agtaattgta ttttaaatcc ttattgtaat attgatttta gaaataagac atggacatgt 240
cctttctcaa atatcaagaa tccatttcct ttacattatg cagagcatat atcagagaag 300
aatttgcctg ccgatgttat gtactccaat attgaataca tccaaccttc caatgtagga 360
gatattcccc ctccaacgtt tttattcgtc atcgatactt gtttactaga agaagagcta 420
gaacaattaa aagattcaat tcaacaatgt attagtttaa tgcctgggga tgcttacata 480
ggtataatta cttttggtaa tatgtgttat gttcatgaaa ttggttttaa cgattgtttg 540
aaatcttatg tatttaaggg gaataaagaa ataagtgctc aagatttaca aaaacaatta 600
aatttaggta gtagaaatga tcctcgtagt tccacaacat ctgcttctgc tcgtcgattt 660
ttacaacccg ttagtgaatg tgaatataat ataaatatgt tattagaaga tatacaaaaa 720
gataactggc caactccacc agatcaaaga gctaaaagat gtaccggtgt agcattgagt 780
gttgctattg gtttattaga atgttgttgt aatcaattaa gtggtcgtgt tatgatgttt 840
ataggtggag cagatactac ttcccctggt aaaattgtag atacgccttt aagtgaatcg 900
ttaagacatc atttagattt acaaaaagaa aattcgaatg ctagacatgt taaaaaagct 960
ttaaaatatt atgtatcact agctaataga gctgtagcat ctggtcatgc tattgatata 1020
tttgcatgtt cattagatca aataggttta tatgaaatga aggtttgttg tgaaaagaca 1080
aatggtttta tggttatggc agattcattt tctatgaatg tatttaaaga ttcttttaaa 1140
aaaatatttg aaacggattc gacggaatat ataaaacatg gttacaatgc aaaattgacg 1200
gttatttgtt caaaagaatt tagagtatgt ggtgcaatcg gtgcatgttc aagtaataaa 1260
aaaacagcta actatgtatc tgatacgtgt gttggagaag gtggtacatg tgaatggact 1320
atatgtgcat tagatagaca atcaacaatt gctttttatt ttgaaatagt aaatcagaat 1380
ttggcttcct tacctccaga tagacaagcg tatttacaat tccaaacatt atatcagcat 1440
cctagtggaa gaagaagatt acgtgttact acaatatctt atagatttgc agaacctaat 1500
atagcagaaa tatcgcaagg ttttgatcaa gaaactgctg ctgttattat ggctcgattt 1560
gctgtattaa aagcagaaac agatgaacct atagatgtat taagatggct tgatagaaaa 1620
cttattagat tagttagtac ttttgcagat tatcaaaaag atgatattaa ttcttttcat 1680
ttatcttccg aattttctat atatcctcaa tttatgtatc atttaagaag atctcatttt 1740
ttacaaacgt ttaatgcaag tcctgatgaa acagcatact atagaagtat attattaaga 1800
gaaaatgtta tgaattcatt aattatgata cagccagcat tacttcaata ttcatttgat 1860
tccccaactc caataccagt attattagat gcacaatctt taaaatcaaa tgtaatactt 1920
ttattagatt catatttcca tatagttata tggtatggag aaatgatata tcaatggaga 1980
gaacagggtt ttcatgagaa gccagaatat gagcatttta gacaattatt gaatgcacca 2040
catgaagatg ctaaatccat tttagaagat agatttccta tacctaaatt tgttttatgt 2100
aatagtggtg gtagtcaaag tagattttta ttagctaagg tgaatccatc aacaacacat 2160
aattcgttaa gtggtagtac ctttggtaca tctagtaatg aatcttatat aattaataca 2220
gatgatgttt ctttaaaaat atttatggat catttagtaa agttagcagt acaaacttaa 2280

<210> SEQ ID NO 61
<211> LENGTH: 4062
<212> TYPE: DNA
<213> ORGANISM: Plasmodium falciparum

<400> SEQUENCE: 61
atggaaggat atgaagaagt atctgatttg attcagaaat ttaagaagga tacttacgtt 60
ttaaattatt acaaaaggat atacgaactt aataaatgta aaagttatag gtctatcatg 120
attaaagata tacaaaataa aatagattac aagaaagagc aagaaaaaaa tataaaaaaa 180
aaaaaaaaaa aggatgaaaa tgacgatgaa attataaatg acgatgaaat tataaatgaa 240
gatgaaaatg ataaaaagga atattattat aatagtgaag agaatgctac aacattagga 300
agagaaactt caaaagataa gatccataca ttacatgaaa attataatga tgataataat 360
aatgatataa tgaaaactat tttaaaaagt atagataaca aactatataa atatacgaat 420
gaagttttag agtattttga tggacaggat aaagaaacct taaatacaaa ctaccaaata 480
aataattgta tagaggcaca tgcatatatc gataatatat tgattacaaa tcaacatgat 540
atacaatata tatgtaagga tattaataat attgaaaagt taacacaaag tataaataac 600
aaattaacaa atcgtaaaat aatcttagag cttttaaata catatattaa aataattatt 660
attacacccc aactaattag aaatataata tatggagata taaatcaaga atttattaaa 720
aatatacata tcttaacaaa taaaattgaa aattgtaaac attgtttata tgatatttat 780
ccaagtatta aatactcata tatagaatta gaaaaattaa aaaaaaaatc agtagatcga 840
atttatttct tcttccttga aaaaataaat aatataaaaa ataaaaatac cgatatttat 900
attatacaac aaaatctact aacctttttt gaattaaata cttttctttt taataacaac 960
agacatgtgt ataattatct tttgaaagaa tatatccatg ttatgaataa aaaatatttc 1020
catttattta aaaattatat aacgaatatg caaaaaaaaa taaaaaaataa taaaaaattgt 1080 acttttataa ataattcaaa tgttggattt acaaataatt acaactcaca agttgaaaga 1140
aatgtaaata ataagataag cgtgaataga aatataaaca ttaacaatat aaacattaac 1200
aatataaaca ttaacaatat aaacattaac aatataaaca ttaacgatgt cgacataaat 1260
aatatcaaca taaataataa taataataat tataattata ataattataa taattattat 1320
tataataata gttgtagtaa caaccatctg gatatcatat cgtcaaatat gaataatgta 1380
acttttcaaa atgcaaaaaa aaccatgatg aattttttag ggatcaaccc caaaaatgat 1440
aatacatgta acacatatga agaaccggat gaaaatattt tctccttaaa ttgtcgacat 1500
aaagtgttgt atgatatgtg ttattttaac aaaacaaagg aagaaaaaaa aaatgatatt 1560
aatataaatg atgataatat aaatgatgat aatataaatg atgataatat aaatgatgat 1620
aatataaatg atgataatat aaatgatgat aatataaatg atgataatat aaatgatgat 1680
aatataaatg atgataatat aaatgatgat aatataaatg atgataatat aaatgatgat 1740
aatataaatg atgataatat aaatgatgat aatataaatg atgataatat atatgatgat 1800
aatataaatg atgataatat aaatgacaat aataatgaca ataataatga gaacattatt 1860
atgaataatt ataattatat taagaattat aataggataa acaatgaaaa aacttttgaa 1920
aacaaaataa ataaagaata tccagtgtcc ttaatttcgg acttagacaa tttaatctac 1980
cattttgaag aaatatacaa atcaataaat aaattatttt tagatactgg ttctttagaa 2040
tattatttta ttttgaattt ttttaaagat tatgaatcac ctgatttttt atttttagag 2100
atatattcaa agaccatatc tctgtgtttt gattttatct atttttatac tatacaaacg 2160
tatgatgtta tatctttata ttgtgtatat attatgaacc tatattatgc ttatattatg 2220
tataaaagaa atatcgtaac cctttatgtg tatattcaaa gaattcaaac ttttttatgg 2280
gataaaatat attacattat tcaagaaaat cttgattcct taaataagaa aaggttagat 2340
gagaagaaat acgtttcgtc aaattttaat gctaagataa atacaaatga acttgaacat 2400
tatcaaaata aaacatgtca cataaataat ttgacatttg ataagtttga aaattttaca 2460
aatgttcata gtaataatta tcaaaatggt gataataagg gtgataatga agataacaac 2520
atggataatg aaaataaaaa attggataat gaagataaaa agagtgataa tgaagataaa 2580
aagagtgata atgaagataa cgataaagat aaagataatc attataataa taacattagt 2640
caacattatt atcataatca taataattat tgtatgaata aaaatatcga actcacaaac 2700
aatttgggta tatataaaac acaagcaaat aaaaatacac atcttgtgaa cattaaacaa 2760
aatgatataa ctaacaaaca tttgaacacg aatctgaata atcaagaaga aaaaaaacat 2820
tcacttcatt tttcaactat tttaaaaaca caagaagtac atagtgttac aaaaaaattt 2880
acagattttt attgctctgt agttatatta tctaatttgt gttttcatat agacacttat 2940
tataaagaaa aaatagataa gcaaaaagta aaagttggat atcaagagca aaaactcaag 3000
gaaaataaaa atcaacatct catgaatatg gaagaaaaag ttgataaaat agagatggat 3060
agaaaaaatt ataatgatca gaaaggatgt aatatattac atggcgaagc ggataaaaat 3120
aaattatcaa atgaacaatt taaagaagat ataataatgg aaaatttata tgataaaaat 3180
gtaaattttg taaaacataa taatgagggt atagaaaaaa ataaagatga atctaaaata 3240
actacagaaa aaaggaaaca taataataat aataatattt gtgcacattc aaatgagaat 3300
agttatttaa acaaaatata tgatgagaat gtaactatgg aagacaaatt aaaaaatgat 3360
aaagaagtaa ataatacaag tatatcggat aaaaaaaata attatttttt aaaatataag 3420
aaaattacta atttgatatc aaaattagaa ggagctatta tacatacatt aataagtata 3480
gataatgaat tggtatgtcc aaaagaaaaa ttattatttt taattaataa ttattattat 3540
attatttata tattaaaaca aaataaatta caagagaaaa tatgtacatt tgaaaaatta 3600
ttaaaaaaag aaataacaac ttatatagaa tatgaattaa atatatatat aaaagatatt 3660
attttatttg taaacaaaca tgaaaatata attaatacta taaaagaaga tatatataat 3720
aaaaatataa agaacaataa taatgatgat catcataatt attatttatc acatgttgat 3780
tttatttcta tggaaaatat agctattcaa tttacaaaaa attggaaact tttatttaaa 3840
aacatcagaa ataatattat tacttcattt ataaatatag acaatgcatt caatatatta 3900
aaattattaa atactcaaat tttgttatac tttacacgtt tctatcaatt gaccaaaaaa 3960
atattttcta atatacaacc acctttatat atacaaaacc ttccatccgt tgatgttatc 4020
atgatacaaa ttaagaaaga tgcaaagaat gtcggtagtt aa 4062

<210> SEQ ID NO 62
<211> LENGTH: 2223
<212> TYPE: DNA
<213> ORGANISM: Plasmodium falciparum

<400> SEQUENCE: 62
atgaaaatca aagagttatt atataatgaa ttaataataa taaagataac ggaattttta 60
accatactag aaatacaaaa tatgattata tccttaagaa ttaatgtaaa gagaaatata 120
tattttatga gagaatgttt atctttaatg aatctagata cagatggata taatcataat 180

-continued

```
gtaagtaata aaaatactcc aaataaaaat aaaaataaaa atacatcgac cacagaacct    240
ttattattat catcgagtgt taatcttact acagatattg atgattatgt acataatgca    300
acttcatatg taggtgatca acacttttta cagcaagaag gtttaaattt aattacgtat    360
gatgatgagt atgatgagta tatatttaac gattataatg aaggaggaaa taatgttgat    420
aatgtgaata attttgataa tgtgaataat attgataatg tgaataattt tgataatgac    480
aataatatgt ataattatag taaccatgat atatataata atactagtta ttataataca    540
cgggcagatg aaaactttga cgagaatttt atgtataaca caaaatattc tcattatgaa    600
gatacattaa atgatatgac acatttaatg tcaacatata cagataataa tataaactat    660
tatgaaacaa ataaaactaa ctttggtgct ctatacgaaa ttaaaaaata tttgaacttc    720
tttgaacaag aaaaagaagg acatgtacaa aaatgtttta ataatgtatg gatatatata    780
catttgaaaa atgaacttat agatataaaa aaaaatttag aaacttattt tatgagaatt    840
aaaatgaaca cccaagttaa tagaaataaa agaatacgta tagatatatt tcaattattt    900
aaatataatc atacttatta ctctttttat gatatgccat gggtctctat ttattatgat    960
tttttcttaa attccatatg tacactttgt aatataaaat tagatcatag atccatctgt   1020
ctttttttcag aaaaatttaa cctaattcaa acaaatgaca agttgctaaa gtatattaat   1080
agtatgtccg atgatatagt aagtaatagg aaaaatgaga aaaaacgaga tcatcaaaag   1140
gttgatatgc tatttgggga ggatgttgaa agggaaaaaa caaaaaaaaa aacagacatg   1200
ataaataatg ataataaaaa tgatagtaat aattatgata ataataatga tagtaataat   1260
tatgataata ataatgatag taataattat gataataaaa atgatagtaa taattatgat   1320
aataataatg atagtaataa ttatgataat aaaaatgata gtaataatta tgataataaa   1380
aatgatagta ataattatga taatatgtat aaccttcatg atgattataa tcaacatcaa   1440
gaaacccttg cagaaattaa actgaataaa gatatattta gttgtaaaaa taaaattaat   1500
acatatgatg aagaatttat ttttataaga aagactcata ttttttgtga agaatgtaca   1560
aaaattattg attataaaat gaacataaat tctttactag aatcaattaa gaaagattat   1620
gaacttttaa aaaaaattcg aataatttat aagatgattg atatcccctc tgatttattt   1680
tgcttttgta attatttctt ttttaaagaa aaatatatta cattctttaa aaatgttagt   1740
aatgatttac aaaatctaag gaaagcttta aaaaagaaat taacaaataa ttttatactc   1800
aatttcagta ttaattttta taaatttgtt attagttctt taatattatg tgatgaaaaa   1860
aaattattca gtcaagaaaa tattttctta tttggatttt atattaaata tagaaatatt   1920
cttaaattat ttagtagtcc tagatgtaca catatctatt tctcttttaa tattatctat   1980
caaaaaattg taaaatttca aagctttttt aaacataaac atttttcaaa attatccaaa   2040
gttttacatt ttgatgttat tacaattctt gaaaaattaa aacattcaaa aaccaaaatg   2100
ttatataaaa atattgcagt atatttatat caacatttaa acgataaaat acttagaaag   2160
tataattatg acgaagccta tgcctatttt tttcagtgtc ttcaacggta tcacttttca   2220
taa                                                                  2223
```

<210> SEQ ID NO 63
<211> LENGTH: 1446
<212> TYPE: DNA
<213> ORGANISM: Plasmodium falciparum

<400> SEQUENCE: 63

```
atggctttaa taaatttcaa agaaaaaatt cagatattgt taaagttaaa agaatcttta     60
```

```
ataccctcaaa ttgatggtaa ttttatagga caatgggaaa tggaagcatt aaaatatcag    120
aatacaagtg agaatataat gatagaatta aaaaatgtaa attttataga aacattggtt    180
agtgctattt cttctcaatt atcctatttg agaataaatt tgcaaaatta tgcaaaaatg    240
aatgaacaag aaaaagataa atttaaaaga ttatatgtat tagcagcttt agggttgata    300
gcaaaattaa aattaatttt atttttttca acatatgtaa attcaagaaa tgagacaaat    360
aatagtaaag cctttcccat aataaatgaa aatacatatc cttcacaatt atctcctaat    420
atggaaaata attatgacat gacaatttca ttaaatatga acaacaacaa taataataat    480
aataataata ataatattaa taatatgaat aataatataa attgtaataa taataataat    540
catagtgaga attttataaa tcctaaagaa tcacaaagta taaatatgta taacaacaat    600
gtagatgaat tttatgtaca ttatcaaaat aacacagagc aatataatga taattttaca    660
aaaagtataa ctcaaaataa tatgatgaat tttaatgcac ctgttaataa cgtaacatca    720
aataataata taaataatct taatataaat aatatgaatg taaataatat gaacgtaaat    780
aatatgaata ttaacaatgt aagcaatata aataatgtaa ataataatag taaaaagaat    840
aataaaagta gtaataataa taataataat ataaattgta ataatagtgg gaataatttt    900
tctagccatt ttactactaa caatacagag gatatacaat taaatgtgct caacaacttt    960
gttacaacaa aaaatgaaaa cctgataaat gcacctttac atacatcaaa aaaaagatct   1020
ttaacaatag ctcaaccaca aaataataat aaatctatta actatataaa aaatttacaa   1080
acaataaatg gaacaaaaaa tattacaaat gaacatatga taaattataa tgaacatgtc   1140
attaatgatg accctcaaag atttttacaa caaaatcaat atacaaagta tacaaataat   1200
aatcatcaaa atgtaacagc aacaaataat gataataatg aattaaccaa ttgttctata   1260
aattttaata attattatca acatcaaaat aatggtaata acagtatcaa caataataat   1320
aacaacaaca acaataataa taataataat aatagtatac aggacaaaac tattctccag   1380
tcatataaca ataataatat gtataccttc agagatgata tttataaaaa tagttattac   1440
atataa                                                              1446
```

<210> SEQ ID NO 64
<211> LENGTH: 5715
<212> TYPE: DNA
<213> ORGANISM: Plasmodium falciparum

<400> SEQUENCE: 64

```
atgagatcca tttctgtcgg tttcaccatt tatgaagcac aaaatttaga agttgacgac     60
aaaaatttat tagatccttt agtagttgtt cgttgttgta ataatgaata cataacaaaa    120
aaaaagaaaa aaaaatataa cgctgtgaat tgggaagaaa gtcatatatg ggatagaatt    180
attttatctg aaattgaatg gaatgtttca aaaatagaat ttgaggttca gagtgctaat    240
attttatggc gaaatgatat aataggtgta atatcatttg aacttaaact tattaagaat    300
aaaagaaatc atcaaattca ggggatctat ccaatacttt gtaagaatgg taccgaaatt    360
cgagggcaat tgcgacttaa agtaatggta tgtgatgaaa atgattatat aagtaataat    420
aatattttta atgatttaac agaaaataat aatgaaaaca gaattgaaga taacgaagaa    480
atatataatg acttaacaaa agctgttgtt gaagaaaatc ttgtaacttt aagagatgaa    540
aaaagtcgtt tttattattt atatgttaat atacataaaa tagaagatat ttataccgat    600
ataagtaaaa aggaatatcg agatttatat ataacatgtg attttaatgg ttgccattta    660
```

-continued

```
aaatctagtc aagcaagaaa ttgtattaat tatacattta atgaatgctt taaaatacct    720
atcgccactc ctatattaga tgattccata atattgaaaa tatgggattg gaattattta    780
tcaaacgatg aattgatagc cataggtgta ttgtcattta accaaataaa aaatgaatgc    840
cttaatccaa catggctcaa tttatatggt tttcacaaaa aagaatttga cttggaaaaa    900
attacaaata attatacaaa caagaataat agtaataatt attatgatat atgtaatgat    960
tacaatttac ttttagaagg gaatttttat ctaggtagaa tatgtatcag tagttatgtg   1020
gaaaggataa ataattttga taatctaaat atagccatta ctcaaagttg tttagcatat   1080
gatgacccat tatatatacc tatcacttta ttatgtgatg tttatttagt taccggaatt   1140
ttgtcaaaaa atatttatgt cgaactaaca tgcggaccac atagaaaaaa aacacaatgc   1200
gtatccgtca atgaaatgtt acaagatgta atgggtaaac aaacaaacca aaaaaaaaaa   1260
acaaaaaaaa aaaaaattat aaaaggtata cacaattcat atatagataa tgaaattgta   1320
aataataatt atgataatac tatttataca tataatcaaa aaactaatcc actattcaca   1380
tttgatgaaa tacttaattt ggataacgtt ttcaataaag tgactgagaa acaacagatt   1440
attgaaaata atgaacatac agaattttat tttagtgcta ataaaggcaa aatagaaaat   1500
atgaaattat gtgttgttca ggaagaatat caacaatggg atatcatcat aaatgtatat   1560
gaaaaggttt ataataattc atatcatgaa aataattttc ttccaagtct tttatataat   1620
aatgaagaga caaaaaatga tgactattca aaattaactg aatatcaaaa atatcaaaaa   1680
aaaaaagaag aaattgatca atatgaacaa aatataccta atcatattga tagaagaatt   1740
gcctattata gaatgccatt aaaaaatgta cttttatata atgaaaaaat atctagatgt   1800
cctatatgga ttccattaaa aaatattcca aaaaatgtac aaggtgattt taattgtatg   1860
tataatattt ttcaaaatgg ttctatatta ttaaacttag aaaaatcttt tgatgtacaa   1920
ttaggaataa atagaagaaa aaaattaata cctgttaatt atgaattaag atgttatata   1980
tatgcttgta gaaatgttat atcacatttt aatgattctc ctaatacatt tgtacatata   2040
tcatgtgcag gtaaaatgaa aattacctct ctttctttaa attcatgtaa tccagtctat   2100
ttacaatgtc tgaaattaaa tattaatatt ttaacagatt attctatagg cctacctacc   2160
atccctctaa tcattgtcac attgtatgaa ttccataatg atacatttta ttacatagga   2220
agatgctatt gtaattatga tatatatctt aaacaaagtg ggaataaata taattttact   2280
gaaaaaggat ccaaatataa tgtagtcgaa caaattaaac cgaaatggat aaaattaaaa   2340
ggaagcaagt acacaaaggc aatgtatgcc aacaatttat ggcaacataa tggaaatgat   2400
aaaagaatta tgcaggaata tttatatgaa aaacaacaag aactaatcaa caatagtact   2460
attaacaaaa acaataataa caataataaa aaagataaca ataataaaaa agataacaat   2520
aataaaaaag ataacaataa taataataat aataattatt attataatag tagtaatgtg   2580
tatcaatata atgacttatt atacggtgaa agagttggag atattctctt atattttgaa   2640
cttgttcaat ctaaagatgc aatgaaattt cctatttatc ctatgattac ggaaattaaa   2700
aaatgcacct tatccttttt ttgcatgtct ttagaaaatc tcatattaat gaaaaaggca   2760
aatttcttaa aaacactatc attcgaacga aataataaat atcagatatc aaccccaatt   2820
atccttttgt ctattacatc ttattcttct tatggaaaaa aaaaaaacga actcatgatt   2880
aaatatgaaa aacattaaa agctaataca aggatacaat taaaaaattg gaaaaattct    2940
ttcaatcaac aaagttttga aatgttctca atagaaaata tgaatattga cattccatta   3000
gatcctatat ttgatcctat acttaatata aaagtatata acaaaaaagt taaatcaaaa   3060
```

```
tattttattg gagaaacaaa tatatctctt gttccatatc tcccatggat taaaaatata   3120
gatgaagtcc tttattattt acaagctcat gatgattatt ccgaaacaat taatatgaaa   3180
aacatagata acacatttaa tatatacaaa aataaaaacg cagctctcgt catatcagca   3240
atttcattgg ctgactgtga ggatacatta tcgttgaagg aagaaattaa taaatatgaa   3300
aacgatgatg acgaagcttg gaaagaaata cctcttttta atttggacca agaaaatcaa   3360
aaggaggata ataaaaatac atcaagtcag catggaaacg taactaataa ttatgatgga   3420
tataataatg gtgcatatga aatgggaatg tataatatgg aaacatacaa tataaaaaat   3480
aatgataata ataataataa taattataat aattataata acaatagtta taataataat   3540
aattattatt ataataatta tgcagctcca tatacatctt ataataataa tgtactacaa   3600
aatgatacga gaaataatgt taggtataat cattcaaaca acatgatgat caataatatg   3660
tataaaaata atatatataa tgcttcccaa tttggtgtaa ttaattataa taattataat   3720
aattattatg ataaaggtaa tacactaaat tttaataata ataacataca ccattttaac   3780
aaattatcaa ataacaaatt tgattcatat ttgtcaagaa ttcaaaaaga tacatataat   3840
ataaaatata ataatagtat atataaatta tttgatgatg gtattcctga aataataaaa   3900
ttaagctata atgtaaagaa ttatccatat ataaaaatat taacaagcaa atatatttta   3960
aatgtacata ttcctccaag atttatttta tatgtagaag gtgataaatt aaatattgag   4020
aaatttataa aaaatattaa tcgtgtatct gttgatggta ttttagaaaa ctatcttgat   4080
gatatattaa ttccttctct acctttaata aaaaagtgca atgatatatc atgtgataat   4140
aattataatg aaaataaaat agaaaagcaa ggtattaaat ttggttgttt tgaacagttt   4200
ccatttgttg aaattatagg tggacaaatt aaatgtttta caaaaattaa atacagaaat   4260
ttagaatctg aaaatatgcc attaagttta aaagatataa caaatcaaaa tatatttaga   4320
aataaattta gagggaaaaa taaaattcct ttatatttaa aaatacgtgt atatgtgtta   4380
agaggcatag gattatatgg tataaataat gaatatactg caaatccata tttgattttt   4440
tcattaggag aaaaaacttc taatttaaga aatgctttca aacgttcaaa tataaatcca   4500
gaatttggat gtctttggga aagtgaagct atatttcctg aagatgaaat attaactatt   4560
agtgtttata gtgctgaaga taattatgat aaacaaataa atgatatata tattggatca   4620
actgaaatta atttatttga tagatggatg agtaaggaat ggagacatat gatgaagaaa   4680
aataaaatac ctgttgaata tagaccattg tatagtaatt atataaaaca tccaaaaatg   4740
gtatcatcta ataattacaa tacaatgaat agttggaata atattttttc atttttttgac   4800
atatttaatt atttaatgac ctatacatca ccaacaaaag gtaacaacaa caacaataat   4860
gataataata ataataatag taatatttat ggaaatcatt ctttgaaaga tacacattca   4920
aatatatcct ttggcaattc acaaaagaga aataatggta tattagaaat gtgggtagaa   4980
attatggatt atgaacaatc caagaaaata cctatacata aaatggttcc accaaaaaaa   5040
acagaaattg aaataagaat aattatatgg agatgtacta tgctaacaaa taaagataat   5100
attaataaaa ctatggattt aaccgtaaca tctgaattag actgtataac atataatggt   5160
aaaaatccga ctatgcaatc aaccgatgta cattataact gtaaaacagg aactgctata   5220
tttaattgga gaattgttta tcctaatatt acgcatcctt taaatacatg ctttttacaa   5280
ctagctgcat ataataataa taatgttgga gttagcgaat ttttaggaga agtcaattta   5340
gaactatcca aatatataca aaaagcatca caaatattaa ataaatttga attagacgca   5400
```

gaacttaaat taaggaaaaa aacagatact gatcataata aaaatactta taatggatat 5460
atacaagtaa ctgttcaatt tattccccaa aataaagcta atataaaacc tgtaggatta 5520
ggtagagatg aaccaaatag aaatccttat ttaaaaacac ctgatagtgg aagggaatgg 5580
aacgatttca tgtattccat aggttttaat gatatatata agcctttctg gaattcttta 5640
aaattggcgt tcatatgcct tctagttata tgggtgtttg tattatcttt cgtttatccg 5700
tcattgttaa ggtga 5715

<210> SEQ ID NO 65
<211> LENGTH: 5115
<212> TYPE: DNA
<213> ORGANISM: Plasmodium falciparum

<400> SEQUENCE: 65
atgtcaagca ttgcgaaaaa gacccaatac aatattaagg tcgatataca cgaagtaaaa 60
gacttaagtt ttcgtgagag tgcgaatgag aaagaaatta taccaaatcc ttatattgaa 120
gtgacagtaa ataatgagaa gaagagtact acaaaaaaga atcaagcagt aaatgttgta 180
tataatacat catttaattt ttcacaagat ttaacagatt ataaatttga aaggactagt 240
gtagatgtat gtgttttaca taaatatact attcagagtg ctttaatagg aaaatgttcc 300
tttggtttaa attttgttta ttccaaagtt caacattggt tatataggat atgggtaaaa 360
ttaagaaatc cagatttgcc attagatgat gttggttttt tattaatatc tgttggtgtt 420
tatggtccag gagattccat acctattgtt aatgatagtg ttaaaacgga tattcatgaa 480
gatgtattta gtaataaagg tttggatata catattacac attatgattt gtgtttgaat 540
atatttagag gtcaagatat agaattaata ggtaatagta cactgttttc taatatactt 600
gaaccatatg taaaagtatc acataatgga tttgaagaat gtactaaagt aataagaaat 660
gatccgaatc cagtatggaa tttaagtatt catattccta catgtactcc ttgttatgat 720
aaaaatattc ttgtcgaatt aataaatgga gaacataatg gtattgttat atatagtatt 780
ctcttagatt tttttgaaat attaaaaaga gaattagcac caagatggtt taatatttat 840
tataatccac aaaatcaaat catgccaaga tatagtgaat atatgcaaaa cggatcaatt 900
cagataaatt taaatagtac tacgactaat aataataata ataatagcac tgctataaac 960
cctttaggta attatctttt ttcaggagca gctgaaaaaa tatttaaaaa tgctacacaa 1020
gctattaata ttaatgatat attaggtgta acgaaagtac aaaatatgtt tactgatgat 1080
acattaaagg agttctattt atatggtggt cgtatttttc tgagtgcaaa tgcaaccaaa 1140
acacattcac caggtcctat ttgtataaaa tcagcaaaag tagaggtaga tgcacctaac 1200
aaagaataca ttttttgtgc tgacatatat gaaatcttat cggttcgaaa taataaaatg 1260
ggaaattatg acgattatga cggtggctac accaccacca acaacaacaa caagaacaaa 1320
aataataata atgaaaataa taataatgac aataatgaca atatttacaa tagtaacaat 1380
atttataata gcgcaagtga aaaaagacga agtcgataca ataataatta tgatgcgagc 1440
ggagaaagca tcatctgcgt ttgtgctctt ggaccacata aactaaaaac cattcctcta 1500
ttaccgaatg aagttggttc ttatgtttta aacgaaaatg ttggtagaat agatgagttt 1560
cgtatatttt taccacaaaa taataatgaa caaatatatg atatattttt atatatatac 1620
ataaaatcga atttggccgt tacaaattgg attaataata gaaggagtat atataatagt 1680
gtcttattaa acaatgaata cgaatccgga gatagaaata aaaaacaggg attacataaa 1740
atgggttcta taaataatat atcagaagat ataatgcaag attcggattt cttaaataat 1800
tataaattaa caagttatgt acgtattcca tataaatatc ttttattaaa tgaaaacaag 1860
cctaaatggt tttctatgaa gaatattgaa acaaatgttc atgaatataa tatatctttt 1920
tttgctaatt taataccttta ccatgcttat aaaaagagac ccaaaagatt agaatataaa 1980
ttatctagat attttttcg tgctttaata tatgaaggat tacattttcc agcaaaagga 2040
tataatgctt ttccagatcc ttatattaaa attgaattag ctggacaagt aattaaaaca 2100
agtactatat tacatacatt gaatccgaat tattatgaag catatgaagt acaagttata 2160
ttacctacta atttaaattt agctcctgat atatctatag aagctttatc tgtaaataaa 2220
tctttttat ataatgatga tatattattg ggatcatgta catttcctat tatgaaagta 2280
ccaactgaat ggaagaaatc accaatatgg ataccccttaa aatcatcaca atataaaaaa 2340
tgtaaagcta aacttcttgt tgcttttgaa ttagtacctg ttgaaaaagt tctagatgat 2400
acatatccat tctatgatga tataagacct tctacattac ctggtcacgt ctctttattt 2460
ttaataggta tacgaatgtt taaaccttta aaagatcctt ccgtaacggt ttgttttggt 2520
agagatgtcg atgatacatc tcaatttttg tggcatgaaa ctactaataa agtaatatca 2580
ggaaaagaag gtaattggaa cttcttaaaa tatttttctt tagatgttat gttacctaaa 2640
agaatgcaac accatagttt tctagaagtt agaatagaag ataggatatt aaatagtggg 2700
ttcacaggaa ctgcatctag taatatgcat gctgtaaatg caacaaataa taatctttta 2760
atagggactg catatataac tctaaatcca ttacttccat ggctagataa ttatgaaaaa 2820
aatgaatgtg tagaattatt taaattacat ttactagaag aagttttaat agaagatgca 2880
gaaatggata gaaaatctta caacagtgca ttgatatata aaaaaagttc aataatgtca 2940
aggaaattgt ctaatgataa ttttgaaacg caacagatgg gagaagaaaa tggtatattt 3000
aatgatatac ccatgaatac tttggaagaa aatgtgacca ttaaagggga tgatagcagc 3060
gatgatgaaa aggataatag ttatgatgat gaaaaggata atagttatga tgatgaaaag 3120
gataatagtt atgatgatga aaaggataat agttatgatg gtgatgataa aagtggtcat 3180
tattatcata catgggaaga taataataac aataataata ataatgtaac tagtgatcat 3240
acttgtaagc ataaaaatga acataataat aataaaaaag aggacgaaaa aagaaaaagg 3300
gaaaaaaaaa atacatatac aacaaaccat gataaaagag aaaataataa cacacatatt 3360
aataacaatt ataaacatgt tatagatata aaaaagaaga aaagaaaaaa gaatataaag 3420
aaatatataa ataatgaata cgttccatac aatgatcccg atttttctaa tgtacgtata 3480
gaagagacat tagaacatgt atgttttaaa ataaatgatt taacaaaaaa agagaataca 3540
tatatttatt ataatgatga acaagaaact ttatgtgata gtatttcaag tgagaaaaga 3600
aaaaaattaa aagatattca ttttttaaa ggtggtaaac atgatgataa agaaaagaaa 3660
agtaccatta tagatggaaa gcaacctaca acgatatatg ggtttaatga agatatgtta 3720
aattttcaat tatcattagc cgacgatgat gaacaagaag aaattcaaag agatgaaatg 3780
ttatatgaat atgaggtaga tatgaataca gatgatttac catatttaag agcaacaatt 3840
tttagatgta cagattcagg agttcctgaa gcggttggat atttgaaata tatatgtaat 3900
gtgtatgatg aaaagacaat gtatttaaaa aaagaaatga taaagaaatg tgatgattta 3960
gtaagagaat atagattaac acgtaattta gtagtacgtg catatattat acaagcaaga 4020
ggtttgaatc caccctcagg tgcaactgat ataacaacat atatatggat aaagaatagt 4080
aatgatatga caaatattcc aggaggatta tctcataata taaaagatac aggtcataca 4140
aagaagcaag gatataaacc agaatttaat agatgttatc aattattatg ttcatttcct 4200
gatgaatcga tagtacaagt atgtataatg aatcagggtt ctttatcaga tgaaattata 4260
ggatatacat atatagatat ggaggataga tattttaatc aaaaaattag acaattaatg 4320
attgatgacc ttatgccaat agaattaaga tctttaaaat tagaaaatag tacaatatct 4380
catggatctt taagatgttg gtttgaaatt tttaatgaag aatttgctca actgaatcct 4440
ataaaagtgt tatgttccaa tgaacctgat gattatcaat taaggcttgt aatatggaaa 4500
gtaaataatg ctgctatgga tgataattcg acaataagtt tatttgttag atgtatttat 4560
accgatgaag atcgtgaaga tataagagat acagatacac attataatag taaagatgga 4620
aaaggaatat ttaattggag atttgtttat aatattaaaa taccaactaa tgcaacaaat 4680
attaaaattc aaattcataa ttatgcttta ttatcatcta atgagcctat aggtgaggca 4740
accttagatc tgtctgctca tttttatagg gcacgtaaga aaaagggtta ttaccccata 4800
cccagatttt ggctatcgtg taaacaccca gctcacaaaa acaaagtaag aggaaatgta 4860
gaaatagaag ggtccattct aataaaatct gaggctgaac ttgacccagt tggtaatgga 4920
agggatgaac ctaataaaga tccttattta cctccagtta ctgaaaatag aacatatgtg 4980
gattgggtga tgataaatga aaaatttggt gctgcaacgg cttcgattat gcatggctta 5040
aaatggacag gtgtatggat tgtagtgggt gttatcgtaa ttgggatatt tttcctcata 5100
tttttgttta aatga 5115

<210> SEQ ID NO 66
<211> LENGTH: 21
<212> TYPE: DNA
<213> ORGANISM: Artificial Sequence
<220> FEATURE:
<223> OTHER INFORMATION: primer

<400> SEQUENCE: 66
cagtggatgc atgaacggtg g 21

<210> SEQ ID NO 67
<211> LENGTH: 22
<212> TYPE: DNA
<213> ORGANISM: Artificial Sequence
<220> FEATURE:
<223> OTHER INFORMATION: primer

<400> SEQUENCE: 67
cctaacttgg aacatgggag tc 22

<210> SEQ ID NO 68
<211> LENGTH: 21
<212> TYPE: DNA
<213> ORGANISM: Artificial Sequence
<220> FEATURE:
<223> OTHER INFORMATION: primer

<400> SEQUENCE: 68
ctgcactctt ccaaagccat g 21

<210> SEQ ID NO 69
<211> LENGTH: 22
<212> TYPE: DNA
<213> ORGANISM: Artificial Sequence
<220> FEATURE:
<223> OTHER INFORMATION: primer

<400> SEQUENCE: 69
accatcgtct ttaccgtgtg ac 22

<210> SEQ ID NO 70
<211> LENGTH: 25
<212> TYPE: DNA
<213> ORGANISM: Artificial Sequence
<220> FEATURE:
<223> OTHER INFORMATION: primer

<400> SEQUENCE: 70
ctcacgacat tcgaaatgta atctc 25

<210> SEQ ID NO 71
<211> LENGTH: 29
<212> TYPE: DNA
<213> ORGANISM: Artificial Sequence
<220> FEATURE:
<223> OTHER INFORMATION: primer

<400> SEQUENCE: 71
gatcatcatg ttgtttgaat gattatacc 29

<210> SEQ ID NO 72
<211> LENGTH: 21
<212> TYPE: DNA
<213> ORGANISM: Artificial Sequence
<220> FEATURE:
<223> OTHER INFORMATION: primer

<400> SEQUENCE: 72
cataatcgaa gccgttgcag c 21

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
gcagcctttg gaaggaaaga 20

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
ggctcctccc ttaaggtgac 20

<210> SEQ ID NO 75
<211> LENGTH: 24
<212> TYPE: DNA
<213> ORGANISM: Artificial Sequence
<220> FEATURE:
<223> OTHER INFORMATION: primer

<400> SEQUENCE: 75
cgtgcagctc tttagtagaa gtgg 24

<210> SEQ ID NO 76
<211> LENGTH: 22
<212> TYPE: DNA

<213> ORGANISM: Artificial Sequence
<220> FEATURE:
<223> OTHER INFORMATION: primer

<400> SEQUENCE: 76
agcattaaca gcagggtaac tg 22

<210> SEQ ID NO 77
<211> LENGTH: 22
<212> TYPE: DNA
<213> ORGANISM: Artificial Sequence
<220> FEATURE:
<223> OTHER INFORMATION: primer

<400> SEQUENCE: 77
tatcgtgcac atatgaccat ct 22

<210> SEQ ID NO 78
<211> LENGTH: 23
<212> TYPE: DNA
<213> ORGANISM: Artificial Sequence
<220> FEATURE:
<223> OTHER INFORMATION: primer

<400> SEQUENCE: 78
catctccctt gtccatttgc aac 23

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
ggtctcaggt atggacaggg 20

<210> SEQ ID NO 80
<211> LENGTH: 22
<212> TYPE: DNA
<213> ORGANISM: Artificial Sequence
<220> FEATURE:
<223> OTHER INFORMATION: primer

<400> SEQUENCE: 80
tcatgatcag gatggggaga tg 22

<210> SEQ ID NO 81
<211> LENGTH: 25
<212> TYPE: DNA
<213> ORGANISM: Artificial Sequence
<220> FEATURE:
<223> OTHER INFORMATION: primer

<400> SEQUENCE: 81
cgacaaatac ataaagatgg acgag 25

<210> SEQ ID NO 82
<211> LENGTH: 26
<212> TYPE: DNA
<213> ORGANISM: Artificial Sequence
<220> FEATURE:
<223> OTHER INFORMATION: primer

<400> SEQUENCE: 82
catggcttgt tggtataaaa catacg 26

<210> SEQ ID NO 83
<211> LENGTH: 21
<212> TYPE: DNA
<213> ORGANISM: Artificial Sequence
<220> FEATURE:
<223> OTHER INFORMATION: primer

<400> SEQUENCE: 83
gcagctctcg tcatatcagc a 21

<210> SEQ ID NO 84
<211> LENGTH: 21
<212> TYPE: DNA
<213> ORGANISM: Artificial Sequence
<220> FEATURE:
<223> OTHER INFORMATION: primer

<400> SEQUENCE: 84
tccaagcttc gtcatcatcg t 21

<210> SEQ ID NO 85
<211> LENGTH: 21
<212> TYPE: DNA
<213> ORGANISM: Artificial Sequence
<220> FEATURE:
<223> OTHER INFORMATION: primer

<400> SEQUENCE: 85
gagcctatag gtgaggcaac c 21

<210> SEQ ID NO 86
<211> LENGTH: 21
<212> TYPE: DNA
<213> ORGANISM: Artificial Sequence
<220> FEATURE:
<223> OTHER INFORMATION: primer

<400> SEQUENCE: 86
ccaactgggt caagttcagc c 21

<210> SEQ ID NO 87
<211> LENGTH: 9
<212> TYPE: PRT
<213> ORGANISM: Artificial Sequence
<220> FEATURE:
<223> OTHER INFORMATION: described fragment of merozoite surface protein 1

<400> SEQUENCE: 87

Tyr Leu Ile Asp Gly Tyr Glu Glu Ile
1 5

<210> SEQ ID NO 88
<211> LENGTH: 9
<212> TYPE: PRT
<213> ORGANISM: Artificial Sequence
<220> FEATURE:
<223> OTHER INFORMATION: described fragment of merozoite surface protein 1

<400> SEQUENCE: 88

Lys Leu Leu Asp Lys Ile Asn Glu Ile
1 5

<210> SEQ ID NO 89

-continued

```
<211> LENGTH: 9
<212> TYPE: PRT
<213> ORGANISM: Artificial Sequence
<220> FEATURE:
<223> OTHER INFORMATION: described fragment of merozoite surface protein
      1

<400> SEQUENCE: 89

Lys Leu Lys Glu Phe Ile Pro Lys Val
1               5
```

MALARIA VACCINES BASED ON PRE-ERYTHROCYTIC ANTIGENS FROM *P. FALCIPARUM*

This application is a Continuation Application of co-pending application Ser. No. 13/988,339, filed Aug. 7, 2013; which is a National Stage Application of International Application Number PCT/EP2011/006110, filed Dec. 6, 2011; which claims the benefit of U.S. Provisional Application No. 61/419,906, filed Dec. 6, 2010; all of which are incorporated herein by reference in their entirety.

The Sequence Listing for this application is labeled "SeqList-04-Dec15.txt" which was created on Dec. 4, 2015 and is 312 KB. The entire content of the Sequence Listing is incorporated herein by reference in its entirety.

The present invention relates to polypeptides or fragments thereof for use as malaria vaccines. It also relates to nucleic acid molecules coding for the polypeptides of the invention. It further relates to compositions comprising such polypeptides or fragments thereof or the nucleic acid molecules, in particular combinations of such polypeptides or fragments thereof, and the use of such compositions as malaria vaccines.

BACKGROUND OF THE INVENTION

Malaria is an infectious disease transmitted by inoculation of infectious sporozoites from the *Plasmodium* parasite via *Anopheles* mosquito bites. There are currently an estimated 500 million annual cases of malaria globally, and infection is lethal in 1-3 million people per year in endemic regions such as sub-Saharan Africa. Among the worst affected are children under the age of 5 years, in which the disease comprises several syndromes such as acute respiratory disease, severe anemia or cerebral malaria. The life cycle of *Plasmodium falciparum*, the parasite causing the most severe form of human malaria, is complex and multifaceted, with local differences within the host tissues and differing morphology corresponding to differential antigen expression. Following sporozoite inoculation, the parasite transforms and expands in an obligate, clinically silent and uni-directional phase in the liver (Prudenco et al., 2006). The release of packages of membrane-enclosed merozoites, termed merosomes, marks the onset of malaria (Sturm et al., 2006) though the symptoms and pathology of malaria, typically recognised by its cyclic pattern of fevers and chills, is caused exclusively during the rapid asexual multiplication phase of the *Plasmodium* parasite inside erythrocytes (Haldar et al., 2007). Thus, only preventative treatments targeting the pre-erythrocytic stages have the potential to prevent disease and offer effective protection. Immunisation of both humans and rodents with gamma-irradiated *P. falciparum* sporozoites (RAS) is the only experimental vaccine that confers essentially complete protection and is the gold standard of protective immunity against mosquito-borne malaria transmission (Nussenzweig et al., 1967; Hoffman et al., 2002). Irradiation disrupts the parasite genetic repertoire and parasites arrest in the liver, where they persist for up to 6 months post-infection (Silvie et al., 2002). However, these parasites are genetically undefined and, until today, have been restricted to experimental studies only. Nonetheless, this model provides proof-of-principle that sterile immunity in man is possible, based on the random genetic attenuation obtained by irradiation. Recent work has elicited sterile immunity in rodent models by genetically attenuated parasites (GAPs) (Mueller et al., 2005 a/b; van Dijk et al., 2005; Tarun et al., 2007; Aly et al., 2008; Silvie et al., 2008). These GAPs arrest at the early liver stage and confer sustained and stage-specific immunity (Mueller et al., 2007; Jobe et al., 2007).

The challenge for malaria vaccination based on genetically attenuated parasites depends on translating the results acquired in the rodent malaria models to human malaria. This has been successfully performed by disrupting p52 in *P. falciparum,* an ortholog of the rodent parasite gene p36p, which has been recently shown to induce sterilising immunity against sporozoite induced malaria (van Schaijk et al., 2008; van Dijk et al., 2005; VanBuskirk et al., 2009). The immune mechanisms conferring resistance to attenuated sporozoites are thought to rely on both humoral and cellular arms of the immune system. Apoptotic RAS-infected hepatocytes lead to presentation of *Plasmodium* antigens to dendritic cells, likely eliciting the protection-conferring immune response (Leiriao et al., 2005). Primarily, protection has been thought to rely on CD8+ T cells as the cytotoxic effector cells (White et al., 1996; Bongfen et al., 2007) and CD4+ T cells providing aid for antibody and optimal memory CD8+ cytotoxic T lymphocyte activity (Carvalho et al., 2002). Sterile immunity can be achieved in the absence of CD8+ T cells, mediated solely by CD4+ T cells and class-II effector mechanisms (Oliveira et al., 2008). Interestingly, a recently published model has been described where primaquine phosphate, a drug that exclusively targets *Plasmodium* liver stages, has been utilised in vivo to elicit vaccine-like protective immunity against subsequent sporozoite-induced rodent malaria in the absence of persistent metabolically active liver stages essential for such a CD8+ T cell response (Putrianti et al., 2009). Moreover, the use of wildtype parasites together with prophylactic chemotherapy (such as Chloroquine) results in protective immunity in *P. falciparum* (Roestenberg et al., 2009). Nonetheless, it has been suggested that long-persisting RAS forms present parasite antigen via MHC class I that induces IFN-gamma-based inducible nitric oxide synthase (iNOS) production by infected hepatocytes (Klotz et al., 1995). The circumsporozoite protein (CSP), the major surface protein of sporozoites, has historically been considered a major antigen and vaccine candidate associated with the liver stages of *Plasmodium.* Several CSP-derived T cell epitopes have been identified to date, some associated with very high levels of protection, as measured by the reduction in liver stage burden following challenge of immunised mice with normal sporozoites. RTS,S/AS02A is a pre-erythrocytic vaccine candidate based on *P. falciparum* CSP developed collaboratively between GlaxoSmithKline (GSK) and the Malaria Vaccine Initiative (MVI) Programme for Appropriate Technology in Health (PATH). However, its results are rather disappointing, with efficacies of between 40 and 60% (Alonso et al., 2004; Alonso et al., 2005; Bejon et al., 2008, Epstein et al., 2011). Such partial protection suggests that CSP may not be the sole protective antigen in attenuated models. Indeed, there is no CSP epitope described in C57B1/6 mice, though in Balb/c there is a well-known and characterised T-cell epitope. Interestingly, a recent study employing a *P. berghei* parasite line expressing heterologous *P. falciparum* CSP demonstrated that sterile immunity can be achieved in the absence of a CSP-specific immune response and concluded that hitherto uncharacterised antigens, and not CSP, may be targeted to induce sterilising immunity (Gruner et al., 2007; Mauduit et al., 2010).

It was an object of the present invention to provide means for an effective malaria vaccine. More specifically, it was an object of the present invention to identify novel liver stage antigens that are protective (i.e. critical for immunity), and thus can be used for vaccination.

SUMMARY OF THE INVENTION

According to the present invention this object is solved by a composition comprising at least two polypeptides selected from polypeptides comprising an amino acid sequence of SEQ ID NOs: 1 to 18 and a polypeptide, which is at least 80% identical to any of the above polypeptides, preferably furthermore selected from polypeptides comprising an amino acid sequence of SEQ ID NOs: 19 to 23 and a polypeptide, which is at least 80% identical to any of the above polypeptides, or comprising at least two fragments of the above polypeptides.

According to the present invention this object is solved by a composition comprising at least two nucleic acid molecules each coding for at least one polypeptide or fragment thereof according to the invention, preferably having a nucleotide sequence selected from SEQ ID NOs: 41 to 63, more preferably SEQ ID NOs: 41 to 65.

According to the present invention this object is solved by providing the compositions of the invention for use as a malaria vaccine, preferably for use as a subunit malaria vaccine or multicomponent malaria vaccine emulating the malarial live attenuated organisms.

According to the present invention this object is furthermore solved by a polypeptide comprising an amino acid sequence selected from SEQ ID NOs: 1 to 23 and a polypeptide, which is at least 80% identical to any of the above polypeptides, or a fragment thereof, for use as a malaria vaccine, preferably for use as a subunit malaria vaccine or multicomponent malaria vaccine emulating the malarial live attenuated organisms.

According to the present invention this object is furthermore solved by a fragment of the above polypeptide, comprising or having an amino acid sequence selected from SEQ ID NOs: 26 to 36 for use as a malaria vaccine, preferably for use as a subunit malaria vaccine or multicomponent malaria vaccine emulating the malarial live attenuated organisms.

According to the present invention this object is furthermore solved by a nucleic acid molecule coding for at least one polypeptide or fragment thereof according to the invention, preferably having a nucleotide sequence selected from SEQ ID NOs: 41 to 63, for use as a malaria vaccine, preferably for use as a subunit malaria vaccine or multicomponent malaria vaccine emulating the malarial live attenuated organisms.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of “from at least two to 23” should be interpreted to include not only the explicitly recited values of 2 to 23, but also include individual values and sub-ranges within the indicated range. Thus, included in this numerical range are individual values such as 3, 4, 5, 6, 7, 8, 9, 10, 11, 12, 13, 14, 15, 16, 17, 18, 19, 20, 21, 22 and 23 and sub-ranges such as from 2 to 5, from 3 to 10, from 4 to 15, from 2 to 8, from 5 to 15, and from 6 to 10, etc. As another illustration, a numerical range of “5 to 50 amino acids” should be interpreted to include not only the explicitly recited values of 5 to 50 amino acids, but also include individual values and sub-ranges within the indicated range. Thus, included in this numerical range are individual values such as 5, 6, 7, 8, 9, 10, 11, 12, 13, 14, 15, 16, 17, 18, 19, 20, 21, 22, 23, . . . , 49 and 50 and sub-ranges such as from 5 to 50, from 8 to 25, from 8 to 15, and from 28 to 40, etc. This same principle applies to ranges reciting only one numerical value. Furthermore, such an interpretation should apply regardless of the breadth of the range or the characteristics being described.

Compositions with Malaria Attenuated Liver Stage (MALS) Antigens

Here we present a novel approach for vaccine development that harnesses the immunological potential of the parasite at the liver stage, the clinically silent incubatory state prior to the onset of the pathological blood stage.

The results of the prior art described above in addition to the fact that eventually clinical immunity to malaria is acquired during natural infections suggested that an efficacious vaccine against malaria may in principle be producible. However, while naturally acquired immunity to malaria is believed to target the erythrocytic stage of infection until today only vaccines targeting the pre-erythrocytic stages have resulted in protection against malaria infection. As irradiated sporozoites (attenuated parasites) are difficult to technically produce and given the fact that pre-erythrocytic vaccine candidates based on *P. falciparum* CSP have been giving disappointing results in terms of efficacy new candidate vaccine antigens are still warranted.

The inventors have found a unique strategy for the identification of such antigens. Now the present invention discloses protective antigens targeting the critical phase of the parasite in the liver. These novel validated antigens isolated from the protection-inducing attenuated parasites—a novelty in malaria vaccine development—can be further translated into a vaccine prototype that mediates immunity by elimination of the parasite at this crucial, pre-pathological bottleneck.

Ultimately, our technology can be further expanded by combining the most potent pre-erythrocytic antigens described within this invention with erythrocytic antigens for a multi-component (-stage) subunit vaccine that both emulates the live-attenuated parasite vaccine and mimics induction of natural aquired immunity and hence paves the way for the preparation of next generation vaccine formulations.

As described above, the present invention provides a composition comprising:

the newly identified MALS antigens (proteins, polypeptides) or fragments thereof or nucleic acid molecules encoding them.

The compositions according to the invention comprise at least two, at least three, at least four, at least five, at least six, up to 23 (at least 2 to 23) of the polypeptides or nucleic acid molecules encoding them, such as from 2 to 5, from 3 to 10, from 4 to 15, from 2 to 8, from 5 to 15, and from 6 to 10.

The compositions according to the invention comprise fragments of at least two, of at least three, of at least four, of at least five, of at least six, of up to 23 (at least 2 to 23) of the polypeptides of the invention, such as of 2 to 5, of 3 to 10, of 4 to 15, of 2 to 8, of 5 to 15, and of 6 to 10.

The proteins or polypeptides which are to be selected for the composition of the invention are proteins or polypeptides comprising or having an amino acid sequence of:

| | | |
|---|---|---|
| MAL13P1.13 | (SEQ ID NO: 1), | (MALS_A) |
| PF14_0480 | (SEQ ID NO: 2), | (MALS_B) |
| MAL13P1.258 | (SEQ ID NO: 3), | (MALS_C) |
| PF14_0435 | (SEQ ID NO: 4), | (MALS_F) |
| PF14_0390 | (SEQ ID NO: 5), | |
| PF13_0242 | (SEQ ID NO: 6), | |
| PF13_0168 | (SEQ ID NO: 7), | |
| PF11_0342/0421 | (SEQ ID NO: 8), | |
| PFc0515c | (SEQ ID NO: 9), | |
| PFc0135c | (SEQ ID NO: 10), | |
| PF14_0533 | (SEQ ID NO: 11), | |
| PF13_0282 | (SEQ ID NO: 12), | |
| PF10_0081 | (SEQ ID NO: 13), | |
| PFF0420c | (SEQ ID NO: 14), | |
| PF14_0323 | (SEQ ID NO: 15), | (MALS_Cal) |
| PF10_0375 | (SEQ ID NO: 16), | |
| PF11_0128 | (SEQ ID NO: 17), | |
| PF14_0548 | (SEQ ID NO: 18), | |

and a polypeptide, which is at least 80%, preferably at least 85%, more preferably at least 90%, even more preferably at least 95% identical to any of the above polypeptides.

They are furthermore selected from proteins or polypeptides comprising or having an amino acid sequence of:

| | |
|---|---|
| PF08_0051 | (SEQ ID NO: 19), |
| PF08_0036 | (SEQ ID NO: 20), |
| PF13_0135 | (SEQ ID NO: 21), |
| PF13_0343 | (SEQ ID NO: 22), |
| PFE1260c | (SEQ ID NO: 23), |

and a polypeptide, which is at least 80%, preferably at least 85%, more preferably at least 90%, even more preferably at least 95% identical to any of the above polypeptides.

For details, see Table 1.

The above accession numbers are PlasmoDB/GeneDB accession numbers.

As described above, the present invention also provides polypeptides which are at least 80%, preferably at least 85%, more preferably at least 90%, even more preferably at least 95% identical to any of the above polypeptides, or fragments thereof.

As used herein, the term "percent (%) identical" or "percent (%) sequence identity" refers to sequence identity between two amino acid sequences. Identity can be determined by comparing a position in both sequences, which may be aligned for the purpose of comparison. When an equivalent position in the compared sequences is occupied by the same amino acid, the molecules are considered to be identical at that position.

Generally, a person skilled in the art is aware of the fact that some amino acid exchanges in the amino acid sequence of a protein or peptide do not have any influence on the (secondary or tertiary) structure, function and activity of the protein or peptide at all. Amino acid sequences with such "neutral" amino acid exchanges as compared to the amino acid sequences disclosed herein fall within the scope of the present invention. Also included are mutations in the original amino acid sequences that allow or facilitate the production of the polypeptide or fragments thereof in an organism different from *P. falciparum,* such as *E. coli.*

Preferably, the composition of the invention comprises at least two polypeptides which are selected from polypeptides comprising or having an amino acid sequence of SEQ ID NOs: 1 to 23 or polypeptides having at least 80% sequence identity to any of the amino acid sequences of SEQ ID NOs: 1 to 23 or fragment(s) thereof.

In a preferred embodiment, a composition of the invention furthermore comprises:

*P. falciparum* Ferlin,

*P. falciparum* Ferlin-like protein and/or another *P. falciparum* C2-domain containing protein, or or a fragment thereof.

*P. falciparum* Ferlin (Pf FER; PF14_0530) has the amino acid sequence of SEQ ID NO: 24,

*P. falciparum* Ferlin-like protein (Pf FLP; MAL8P1.134) has the amino acid sequence of SEQ ID NO: 25.

A composition of the invention can furthermore comprise polypeptide(s) comprising or having an amino acid sequence selected from:

| | | |
|---|---|---|
| PF14_0530 | (SEQ ID NO: 24), | (MALS_E), |
| Mal8P1.134 | (SEQ ID NO: 25), | (MALS_G), |

and polypeptides having at least 80% sequence identity to any of the amino acid sequences of SEQ ID NOs: 24 and 25, or fragment(s) thereof.

Preferably, the composition of the invention comprises at least two polypeptides which are selected from polypeptides comprising or having an amino acid sequence of SEQ ID NOs: 1 to 25 or polypeptides having at least 80% sequence identity to any of the amino acid sequences of SEQ ID NOs: 1 to 25 or fragment(s) thereof.

Preferred Compositions

A preferred composition of the invention comprises at least two of:

| | | |
|---|---|---|
| MAL13P1.13 | (SEQ ID NO: 1), | (MALS_A), |
| PF14_0480 | (SEQ ID NO: 2), | (MALS_B), |
| MAL13P1.258 | (SEQ ID NO: 3), | (MALS_C), |
| PF14_0435 | (SEQ ID NO: 4), | (MALS_F), |

and polypeptides having at least 80% sequence identity to any of the amino acid sequences of SEQ ID NOs: 1 to 4, or fragment(s) thereof.

A preferred composition of the invention comprises at least two of:

| | | |
|---|---|---|
| MAL13P1.13 | (SEQ ID NO: 1), | (MALS_A), |
| PF14_0480 | (SEQ ID NO: 2), | (MALS_B), |
| MAL13P1.258 | (SEQ ID NO: 3), | (MALS_C), |
| PF14_0435 | (SEQ ID NO: 4), | (MALS_F), |
| PF14_0530 | (SEQ ID NO: 24), | (MALS_E), |
| PF14_0323 | (SEQ ID NO: 15), | (MALS_Cal) |

and polypeptides having at least 80% sequence identity to any of the amino acid sequences of SEQ ID NOs: 1 to 4, 15 or 24, or fragment(s) thereof.

Fragments

In an embodiment of the invention, the composition comprises fragments of the polypeptides of the invention.

Preferably, a fragment of the polypeptide(s) of the invention, namely the polypeptides comprising or having the amino acid sequence of SEQ ID NOs: 1 to 23 (or SEQ ID NOs: 1 to 25), comprises at least one antigenic determinant or epitope of the polypeptide.

In one embodiment, the amino acid sequence of the antigenic determinant or epitope has a length of at least 8 amino acids. Thus, in a preferred embodiment, the fragment has a length of at least 8 amino acids. In an embodiment, the fragment or peptide has a length in the range of 5 to 50 amino acids, preferably 8 to 25 amino acids, more preferably 8 to 15 amino acids. In an embodiment, the fragment or peptide has a length in the range of 28 to 40 amino acids.

In one embodiment, the antigenic determinant or epitope is a CD8+ T cell epitope, a CD4+ T cell epitope or a B cell epitope, preferably a CD8+ T cell epitope. Preferably, the CD8+ T cell epitope is a *P. falciparum*-specific CD8+ T cell epitope, such as a HLA-A 0201-restricted CD8+ T cell epitope. A person skilled in the art knows how to identify/predict CD8+ T cell epitopes in a given amino acid sequence, e.g. by epitope prediction programs, such as SYFPEITHI.

In a preferred composition (of at least two fragments) the fragments are selected from fragments comprising or having an amino acid sequence of:

```
(fragment of MALS_A)
                                  (SEQ ID NO: 26)
SLICGLYLL,

(fragment of MALS_A)
                                  (SEQ ID NO: 27)
ILYSLMINSL,

(fragment of MALS_A)
                                  (SEQ ID NO: 28)
LICGLYLLTL,

(fragment of MALS_B)
                                  (SEQ ID NO: 29)
VLLEKINVI,

(fragment of MALS_B)
                                  (SEQ ID NO: 30)
YLSPNFINKI,

(fragment of MALS_C)
                                  (SEQ ID NO: 31)
ILHGGVYRL,

(fragment of MALS_C)
                                  (SEQ ID NO: 32)
ILFLFILSI,

(fragment of MALS_C)
                                  (SEQ ID NO: 33)
LLFINEINKL,
```

-continued

```
(fragment of MALS_F)
                                  (SEQ ID NO: 34)
SLISLYIYYV,

(fragment of MALS_F)
                                  (SEQ ID NO: 35)
FLLLMLVSI,
and/or

(fragment of MALS_Cal)
                                  (SEQ ID NO: 36)
FLTLMARKL.
```

They can furthermore be selected from fragments comprising or having an amino acid sequence of:

```
(fragment of MALS_E)
                                  (SEQ ID NO: 37)
NLLDPLVVV,

(fragment of MALS_E)
                                  (SEQ ID NO: 38)
LLLEGNFYL,

(fragment of MALS_E)
                                  (SEQ ID NO: 39)
KLIPVNYEL, and,
and/or

(fragment of MALS_E)
                                  (SEQ ID NO: 40)
ILIPSLPLI.
```

In a preferred composition (of at least two fragments) the fragments are selected from fragments of MALS_A (SEQ ID NO: 1), MALS_B (SEQ ID NO: 2), MALS_C (SEQ ID NO: 3), MALS_F (SEQ ID NO: 4) and optionally MALS_Cal (SEQ ID NO: 15) and MALS_E (SEQ ID NO: 24).

The following mixtures/pools of fragments (peptide pools of antigens) are preferred:

| | |
|---|---|
| Fragments of MALS_A | SEQ ID NOs: 26 to 28, |
| Fragments of MALS_B | SEQ ID NOs: 29 and 30, |
| Fragments of MALS_C | SEQ ID NOs: 31 to 33, |
| Fragments of MALS_F | SEQ ID NOs: 34 and 35, |
| Fragments of MALS_Cal | SEQ ID NO: 36, |
| Fragments of MALS_E | SEQ ID NOs: 37 to 40. |

A preferred composition comprises fragments comprising or having an amino acid sequence of:

SEQ ID NOs: 26 to 28, and/or
SEQ ID NOs: 29 and 30, and/or
SEQ ID NOs: 31 to 33, and/or
SEQ ID NOs: 34 and 35, and/or preferably furthermore
SEQ ID NO: 36, and/or
SEQ ID NOs: 37 to 40.

The use of antigenic peptides of Ferlin, Ferlin-like protein and other C2-domain containing proteins for malaria vaccines is also disclosed in WO 2011/066995.

Modifications

In one embodiment, the polypeptide(s) of the invention or fragment(s) thereof comprise further component(s), such as label(s), N- and/or C-terminal modification(s), further drug(s) or agent(s). The skilled artisan will be able to select suitable further components.

Nucleic Acid Molecules Coding for the Polypeptide(s) of the Invention

In an embodiment of the invention, the composition comprises nucleic acid molecules coding for the polypeptides of the invention.

Preferred nucleic acid molecules have a nucleotide sequence selected from SEQ ID NOs: 41 to 63 or SEQ ID NOs: 41 to 65.

A preferred composition of the invention comprises at least two nucleic acid molecules each coding for at least one polypeptide of the invention or fragment thereof, preferably having a nucleotide sequence selected from SEQ ID NOs: 41 to 63, more preferably SEQ ID NOs: 41 to 65.

The nucleic acid molecules can be isolated nucleic acid molecules, plasmids comprising them, expression constructs comprising them, such as expression systems for DNA vaccines.

Further Components of the Compositions

The compositions according to the invention can further comprise"

a carrier and/or an adjuvant.

In one embodiment, the carrier is fused to the polypeptide(s) or fragment(s) thereof or nucleic acid molecule(s) encoding them (i.e. the components of the composition as described above).

In one embodiment, the carrier is a virus particle or parts thereof, an envelope protein of a viral vector or of a virus particle, a nanocarrier.

In one embodiment, the virus particle is Hepatitis B virus particle or parts thereof.

In such an embodiment, the carrier, e.g. Hepatitis B virus particle or parts thereof, is suitable for liver targeting of the polypeptide or fragment thereof.

In one embodiment, the nanocarrier is a cell-targeted nanocarrier, such as the cell-targeted nanocarriers available from Rodos BioTarget GmbH, Hannover, e.g. the TARGOSPHERE® delivery system. These nanocarriers can be combined with the desired polypeptide or fragment thereof and specifically directed to antigen-presenting immuno cells (like APCs, DCs, macrophages etc).

In one embodiment, the adjuvant is triggering CD8 T cell responses in general. Preferably, the adjuvant is a commercially available adjuvant system, e.g. IC31 (Intercell company, Vienna) since that adjuvant system is triggering CD8 T cell responses rather than antibody-mediated immunity.

Use of the Compositions as Malaria Vaccine

As described above, the present invention provides the compositions for use as a malaria vaccine.

The compositions are preferably for use as a subunit malaria vaccine or multicomponent malaria vaccine emulating the malarial live attenuated organisms.

In comparison to a vaccine based on attenuated whole organisms (live attenuated vaccines), a "subunit vaccine" consists of at least one component (protein, protein fragment) of the respective pathogen.

A "multicomponent vaccine" refers to a vaccine comprising more than one component (protein, protein fragment) of the respective pathogen, preferably from different developmental and disease-inducing life cycle stages (multi-component (-stage) vaccine).

A "subunit vaccine emulating the malarial live attenuated organisms" refers to the minimal combination of immunogenic protein components derived from the protection-inducing attenuated malarial liver stage parasite.

As discussed above, the invention presents a novel approach for vaccine development that harnesses the immunological potential of the parasite at the liver stage, the clinically silent incubatory state prior to the onset of the pathological blood stage.

The herein disclosed and newly identified protective antigens target the critical phase of the parasite in the liver. These novel validated antigens isolated from the protection-inducing attenuated parasites—a novelty in malaria vaccine development—can be further translated into a vaccine prototype that mediates immunity by elimination of the parasite at this crucial, pre-pathological bottleneck.

The present invention can be further expanded by combining the most potent pre-erythrocytic antigens described within this invention with erythrocytic antigens for a multi-component (-stage) subunit vaccine that both emulates the live-attenuated parasite vaccine and mimics induction of natural aquired immunity and hence paves the way for the preparation of next generation vaccine formulations.

MALS Antigens, Fragments, Nucleic Acid Molecules as Targets for Malaria Vaccines As described above, the present invention furthermore provides a polypeptide comprising or having an amino acid sequence selected from:

| | | |
|---|---|---|
| MAL13P1.13 | (SEQ ID NO: 1), | (MALS_A) |
| PF14_0480 | (SEQ ID NO: 2), | (MALS_B) |
| MAL13P1.258 | (SEQ ID NO: 3), | (MALS_C) |
| PF14_0435 | (SEQ ID NO: 4), | (MALS_F) |
| PF14_0390 | (SEQ ID NO: 5), | |
| PF13_0242 | (SEQ ID NO: 6), | |
| PF13_0168 | (SEQ ID NO: 7), | |
| PF11_0342/0421 | (SEQ ID NO: 8), | |
| PFc0515c | (SEQ ID NO: 9), | |
| PFc0135c | (SEQ ID NO: 10), | |
| PF14_0533 | (SEQ ID NO: 11), | |
| PF13_0282 | (SEQ ID NO: 12), | |
| PF10_0081 | (SEQ ID NO: 13), | |
| PFF0420c | (SEQ ID NO: 14), | |
| PF14_0323 | (SEQ ID NO: 15), | (MALS_Cal) |
| PF10_0375 | (SEQ ID NO: 16), | |
| PF11_0128 | (SEQ ID NO: 17), | |
| PF14_0548 | (SEQ ID NO: 18), | |
| PF08_0051 | (SEQ ID NO: 19), | |
| PF08_0036 | (SEQ ID NO: 20), | |
| PF13_0135 | (SEQ ID NO: 21), | |
| PF13_0343 | (SEQ ID NO: 22), | |
| PFE1260c | (SEQ ID NO: 23), | |

and a polypeptide, which is at least 80%, preferably at least 85%, more preferably at least 90%, even more preferably at least 95% identical to any of the above polypeptides, or a fragment thereof, for use as a malaria vaccine, preferably for use as a subunit malaria vaccine or multicomponent malaria vaccine emulating the malarial live attenuated organisms.

As described above, the present invention furthermore provides a fragment of a polypeptide of the invention, comprising or having an amino acid sequence selected from:

```
(fragment of MALS_A)
                                    (SEQ ID NO: 26)
SLICGLYLL,

(fragment of MALS_A)
                                    (SEQ ID NO: 27)
ILYSLMINSL,

(fragment of MALS_A)
                                    (SEQ ID NO: 28)
LICGLYLLTL,

(fragment of MALS_B)
                                    (SEQ ID NO: 29)
VLLEKINVI,

(fragment of MALS_B)
                                    (SEQ ID NO: 30)
YLSPNFINKI,
```

-continued (fragment of MALS_C)
(SEQ ID NO: 31)
ILHGGVYRL, (fragment of MALS_C)
(SEQ ID NO: 32)
ILFLFILSI, (fragment of MALS_C)
(SEQ ID NO: 33)
LLFINEINKL, (fragment of MALS_F)
(SEQ ID NO: 34)
SLISLYIYYV, (fragment of MALS_F)
(SEQ ID NO: 35)
FLLLMLVSI,
and/or (fragment of MALS_Cal)
(SEQ ID NO: 36)
FLTLMARKL.

for use as a malaria vaccine, preferably for use as a subunit malaria vaccine or multicomponent malaria vaccine emulating the malarial live attenuated organisms.

As described above, the present invention furthermore provides a nucleic acid molecule coding for at least one polypeptide of the invention or fragment thereof, preferably having a nucleotide sequence selected from SEQ ID NOs: 41 to 63, for use as a malaria vaccine, preferably for use as a subunit malaria vaccine or multicomponent malaria vaccine emulating the malarial live attenuated organisms.

In another aspect, the present invention relates to a plasmid comprising at least one nucleic acid molecule or sequence as defined above.

In another aspect, the present invention relates to an antibody against a polypeptide or fragment thereof as defined above.

In another aspect, the present invention relates to a method of producing a composition as defined above comprising the step of admixing at least two polypeptides or fragments thereof as defined above or at least two nucleic acid molecules as defined above.

In yet another aspect, the present invention relates to a method of prevention of malaria, comprising the step of administering a polypeptide or fragment thereof as defined above, or a nucleic acid molecule or plasmid as defined above, or a composition as defined above to a person in need thereof.

TABLE 1

Overview of the 24 most abundantly upregulated transcripts in malaria attenuated liver stages (MALS).

| Gene | *P. falciparum* | *P. berghei* | *P. yoelii* | Function | p-value | SEQ ID NO: |
|---|---|---|---|---|---|---|
| 1 | PF13_0242 | PBANKA_135860 | PY02505 | isocitrate dehydrogenase, mitochondrium | 1.6e−32 | 6 |
| 2 | PF14_0480 | PBANKA_131420 | PY01987 | C-terminal TM, ARM | 0.0001 | 2 |
| 3 | PF14_0530 | PBANKA_131930 | PY05745 | Ferlin, putative | 0.0001 | 24 |
| 4 | PF13_0168 | PBANKA_134630 | PY04297 | CPW-WPC family protein, apicoplast | 0.0001 | 7 |
| 5 | Mal13P1.13 | PBANKA_140100 | PY02854 | Cytoplasmic, transcription, SEN-1 related | 0.0001 | 1 |
| 6 | PF11_0342/0421 | PBANKA_091520 | PY01035 (PfEMP3) | Actin binder | 0.0007 | 8 |
| 7 | PFc0515c/0135c (ARM) | PBANKA_041020 | PY01708 | TPR domain containing protein | 0.001 | 9, 10 |
| 8 | Mal13P1.258 | PBANKA_136400 | none | Extracellular, metabolic carbohydrates | 0.0011 | 3 |
| 9 | PF14_0533 | PBANKA_131970 | PY00668 | ApiAP2, apicoplast | 0.0011 | 11 |
| 10 | PF14_0435 | PBANKA_130960 | PY05937 | Membrane protein, apicoplast | 0.0012 | 4 |
| 11 | PF13_0282 | PBANKA_113040 | PY02352 | Proteasome | 0.0012 | 12 |
| 12 | PF10_0081 | PBANKA_120660 | PY00768 | 26S Proteasome subunit | 0.0013<br>0.0013 | 13<br>14 |
| 13 | PFF0420c | PBANKA_010710 | PY03034 | 20S Proteasome | | |
| 14 | Mal8P1.134 | PBANKA_122440 | PY04695 | Ferlin like protein, putative | 0.0013 | 25 |
| 15 | PF14_0323 | PBANKA_101060 | PY06908 | Calmodulin | 0.0013 | 15 |
| 16 | PF10_0375 | none | none | Plasmodium exported protein | 0.0023 | 16 |
| 17 | PF11_0128 | PBANKA_093540 | PY05764 | Coq4 homolog, Proteasome | 0.005 | 17 |
| 18 | PF08_0051 | PBANKA_071150 | none | TNF-like domain | 0.0057 | 19 |
| 19 | PF08_0036 | PBANKA_070800 | PY02497 | Pfsec23 | 0.007 | 20 |
| 20 | PF14_0548 | PBANKA_132120 | PY00672 | PfVps4, AAA domain | 0.0076 | 18 |
| 21 | PF13_0135 | PBANKA_133900 | PY06640 | vacuolar protein sorting 52 homologue, 2TM domains | 0.008 | 21 |

TABLE 1-continued

Overview of the 24 most abundantly upregulated transcripts in malaria attenuated liver stages (MALS).

| Gene | *P. falciparum* | *P. berghei* | *P. yoelii* | Function | p-value | SEQ ID NO: |
|---|---|---|---|---|---|---|
| 22 | PF13_0343 | PBANKA_114110 | none | cytosolic | 0.012 | 22 |
| 23 | PFE1260c | PBANKA_124010 | PY06789 | MAL5P1.252, TM | 0.041 | 23 |
| 24 | PF14_0390 | none | none | Transcription, membrane | 0.07 | 5 |

The following examples and drawings illustrate the present invention without, however, limiting the same thereto.

For statistical analysis we performed a Mann-Whitney U-Test.

FIGS. 5A-5D show Cultured ELISpot analysis for detecting antigen-specific CD830 T cells in malaria-exposed Ghanian adults.

Freshly isolated PBMCs from the blood of malaria-exposed (26 blood samples) and non-exposed (naïve) individuals (8 blood samples) were stimulated with peptide pools of antigen (5A) MALS_A (Mal13P1.13) (SLICGLYLL (SEQ ID NO:26), ILYSLMINSL (SEQ ID NO:27), LICGLYLLTL (SEQ ID NO:38)), (5B) MALS_B (PF14_0480) (VLLEKINVI (SEQ ID NO:29), YLSPNFINKI (SEQ ID NO:30)), (5C) MALS_Cal (PF14_0323) (FLTLMARKL (SEQ ID NO:36)) as well as peptides derived from the described blood-stage antigen MSPI (5D) (merozoite surface protein 1) (YLIDGYEEI (SEQ ID NO:87), KLLDKINEI (SEQ ID NO:88), KLKEFIPKV (SEQ ID NO:89)).

The secretion of IFN-gamma has been analysed by cultured ELISpot assay. For statistical analysis we performed a Mann-Whitney U-Test.

FIG. 6A-6E show Cultured ELISpot analysis for detecting antigen-specific CD8+ T cells in malaria-exposed Ghanian adults.

Freshly isolated PBMCs from the blood of malaria-exposed (26 blood samples) and non-exposed (naïve) individuals were stimulated with peptide pools of antigen (6A) MALS _C (Mal13P1.258) (ILHGGVYRL (SEQ ID NO:31), ILFLFILSI (SEQ ID NO:32), LLFINEINKL (SEQ ID NO:33)), (6B) MALS_F (PF14_0435) (SLISLYIYYV (SEQ ID NO:34)), (6C) MALS_E (NLLDPLVVV (SEQ ID NO:37), LLLEGNFYL (SEQ ID NO:38), KLIPVNYEL (SEQ ID NO:39), ILIPSLPLI (SEQ ID NO:40)), (6D) Antigen mixture (MALS_A: SLICGLYLL (SEQ ID NO:26), ILYSLMINSL (SEQ ID NO:27), LICGLYLLTL (SEQ ID NO:28); MALS_B: VLLEKINVI (SEQ ID NO:29), YLSPNFINKI (SEQ ID NO:30); MALS_C: ILHGGVYRL (SEQ ID NO:31), ILFLFILSI (SEQ ID NO:32), LLFINEINKL (SEQ ID NO:33); MALS_E: NLLDPLVVV (SEQ ID NO:37), LLLEGNFYL (SEQ ID NO:38), KLIPVNYEL (SEQ ID NO:39), ILIPSLPLI (SEQ ID NO:40); MALS_F: SLISLYIYYV (SEQ ID NO:34); MALS_Cal: FLTLMARKL (SEQ ID NO:36)) as well as peptides derived from (6E) MSPI (merozoite surface protein 1) a described blood-stage antigen (YLIDGYEEI (SEQ ID NO:87), KLLDKINEI (SEQ ID NO:88), KLKEFIPKV (SEQ ID NO:89)).

The secretion of IFN-gamma has been analysed by a cultured ELISpot assay. For statistical analysis we performed a Mann-Whitney U-Test.

EXAMPLES

Example 1

Figure 1:
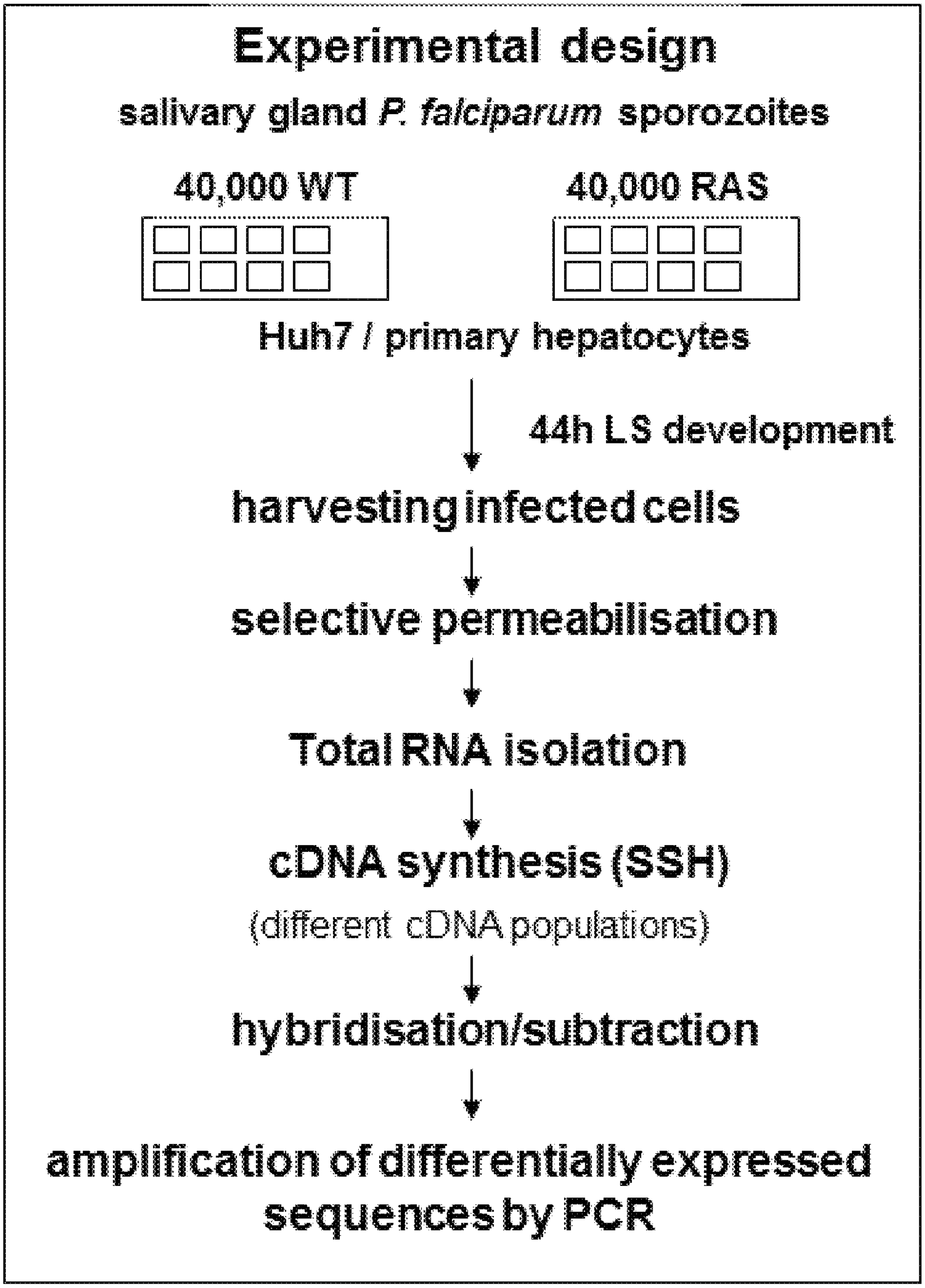
FIG. 1 shows the experimental setup of the modified suppression subtractive hybridisation (SSII) assay for comparing the transcripts of *P. falciparum* WT and RAS parasites after mid-liver stage development.
Figure 2A:
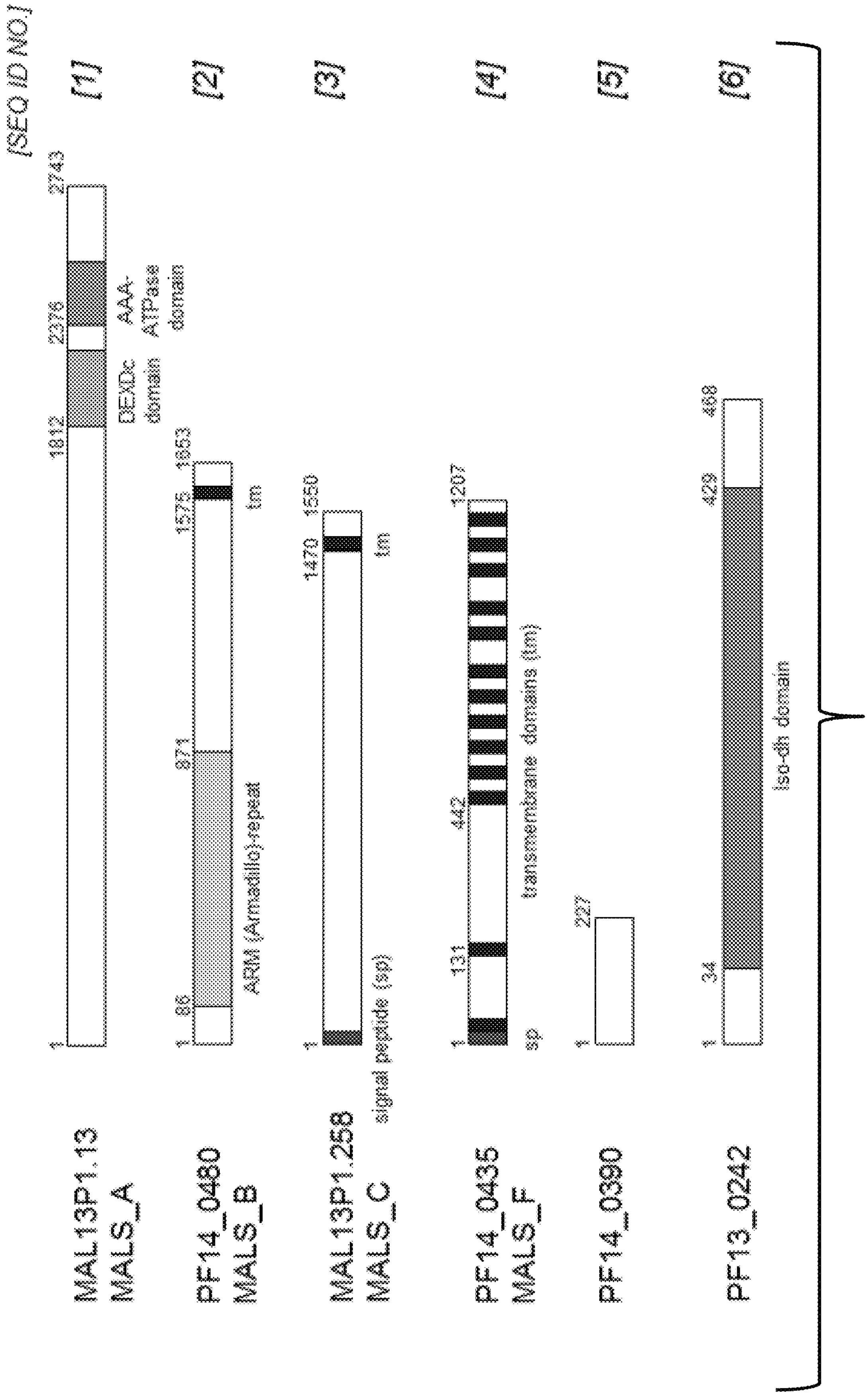
FIGS. 2A-2D show the predicted primary structure of the indicated *P. falciparum* proteins, as predicted by the SMART algorithm (www.smart.embl-heidelberg.de, version 7.0, November 2011), Pfam, EMBL and PlasmoDB.org.
Figure 2B:
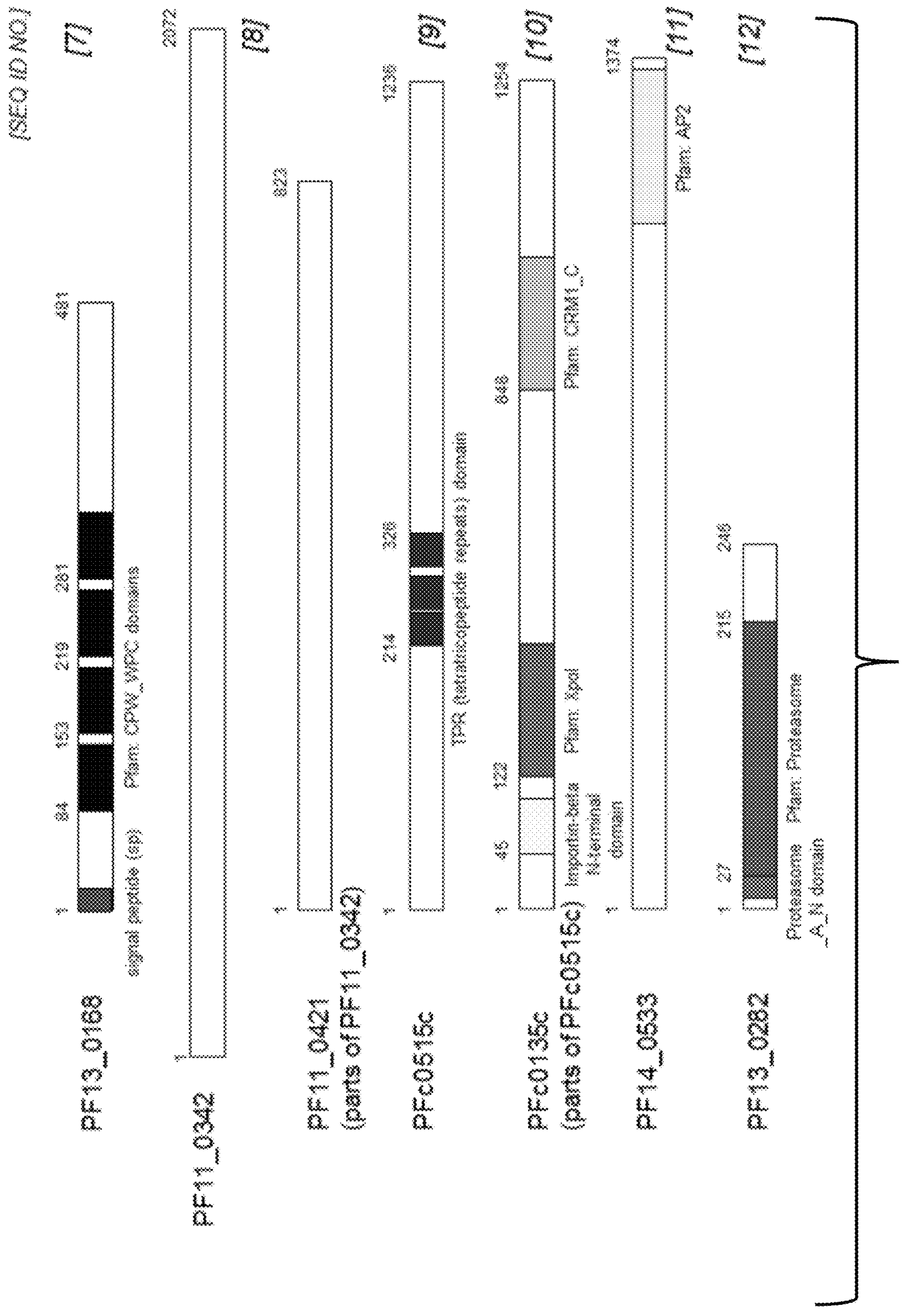
Figure 2C:
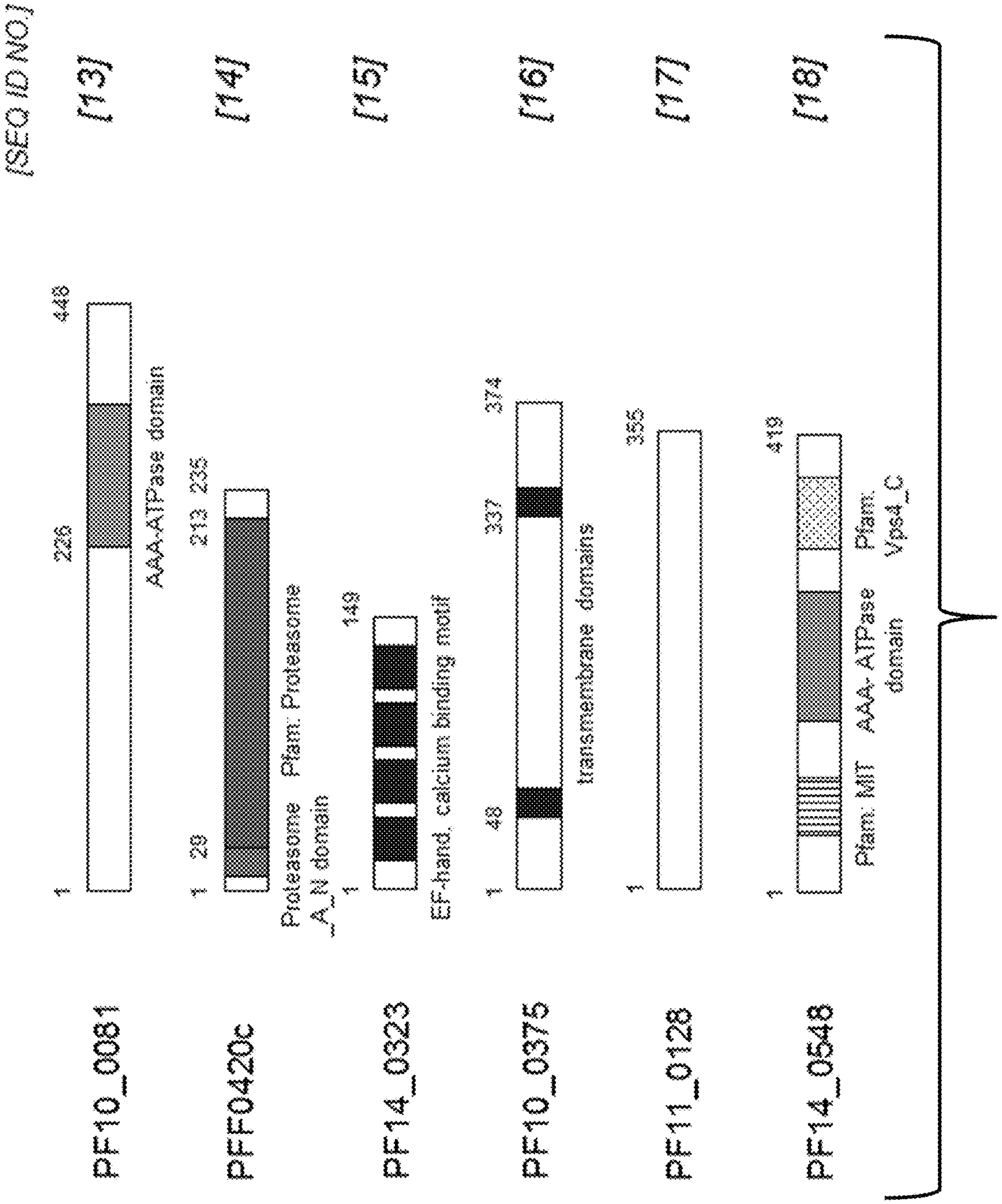
Figure 2D:
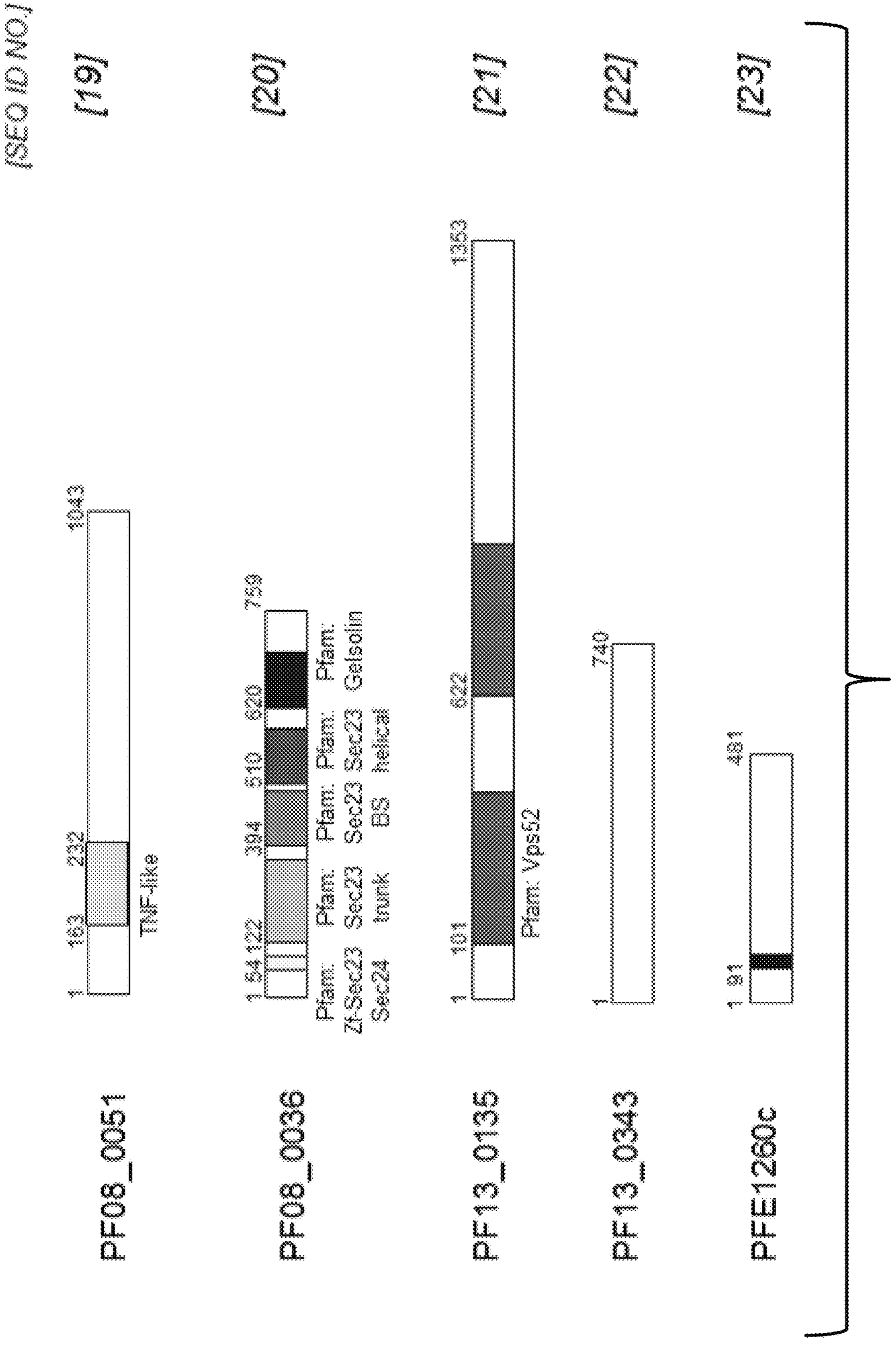

Identification of Potentially Immunogenic Antigens in the Liver Stages Of *P. falciparum* by a SSH Screen It has been shown that immunisation with attenuated parasites confer sterile protection in mice (RAS and GAP) and also in humans (RAS). By applying the SSH (suppressive subtractive hybridisation) technology in order to analyse differentially expressed genes the inventors identified critical/potential targets of protective liver-stage immunity. For that purpose, they compared the transcriptional profile of liver stages from wildtype and attenuated (RAS) parasites, i.e. the cDNA populations of the protected RAS forms and the unprotected WT forms. Their modified suppressive subtractive hybridisation (SSH) screening (FIG. 1) allowed selective enrichment of differentially regulated cDNAs of high and low abundance that are exclusively present in one population. A combination of hybridisation and PCR amplification steps allowed simultaneous normalisation and subtraction of the cDNA populations. Since protective antigens are expressed very early, malaria infected hepatocytes were harvested at early time points after host cell invasion. SMART PCR cDNA Synthesis and PCR-Select cDNA subtraction kits were used to identify differentially expressed genes between the two populations.

Sequencing of the identified differentially expressed genes was conducted by a sequencing company GATC, Konstanz and the data obtained were evaluated with BLAST algorithms (PlasmoDB version: 8.1, Oct. 8, 2011, NCBI, Sanger/GeneDB as of November, 2010, SMART). After sequencing and bioinformatical analysis of 672 RAS-specific clones the inventors were able to describe the 24 most abundantly transcribed antigens as listed in Table 1.

Their predicted primary structures are shown in FIGS. 2A-2D.

Example 2

Validation of Upregulation of RAS-Specific Antigens by Quantitative RT-PCR

The results obtained from the differential expression analyses (Suppression Subtractive Hybridisation screening) have been validated by performing quantitative Real-time PCR (qRT-PCR) for selected antigens. Total RNA isolated from *P. falciparum* wildtype and radiation-attenuated (RAS) liver stage parasites have been used to quantify the respective transcripts in both populations. *Plasmodium* liver stages were obtained by infecting cultured primary human hepatocytes with *P. falciparum* salivary gland sporozoites (strain NF54, Prof. Robert Sauerwein, Nijmegen, Netherlands; Delemarre BJM & Van der Kaay HJ, Ned. T. Geneesk 123 (1979).

Infection of host cells was conducted in close collaboration with the laboratory of Prof. D. Mazier at INSERM, Paris (Semblat et al., 2002). Purified human hepatocytes were plated on collagen I-coated wells ($2.5\times10^6$ cells/well in a 6-well plate) and maintained until infection with salivary gland sporozoites. Cells have been infected with $1.5\times10^6$ sporozoites per well. To obtain liver stages from radiation-attenuated parasites, sporozoites were irradiated at 150 Gray prior infection of liver cells. Two days post infection cells were harvested and total RNA has been purified using TRIzol™ Reagent (a monophasic solution including phenol, and guanidine isothiocyanate which facilitate the isolation of a variety of RNA species of large or small molecular size). First strand cDNA synthesis (Superscript III 1st strand synthesis Kit, Invitrogen) was performed with gene-specific primers (Invitrogen) in a nested first-strand reaction.

Subsequently, cDNA was used to amplify the corresponding transcripts. SYBR Green has been used for quantification (Power SYBR Green Mastermix, Applied Biosystems). For normalisation, parasite specific GAPDH has been used. We also included as a positive control in this analysis the candidate antigens Pf Ferlin (PF14_0530; MALS_E) and Pf Ferlin-like protein (Mal8P1.134; MALS_G) (as described and disclosed in WO 2011/066995).

The following oligonucleotides have been used for the nested first strand cDNA synthesis:

```
Pf G APDH nested rev
                                        [SEQ ID NO: 66]
5' CAGTGGATGCATGAACGGTGG,

MALS_B (PF14 0840) nested rev
                                        [SEQ ID NO: 67]
5' CCTAACTTGGAACATGGGAGTC,

MALS_A (Mal13P1.13) nested rev
                                        [SEQ ID NO: 68]
5' TGCACTCTTCCAAAGCCATG,

MALS_C (Mal13P1.258) nested rev
                                        [SEQ ID NO: 69]
5' ACCATCGTCTTTACCGTGTGAC,

MALS_F (PF14_0435) nested rev
                                        [SEQ ID NO: 70]
5' CTCACGACATTCGAAATGTAATCTC,

MALS_E (PF14_0530) nested rev
                                        [SEQ ID NO: 71]
5' GATCATCATGTTGTTTGAATGATTATACC,

MALSG (Mal8P1.134) nested rev
                                        [SEQ ID NO: 72]
5' CATAATCGAAGCCGTTGCAGC.
```

The following oligonucleotides have been used for amplification of the corresponding transcripts:

```
Pf GAPDH for
                                        [SEQ ID NO: 73]
5' GCAGCCTTTGGAAGGAAAGA
and

Pf GAPDH rev
                                        [SEQ ID NO: 74]
5' GGCTCCTCCCTTAAGGTGAC,

MALS_B (PF14_0840) for
                                        [SEQ ID NO: 75]
5' CGTGCAGCTCTTTAGTAGAAGTGG
and

MALS_B rev
                                        [SEQ ID NO: 76]
5' AGCATTAACAGCAGGGTAACTG,

MALS_A (Mal13P1.13) for
                                        [SEQ ID NO: 77]
5' ATCGTGCACATATGACCATCT
and

MALS_A rev
                                        [SEQ ID NO: 78]
5' CATCTCCCTTGTCCATTTGCAAC,

MALS_C (Mal13P1.258) for
                                        [SEQ ID NO: 79]
5' GGTCTCAGGTATGGACAGGG
and

MALS_C rev
                                        [SEQ ID NO: 80]
5' TCATGATCAGGATGGGGAGATG,

MALS_F (PF14_0435) for
                                        [SEQ ID NO: 81]
5' CGACAAATACATAAAGATGGACGAG
and

MALS_F rev
                                        [SEQ ID NO: 82]
5' CATGGCTTGTTGGTATAAAACATACG,
```

-continued

```
MALS_E (PF14_0530) for
                                        [SEQ ID NO: 83]
5' GCAGCTCTCGTCATATCAGCA
and

MALS_E rev
                                        [SEQ ID NO: 84]
5' TCCAAGCTTCGTCATCATCGT,

MALS_G (Mal8P1.134) for
                                        [SEQ ID NO: 85]
5' GAGCCTATAGGTGAGGCAACC
and

MALS_G rev
                                        [SEQ ID NO: 86]
5' CCAACTGGGTCAAGTTCAGCC.
```

Figure 3:
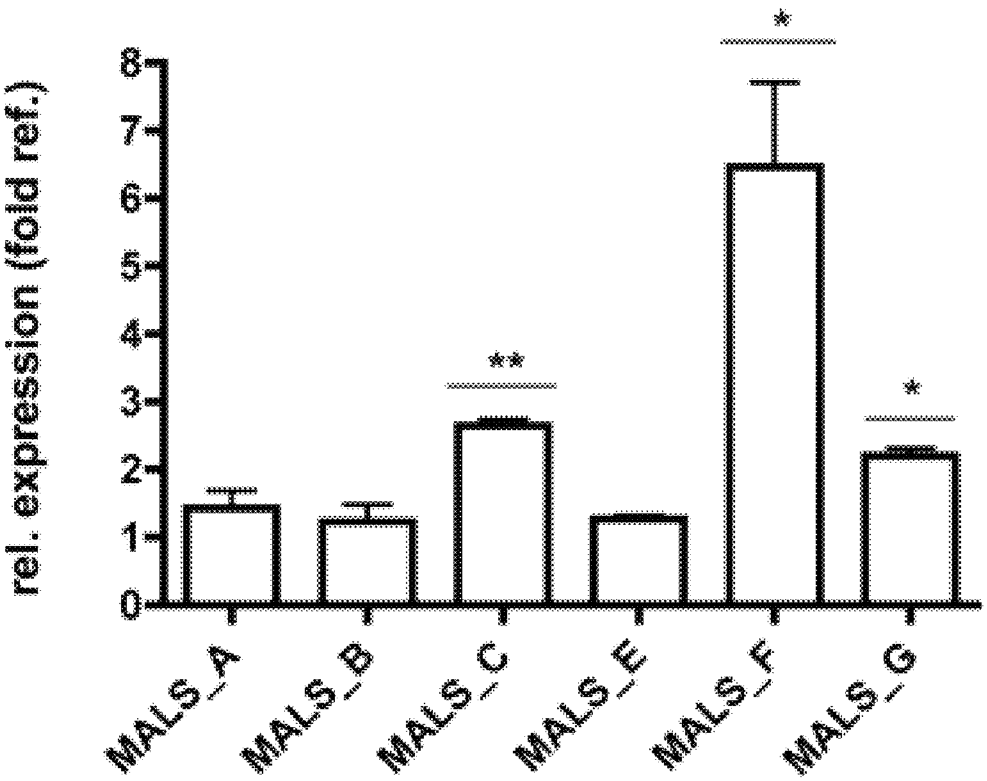
FIG. 3 shows Validation of upregulation of RAS-specific antigens by quantitative RT-PCR. Total RNA has been isolated from *P. falciparum* liver stages (2 days post infection) of Wildtype and RAS followed by first strand cDNA synthesis. cDNA was then subjected for gene-specific qRT-PCR. Statistical analysis was performed by t-test.
Figure 4A:
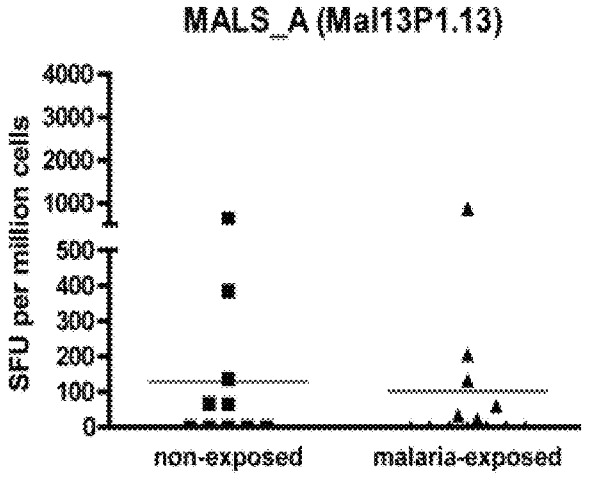
FIG. 4A-4D show Cultured ELISpot analysis for detecting antigen-specific CD8+ T cells in malaria-exposed Kenyan adults. Freshly isolated PBMCs from the blood of malaria-exposed (13 blood samples) and non-exposed (naïve) individuals (8 blood samples) were stimulated with peptide pools of antigen (4A) MALS_A (Mal13P1.13) (SLICGLYLL (SEQ ID NO:26), ILYSLMINSL (SEQ ID NO:27), LICGLYLLTL (SEQ ID NO:33)), (4B) MALS_B (PF14_0480) (VLLEKINVI (SEQ ID NO:26), YLSPNFINKI (SEQ ID NO:30)), (4C) MALS_C (Mal13P1.258) (ILHGGVYRL (SEQ ID NO:31), ILFLFILSI (SEQ ID NO:32), LLFINEINKL (SEQ ID NO:33)), (4D) MALS_F (PF14_0435) (FLLLMLVSI (SEQ ID NO:34), SLISLYIYYV (SEQ ID NO:35)).
Figure 4B:
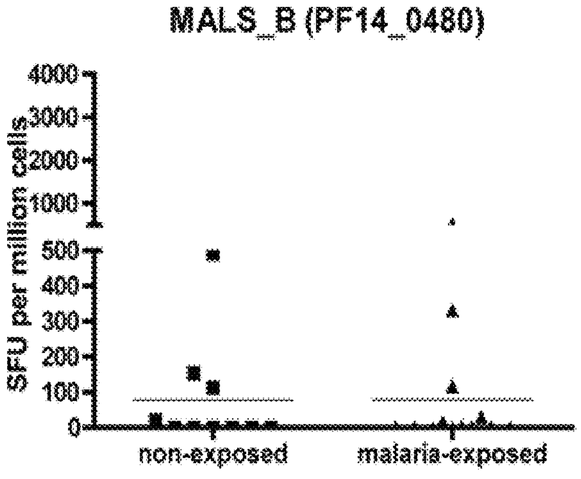
Figure 4C:
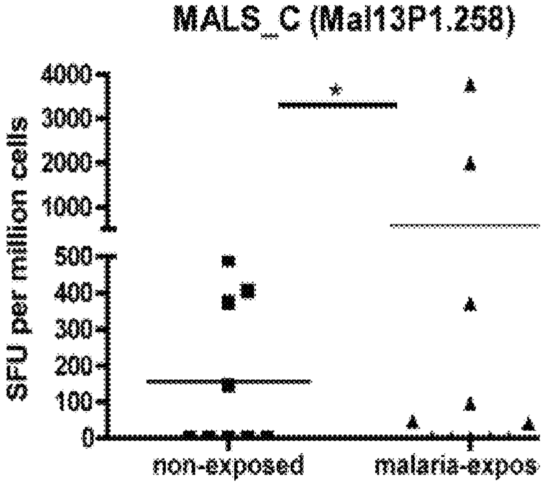
Figure 4D:
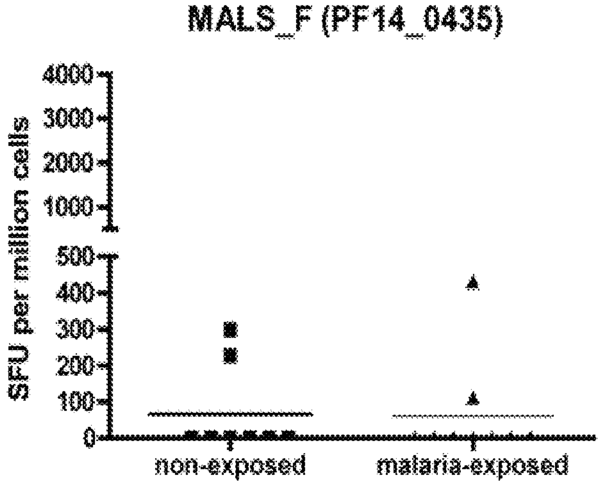
Figure 5A:
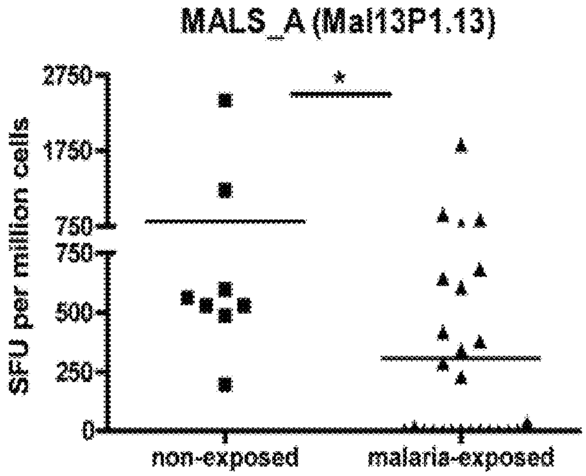
Figure 5B:
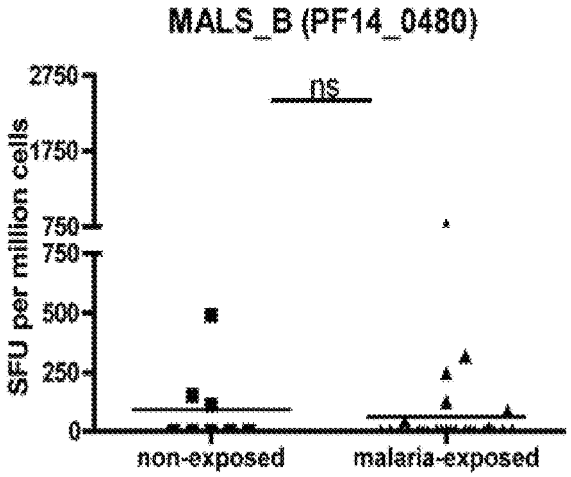
Figure 5C:
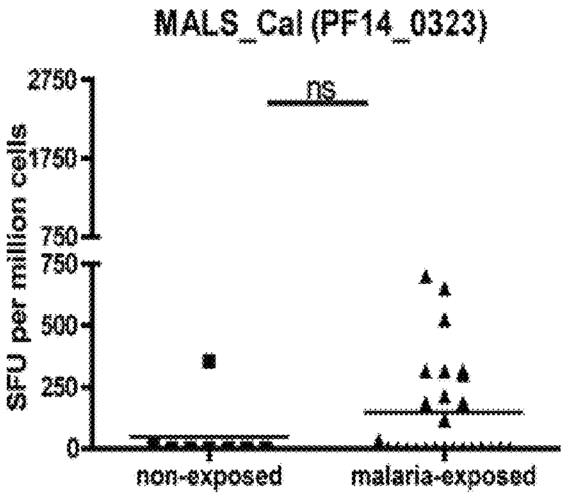
Figure 5D:
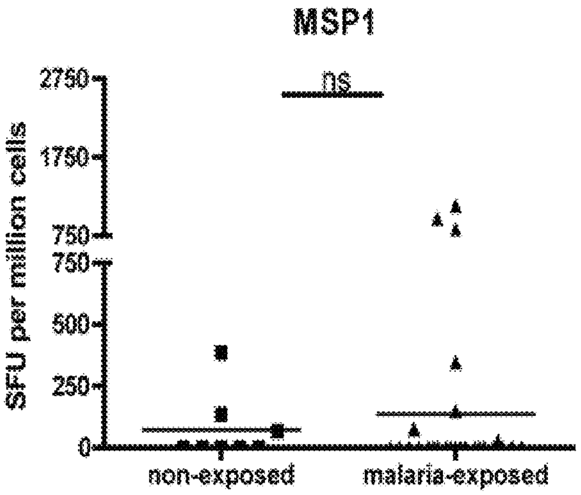
Figure 6A:
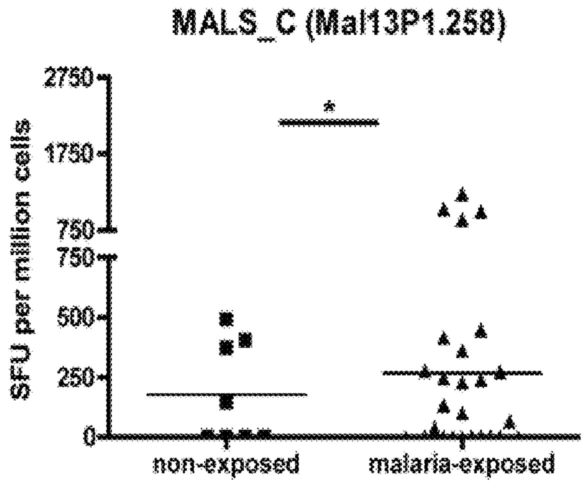
Figure 6B:
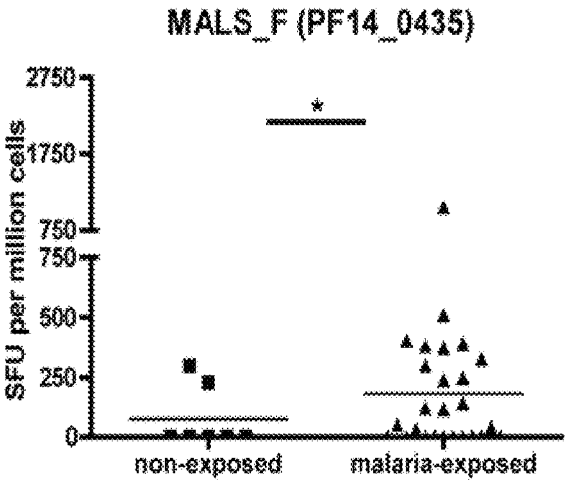
Figure 6C:
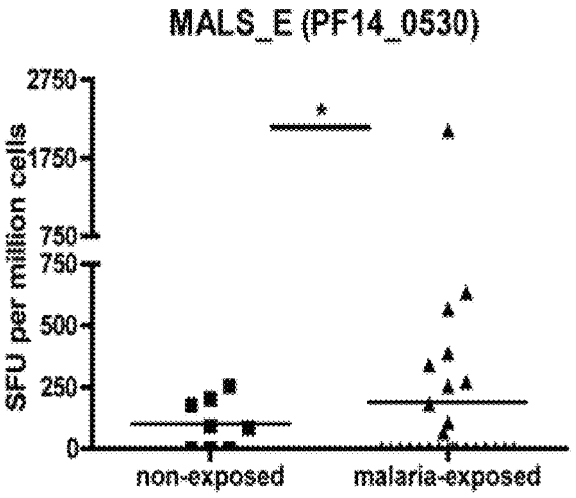
Figure 6D:
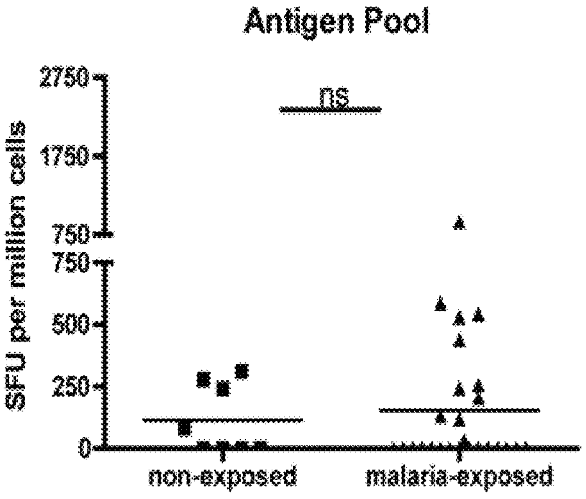
Figure 6E:
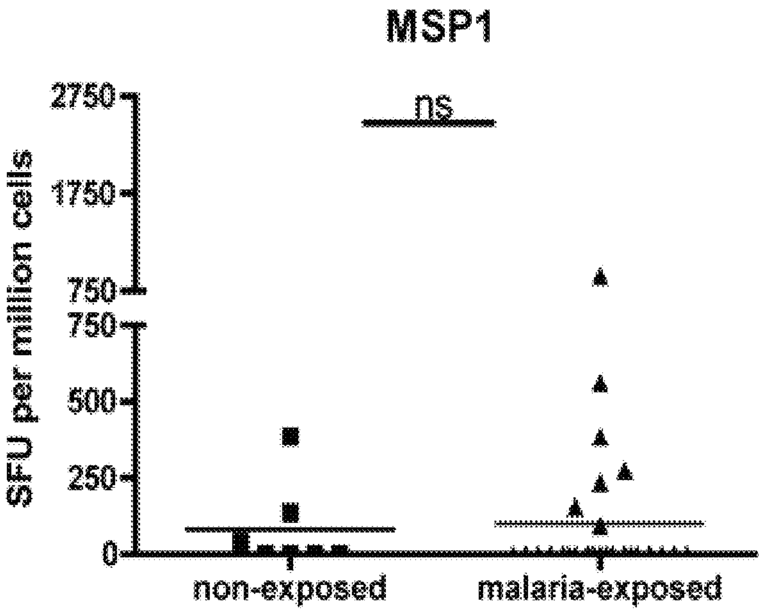

The quantification of the transcript copies clearly shows a 1.2 to 6.5-fold up-regulation of the tested antigens in liver stages of radiation-attenuated parasites compared to wild-type liver stages (see FIG. 3).

Example 3

Presence of Antigen-Specific T Cells Recognising Peptides Derived from Selected Antigen Candidates in Malaria-Exposed Kenyan Adults In order to investigate the presence of antigen-specific T cells in malaria-exposed individuals, T-cell responses to peptides from a first selection of antigens MAL13P1.13 (SLICGLYLL (SEQ ID NO:26), ILYSLMINSL (SEQ ID NO:27), LICGLYLLTL (SEQ ID NO:28)), PF14_0480 (VLLEKINVI (SEQ ID NO:29), YLSPNFINKI (SEQ ID NO:30)), MAL13P1.258 (ILHGGVYRL (SEQ ID NO:31), ILFLFILSI (SEQ ID NO:32), LLFINEINKL (SEQ ID NO:33)), and PF14_0435 (FLLLMLVSI (SEQ ID NO:35), SLISLYIYYV (SEQ ID NO:34)) were tested in semi-immune Kenyan adults in collaboration with Dr. Britta Urban at the Kenyan Medical Research Institute-Wellcome Trust Research Programme (KEMRI). All adults are resident in Junju District, about 60 km north of Mombasa at the Kenyan coast. The area has two high transmission seasons but low-level transmission occurs all year round (infectious bites per year: 23-53) (Mwangi et al., 2005).

In order to determine the production of antigen-specific IFN-gamma by activated peripheral blood mononuclear cells (PBMC), cultured ELISpot analysis was carried out over a period of 10 days. Peripheral blood mononuclear cells (PBMCs) were purified from fresh blood samples by gradient centrifugation using Lymphoprep and resuspended in RPMI 1640 medium containing 10% heat-inactivated FCS, 2 mM L-Glutamine and Penicillin (100 U/ml)/Streptomycin (100 μg/ml). $1\times10^6$ cells were cultured with 10 μg/ml of peptides in a volume of 500 μl. On day 3 and day 7, 250 μl culture medium was removed and replaced with fresh medium containing human IL2 (final concentration 20 U/ml). On day 9, cells were washed three times, resuspended in 500 μl medium and rested overnight before proceeding to an IFN-gamma ELISpot assay (IFN-gamma ELISpot kit, Mabtech). Cells (100.000 cells/well) were transferred to MultiScreen filter plates coated with 10 μg/ml anti-human IFN-gamma antibody and incubated with indicated peptide pools or medium (non stimulated control) overnight (in each case in triplicates). After removing the cells and several washing steps, secreted IFN-gamma was detected by using a second antibody against human IFN-gamma coupled with biotin (1 μg/ml) and subsequent addition of streptavidin-ALP followed by substrate solution.

The detected IFN-gamma response is shown as counted spots per million cells. FIGS. 4A-4D summarize the specific T-cell responses to individual peptide pools from antigens Mal13P1.13, PF14_0840, Mal13P1.258 (high responder) as well as PF14_0435 (mediate responder), which therefore can be considered as valuable candidate antigens for a potential subunit vaccine against malaria.

Example 4

Presence of Antigen-Specific T Cells Recognizing Peptides Derived from Selected Antigen Candidates in Semi-Immune Ghanaian Adults We have been able to expand our investigations on testing reactivity of T cells to our critical target antigens in a malaria holo-endemic region in Ghana.

In close collaboration with Prof Dr. Achim Hoerauf (University of Bonn, Germany) and the Kumasi Center for Collaborative Research, Kumasi, Ghana (KCCR), we investigated the presence of antigen-specific T cells recognising peptides derived from selected antigen candidates in semi-immune Ghanaian adults. Most of the analysed peptides have already been tested in studies in Kilifi, Kenya as described as part of this invention. Within this study the following antigen candidates and corresponding peptides were used: MALS_A=Mal13P1.13 (SLICGLYLL (SEQ ID NO:26), ILYSLMINSL (SEQ ID NO:27), LICGLYLLTL (SEQ ID NO:28)), MALS_B=PF14_0840 (VLLEKINVI (SEQ ID NO:29), YLSPNFINKI (SEQ ID NO:30)), MALS_C =Mal13P1.258 (ILHGGVYRL (SEQ ID NO:31), ILFLFILSI (SEQ ID NO:32), LLFINEINKL (SEQ ID NO:33)), MALS_F=PF14_0435 (SLISLYIYYV (SEQ ID NO:34)) and MALS_Cal=PF14_0323 (FLTLMARKL (SEQ ID NO:36)). In addition to that we included peptides derived from the candidate antigen Pf Ferlin (PF14_0530) as described below (and disclosed in WO 2011/066995).

In order to determine the production of antigen-specific IFN-gamma by activated peripheral blood mononuclear cells (PBMC), cultured ELISpot analyses were carried out over a period of 10 days. Briefly, Peripheral Blood Mononuclear Cells (PBMCs) were purified from fresh blood samples by gradient centrifugation using Lymphoprep and resuspended in RPMI 1640 medium containing 10% heat-inactivated FBS, 2 mM L-Glutamine and Penicillin (100 U/ml)/Streptomycin (100 μg/ml). $1\times10^6$ cells were cultured with 10 μg/ml (except for the tested antigen mixture, described below) of peptides in a volume of 800 μl. On day 3 and day 7, 400 μl culture medium was removed and replaced with fresh medium containing human IL2 (final concentration 20 U/ml), On day 9 cells were washed three times, resuspended in 500 μl medium and rested overnight before proceeding with an IFN-gamma ELISpot assay (IFN-gamma ELISpot kit, Mabtech). Cells (100,000 cells/well) were transferred to MultiScreen filter plates coated with 10 μg/ml anti-human IFN-gamma antibody and incubated with indicated peptide pools or medium (non stimulated control) overnight (in each case in triplicates). After removing the cells and several washing steps, secreted IFN-gamma was detected by using a secondary antibody against human IFN-gamma coupled with biotin (1 μg/ml) and subsequent addition of Streptavidin-ALP followed by substrate solution. The detected IFN-gamma response is shown as counted spots per million cells. In addition to analysing peptide pools from individual antigens, we investigated T cell activation in response to a mixture of antigens (peptide pool). In this experimental set-up, peptides derived from antigen candidates Mal13P1.13 (SLICGLYLL (SEQ ID NO:26), ILYSLMINSL (SEQ ID NO:27), LICGLYLLTL (SEQ ID NO:28)), PF14_0840 (VLLEKINVI(SEQ ID NO:29), YLSPNFINKI (SEQ ID NO:30)), Mal13P1.258 (ILHGGVYRL (SEQ ID NO:31), ILFLFILSI (SEQ ID NO:32), LLFINEINKL (SEQ ID NO:33)), PF14_0435 (SLISLYIYYV (SEQ ID NO:34)), PF14_0323 (FLTLMARKL (SEQ ID NO:36)) and PF14_0530 (NLLDPLVVV (SEQ ID NO:37), LLLEGNFYL (SEQ ID NO:38), KLIPVNYEL (SEQ ID NO:39), ILIPSLPLI (SEQ ID NO:40)) were combined at a concentration of 1.25 μg/ml per peptide (considered as peptide pool).

Two different sets of experiments have been carried out using 26 blood samples of malaria-exposed individuals (semi-immune adults) each (FIGS. 5A-5D and FIGS. 6A-6E, respectively). In parallel CD8+ T cell responses to peptides derived from a known blood-stage vaccine candidate MSP-1 (Merozoite Surface Protein 1) have been determined (Goodman et al., 2010). In good agreement with our hypothesis that parasite transcripts isolated from the protection-mediated attenuated parasite line may serve as critical targets of anti-liver stage immunity we could nicely confirm a significant interaction of these candidate antigens with the host's immune system. Cultured ELISpot analysis hence revealed significant T cell activation as measured by IFN-gamma secretion for the target antigens MALS_A (Mal13P1.13), MALS_C (Mal13P1.258), MALS_E (PF14_0530) and MALS_F (PF14_0435).

With respect to the results shown in FIGS. 5A-5D: Contrary to what was expected we measured IFN-gamma responses against MALS_A in a few individuals from the non-exposed group. We excluded specific restimulation of PBMCs from non-exposed individuals by MALS_A derived peptides after BLAST searches of the specific peptide sequence against human and other apicomplexan parasites (including Toxoplasma) sequences. Evidence from the literature suggests that *Plasmodium* antigens are thought to mimic antigens from other microbes thereby soliciting the reactivation of cross-reactively primed memory T cells rapid (Riley et al, 1999).

The features disclosed in the foregoing description, in the claims and/or in the accompanying drawings may, both separately and in any combination thereof, be material for realizing the invention in diverse forms thereof.

REFERENCES

Alonso, P. L., Sacarlal, J., Aponte, J. J., Leach, A., Macete, E., Milman, J., Mandomando, I., Spiessens, B., Guinovart, C., Espasa, M., Bassat, Q., Aide, P., Ofori-Anyinam, O., Navia, M. M., Corachan, S., Ceuppens, M., Dubois, M. C., Demoitie, M. A., Dubovsky, F., Menendez, C., Tornieporth, N., Ballou, W. R., Thompson, R., Cohen, J. (2004) Efficacy of the RTS,S/AS02A vaccine against *Plasmodium falciparum* infection and disease in young African children: randomised controlled trial. *Lancet* 364, 1411-20.

Alonso, P. L., Sacarlal, J., Aponte, J. J., Leach, A., Macete, E., Aide, P., Sigauque, B., Milman, J., Mandomando, I., Bassat, Q., Guinovart, C., Espasa, M., Corachan, S., Lievens, M., Navia, M. M., Dubois, M. C., Menendez, C., Dubovsky, F., Cohen, J., Thompson, R., Ballou, W. R. (2005) Duration of protection with RTS,S/AS02A malaria vaccine in prevention of *Plasmodium falciparum* disease in Mozambican children: single-blind extended follow-up of a randomised controlled trial. *Lancet* 366, 2012-8.

Aly, A. S., Mikolajczak, S. A., Rivera, H. S., Camargo, N., Jacobs-Lorena, V., Labaied, M., Coppens, I., Kappe, S. H. (2008) Targeted deletion of SAP1 abolishes the expression of infectivity factors necessary for successful malaria parasite liver infection. *Mol Microbiol.* 69, 152-63.

Bejon, P., Lusingu, J., Olotu, A., Leach, A., Lievens, M., Vekemans, J., Mshamu, S., Lang, T., Gould, J., Dubois, M. C., Demoitie, M. A., Stallaert, J. F., Vansadia, P., Carter, T., Njuguna, P., Awuondo, K. O., Malabeja, A., Abdul, O., Gesase, S., Mturi, N., Drakeley, C. J., Savarese, B., Villafana, T., Ballou, W. R., Cohen, J., Riley, E. M., Lemnge, M. M., Marsh, K., von Seidlein, L. (2008) Efficacy of RTS,S/AS01E vaccine against malaria in children 5 to 17 months of age. *N Engl J Med* 359, 2521-32.

Bongfen, S. E., Torgler, R., Romero, J. F., Renia, L., Corradin, G. (2007) *Plasmodium berghei* infected primary hepatocytes process and present the circumsporozoite protein to specific CD8+ T cells in vitro. *J Immunol* 178,7054-7063.

Carvalho, L. H., Sano, G., Hafalla, J. C., Morrot, A., Curotto de Lafaille, M. A., Zavala, F. (2002) IL-4 secreting CD4+ T cells are crucial to the development of CD8+ T-cell-responses against malaria liver stages. *Nat Med* 8,166-170.

Epstein J E, Tewari K, Lyke K E, Sim B K, Billingsley P F, Laurens M B, Gunasekera A, Chakravarty S, James E R, Sedegah M, Richman A, Velmurugan S, Reyes S, Li M, Tucker K, Ahumada A, Ruben A J, Li T, Stafford R, Eappen A G, Tamminga C, Bennett J W, Ockenhouse C F, Murphy J R, Komisar J, Thomas N, Loyevsky M, Birkett A, Plowe C V, Loucq C, Edelman R, Richie T L, Seder R A, Hoffman S L (2011) Live attenuated malaria vaccine designed to protect through CD8+ T cell immunity. *Science.* October 28; 334(6055):475-80. Epub 2011 September 8.

Goodman A L, Epp C, Moss D, Holder A A, Wilson J M, Gao G P, Long C A, Remarque E J, Thomas A W, Ammendola V, Colloca S, Dicks M D, Biswas S, Seibel D, van Duivenvoorde L M, Gilbert S C, Hill A V, Draper S J. (2010) New candidate vaccines against blood-stage *Plasmodium falciparum* malaria: prime-boost immunization regimens incorporating human and simian adenoviral vectors and poxviral vectors expressing an optimized antigen based on merozoite surface protein 1. *Infect Immun.* 78(11):4601-4612.

Gruner, A. C., Mauduit, M., Tewari, R., Romero, J. F., Depinay N., Kayibanda, M., Lallemand, E., Chavatte, J. M., Crisanti, A., Sinnis, P., Mazier, D., Corradin, G., Snounou, G., Renia, L. (2007) Sterile protection against malaria is independent of immune responses to the circumsporozoite protein. *PLoS One* 2, e1371.

Haldar, K., Murphy, S. C., Milner, D. A. Jr, Taylor, T. E. (2007) Malaria: mechanisms of erythrocytic infection and pathologic correlates of severe disease. *Annu Rev Pathol Mech Dis* 2, 217-249.

Hoffman, S. L., Goh, L. M. L., Luke, T. C., Schneider, I., Le, T. P., Doolan, D. L., Sacci, J., de la Vega, P., Dowler, M., Paul, C., Gordon, D. M., Stoute, J. A., Church, L. W., Sedegah, M., Heppner, D. G., Ballou, W. R., Richie, T. L. (2002) Protection of humans against malaria with radiation-attenuated *Plasmodium falciparum* sporozoites. *J Infect Dis* 185,1155-64.

Jobe, O., Lumsden, J., Mueller, A. K., Williams, J., Silva-Rivera, H., Kappe, S. H., Schwenk, R. J., Matuschewski, K., Krzych, U. (2007) Genetically attenuated *Plasmodium berghei* liver stages induce sterile protracted protection that is mediated by major histocompatibility complex Class I-dependent interferon-gamma-producing CD8+ T cells. *J Infect Dis.* 196, 599-607.

Klotz, F. W., Scheller, L. F., Seguin, M. C., Kumar, M. A., Marietta, A., Green, S. J., Azad, A. F. (1995) Co-localization of inducible nitric oxide synthase and *Plasmodium berghei* in hepatocytes from rats immunized with irradiated sporozoites. *J Immunol.* 154, 3391-3395.

Leiriao, P., Mota, M. M., Rodriguez, A. (2005) Apoptoptic *Plasmodium*-infected hepatocytes provide antigens to liver dendritic cells. *J Infect Dis.* 191,1576-1581.

Mauduit, M., Tewari, R., Depinay, N., Kayibanda, M., Lallemand, E., Chavatte, J. M., Snounou, G., Renia, L., Grüner, A. C. (2010) Minimal role for the circumsporozoite protein in the induction of sterile immunity by vaccination with live rodent malaria sporozoites. *Infect Immun.* 78, 2182-8.

Mueller, A. K., Labaied, M., Kappe, S. H. & Matuschewski, K. (2005 a) Genetically modified *Plasmodium* parasites as a protective experimental malaria vaccine. *Nature* 433, 164-7.

Mueller, A. K., Camargo, N., Kaiser, K., Andorfer, C., Frevert, U., Matuschewski, K., Kappe, S. H. (2005 b) *Plasmodium* liver stage developmental arrest by depletion of a protein at the parasite-host interface. *Proc Natl Acad Sci USA* 102, 3022-7.

Mueller, A. K., Deckert, M., Heiss, K., Goetz, K., Matuschewski, K., Schluter, D. (2007) Genetically attenuated *Plasmodium berghei* liver stages persist and elicit sterile protection primarily via CD8 T cells. *Am J Pathol* 171, 107-115.

Mwangi, T. W., Ross, A., Snow, R. W., Marsh, K. (2005) Case definitions of clinical malaria under different transmission conditions in Kilifi District, Kenya. *J Infect Dis* 191, 1932-9.

Nussenzweig, R. S., Vanderberg, J., Most, H. & Orton, C. (1967) Protective immunity produced by the injection of γ-irradiated sporozoites of *Plasmodium berghei. Nature* 216, 160-2.

Oliveira, G. A., Kumar, K. A., Calvo-Calle J. M., Othoro, C., Altszuler, D., Nussenzweig, V., Nardin, E. H. (2008) Class II restricted immunity induced by malaria sporozoites. *Infect Immun.* 76, 200-1206.

Prudenco, M., Rodriguez, A., Mota, M. M. (2006) The silent path to thousands of merozoites: the *Plasmodium* liver stage. *Nat Rev Microbiol* 4, 849-856.

Putrianti, E. D., Silvie, 0., Kordes M., Borrmann, S., Matuschewski K. (2009) Vaccine-like immunity against malaria by repeated causal-prophylactic treatment of liver-stage *Plasmodium* parasites. *J Infect Dis* 199, 899-903.

Riley E. M. (1999) Is T-cell priming required for initiation of pathology in malaria infections? *Immunol Today.* 20:228-33.

Roestenberg, M., McCall, M., Hopman, J., Wiersma, J., Luty, A. J., van Gemert, G. J., van de Vegte-Bolmer, M., van Schaijk, B., Teelen, K., Arens, T., Spaarman, L., de Mast, Q., Roeffen, W., Snounou, G., Renia, L., van der Ven, A., Heimsen, C. C., Sauerwein, R. (2009) Protection against a malaria challenge by sporozoite inoculation. *N Engl J Med* 361, 468-77.

Semblat J P, Silvie O, Franetich J F, Mazier D. (2005) Laser capture microdissection of hepatic stages of the human parasite *Plasmodium falciparum* for molecular analysis. *Methods Mol Biol.* 293:301-7.

Silvie, O., Semblat, J. P., Franetich, J. F., Hannoun, L., Eling, W., Mazier, D. (2002) Effects of irradiation on *Plasmodium falciparum* sporozoite hepatic development: implications for the design of pre-erythrocytic malaria vaccines. *Parasite Immunol.* 24, 221-3.

Silvie, O., Goetz, K., Matuschewski, K. (2008) A sporozoite asparagine-rich protein controls initiation of *Plasmodium* liver stage development. *PLoS Pathog.* 4(6), e1000086.

Sturm, A., Amino, R., van de Sand, C., Regen, T., Retzlaff, S., Rennenberg, A., Krueger, A., Pollok, J. M., Menard, R., Heussler, V. T. (2006) Manipulation of host hepatocytes by the malaria parasite for delivery into liver sinusoids. *Science* 313, 1287-1290.

Tarun, A. S., Dumpit, R. F., Camargo, N., Labaied, M., Liu, P., Takagi, A., Wang, R., Kappe, S. H. (2007) Protracted sterile protection with *Plasmodium yoelii* pre-erythrocytic genetically attenuated parasite malaria vaccines is independent of significant liver stage persistence and is mediated by CD8+ T cells. *J Infect Dis* 196, 608-16.

van Dijk, M. R., Douradinha, B., Franke-Fayard, B., Heussler, V., van Dooren, M. W., van Schaijk, B., van Gemert, G. J., Sauerwein, R. W., Mota, M. M., Waters, A. P., Janse, C. J. (2005) Genetically attenuated, P36p-deficient malarial sporozoites induce protective immunity and apoptosis of infected liver cells. *Proc Natl Acad Sci USA.* 102, 12194-9.

van Schaijk, B. C., Janse, C. J., van Gemert, G. J., van Dijk, M. R., Gego, A., Franetich, J. F., van de Vegte-Bolmer, M., Yalaoui, S., Silvie, O., Hoffman, S. L., Waters, A. P., Mazier, D., Sauerwein, R. W., Khan, S. M. (2008) Gene disruption of *Plasmodium falciparum* p52 results in attenuation of malaria liver stage development in cultured primary hepatocytes. *PLoS ONE.* 3:e3549.

VanBuskirk, K. M., O'Neill, M. T., De La Vega, P., Maier, A. G., Krzych, U., Williams, J., Dowler, M. G., Sacci, J. B. Jr., Kangwanrangsan, N., Tsuboi, T., Kneteman, N. M., Heppner, D. G. Jr., Murdock, B. A., Mikolajczak, S. A., Aly, S. A., Cowman, A. F., Kappe, S. H. (2009) Preerythrocytic, live-attenuated *Plasmodium falciparum* vaccine candidates by design. *Proc Natl Acad Sci USA.* 106, 13004-9.

White, K. L., Synder, H. L., Krzych, U. (1996) MHC class-I dependent presentation of exoerythrocytic antigens to CD8+ T lymphocytes is required for protective immunity against *Plasmodium berghei. J Immunol.* 156, 3374-3381.

We claim:

1. A multicomponent composition, which is immunogenic, comprising at least two polypeptides and an adjuvant, wherein each of said at least two polypeptides has a length in the range of 5 to 50 amino acids, wherein at least one of the two polypeptides comprises an amino acid sequence

SLICGLYLL, (SEQ ID NO: 26)

and at least one of the two polypeptides comprises an amino acid sequence

LLFINEINKL. (SEQ ID NO: 33)

2. The multicomponent composition, according to claim 1, wherein the composition further comprises a mixture of polypeptides comprising the sequences of SEQ ID NOs: 27, 28, 31 and 32, wherein each of these further polypeptides has a length in the range of 5 to 50 amino acids.

3. The multicomponent composition, according to claim 1, wherein the composition further comprises a polypeptide comprising an amino acid sequence selected from:

VLLEKINVI, (SEQ ID NO: 29)

YLSPNFINKI, (SEQ ID NO: 30)

SLISLYIYYV, (SEQ ID NO: 34)

FLLLMLVSI, (SEQ ID NO: 35)

-continued

FLTLMARKL, (SEQ ID NO: 36)

NLLDPLVVV, (SEQ ID NO: 37)

LLLEGNFYL, (SEQ ID NO: 38)

KLIPVNYEL, (SEQ ID NO: 39)
or

ILIPSLPLI, (SEQ ID NO: 40)

wherein the polypeptide has a length in the range of 5 to 50 amino acids.

4. The multicomponent composition, according to claim 1, wherein the composition further comprises polypeptides selected from the following polypeptides:

a mixture of SEQ ID NOs: 29 and 30;

a mixture of SEQ ID NOs: 34 and 35;

SEQ ID NO: 36; and a mixture of SEQ ID NOs: 37 to 40, wherein each of these further polypeptides has a length in the range of 5 to 50 amino acids.

5. The multicomponent composition, according to claim 1, wherein the polypeptides comprise one or more labels, N- and/or C-terminal modifications, or a drug.

6. The multicomponent composition, according to claim 1, wherein the adjuvant triggers a CD8 T cell response.

7. A method for activating an immune response, wherein said method comprises administering, to a subject in need of such activation, the multicomponent composition according to claim 1.

8. The multicomponent composition, according to claim 1, wherein each of at least two polypeptides has a length of 8 to 25 amino acids.

* * * * *